(12) United States Patent
Fairhurst et al.

(10) Patent No.: US 8,193,164 B2
(45) Date of Patent: Jun. 5, 2012

(54) ORGANIC COMPOUNDS

(75) Inventors: Robin Alec Fairhurst, Horsham (GB); Roger John Taylor, Horsham (GB)

(73) Assignee: Novartis AG, Basel (CH)

( * ) Notice: Subject to any disclaimer, the term of this patent is extended or adjusted under 35 U.S.C. 154(b) by 565 days.

(21) Appl. No.: 12/297,491

(22) PCT Filed: Apr. 19, 2007

(86) PCT No.: PCT/EP2007/003439
§ 371 (c)(1),
(2), (4) Date: Oct. 17, 2008

(87) PCT Pub. No.: WO2007/121924
PCT Pub. Date: Nov. 1, 2007

(65) Prior Publication Data
US 2010/0190784 A1 Jul. 29, 2010

(30) Foreign Application Priority Data
Apr. 21, 2006 (GB) .................................. 0607950.3

(51) Int. Cl.
C07D 519/00 (2006.01)
A61K 31/52 (2006.01)
A61P 17/06 (2006.01)
A61P 29/00 (2006.01)
A61P 11/06 (2006.01)
A61P 11/00 (2006.01)
A61P 37/08 (2006.01)
C07D 473/40 (2006.01)
C07D 251/54 (2006.01)
C07D 251/50 (2006.01)
C07D 473/16 (2006.01)

(52) U.S. Cl. ..................... 514/46; 514/263.4; 514/232.5; 514/245; 544/81; 544/198; 544/277; 544/209; 544/264; 536/27.23; 536/27.61

(58) Field of Classification Search .................. 544/81, 544/198, 277; 514/46, 263.4, 232.5, 245; 536/27.23, 27.61
See application file for complete search history.

(56) References Cited

U.S. PATENT DOCUMENTS

| | | |
|---|---|---|
| 4,008,125 A | 2/1977 | Kurozumi et al. |
| 4,738,954 A | 4/1988 | Hamilton et al. |
| 4,873,360 A | 10/1989 | Johnson et al. |
| 4,954,504 A | 9/1990 | Chen et al. |
| 5,688,774 A | 11/1997 | Jacobson et al. |
| 6,307,054 B1 | 10/2001 | Truesdale et al. |
| 6,376,472 B1 | 4/2002 | Myers et al. |
| 6,403,567 B1 | 6/2002 | Zablocki et al. |
| 6,429,315 B1 | 8/2002 | Sledeski et al. |
| 6,492,348 B1 | 12/2002 | Bays et al. |
| 6,559,313 B2 | 5/2003 | Myers et al. |
| 6,677,316 B2 | 1/2004 | Bays et al. |
| 7,553,823 B2 | 6/2009 | Zablocki et al. |
| 7,737,126 B2 * | 6/2010 | Blatcher et al. .................. 514/46 |
| 2003/0092668 A1 | 5/2003 | Liang et al. |
| 2003/0176390 A1 | 9/2003 | Herling et al. |
| 2004/0106572 A1 | 6/2004 | Fishman et al. |
| 2004/0162422 A1 | 8/2004 | Hall et al. |
| 2005/0101551 A1 | 5/2005 | Sevillano et al. |
| 2005/0182018 A1 | 8/2005 | Linden et al. |
| 2006/0142237 A1 | 6/2006 | Fishman et al. |
| 2006/0189636 A1 | 8/2006 | Critchley et al. |
| 2007/0099865 A1 | 5/2007 | Fishman et al. |
| 2007/0191293 A1 | 8/2007 | Langston et al. |
| 2007/0232626 A1 | 10/2007 | Jacobson et al. |
| 2008/0027022 A1 | 1/2008 | Linden et al. |
| 2008/0051364 A1 | 2/2008 | Fishman et al. |
| 2008/0051404 A1 | 2/2008 | Claiborne et al. |
| 2008/0200483 A1 | 8/2008 | Fairhurst et al. |
| 2008/0207648 A1 | 8/2008 | Fairhurst et al. |
| 2008/0214581 A1 | 9/2008 | Allen et al. |
| 2008/0242683 A1 | 10/2008 | Fairhurst et al. |
| 2008/0262001 A1 | 10/2008 | Kranenburg et al. |
| 2008/0300213 A1 | 12/2008 | Fishman |
| 2008/0312160 A1 | 12/2008 | Guerrant et al. |
| 2009/0012035 A1 | 1/2009 | Jacobson et al. |

(Continued)

FOREIGN PATENT DOCUMENTS
EP 0 267 878 A1 5/1988
(Continued)

OTHER PUBLICATIONS

Bressi, J. Med. Chem. 2000, 43, 4135-4150.*
Wanner, Martin J.; Koomen, Gerrit-Jan, J. Chem. Soc. Perkin Trans. 1, (2001), 1908-1915.*
Fairhurst et al., U.S. PTO Office Action, U.S. Appl. No. 12/297,727, filed Oct. 4, 2010, 13 pgs.
Baraldi et al., "Recent improvements in the field of A3 adenosine receptor ligands", Expert Opinion on Therapeutic Patents, vol. 15, No. 11 (2005), pp. 1507-1519.

(Continued)

Primary Examiner — Mark Berch
(74) Attorney, Agent, or Firm — Paul D. Strain, Esq.; Strain & Strain PLLC

(57) ABSTRACT

A compound of formula (I), or stereoisomers or pharmaceutically acceptable salts thereof, (I)

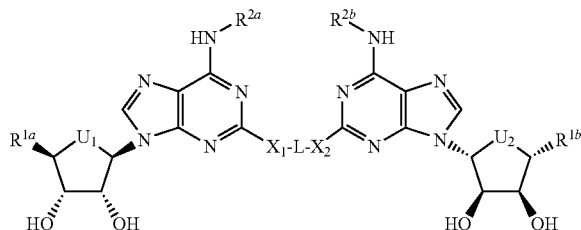

wherein, $R^{1a}$, $R^{1b}$, $R^{2a}$, $R^{2b}$, $U_1$, $U_2$, $X_1$, $X_2$ and L are as defined herein.

4 Claims, No Drawings

U.S. PATENT DOCUMENTS

| | | |
|---|---|---|
| 2009/0054476 A1 | 2/2009 | Goblyos et al. |
| 2009/0081764 A1 | 3/2009 | Pausch et al. |
| 2009/0093633 A1 | 4/2009 | Fairhurst et al. |
| 2009/0099214 A1 | 4/2009 | Fairhurst et al. |
| 2009/0105476 A1 | 4/2009 | Fairhurst et al. |
| 2009/0123510 A1 | 5/2009 | Cronstein et al. |
| 2009/0181920 A1 | 7/2009 | Watkins et al. |
| 2009/0181934 A1 | 7/2009 | Fairhurst |
| 2009/0240045 A1 | 9/2009 | Fairhurst et al. |
| 2009/0281126 A1 | 11/2009 | Fairhurst et al. |
| 2009/0281127 A1 | 11/2009 | Fairhurst et al. |
| 2009/0325967 A1 | 12/2009 | Fairhurst et al. |
| 2010/0041918 A1 | 2/2010 | Laumen |
| 2010/0197914 A1 | 8/2010 | Fairhurst et al. |
| 2010/0240680 A1 | 9/2010 | Fairhurst et al. |
| 2010/0286126 A1 | 11/2010 | Fairhurst et al. |

FOREIGN PATENT DOCUMENTS

| | | |
|---|---|---|
| JP | 63-219387 | 9/1988 |
| WO | WO 92/05177 A1 | 4/1992 |
| WO | WO 93/22328 | 11/1993 |
| WO | WO 98/50047 A1 | 11/1998 |
| WO | WO 99/67263 A1 | 12/1999 |
| WO | WO 99/67265 A1 | 12/1999 |
| WO | WO 99/67266 A1 | 12/1999 |
| WO | WO 00/23457 | 4/2000 |
| WO | WO 00/78774 A2 | 12/2000 |
| WO | WO 00/78779 A2 | 12/2000 |
| WO | WO 01/60835 A1 | 8/2001 |
| WO | WO 02/22630 A1 | 3/2002 |
| WO | WO 02/055085 A2 | 7/2002 |
| WO | WO 02/070534 A1 | 9/2002 |
| WO | WO 03/029264 A2 | 4/2003 |
| WO | WO 03/086408 A1 | 10/2003 |
| WO | WO 2005/063246 A1 | 7/2005 |
| WO | WO 2005/084653 A2 | 9/2005 |
| WO | WO 2005/107463 A1 | 11/2005 |
| WO | WO2005/116037 A1 | 12/2005 |
| WO | WO 2006/011130 A1 | 2/2006 |
| WO | WO 2006/045552 A1 | 5/2006 |
| WO | WO 2006/074925 A1 | 7/2006 |
| WO | WO 2006/097260 A1 | 9/2006 |
| WO | WO 2007/121917 A2 | 11/2007 |
| WO | WO 2007/121919 A1 | 11/2007 |
| WO | WO 2007/121920 A2 | 11/2007 |
| WO | WO 2007/121921 A2 | 11/2007 |
| WO | WO 2007/121923 A1 | 11/2007 |
| WO | WO 2007/121924 A2 | 11/2007 |
| WO | WO 2007/147659 A1 | 12/2007 |
| WO | WO 2008/006563 A1 | 1/2008 |

OTHER PUBLICATIONS

Barnard et al., "Inhibition of measles virus replication by 5'-nor carbocyclic adenosine analogues", Antiviral Chemistry & Chemotherapy, vol. 12, No. 4 (2001), pp. 241-250.
Broadley et al., "Drugs Modulating Adenosine Receptors as Potential Therapeutic Agents for Cardiovascular Diseases", Expert Opinion on Therapeutic Patents, vol. 10, No. 11 (2000), pp. 1669-1692.
Cowart et al., "Synthesis of Novel Carbocyclic Adenosine Analogues as Inhibitors of Adenosine Kinase", J. Org. Chem., vol. 64, No. 7 (1999), pp. 2240-2249.
Curran et al., "The Preparation of Optically Active 2, Cyclopenten-1,4-Diol Derivatives from Furfuryl Alcohol", Tetrahedron, vol. 53, No. 6 (1997), pp. 1983-2004.
Duhamel et al., "Acylation Enatioselective D'un Diol, Meso: Le Cis-Cyclopenthen-2 Diol-1,4", Tetrahedron Letters, vol. 26, No. 26 (1985), pp. 3099-3102.
Galkina et al., "Studies on an Oixdative, 1,4-Addition to s-trans-1,3-Dienes, a Key Reaction in a Strigol Total Synthesis", Eur. J. Org. Chem., (2003), pp. 4640-4653.
Ghosh et al. "Synthesis of Enantiomerically Pure 5'-Aza Noraristeromycin Analogs", J. Org. Chem., vol. 60, No. 18 (1995), pp. 5808-5813.
Hegde et al., "5'-Amino-5'-deoxy-5'-noraristeromycin", Chemical Abstracts Index entry for Journal of Organic Chemistry, vol. 63, No. 20 (1998), pp. 7092-7094.
Hegde et al., "5'-Amino-5'-deoxy-5'noraristeromycin", J. Org. Chem., vol. 63, No. 20 (1998), pp. 7092-7094.
Marlene A Jacobsen, "Adenosine receptor agonists", Expert Opinion Therapeutic Targets, vol. 12, No. 4 (2002), pp. 489-501.
Marumoto et al., "Synthesis and Coronary Vasodilating Activity of 2-Substituted Adenosines", Chemical and Pharmaceutical Bulletin, vol. 23, No. 4 (1975), pp. 759-774.
Oriyama et al., "Catalytic Asymmetrization of CIS-2-Cyclopentene-1,4-Diol. Highly Efficient and Practical Synthesis . . . ", Heterocycles, vol. 52, No. 3 (2000), pp. 1055-1069.
Palle et al., "Structure-Affinity Relationships of the Affinity of 2-Pyrazolyl Adenosine Analogues for the Adenosine A2A Receptor", Bioorganic & Medicinal Chemistry Letters, vol. 12, No. 20 (2002), pp. 2935-2939.
Silverman J, Rheumatol, vol. 35, No. 4(2008), pp. 1-8.
Terashima et al., "Novel Use of Meso-Compound for the Preparation of Optically Active Compounds . . . ", Tetrahedron Letters, vol. 11 (1977), pp. 1001-1004.
Yang et al., "Amino substituted derivatives of 5'-amino-5'-deoxy-5'-noraristeromycin", Bioorganic & Medicinal Chemistry, vol. 13, No. 3 (2005), pp. 877-882.
Fairhurst, U.S. PTO Office Action, U.S. Appl. No. 11/576,607, Jan. 11, 2010, 39 pgs.
Fairhurst, U.S. PTO Office Action, U.S. Appl. No. 11/576,607, Dec. 23, 2009, 43 pgs.
Fairhurst, U.S. PTO Office Action, U.S. Appl. No. 11/576,607, Jul. 16, 2010, 40 pgs.
Fairhurst, U.S. PTO Office Action, U.S. Appl. No. 11/722,835, Dec. 22, 2009, 37 pgs.
Fairhurst, U.S. PTO Office Action, U.S. Appl. No. 11/722,835, Jul. 16, 2010, 32 pgs.
Fairhurst, U.S. PTO Office Action, U.S. Appl. No. 12/296,714, Jan. 5, 2010, 4 pgs.
Fairhurst, U.S. PTO Office Action, U.S. Appl. No. 12/296,714, May 19, 2010, 63 pgs.
Fairhurst, U.S. PTO Office Action, U.S. Appl. No. 12/296,714, Dec. 23, 2009, 12 pgs.
Fairhurst, U.S. PTO Office Action, U.S. Appl. No. 12/296,714, Dec. 30, 2009, 10 pgs.
Fairhurst, U.S. PTO Office Action, U.S. Appl. No. 12/297,373, Dec. 22, 2009, 8 pgs.
Fairhurst, U.S. PTO Office Action, U.S. Appl. No. 12/297,373, Jul. 15, 2010, 8 pgs.
Fairhurst, U.S. PTO Office Action, U.S. Appl. No. 12/297,404, Dec. 30, 2009, 18 pgs.
Fairhurst, U.S. PTO Office Action, U.S. Appl. No. 12/297,404, Jul. 15, 2010, 38 pgs.
Fairhurst, U.S. PTO Office Action, U.S. Appl. No. 12/297,940, Jan. 22, 2010, 15 pgs.
Fairhurst, U.S. PTO Office Action, U.S. Appl. No. 12/297,007, Dec. 23, 2009, 11 pgs.
Fairhurst, U.S. PTO Office Action, U.S. Appl. No. 12/297,007, Jul. 15, 2010, 32 pgs.
International Search Report, PCT/EP2007/006156, Oct. 12, 2007, 3 pgs.
International Search Report, PCT/EP2007/059666, Jan. 18, 2008, 3 pgs.
Kerns et al., "Drug-like Properties: Concepts, Structure Design and Methods: from ADME to Toxicity Optimization", Elsevier (2008), pp. 92-93.
Goosen et al., "Physicochemical Characterization and Solubility Analysis of Thalidomide and Its N-Alkyl Analogs", Pharmaceutical Research, vol. 19, No. 1 (2002), pp. 13-19.
Fourie et al., "Percutaneous delivery of carbamazepine and selected N-alkyl and N-hydroxyalkyl analogues", International Journal of Pharmaceutics, vol. 279, Issues 1-2 (2004), pp. 59-66.
Edwards et al., "Nonpeptidic Inhibitors of Human Neutrophil Elastase. 7. Design, Synthesis, and in Vitro Activity of a Series of Pyridopyrimidine Trifluoromethyl Ketones", J. Med. Chem., vol. 39 (1996), pp. 1112-1124.
Rautio et al., "Piperazinylalkyl prodrugs of naproxen improve in vitro skin permeation", European Journal of Pharmaceutical Sciences, vol. 11 (2000), pp. 157-163.

Pending U.S. Appl. No. 12/297,291, Fairhurst et al., filed Oct. 15, 2008.
Kikugawa et al., "Platelet Aggregation Inhibitors. 6.12-Thioadenosine Derivatives", Journal of Medicinal Chemistry, 1973 vol. 16 No. 12 pp. 1381-1388.
Pending U.S. Appl. No. 13/218,865, Robin Alec Fairhurst et al., filed Aug. 26, 2011.
Pending U.S. Appl. No. 13/218,887, Robin Alec Fairhurst et al., filed Aug. 26, 2011.
Fairhurst, U.S. PTO Notice of Allowance, U.S. Appl. No. 11/576,607, Jun. 9, 2011, 7 pgs.
Fairhurst, U.S. PTO Notice of Allowance, U.S. Appl. No. 11/722,835, May 27, 2011, 7 pgs.
Fairhurst, U.S. PTO Office Action, U.S. Appl. No. 11/576,607, Feb. 17, 2011, 12 pgs.
Fairhurst, U.S. PTO Office Action, U.S. Appl. No. 11/722,835, Jan. 3, 2011, 12 pgs.
Fairhurst, U.S. PTO Office Action, U.S. Appl. No. 12/296,714, Jan. 3, 2011, 16 pgs.
Fairhurst, U.S. PTO Office Action, U.S. Appl. No. 12/296,714, Apr. 28, 2011, 7 pgs.
Fairhurst, U.S. PTO Office Action, U.S. Appl. No. 12/297,291, Mar. 21, 2011, 41 pgs.
Fairhurst, U.S. PTO Office Action, U.S. Appl. No. 12/297,291, Dec. 1, 2010, 21 pgs.
Fairhurst, U.S. PTO Office Action, U.S. Appl. No. 12/308,637, Feb. 24, 2011, 23 pgs.
Fairhurst, U.S. PTO Office Action, U.S. Appl. No. 12/310,254, Mar. 24, 2011, 18 pgs.
Fairhurst, U.S. PTO Office Action, U.S. Appl. No. 12/679,663, Feb. 28, 2011, 21 pgs.
Fairhurst, U.S. PTO Supplemental Notice of Allowance, U.S. Appl. No. 11/576,607, Jun. 15, 2011, 3 pgs.
Ghosh et al., "Synthesis and Biological Evaluation of a Carbocyclic Azanoraristeromycin Siderophore Conjugate", Nucleosides & Nucleotides, vol. 18, No. 2 (1999), pp. 217-225.
Fairhurst, U.S. PTO Notice of Allowance, U.S. Appl. No. 12/297,291, Jul. 14, 2011, 9 pgs.
Laumen, U.S. PTO Office Action, U.S. Appl. No. 12/312,311, Aug. 9, 2011, 20 pgs.
Siddiqi et al., "Enantiospecific Synthesis of the Fluoro and Epimeric Derivatives of 5'-Noraristeromycin", J. Chem. Soc., Chem. Commun., 1993, pp. 708-709.
Fairhurst, U.S. PTO Restriction Requirement, U.S. Appl. No. 12/247,764, Jul. 15, 2011, 14 pgs.
International Search Report, PCT/EP2008/063869, Jul. 21, 2009, 7 pgs.
Fairhurst, U.S. PTO Notice of Allowance, U.S. Appl. No. 11/722,835, Oct. 21, 2011, 10 pgs.
Fairhurst, U.S. PTO Notice of Allowance, U.S. Appl. No. 12/308,637, Sep. 26, 2011, 13 pgs.
Fairhurst, U.S. PTO Office Action, U.S. Appl. No. 12/310,254, Oct. 12, 2011, 11 pgs.
Fairhurst, U.S. PTO Office Action, U.S. Appl. No. 12/247,764, Oct. 26, 2011, 17 pgs.
Fairhurst, U.S. Notice of Allowance, U.S. Appl. No. 12/297,291, Nov. 10, 2011, 9 pgs.
Fairhurst, U.S. PTO Notice of Allowance, U.S. Appl. No. 11/576,607, Nov. 14, 2011, 9 pgs.
Fairhurst, U.S. PTO Notice of Allowance, U.S. Appl. No. 12/310,254, Feb. 2, 2012, 7 pgs.
Fairhurst, U.S. PTO Office Action, U.S. Appl. No. 13/218,865, Jan. 27, 2012, 21 pgs.
Fairhurst, U.S. PTO Office Action, U.S. Appl. No. 13/218,887, Feb. 1, 2012, 21 pgs.
Fairhurst, U.S. PTO Advisory Action, U.S. Appl. No. 12/310,254, Jan. 18, 2012, 10 pgs.

* cited by examiner

ORGANIC COMPOUNDS

This application is a U.S. National Phase filing of International Application Serial No. PCT/EP2007/003439 filed 19 Apr. 2007, and claims priority to G.B. Application Serial No. 0607950.3 filed 21 Apr. 2006, the contents of which are incorporated herein by reference in their entirety.

This invention relates to organic compounds, their preparation and use as pharmaceuticals.

An aspect of the invention provides compounds of formula (I):

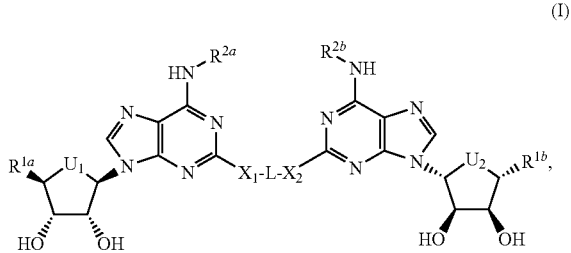

(I)

or stereoisomers or pharmaceutically acceptable salts thereof, wherein $U_1$ and $U_2$ are independently selected from $CH_2$ and O with the proviso that when $U_1$ is O then $R^{1a}$ is not a N-bonded substituent, and when $U_2$ is O then $R^{1b}$ is not a N-bonded substituent;

$R^{1a}$ and $R^{1b}$ are independently selected from a 3- to 12-membered heterocyclic group containing from 1 to 4 ring nitrogen atoms and optionally containing from 1 to 4 other heteroatoms selected from the group consisting of oxygen and sulfur, that group being optionally substituted by oxo, O—$C_1$-$C_8$-alkyl, $C_6$-$C_{10}$-aryl, $R^{1c}$ or by $C_1$-$C_8$-alkyl optionally substituted by OH, or $R^{1a}$ and $R^{1b}$ are independently selected from —$NR^4R^4$, —$NR^5$—$C_1$-$C_8$-alkylcarbonyl, —$NR^5$—$C_3$-$C_8$-cycloalkylcarbonyl, —$NR^5SO_2$—$C_1$-$C_8$-alkyl, —$NR^5$—$C_7$-$C_{14}$-aralkylcarbonyl and —$NR^5C(=O)$—C(=O)—$NR^5$—$C_1$-$C_8$-alkyl optionally substituted by $R^{1c}$, or $R^{1a}$ and $R^{1b}$ are independently selected from $NR^4$—$C_1$-$C_8$-alkyl, $NR^5C(O)C_1$-$C_8$ hydroxyalkyl, $NR^5CO_2C_1$-$C_8$-alkyl, and $NR^5CO_2C_2$-$C_8$-hydroxyalkyl, or $R^{1a}$ and $R^{1b}$ are independently selected from $C_1$-$C_8$-hydroxyalkyl, $CH_2$—O—$C_1$-$C_8$-alkyl, $C(O)$—O—$C_1$-$C_8$-alkyl, $C(O)NR^5R^5$, and $C(O)$—NH—$C_1$-$C_8$-alkyl;

$R^{1c}$ is a 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl;

$R^{2a}$ and $R^{2b}$ are independently $C_1$-$C_8$-alkyl optionally substituted by OH, halogen $C_6$-$C_{10}$-aryl optionally substituted by OH, $SO_2R^{10}$, $SC_1$-$C_8$-alkyl, CN, halogen, O—$C_7$-$C_{14}$-aralkyl, or O—$C_1$-$C_8$-alkyl, a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, $C_2$-$C_8$-alkenyl, $C_2$-$C_8$-alkynyl or $C_1$-$C_8$-alkyl, O—$C_1$-$C_8$-alkyl, —$SO_2$—$C_1$-$C_8$-alkyl, a 3- to 12-membered heterocyclic group containing from 1 to 4 ring nitrogen atoms and optionally containing from 1 to 4 other heteroatoms selected from the group consisting of oxygen and sulfur, that group being optionally substituted by 3- to 12-membered heterocyclic group containing from 1 to 4 ring nitrogen atoms and optionally containing from 1 to 4 other heteroatoms selected from the group consisting of oxygen and sulfur, $C_7$-$C_{14}$-aralkyl, or $C_6$-$C_{14}$-aryl optionally substituted by O—$C_7$-$C_{14}$-aralkyl, or $R^{2a}$ and $R^{2b}$ are independently $C_3$-$C_{15}$-carbocyclic group optionally substituted by O—$C_7$-$C_{14}$-aralkyl, $C_3$-$C_{15}$-carbocyclic group, O—$C_1$-$C_8$-alkyl, or $C_1$-$C_8$-alkyl, or $R^{2a}$ and $R^{2b}$ are independently a 3- to 12-membered heterocyclic group containing from 1 to 4 ring nitrogen atoms and optionally containing from 1 to 4 other heteroatoms selected from the group consisting of oxygen and sulfur, that group being optionally substituted by 3- to 12-membered heterocyclic group containing from 1 to 4 ring nitrogen atoms and optionally containing from 1 to 4 other heteroatoms selected from the group consisting of oxygen and sulfur, $C_1$-$C_{14}$-aralkyl, or $C_6$-$C_{14}$-aryl optionally substituted by O—$C_7$-$C_{14}$-aralkyl;

$X_1$ and $X_2$ are, independently, a bond, $C_1$-$C_8$-alkylaminocarbonyl, $C_2$-$C_8$-alkenyl, $C_2$-$C_8$-alkynyl, or a N-bonded 3- to 12-membered heterocyclic group containing from 1 to 4 ring nitrogen atoms and optionally containing from 1 to 4 other heteroatoms selected from the group consisting of oxygen and sulfur;

L is selected from —$NR^4C(O)$—W—$NR^4C(O)NR^4$—, —$NR^5$—$C(=NR^5)$—$NR^5$—, —$NR^5$—Y—$NR^5$—, $NR^4C(O)NR^4$—, $NR^4C(O)NR^4$—Z—$NR^5$—, $NR^4C(O)$—$(CR^6R^7)_n$—$C(O)NR^4$—, and $NR^4C(O)NR^4$—W—$NR^4C(O)NR^4$—;

W is selected from $C_3$-$C_{15}$-carbocyclic group, a $C_6$-$C_{10}$-aryl optionally substituted by OH, O—$C_1$-$C_8$-alkyl, and —$W^a$—$C(O)NR^4$—$W^b$—$NR^4C(O)$—$W^a$—;

each $W^a$ is independently selected from a 3- to 12-membered heterocyclic group containing from 1 to 4 ring nitrogen atoms and optionally containing from 1 to 4 other heteroatoms selected from the group consisting of oxygen and sulfur, a $C_3$-$C_{15}$-carbocyclic group optionally substituted by $C_1$-$C_8$-alkyl, and $C_6$-$C_{10}$-aryl optionally substituted by HO, halogen;

$W^b$ is selected from a 3- to 12-membered heterocyclic group containing from 1 to 4 ring nitrogen atoms and optionally containing from 1 to 4 other heteroatoms selected from the group consisting of oxygen and sulfur, a $C_3$-$C_{15}$-carbocyclic group optionally substituted by HO, halogen, oxo, dialkylamino, and $C_6$-$C_{10}$-aryl;

Y is selected from selected from a 3- to 12-membered heterocyclic group containing from 1 to 4 ring nitrogen atoms and optionally containing from 1 to 4 other heteroatoms selected from the group consisting of oxygen and sulfur optionally substituted by halogen, and $R^9$, a $C_3$-$C_{15}$-carbocyclic group optionally substituted by alkyl, and $C_6$-$C_{10}$-aryl;

Z is selected from $C_6$-$C_{10}$-aryl, $SO_2$, and $C_6$-$C_{10}$-aryl-$SO_2$—;

each $R^4$ is independently selected from H, $C_1$-$C_8$-alkyl, and $C_6$-$C_{10}$-aryl;

each $R^5$ is independently selected from H, —CN, $C_1$-$C_8$-alkyl, and $C_6$-$C_{10}$-aryl;

each $R^6$ and each $R^7$ are independently selected from H, halogen, OH, $C_1$-$C_8$-alkyl, and $C_6$-$C_{10}$-aryl;

$R^8$ is selected from $C_1$-$C_8$-alkyl optionally substituted by halogen, $C_6$-$C_{10}$-aryl optionally substituted by OH, $C_1$-$C_8$-alkyl, O—$C_1$-$C_8$-alkyl or halogen, and $NR^4R^4$;

$R^9$ is 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl; and n is an integer selected from 1-8.

According to formula (I), $R^{1a}$ and $R^{1b}$ are, independently, suitably a N-bonded 3- to 12-membered heterocyclic group containing from 1 to 4 ring nitrogen atoms and optionally containing from 1 to 4 other heteroatoms selected from the group consisting of oxygen and sulfur, that group being optionally substituted by oxo, O—$C_1$-$C_8$-alkyl, $C_6$-$C_{10}$-aryl, $R^{1c}$ or by $C_1$-$C_8$-alkyl optionally substituted by OH. The 3- to 12-membered heterocyclic groups are preferably 5- to 6-membered heterocyclic groups (e.g. tetrazole groups, pyrrole groups, pyrazole groups, pyridine groups, isoxazole groups, triazole groups, or hydantoin groups). The $R^{1a}$ and $R^{1b}$ heterocyclic groups can be N-bonded where possible. The heterocyclic groups are preferably substituted by at least one group selected from $C_1$-$C_8$-alkyl optionally substituted by OH (e.g. an ethyl group, a hydroxymethyl group or a hydroxyethyl group). These substitution groups on the heterocyclic groups can be C- or N-bonded to the heterocyclic group where possible.

According to formula (I), $R^{1a}$ and $R^{1b}$ are also, independently, suitably —NH—$C_1$-$C_8$-alkylcarbonyl or —NH—$C_3$-$C_8$-cycloalkylcarbonyl. The —NH—$C_1$-$C_8$-alkylcarbonyl group is preferably a acetamide group or a propionamide group. The —NH—$C_3$-$C_8$-cycloalkylcarbonyl is preferably a cyclobutane carboxylic acid amide group.

According to formula (I), $R^{1a}$ and $R^{1b}$ are also, independently suitably $C_1$-$C_8$-hydroxy alkyl or $CH_2$—O—$C_1$-$C_8$-alkyl.

According to formula (I) $R^{1a}$ and $R^{1b}$ are also, independently, suitably NHC(O)$C_1$-$C_8$-hydroxyalkyl. $R^1$ is preferably NHC(O)$C_1$-$C_2$-hydroxyalkyl (e.g. a 2-hydroxy-acetamide group, a 2-hydroxy-propionamide group, or a 3-hydroxy-propionamide group).

According to formula (I) $R^{1a}$ and $R^{1b}$ are preferably equivalent.

According to formula (I), $R^{2a}$ and $R^{2b}$ are independently, suitably H, $C_1$-$C_8$-alkyl optionally substituted by OH, halogen or $C_6$-$C_{10}$-aryl optionally substituted by OH or O—$C_1$-$C_8$-alkyl. When substituted, suitably the $C_1$-$C_8$-alkyl is substituted by OH, phenyl, naphthalene, or preferably by two phenyl groups. When the $C_1$-$C_8$-alkyl is substituted by two phenyl groups, either or both phenyl groups are preferably unsubstituted, or substituted by at least one $OCH_3$, one OH or one halogen.

According to formula (I), $R^{2a}$ and $R^{2b}$ are also, independently, suitably $C_1$-$C_8$-alkyl substituted by a phenyl. This phenyl can be further substituted by a phenyl where this phenyl is substituted by CN, halogen, or $C_1$-$C_8$-alkyl.

According to formula (I), $R^{2a}$ and $R^{2b}$ are also, independently, suitably a $C_3$-$C_{15}$-carbocyclic group (e.g. a fluorene group).

According to formula (I), $R^{2a}$ and $R^{2b}$ are preferably equivalent.

According to formula (I), $X_1$ and $X_2$ are, independently, suitably a 3- to 10-membered heterocyclic group containing from 1 to 4 ring nitrogen atoms and optionally containing from 1 to 4 other heteroatoms selected from the group consisting of oxygen and sulfur. Preferably a 5-membered heterocyclic group such as pyrrolidine, triazole, imidazole or pyrazole.

According to formula (I), $X_1$ and $X_2$ are preferably equivalent.

According to formula (I), L is suitably —$NR^4C(O)$—W—$NR^4C(O)NR^4$—, —$NR^5$—Y—$NR^5$—, $NR^4C(O)NR^4$—, $NR^4C(O)NR^4$—Z—$NR^5$—, $NR^4C(O)$—$(CR^6R^7)_n$—$C(O)NR^4$—, and $NR^4C(O)NR^4$—W—$NR^4C(O)NR^4$—, where W is preferably a $C_6$-$C_{10}$-aryl (e.g. phenyl), a $C_3$-$C_{15}$-carbocyclic group (e.g. cyclohexyl), or —$W^a$—$C(O)NR^4$—$W^b$—$NR^4C(O)$—$W^a$—. Each $W^a$ is independently suitably a 3- to 12-membered heterocyclic group containing from 1 to 4 ring nitrogen atoms and optionally containing from 1 to 4 other heteroatoms selected from the group consisting of oxygen and sulfur (e.g. pyrrolidine). $W^b$ is suitably a 3- to 12-membered heterocyclic group containing from 1 to 4 ring nitrogen atoms and optionally containing from 1 to 4 other heteroatoms selected from the group consisting of oxygen and sulfur, or a $C_3$-$C_{15}$-carbocyclic group or a $C_6$-$C_{10}$-aryl.

L is also suitably —$NR^5C(O)NR^5$—, —$NR^5C(=NR^5)NR^5$—, where $R^5$ is preferably H and the (=$NR^5$) of —$NR^5C(=NR^5)NR^5$— is preferably (=NH) or (=N—CN).

According to formula (I), Y is suitably a 3- to 12-membered heterocyclic group containing from 1 to 4 ring nitrogen atoms and optionally containing from 1 to 4 other heteroatoms selected from the group consisting of oxygen and sulfur optionally substituted by $R^9$, a $C_3$-$C_{15}$-carbocyclic group optionally substituted by OH, and $C_6$-$C_{10}$-aryl optionally substituted by HO. Y is a preferably a 5- to 6-membered heterocyclic group.

Y is also suitably a $C_3$-$C_{15}$-carbocyclic group, e.g.

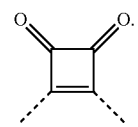

According to formula (I), Z is suitably $C_6$-$C_{10}$-aryl (e.g. phenyl), $SO_2$, and $C_6$-$C_{10}$-aryl-$SO_2$—, preferably phenyl-$SO_2$.

Another aspect of the invention provides compounds of formula (Ia):

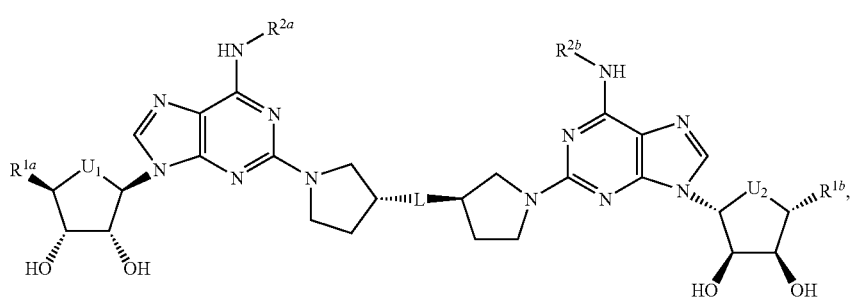

(Ia)

or stereoisomers or pharmaceutically acceptable salts thereof, wherein $U_1$ and $U_2$ are independently selected from $CH_2$ and O with the proviso that when $U_1$ is O then $R^{1a}$ is not a N-bonded substituent, and when $U_2$ is O then $R^{1b}$ is not a N-bonded substituent;

$R^{1a}$ and $R^{1b}$ are independently selected from a 3- to 12-membered heterocyclic group containing from 1 to 4 ring nitrogen atoms and optionally containing from 1 to 4 other heteroatoms selected from the group consisting of oxygen and sulfur, that group being optionally substituted by oxo, O—$C_1$-$C_8$-alkyl, $C_6$-$C_{10}$-aryl, $R^{1c}$ or by $C_1$-$C_8$-alkyl optionally substituted by OH, or $R^{1a}$ and $R^{1b}$ are independently selected from —$NR^5$—$C_1$-$C_8$-alkylcarbonyl, —$NR^5$—$C_3$-$C_8$-cycloalkylcarbonyl, or $R^{1a}$ and $R^{1b}$ are independently selected from $NR^4$—$C_1$-$C_8$-alkyl, $NR^5C(O)C_1$-$C_8$-hydroxyalkyl, $NR^5CO_2C_1$-$C_8$-alkyl, $NR^5CO_2C_2$-$C_8$-hydroxyalkyl, or $R^{1a}$ and $R^{1b}$ are independently selected from $C_1$-$C_8$-hydroxyalkyl, $CH_2$—O—$C_1$-$C_8$-alkyl, C(O)—O—$C_1$-$C_8$-alkyl, $C(O)NR^5R^5$, and C(O)—NH—$C_1$-$C_8$-alkyl;

$R^{1c}$ is a 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl;

$R^{2a}$ and $R^{2b}$ are independently selected from hydrogen, $C_1$-$C_8$-alkyl optionally substituted by OH, O—$C_1$-$C_8$-alkyl, or $C_6$-$C_{10}$-aryl optionally substituted by OH, halogen, $SO_2R^8$, CN, O—$C_7$-$C_{14}$-aralkyl, $C_3$-$C_{15}$-carbocyclic group, O—$C_1$-$C_8$-alkyl, —$SO_2$—$C_1$-$C_8$-alkyl, $C_3$-$C_8$-cycloalkyl optionally substituted by $C_3$-$C_8$-cycloalkyl, O—$C_7$-$C_{14}$ aralkyl, $C_1$-$C_8$-alkyl, or $C_2$-$C_8$-alkenyl, and $C_2$-$C_8$-alkynyl, or $R^{2a}$ and $R^{2b}$ are, independently, $C_7$-$C_{14}$-aralkyl optionally substituted by $C_6$-$C_{10}$-aryl optionally substituted by OH, halogen, or CN, L is selected from —$NR^4C(O)$—W—$NR^4C(O)NR^4$—, —$NR^4C(O)NR^4$—, $NR^4C(O)NR^4$—Z—$NR^5$—, $NR^4C(O)$—$(CR^6R^7)_n$—$C(O)NR^4$—, and $NR^4C(O)NR^4$—W—$NR^4C(O)NR^4$—;

W is selected from $C_3$-$C_{15}$-carbocyclic group optionally substituted by HO, a $C_6$-$C_{10}$-aryl optionally substituted by OH, $C_1$-$C_8$-alkyl, halogen, and —$W^a$—$C(O)NR4$—$W^b$—$NR^4C(O)$—$W^a$—;

each $W^a$ is independently selected from a 3- to 12-membered heterocyclic group containing from 1 to 4 ring nitrogen atoms and optionally containing from 1 to 4 other heteroatoms selected from the group consisting of oxygen and sulfur, a $C_3$-$C_{15}$-carbocyclic group optionally substituted by HO, and $C_6$-$C_{10}$-aryl;

$W^b$ is selected from a 3- to 12-membered heterocyclic group containing from 1 to 4 ring nitrogen atoms and optionally containing from 1 to 4 other heteroatoms selected from the group consisting of oxygen and sulfur, a $C_3$-$C_{15}$-carbocyclic group, and $C_6$-$C_{10}$-aryl optionally substituted by OH;

Y is selected from selected from a 3- to 12-membered heterocyclic group containing from 1 to 4 ring nitrogen atoms and optionally containing from 1 to 4 other heteroatoms selected from the group consisting of oxygen and sulfur optionally substituted by $R^9$, a $C_3$-$C_{15}$-carbocyclic group optionally substituted by OH, and $C_6$-$C_{10}$-aryl optionally substituted by OH;

Z is selected from $C_6$-$C_{10}$-aryl, $SO_2$, and $C_6$-$C_{10}$-aryl-$SO_2$—;

each $R^4$ is independently selected from H, and $C_1$-$C_8$-alkyl;

each $R^5$ is independently selected from H, and $C_1$-$C_8$-alkyl;

each $R^6$ and each $R^7$ are independently selected from H, halogen, OH, and $C_1$-$C_8$-alkyl;

$R^8$ is selected from $C_1$-$C_8$-alkyl optionally substituted by halogen, $C_6$-$C_{10}$-aryl optionally substituted by OH, $C_1$-$C_8$-alkyl, O—$C_1$-$C_8$-alkyl or halogen, and $NR^4R^4$;

$R^9$ is 3- or 12-membered heterocyclic ring containing at least one ring heteroatom selected from the group consisting of nitrogen, oxygen and sulfur, said 3- or 12-membered heterocyclic ring being optionally substituted by halo, cyano, OH, carboxy, amino, nitro, $C_1$-$C_8$-alkyl, and n is an integer selected from 1-4.

Another aspect of the invention provides compounds of formula (Ia), or stereoisomers or pharmaceutically acceptable salts thereof, wherein $U_1$ and $U_2$ are independently selected from $CH_2$ and O with the proviso that when $U_1$ is O then $R^{1a}$ is not a N-bonded substituent, and when $U_2$ is O then $R^{1b}$ is not a N-bonded substituent;

$R^{1a}$ and $R^{1b}$ are independently selected from a 3- to 12-membered heterocyclic group containing from 1 to 4 ring nitrogen atoms and optionally containing from 1 to 4 other heteroatoms selected from the group consisting of oxygen and sulfur, that group being optionally substituted by $C_1$-$C_8$-alkyl, or $R^{1a}$ and $R^{1b}$ are independently selected from —NH—$C_1$-$C_8$-alkylcarbonyl, and —NH—$C_3$-$C_8$-cycloalkylcarbonyl, or $R^{1a}$ and $R^{1b}$ are independently selected from NH—$C_1$-$C_8$-alkyl, $NHC(O)C_1$-$C_8$-hydroxyalkyl, $NHCO_2C_1$-$C_8$-alkyl, and $NHCO_2C_1$-$C_8$-hydroxyalkyl;

$R^{1a}$ and $R^{1b}$ are independently selected from $C_1$-$C_8$-hydroxyalkyl, and $CH_2$—O—$C_1$-$C_8$-alkyl;

$R^{2a}$ and $R^{2b}$ are independently selected from hydrogen, $C_1$-$C_8$-alkyl optionally substituted by OH, $C_3$-$C_{35}$-carbocyclic group, or $C_6$-$C_{10}$-aryl optionally substituted by OH, halogen, or O—$C_1$-$C_8$-alkyl;

$R^{2a}$ and $R^{2b}$ are independently is $C_2$-$C_{14}$-aralkyl optionally substituted by OH, halogen, or CN;

L is selected from —NHC(O)—W—NHC(O)NH—, —NH—Y—NH—, NHC(O)NH—, NHC(O)NH—Z—NH—, $NHC(O)$—$(CH_2)_n$—$C(O)NH$—, and NHC(O)NH—W—NHC(O)NH—;

W is selected from $C_3$-$C_{15}$-carbocyclic group, a $C_6$-$C_{10}$-aryl, and —$W^a$—$C(O)NH$—$W^b$—$NHC(O)$—$W^a$—;

each $W^a$ is independently selected from a 3- to 12-membered heterocyclic group containing from 1 to 4 ring nitrogen atoms and optionally containing from 1 to 4 other heteroatoms selected from the group consisting of oxygen and sulfur, a $C_3$-$C_{15}$-carbocyclic group optionally substituted by HO, and $C_6$-$C_{10}$-aryl optionally substituted by OH;

$W^b$ is selected from a 3- to 12-membered heterocyclic group containing from 1 to 4 ring nitrogen atoms and optionally containing from 1 to 4 other heteroatoms selected from the group consisting of oxygen and sulfur, a $C_3$-$C_{15}$-carbocyclic group optionally substituted by OH, and $C_6$-$C_{10}$-aryl optionally substituted by OH;

Y is selected from selected from a 3- to 12-membered heterocyclic group containing from 1 to 4 ring nitrogen atoms and optionally containing from 1 to 4 other heteroatoms selected from the group consisting of oxygen and sulfur optionally substituted by $R^9$, a $C_3$-$C_{15}$-carbocyclic group optionally substituted by OH, and $C_6$-$C_{10}$-aryl optionally substituted by OH;

Z is selected from $C_6$-$C_{10}$-aryl, $SO_2$, and $C_6$-$C_{10}$-aryl-$SO_2$—; and n is an integer selected from 1-4.

Another aspect of the invention provides compounds of formula (Ia) or stereoisomers or pharmaceutically acceptable salts thereof,
wherein
$U_1$, $U_2$, $R^{1a}$, $R^{1b}$, $R^{2a}$, $R^{2b}$ are as hereinbefore defined; and
L is selected from:

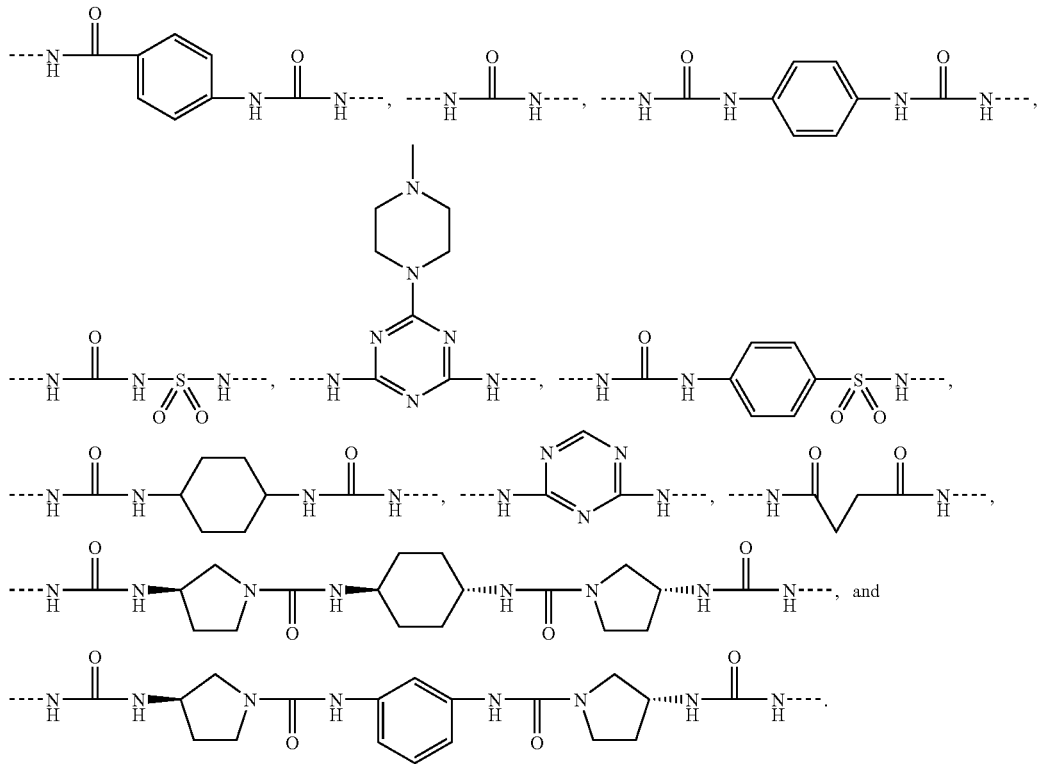

Another aspect of the invention provides compounds of formula (II):

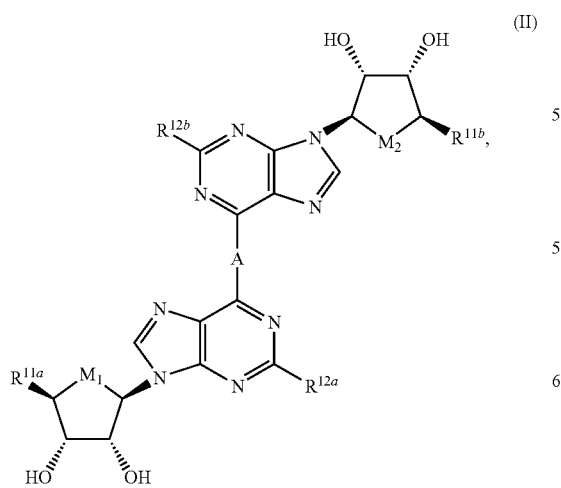

or stereoisomers or pharmaceutically acceptable salts thereof, wherein $M_1$ and $M_2$ are independently selected from $CH_2$ and O with the proviso that when $M_1$ is O then $R^{11a}$ is not a N-bonded substituent, and when $M_2$ is O then $R^{11b}$ is not a N-bonded substituent;

$R^{11a}$ and $R^{11b}$ are independently selected from a 3- to 12-membered heterocyclic group containing from 1 to 4 ring nitrogen atoms and optionally containing from 1 to 4 other heteroatoms selected from the group consisting of oxygen and sulfur, that group being optionally substituted by oxo, O—$C_1$-$C_8$-alkyl, $C_6$-$C_{10}$-aryl, R or by $C_1$-$C_8$-alkyl optionally substituted by OH, or $R^{11a}$ and $R^{11b}$ are independently selected from —$NR^{14}R^{14}$, —$NR^{15}$—$C_1$-$C_8$-alkylcarbonyl, —$NR^{15}$—$C_3$-$C_8$-cycloalkylcarbonyl, —$NR^{15}SO_2$—$C_1$-$C_8$-alkyl, —$NR^{15}$—$C_7$-$C_{14}$-aralkylcarbonyl and —$NR^{15}C(=O)$—$C(=O)$—$NR^{15}$—$C_1$-$C_8$-alkyl optionally substituted by $R^{11c}$, or $R^{11a}$ and $R^{11b}$ are independently selected from $NR^{14}$—$C_1$-$C_8$-alkyl, $NR^{15}C(O)C_1$-$C_8$-hydroxyalkyl, $NR^{15}CO_2C_1$-$C_8$-alkyl, $NR^{15}CO_2C_2$-$C_8$-hydroxyalkyl, or $R^{11a}$ and $R^{11b}$ are independently selected from $C_1$-$C_8$-hydroxyalkyl, $CH_2$—O—$C_1$-$C_8$-alkyl, C(O)—O—$C_1$-$C_8$-alkyl, $C(O)NR^{15}R^{15}$, and C(O)—NH—$C_1$-$C_8$-alkyl;

$R^{11c}$ is a 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl;

$R^{12a}$ and $R^{12b}$ are independently selected from hydrogen, halo, $C_2$-$C_8$-alkenyl, $C_2$-$C_8$-alkynyl and $C_1$-$C_8$-alkoxycarbonyl, or $R^{12a}$ and $R^{12b}$ are independently selected from amino optionally substituted by $C_3$-$C_8$-cycloalkyl optionally substituted by amino, hydroxy, $C_7$-$C_{14}$-aralkyloxy, —$SO_2$—$C_6$-$C_{10}$-aryl and —NH—C(=O)—NH—$R^{12e}$, —NH—C(=O)—$R^{12e}$, or $R^{12a}$ and $R^{12b}$ are independently selected from amino substituted by $R^{12c}$, aralkyl, $C_1$-$C_8$-alkyl optionally substituted by $R^{12c}$, and a $C_5$-$C_{15}$-carbocyclic group optionally substituted by OH, $C_1$-$C_8$-alkyl or $C_1$-$C_8$-alkoxycarbonyl, or $R^{12a}$ and $R^{12b}$ are independently selected from aminocarbonyl optionally substituted by $R^{12d}$, or $R^{12a}$ and $R^{12b}$ are independently selected from $C_1$-$C_8$-alkylamino optionally substituted by OH, $R^{12d}$, amino, di($C_1$-$C_8$-alkyl)amino, —NH—C(=O)—$C_1$-$C_8$-alkyl, —NH—$SO_2$—$C_1$-$C_8$-alkyl, —NH—C(=O)—NH—$R^{12e}$, —NH—C(=O)—NH—$C_1$-$C_8$-alkyl-$R^{12d}$, a $C_5$-$C_{15}$-carbocyclic group and by $C_6$-$C_{10}$-aryl optionally substituted by $C_6$-$C_{10}$-aryloxy, or $R^{12a}$ and $R^{12b}$ are independently selected from $C_1$-$C_8$-alkylaminocarbonyl and $C_3$-$C_8$-cycloalkylamino-carbonyl optionally substituted by amino, $C_1$-$C_8$-alkylamino, di($C_1$-$C_8$-alkyl)amino or —NH—C(=O)—NH—$R^{12f}$, or $R^{12a}$ and $R^{12b}$ are independently selected from a 3- to 12-membered heterocyclic group containing from 1 to 4 ring nitrogen atoms and optionally containing from 1 to 4 other heteroatoms selected from the group consisting of oxygen and sulfur, that group being optionally substituted by 0-3$R^{20}$;

$R^{12c}$ and $R^{12d}$ are each independently a 3- to 12-membered heterocyclic group containing at least one ring heteroatom selected from the group consisting of nitrogen, oxygen and sulfur; optionally substituted by halo, cyano, oxo, OH, carboxy, nitro, $C_1$-$C_8$-alkyl, $C_1$-$C_8$-alkylcarbonyl, OH—$C_1$-$C_8$-alkyl, $C_1$-$C_8$-haloalkyl, amino-$C_1$-$C_8$-alkyl, amino(OH)$C_1$-$C_8$-alkyl and $C_1$-$C_8$-alkoxy optionally substituted by aminocarbonyl;

$R^{12e}$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur;

$R^{12e}$ is a 5- or 6-membered heterocyclic ring containing at least one ring heteroatom selected from the group consisting of nitrogen, oxygen and sulfur, said 5- or 6-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl, or a 5- or 6-membered heterocyclic ring containing at least one ring heteroatom selected from the group consisting of nitrogen, oxygen and sulfur, said ring also being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl;

A is selected from —$NR^{14}C(O)$-E-$NR^{14}C(O)NR^{14}$—, —$NR^{15}$-G-$NR^{15}$—, —$NR^{15}$—$(CR^{16}R^{17})_n$—$NR^{15}$—, —$NR^{15}$—$X_3$-G-$X_4$—$NR^{15}$—, —$NR^{14}C(O)NR^{14}$—, $NR^{14}C(O)NR^{14}$-J-$NR^{15}$—, $NR^{14}C(O)$—$(CR^{16}R^{17})_n$—$C(O)NR^{14}$—, and $NR^{14}C(O)NR^{14}$-E-$NR^{14}C(O)NR^{14}$—;

E is selected from $C_3$-$C_{15}$-carbocyclic group optionally substituted by HO, $C_1$-$C_8$-alkyl, $C_6$-$C_{10}$-aryl, 3- to 12-membered heterocyclic group, a $C_6$-$C_{10}$-aryl optionally substituted by HO, $C_1$-$C_8$-alkyl, O—$C_1$-$C_8$-alkyl, halogen, and -$E^a$-C(O)$NR^4$-$E^b$-$NR^4C(O)$-$E^a$-;

each $E^a$ is independently selected from a 3- to 12-membered heterocyclic group containing from 1 to 4 ring nitrogen atoms and optionally containing from 1 to 4 other heteroatoms selected from the group consisting of oxygen and sulfur, a $C_3$-$C_{15}$-carbocyclic group, and $C_6$-$C_{10}$-aryl optionally substituted by HO, $C_1$-$C_8$-alkyl, O—$C_1$-$C_8$-alkyl, and halogen;

$E^b$ is selected from a 3- to 12-membered heterocyclic group containing from 1 to 4 ring nitrogen atoms and optionally containing from 1 to 4 other heteroatoms selected from the group consisting of oxygen and sulfur, a $C_3$-$C_{15}$-carbocyclic group, and $C_6$-$C_{10}$-aryl optionally substituted by HO, $C_1$-$C_8$-alkyl, O—$C_1$-$C_8$-alkyl, halogen;

G is selected from selected from C(O), $NR^{14}$C(O), C(O)$NR^{14}$, $C_1$-$C_8$-alkyl optionally substituted by OH, halogen or $C_6$-$C_{10}$-aryl, a 3- to 12-membered heterocyclic group containing from 1 to 4 ring nitrogen atoms and optionally containing from 1 to 4 other heteroatoms selected from the group consisting of oxygen and sulfur optionally substituted by $R^{19}$, a $C_3$-$C_{15}$-carbocyclic group optionally substituted by HO, $C_1$-$C_8$-alkyl, and $C_6$-$C_{10}$-aryl optionally substituted by HO, $C_1$-$C_8$-alkyl, O—$C_1$-$C_8$-alkyl, halogen;

J is selected from $C_6$-$C_{10}$-aryl, $SO_2$, and $C_6$-$C_{10}$-aryl-$SO_2$—;

$X_3$ and $X_4$ are independently selected from $C_1$-$C_8$-alkyl optionally substituted by OH, halogen or $C_6$-$C_{10}$-aryl, a 3- to 12-membered heterocyclic group containing from 1 to 4 ring nitrogen atoms and optionally containing from 1 to 4 other heteroatoms selected from the group consisting of oxygen and sulfur optionally substituted by $R^{19}$, a $C_3$-$C_{15}$-carbocyclic group, and $C_6$-$C_{10}$-aryl;

each $R^{14}$ is independently selected from H, $C_1$-$C_8$-alkyl, $C_6$-$C_{10}$-aryl;

each $R^{15}$ is independently selected from H, $C_1$-$C_8$-alkyl, $C_6$-$C_{10}$-aryl;

each $R^{16}$ and each $R^{17}$ are independently selected from H, halogen, OH, $C_1$-$C_8$-alkyl, and $C_6$-$C_{10}$-aryl;

$R^{18}$ is $C_1$-$C_8$-alkyl optionally substituted by halogen, $C_6$-$C_{10}$-aryl optionally substituted by OH, $C_1$-$C_8$-alkyl, O—$C_1$-$C_8$-alkyl or halogen, or $NR^{14a}R^{14b}$;

$R^{19}$ is 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl;

$R^{20}$ is selected from OH, $C_1$-$C_8$-alkyl optionally substituted by OH, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl or -halogen, O—$C_6$-$C_{10}$-aryl optionally substituted by OH, $C_1$-$C_8$-alkyl, O—$C_1$-$C_8$-alkyl or -halogen, $NR^{20a}R^{20b}$, $NHC(O)R^{20c}$, $NHS(O)_2R^{20d}$, $NHS(O)_2R^{20e}$, $NR^{20f}C(O)NR^{20e}R^{20h}$, $NR^{20f}C(O)NR^{20g}R^{20h}$, $NR^{20i}C(O)OR^{20j}$, $C_1$-$C_8$-alkylcarbonyl, $C_1$-$C_8$-alkoxycarbonyl, di($C_1$-$C_8$-alkyl)aminocarbonyl, $COOR^{20k}$, $C(O)R^{4l}$, $NHC(O)R^{20q}$, $NHC(=NR^{20m})N(R^{20n})R^{20o}$, and a 3- to 12-membered heterocyclic group containing at least one ring heteroatom selected from the group consisting of nitrogen, oxygen and sulfur optionally substituted by $COOR^{20p}$;

$R^{20a}$, $R^{20c}$, $R^{20f}$, $R^{20h}$ and $R^{20i}$ are, independently, H, or $C_1$-$C_8$-alkyl;

$R^{20b}$ is H, $C_1$-$C_8$-alkyl a 3- to 12-membered heterocyclic group containing at least one ring heteroatom selected from the group consisting of nitrogen, oxygen and sulfur, optionally substituted by 0-3$R^{21}$ or $C_6$-$C_{10}$-aryl;

$R^{20d}$, $R^{20e}$, and $R^{20j}$ are, independently, $C_1$-$C_8$-alkyl or a 3- to 12-membered heterocyclic group containing at least one ring heteroatom selected from the group consisting of nitrogen, oxygen and sulfur, optionally substituted by 0-3$R^{21}$;

$R^{20g}$ is $C_1$-$C_8$-alkyl optionally substituted by a 3- to 12-membered heterocyclic group containing at least one ring heteroatom selected from the group consisting of nitrogen, oxygen and sulfur, optionally substituted with $SO_2R^{18}$, CN, or O-3$R^{21}$, or $R^{20g}$ is a $C_6$-$C_{10}$-aryl optionally substituted by OH, $C_1$-$C_8$-alkyl, O—$C_1$-$C_8$-alkyl, $SO_2R^{18}$ or -halogen, or $R^{20g}$ is a $C_1$-$C_{14}$-aralkyl optionally substituted by OH, O—$C_1$-$C_8$-alkyl, halogen, $C_6$-$C_{10}$-aryl, $SO_2R^{18}$, CN, —C(=NH)NH$_2$, or O—$C_6$-$C_{10}$-aryl, or $R^{20g}$ is a 3- to 12-membered heterocyclic group containing at least one ring heteroatom selected from the group consisting of nitrogen, oxygen and sulfur, optionally substituted by 0-3$R^{21}$;

$R^{20k}$ is H, $C_1$-$C_8$-alkyl, $C_6$-$C_{10}$-aryl or a 3- to 12-membered heterocyclic group containing at least one ring heteroatom selected from the group consisting of nitrogen, oxygen and sulfur;

$R^{20l}$ is $C_1$-$C_8$-alkyl, $C_6$-$C_{10}$-aryl, $NHR^{16}$ or a 3- to 12-membered heterocyclic group containing at least one ring heteroatom selected from the group consisting of nitrogen, oxygen and sulfur;

$R^{20m}$ is CN or H;

$R^{20n}$ is H or $C_1$-$C_8$-alkyl;

$R^{20o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with $SO_2R^{18}$, CN, or 0-3$R^{21}$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl $SO_2R^{10}$ or -halogen;

$R^{20p}$ is H, $C_1$-$C_8$-alkyl or $C_7$-$C_{14}$-aralkyl;

$R^{20q}$ is $C_6$-$C_{10}$-aryl optionally substituted by OH, C(=NH)NH$_2$, or $SO_2NH_2$, or a 3- to 12-membered heterocyclic group containing at least one ring heteroatom selected from the group consisting of nitrogen, oxygen and sulfur optionally substituted by 0-3$R^{21}$ or a 3- to 12-membered heterocyclic group containing at least one ring heteroatom selected from the group consisting of nitrogen, oxygen and sulfur, optionally substituted by 0-3$R^{21}$;

$R^{21}$ is selected from OH, $C_1$-$C_8$-alkyl optionally substituted by OH, CN, $SO_2R^{18}$ or halogen, $C_7$-$C_{14}$-aralkyl optionally substituted with OH, O—$C_1$-$C_8$-alkyl, $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl or -halogen, O—$C_6$-$C_{10}$-aryl optionally substituted by OH, $C_1$-$C_8$-alkyl, O—$C_1$-$C_8$-alkyl optionally substituted by halogen, $NR^{21a}R^{21b}$, $NHC(O)R^{21c}$, NHS(O)$_2R^{21d}$, $NHS(O)_2R^{21e}$, $NR^{21f}C(O)NR^{21g}R^{21h}$, $NR^{21i}C(O)OR^{21j}$, $C_1$-$C_8$-alkylcarbonyl, $C_1$-$C_8$-alkoxycarbonyl, di($C_1$-$C_8$-alkyl)aminocarbonyl, $COOR^{21k}$, $C(O)R^{21l}$, a C(O)—$C_6$-$C_{10}$-aryl optionally substituted by OH, —COOH, $C_1$-$C_8$-alkyl, O—$C_1$-$C_8$-alkyl, -halogen, or $SO_2R^{18}$, $C(O)NHR^{21m}$ or a 3- to 12-membered heterocyclic group containing at least one ring heteroatom selected from the group consisting of nitrogen, oxygen and sulfur, optionally substituted by 0-3$R^{17}$;

$R^{21a}$, $R^{21b}$, $R^{21c}$, $R^{21f}$, $R^{21h}$ and $R^{21i}$ are, independently, H, $C_1$-$C_8$-alkyl or $C_6$-$C_{10}$-aryl;

$R^{21d}$, $R^{21e}$, $R^{21g}$, $R^{21j}$ and $R^{21m}$ are, independently, $C_1$-$C_8$-alkyl or a 3- to 12-membered heterocyclic group containing at least one ring heteroatom selected from the group consisting of nitrogen, oxygen and sulfur, optionally substituted by $COOR^{24}$;

$R^{21k}$ is H, $C_6$-$C_{10}$-aryl or a 3- to 12-membered heterocyclic group containing at least one ring heteroatom selected from the group consisting of nitrogen, oxygen and sulfur;

$R^{21l}$ is $C_1$-$C_8$-alkyl, $C_6$-$C_{10}$-aryl or a 3- to 12-membered heterocyclic group containing at least one ring heteroatom selected from the group consisting of nitrogen, oxygen and sulfur, optionally substituted by $COOR^{25}$;

$R^{22}$ is $COOR^{22a}$ or a 3- to 12-membered heterocyclic group containing at least one ring heteroatom selected from the group consisting of nitrogen, oxygen and sulfur, optionally substituted by $COOR^{22b}$;

$R^{22a}$, $R^{22b}$, $R^{24}$ and $R^{25}$ are selected from H, $C_1$-$C_8$-alkyl and $C_7$-$C_{14}$-aralkyl; and n is an integer selected from 1-8, with the proviso that when A is

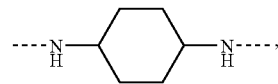

then $R^{12a}$ and $R^{12b}$ are not

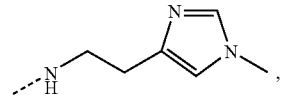

$R^{11a}$ and $R^{11b}$ are not

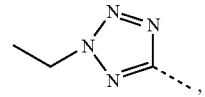

and $M_1$ and $M_2$ are not O.

According to formula (II), $R^{11a}$ and $R^{11b}$ are, independently, suitably a N-bonded 3- to 12-membered heterocyclic group containing from 1 to 4 ring nitrogen atoms and optionally containing from 1 to 4 other heteroatoms selected from the group consisting of oxygen and sulfur, that group being optionally substituted by oxo, $C_6$-$C_{10}$-aryl, $R^{11c}$ or by $C_1$-$C_8$-alkyl optionally substituted by OH. The 3- to 12-membered heterocyclic groups are preferably 5- to 6-membered heterocyclic groups (e.g. tetrazole groups, pyrrole groups, pyrazole groups, pyridine groups, isoxazole groups, triazole groups, or morpholine groups). The $R^{11a}$ and $R^{11b}$ heterocyclic groups can be N-bonded where possible. The heterocyclic groups are preferably substituted by at least one group selected from $C_1$-$C_8$-alkyl optionally substituted by OH (e.g. an ethyl group, a hydroxymethyl group or a hydroxyethyl group). These substitution groups on the heterocyclic groups can be N-bonded to the heterocyclic group where possible.

According to formula (II), $R^{11a}$ and $R^{11b}$ are also, independently, suitably —NH—$C_1$-$C_8$-alkylcarbonyl or —NH—$C_3$-$C_8$-cycloalkylcarbonyl. The —NH—$C_1$-$C_8$-alkylcarbonyl group is preferably a acetamide group or a propionamide group. The —NH—$C_3$-$C_8$-cycloalkylcarbonyl is preferably a cyclobutane carboxylic acid amide group.

According to formula (II) $R^{11a}$ and $R^{11b}$ are also, independently, suitably NHC(O)$C_1$-$C_8$ hydroxyalkyl. $R^{11a}$ and $R^{11b}$ are, independently, preferably NHC(O)$C_1$-$C_2$-hydroxyalkyl (e.g. a 2-hydroxy-acetamide group, a 2-hydroxy-propionamide group, or a 3-hydroxy-propionamide group).

According to formula (II) $R^{11a}$ and $R^{11b}$ are preferably equivalent.

According to formula (II), $R^{12a}$ and $R^{12b}$ are independently selected from amino substituted by $R^{12c}$, —$R^{12c}$—$C_7$-$C_{14}$-aralkyl, $C_1$-$C_8$-alkyl optionally substituted by $R^{12c}$, and a $C_5$-$C_{15}$-carbocyclic group optionally substituted by OH, $C_1$-$C_8$-alkyl or $C_1$-$C_8$-alkoxycarbonyl. $R^{12c}$ is suitably a 3- to 12-membered heterocyclic group containing at least one ring heteroatom selected from the group consisting of nitrogen, oxygen and sulfur (e.g. a pyrrolidine or a pyrazole) optionally substituted by halo, cyano, oxo, OH, carboxy, nitro, $C_1$-$C_8$-alkyl, $C_1$-$C_8$-alkylcarbonyl, OH—$C_1$-$C_8$-alkyl, $C_1$-$C_8$-haloalkyl, amino-$C_1$-$C_8$-alkyl, amino(OH)$C_1$-$C_8$-alkyl and $C_1$-$C_8$-alkoxy optionally substituted by aminocarbonyl. Preferably the 3- to 12-membered heterocyclic group is substituted by at least one $C_1$-$C_8$-alkyl group.

According to formula (II), $R^{12a}$ and $R^{12b}$ are also independently suitably a N-bonded 3- to 12-membered heterocyclic group containing at least one ring heteroatom selected from the group consisting of nitrogen, oxygen and sulfur. This heterocyclic group is preferably a pyrrolidine, pyrazole, triazole, tetrazole, or imidazole. The heterocyclic group is optionally substituted by NR$^{20f}$C(O)NR$^{20g}$R$^{20h}$, NR$^{20a}$R$^{20b}$, NHC(O)R$^{20q}$ and where R$^{20a}$ and R$^{20b}$ are preferably H or $C_1$-$C_8$-alkyl (e.g. methyl) and R$^{4f}$ and R$^{4h}$ are preferably H.

According to formula (II), A is suitably —NR$^{15}$-G-NR$^{15}$—, where G is suitably a 5- to 6-membered carbocyclic group, such as cyclohexyl group.

According to formula (II), A is also suitably —NR$^{15}$—(CR$^{16}$R$^{17}$)$_n$—NR$^{15}$—, where (CR$^{16}$R$^{17}$)$_n$, is suitably a $C_1$-$C_8$-alkyl optionally substituted by OH or $C_6$-$C_{10}$-aryl. Preferably when substituted the $C_1$-$C_8$-alkyl can be mono-substituted by OH or phenyl or the $C_1$-$C_8$-alkyl can be disubstituted by both OH and phenyl.

According to formula (II), A is also suitably —NR$^{15}$—X$_3$-G-X$_4$—NR$^{15}$—, where X$_3$ and X$_4$ are suitably a 3- to 12-membered heterocyclic group containing from 1 to 4 ring nitrogen atoms and optionally containing from 1 to 4 other heteroatoms selected from the group consisting of oxygen and sulfur and a $C_3$-$C_{15}$-carbocyclic group. G is preferably NHC(O), C(O), C(O)NH, a 3- to 12-membered heterocyclic group containing from 1 to 4 ring nitrogen atoms and optionally containing from 1 to 4 other heteroatoms selected from the group consisting of oxygen and sulfur optionally substituted by halogen.

Also, X$_3$ and X$_4$ are suitably $C_1$-$C_8$-alkyl and G is suitably $C_6$-$C_{10}$-aryl. Preferably both X$_3$ and X$_4$ can be ethyl when G is phenyl.

According to formula (II), leg is suitably $C_1$-$C_8$-alkyl optionally substituted by a 3- to 12-membered heterocyclic group containing at least one ring heteroatom selected from the group consisting of nitrogen, oxygen and sulfur, optionally substituted with SO$_2$R$^{18}$, CN, or 0-3R$^{21}$. R$^{20g}$ is preferably a methylene substituted by a pyridine where the pyridine is optionally substituted by one CN.

According to formula (II), R$^{20g}$ is also suitably $C_6$-$C_{10}$-aryl optionally substituted by OH, $C_1$-$C_8$-alkyl, O—$C_1$-$C_8$-alkyl, SO$_2$R$^{18}$, or -halogen. R$^{20g}$ is preferably a phenyl that is optionally substituted by one OH or one SO$_2$NH$_2$.

According to formula (II), R$^{20g}$ is also suitably $C_7$-$C_{14}$-aralkyl optionally substituted by OH, O—$C_1$-$C_8$-alkyl, halogen, $C_6$-$C_{10}$-aryl, SO$_2$R$^{18}$, CN, —C(=NH)NH$_2$, or O—$C_6$-$C_{10}$-aryl. R$^{4g}$ is preferably a benzyl group optionally substituted by one OH or one —C(=NH)NH$_2$.

According to formula (II), R$^{20g}$ is also suitably 3- to 12-membered heterocyclic group containing at least one ring heteroatom selected from the group consisting of nitrogen, oxygen and sulfur, optionally substituted by 0-3R$^{21}$; R$^{20g}$ is preferably a pyrrolidine.

According to formula (II), R$^{20q}$ is suitably phenyl substituted by OH, C(=NH)NH$_2$, or SO$_2$NH$_2$.

According to formula (I), R$^{20q}$ is also suitably 3- to 12-membered heterocyclic group containing at least one ring heteroatom selected from the group consisting of nitrogen, oxygen and sulfur optionally substituted by a 3- to 12-membered heterocyclic group containing at least one ring heteroatom selected from the group consisting of nitrogen, oxygen and sulfur, optionally substituted by 0-3R$^{21}$. Preferably leg is a 6-membered heterocyclic group (e.g. pyridine) substituted by a 6-membered heterocyclic group (e.g. morpholine).

An aspect of the invention provides compounds of formula (II), or stereoisomers or pharmaceutically acceptable salts thereof,
wherein
  $M_1$ and $M_2$ are independently selected from CH$_2$ and O with the proviso that when $M_1$ is O then R$^{11a}$ is not a N-bonded substituent, and when $M_2$ is O then R$^{11b}$ is not a N-bonded substituent;
  R$^{11a}$ and R$^{11b}$ are independently selected from a 3- to 12-membered heterocyclic group containing from 1 to 4 ring nitrogen atoms and optionally containing from 1 to 4 other heteroatoms selected from the group consisting of oxygen and sulfur, that group being optionally substituted by oxo, O—$C_1$-$C_8$-alkyl, $C_6$-$C_{10}$-aryl, R$^{11c}$ or by $C_1$-$C_8$-alkyl optionally substituted by OH, or
  R$^{11a}$ and R$^{11b}$ are independently selected from NR$^{15}$—$C_1$-$C_8$-alkylcarbonyl, —NR$^{15}$—$C_3$-$C_8$-cycloalkylcarbonyl, or
  R$^{11a}$ and R$^{11b}$ are independently selected from NR$^{14}$—$C_1$-$C_8$-alkyl, NR$^{15}$C(O)$C_1$-$C_8$-hydroxyalkyl, NR$^{15}$CO$_2$C$_1$-$C_8$-alkyl, NR$^{15}$CO$_2$C$_2$-$C_8$-hydroxyalkyl;
  R$^{11a}$ and R$^{11b}$ are independently selected from $C_1$-$C_8$-hydroxyalkyl, CH$_2$—O—$C_1$-$C_8$-alkyl, C(O)—O—$C_1$-$C_8$-alkyl, C(O)NR$^{15}$R$^{15}$, and C(O)—NH—$C_1$-$C_8$-alkyl;
  R$^{11c}$ is a 3- to 12-membered heterocyclic ring containing at least one ring heteroatom selected from the group consisting of nitrogen, oxygen and sulfur, said 3- to 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl;
  R$^{12a}$ and R$^{12b}$ are independently selected from amino substituted by R$^{12c}$, —R$^{12c}$—$C_7$-$C_{14}$-aralkyl, $C_1$-$C_8$-alkyl optionally substituted by R$^{12c}$, and a $C_5$-$C_{15}$-carbocyclic group optionally substituted by OH, $C_1$-$C_8$-alkyl or $C_1$-$C_8$-alkoxycarbonyl;
  R$^{12c}$ is a 3- to 12-membered heterocyclic group containing at least one ring heteroatom selected from the group consisting of nitrogen, oxygen and sulfur optionally substituted by halo, cyano, oxo, OH, carboxy, nitro, $C_1$-$C_8$-alkyl, $C_1$-$C_8$-alkylcarbonyl, OH—$C_1$-$C_8$-alkyl, $C_1$-$C_8$-haloalkyl, amino-$C_1$-$C_8$-alkyl, amino(OH)$C_1$-$C_8$-alkyl and $C_1$-$C_8$-alkoxy optionally substituted by aminocarbonyl, or $R^{12a}$ and $R^{12b}$ are independently a N-bonded 3- to 12-membered heterocyclic group containing at least one ring heteroatom selected from the group consisting of nitrogen, oxygen and sulfur; optionally substituted by $NR^{20f}C(O)NR^{20g}R^{20h}$, $NR^{20a}R^{20b}$, $NHC(O)R^{20q}$;

A is selected from —$NR^{15}$-G-$NR^{15}$, —$NR^{15}$—($CR^{16}R^{17}$)$_n$—$NR^{15}$—, and —$NR^{15}$—$X_3$-G-$X_4$—$NR^{15}$;

G is selected from selected from C(O), $NR^{14}$C(O), C(O)$NR^{14}$, $C_1$-$C_8$-alkyl optionally substituted by OH, halogen or $C_6$-$C_{10}$-aryl, a 3- to 12-membered heterocyclic group containing from 1 to 4 ring nitrogen atoms and optionally containing from 1 to 4 other heteroatoms selected from the group consisting of oxygen and sulfur optionally substituted by $R^{19}$, a $C_3$-$C_{15}$-carbocyclic group optionally substituted by HO, $C_1$-$C_8$-alkyl, and $C_6$-$C_{10}$-aryl optionally substituted by HO, $C_1$-$C_8$-alkyl, O—$C_1$-$C_8$-alkyl, halogen;

$X_3$ and $X_4$ are independently selected from $C_1$-$C_8$-alkyl optionally substituted by OH, halogen or $C_6$-$C_{10}$-aryl, a 3- to 12-membered heterocyclic group containing from 1 to 4 ring nitrogen atoms and optionally containing from 1 to 4 other heteroatoms selected from the group consisting of oxygen and sulfur optionally substituted by $R^{19}$, a $C_3$-$C_{15}$-carbocyclic group, and $C_6$-$C_{10}$-aryl;

each $R^{14}$ is independently selected from H, $C_1$-$C_8$-alkyl, and $C_6$-$C_{10}$-aryl;

each $R^{15}$ is independently selected from H, $C_1$-$C_8$-alkyl, and $C_6$-$C_{10}$-aryl;

$R^{20a}$, $R^{20f}$, and $R^{20h}$ are, independently, H, or $C_1$-$C_8$-alkyl;

$R^{20b}$ is H, $C_1$-$C_8$-alkyl, a 3- to 12-membered heterocyclic group containing at least one ring heteroatom selected from the group consisting of nitrogen, oxygen and sulfur, optionally substituted by 0-3$R^{21}$ or $C_6$-$C_{10}$-aryl;

$R^{20g}$ is $C_1$-$C_8$-alkyl optionally substituted by a 3- to 12-membered heterocyclic group containing at least one ring heteroatom selected from the group consisting of nitrogen, oxygen and sulfur, optionally substituted with $SO_2NH_2$, CN, or 0-3$R^{21}$, or $R^{20g}$ is a $C_6$-$C_{10}$-aryl optionally substituted by OH, $C_1$-$C_8$-alkyl, O—$C_1$-$C_8$-alkyl, $SO_2NH_2$ or -halogen, or $R^{20g}$ is a $C_7$-$C_{14}$-aralkyl optionally substituted by OH, O—$C_1$-$C_8$-alkyl, halogen, $C_6$-$C_{10}$-aryl, $SO_2NH_2$, CN, —C(=NH)$NH_2$, or O—$C_6$-$C_{10}$-aryl, or $R^{20g}$ is a 3- to 12-membered heterocyclic group containing at least one ring heteroatom selected from the group consisting of nitrogen, oxygen and sulfur, optionally substituted by 0-3$R^{21}$;

$R^{20g}$ is $C_6$-$C_{10}$-aryl optionally substituted by OH, C(=NH)$NH_2$, or $SO_2NH_2$, or a 3- to 12-membered heterocyclic group containing at least one ring heteroatom selected from the group consisting of nitrogen, oxygen and sulfur optionally substituted by a 3- to 12-membered heterocyclic group containing at least one ring heteroatom selected from the group consisting of nitrogen, oxygen and sulfur; and $R^{21}$ is C(O)—$C_6$-$C_{10}$-aryl optionally substituted by OH, —COOH, $C_1$-$C_8$-alkyl, O—$C_1$-$C_8$-alkyl, -halogen, or $SO_2NH_2$.

DEFINITIONS

Terms used in the specification have the following meanings:

"Optionally substituted" means the group referred to can be substituted at one or more positions by any one or any combination of the radicals listed thereafter.

"Halo" or "halogen", as used herein, may be fluorine, chlorine, bromine or iodine. Preferably halo is chlorine.

"Hydroxy", as used herein, is OH.

"$C_1$-$C_8$-Alkyl", as used herein, denotes straight chain or branched alkyl having 1 to 8 carbon atoms. Preferably $C_1$-$C_8$-alkyl is $C_1$-$C_8$-alkyl.

"$C_1$-$C_8$-Alkoxy", or as used herein, denotes straight chain or branched alkoxy having 1 to 8 carbon atoms (e.g. O—$C_1$-$C_8$-alkyl). Preferably, $C_1$-$C_8$-alkoxy is $C_1$-$C_4$-alkoxy.

"$C_3$-$C_8$-Cycloalkyl", as used herein, denotes cycloalkyl having 3 to 8 ring carbon atoms, e.g., a monocyclic group, such as a cyclopropyl, cyclobutyl, cyclopentyl, cyclohexyl, cycloheptyl or cyclooctyl, any of which can be substituted by one or more, usually one or two, $C_1$-$C_8$-alkyl groups; or a bicyclic group, such as bicycloheptyl or bicyclooctyl.

"$C_1$-$C_8$-Alkylamino" and "di($C_1$-$C_8$-alkyl)amino", as used herein, denote amino substituted respectively by one or two $C_1$-$C_8$-alkyl groups as hereinbefore defined, which may be the same or different.

"$C_1$-$C_8$-Alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined attached by a carbon atom to a carbonyl group.

"$C_6$-$C_{10}$-Aaryl", as used herein, denotes a monovalent carbocyclic aromatic group that contains 6 to 10 carbon atoms and which may be, e.g., a monocyclic group, such as phenyl; or a bicyclic group, such as naphthyl.

"$C_7$-$C_{14}$-Aralkyl", as used herein, denotes alkyl, e.g., $C_1$-$C_8$-alkyl, as hereinbefore defined, substituted by $C_6$-$C_{10}$-aryl as hereinbefore defined. Preferably, $C_7$-$C_{14}$-aralkyl is $C_7$-$C_{10}$-aralkyl, such as phenyl-$C_1$-$C_4$-alkyl.

"$C_1$-$C_8$-Alkylaminocarbonyl" and "$C_3$-$C_8$-cycloalkylaminocarbonyl", as used herein, denote $C_1$-$C_8$-alkylamino and $C_3$-$C_8$-cycloalkylamino, respectively, as hereinbefore defined, attached by a carbon atom to a carbonyl group. Preferably $C_1$-$C_8$-alkylaminocarbonyl and $C_3$-$C_8$-cycloalkyl-aminocarbonyl are $C_1$-$C_4$-alkylaminocarbonyl and $C_3$-$C_8$-cycloalkylaminocarbonyl, respectively.

"$C_3$-$C_{15}$-Carbocyclic group", as used herein, denotes a carbocyclic group having 3 to 15 ring carbon atoms, e.g., a monocyclic group, either aromatic or non-aromatic, such as a cyclopentyl, cyclohexyl, cycloheptyl, cyclooctyl or phenyl; or a bicyclic group, such as bicyclooctyl, bicyclononyl, bicyclodecyl, indanyl or indenyl, again any of which can be substituted by one or more, usually one or two, $C_1$-$C_8$-alkyl groups. Preferably the $C_3$-$C_{15}$-carbocyclic group is a $C_5$-$C_{10}$-carbocyclic group, especially phenyl, cyclohexyl or indanyl. The $C_5$-$C_{15}$-carbocyclic group can unsubstituted or substituted. Substituents on the heterocyclic ring include halo, cyano, OH, carboxy, amino, aminocarbonyl, nitro, $C_1$-$C_{10}$-alkyl, $C_1$-$C_{10}$-alkoxy and $C_3$-$C_{10}$-cycloalkyl.

"3- to 12-Membered heterocyclic ring containing at least one ring heteroatom selected from the group consisting of nitrogen, oxygen and sulfur", as used herein, may be, e.g., furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, morpholino, triazine, oxazine or thiazole. Preferred heterocyclic rings include piperazine, pyrrolidine, morpholino, imidazole, isotriazole, pyrazole, tetrazole, thiazole, triazole, thiadiazole, pyridine, piperidine, pyrazine, furan, oxazole, isoxazole, oxadiazole and azetidine. The 3- to 12-membered heterocyclic ring can be unsubstituted or substituted.

"5- or 6-Membered heterocyclic group containing at least one ring heteroatom selected from the group consisting of nitrogen, oxygen and sulfur", as used herein, may be, for example, a saturated or unsaturated heterocyclic group such as furanyl, pyrrolyl, pyrrolidinyl, pyrazolyl, imidazolyl, triazolyl, isotriazolyl, tetrazolyl, thiadiazolyl, isothiazolyl, oxadiazolyl, pyridinyl, piperidinyl, pyrazinyl, oxazolyl, isoxazolyl, pyrazinyl, pyridazinyl, pyrimidinyl, piperazinyl, pyrrolidinyl, morpholinyl, triazinyl, oxazinyl or thiazolyl. Preferred 5- or 6-membered heterocyclic groups include pyrazolyl, imidazolyl, pyrrolidinyl, pyridinyl and piperidinyl. The 5- or 6-membered heterocyclic group can be unsubstituted or substituted. Preferred substituents include halo, cyano, oxo, OH, carboxy, amino, nitro, $C_1$-$C_8$-alkyl (optionally substituted by hydroxy), $C_1$-$C_8$-alkylsulfonyl, aminocarbonyl, $C_1$-$C_8$-alkylcarbonyl, $C_1$-$C_8$-alkoxycarbonyl, and $C_1$-$C_8$-alkoxy optionally substituted by aminocarbonyl. Especially preferred substituents include chloro, cyano, carboxy, amino, $C_1$-$C_8$-alkoxycarbonyl, $C_1$-$C_4$-alkoxy and $C_1$-$C_4$-alkyl optionally substituted by OH.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps. As understood by one skilled in the art only combinations of substituents that are chemically possible are embodiments of the invention.

Especially preferred specific compounds of formulae (I) and (II) are those described hereinafter in the Examples.

Stereoisomers are those compounds where there is an asymmetric carbon atom. The compounds exist in individual optically active isomeric forms or as mixtures thereof, e.g., as diastereomeric mixtures. The present invention embraces both individual optically active R and S isomers, as well as mixtures thereof. Individual isomers can be separated by methods well known to those skilled in the art, e.g. chiral high performance liquid chromatography (HPLC).

Tautomers are one of two or more structural isomers that exist in equilibrium and are readily converted from one isomeric form to another.

The compounds of the invention may exist in both unsolvated and solvated forms. The term "solvate", is used herein, to describe a molecular complex comprising the compound of the invention and one or more pharmaceutically acceptable solvent molecules, for example, ethanol. The term "hydrate" is employed when said solvent is water.

Synthesis

Another embodiment of the present invention provides a process for the preparation of compounds of formula (I) in free or pharmaceutically acceptable salt form, which comprises the steps of:

(i) reacting a compound of formula (III):

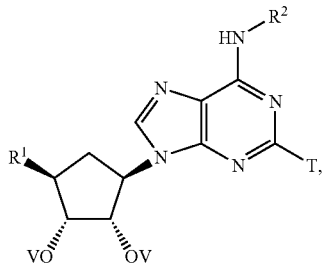

(III)

wherein
$R^1$ is equivalent to $R^{1a}$ and $R^{1b}$;
$R^2$ is equivalent to $R^{2a}$ and $R^{2b}$; and
U is equivalent to $U_1$ and $U_2$, and are as defined in claim 1;
V is H or a protecting group; and T is a leaving group, with a compound of formula (IV):

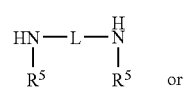

(IV)

or

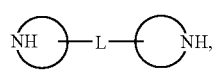

(V)

wherein L and each $R^5$ are as defined in claim 1, and each

is a 3- to 12-membered heterocyclic group containing from 1 to 4 ring nitrogen atoms and optionally containing from 1 to 4 other heteroatoms selected from the group consisting of oxygen and sulfur; and (ii) removing any protecting groups and recovering the resultant compound of formula (I), in free or pharmaceutically acceptable salt form.

The compound of formula (III) may be prepared by reacting a compound of formula (VI):

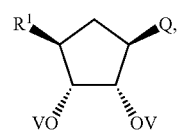

(VI)

wherein
$R^1$ is equivalent to $R^{1a}$ and $R^{1b}$;
U is equivalent to $U_1$ and $U_2$; and
V are as defined in claim 1; and
Q represents a leaving group or a protected derivative thereof with a 2,6-dihalopurine, e.g. 2,6-dichloropurine to provide a compound of formula (VII):

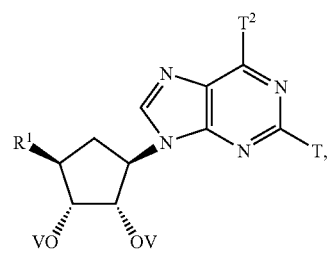

(VIII)

wherein
$R^1$ is equivalent to $R^{1a}$ and $R^{1b}$;
U is equivalent to $U_1$ and $U_2$; and
V are defined in claim 1; and
T and $T^2$ are halogen.

Compound of formula (VII) can be reacted with $R^2NH_2$ under conventional conditions to provide compound of formula (III).

Another embodiment of the present invention provides a process for the preparation of compounds of formula (II), in free or pharmaceutically acceptable salt form, which comprises the steps of
(i) reacting a compound of formula (VIII):

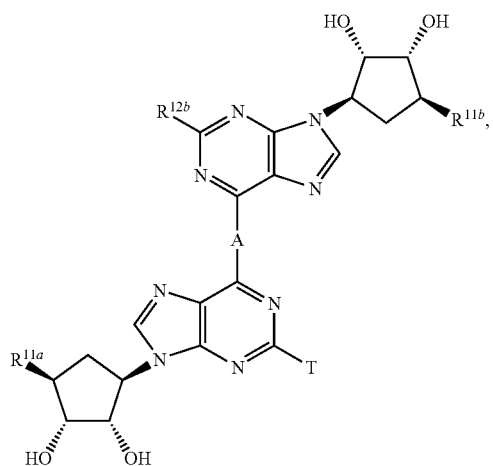

wherein
$R^{11a}$, $R^{11b}$, $R^{12b}$, $M_1$, $M_2$ and A are as defined in claim 1; and
T is a leaving group, with a compound of formula (IX):

H—$R^{12a}$     (IX)

wherein
$R^{12a}$ is as defined in claim 1; and
(ii) removing any protecting groups and recovering the resultant compound of formula (II), in free or pharmaceutically acceptable salt form.

The compound of formula (VIII) may be prepared by reacting a compound of formula (X):

wherein
$R^{11}$ is equivalent to $R^{11a}$ and $R^{11b}$;
M is equivalent to $M_1$ and $M_2$; and
V are as defined in claim 1; and
Q represents a leaving group or a protected derivative thereof with a 2,6-dihalopurine, e.g. 2,6-dichloropurine to provide a compound of formula (XI):

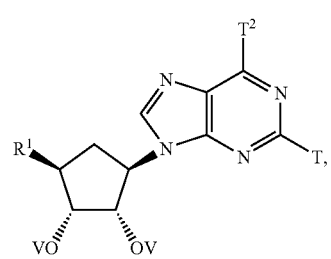

wherein
$R^1$ is equivalent to $R^{1a}$ and $R^{1b}$;
M is equivalent to $M_1$ and $M_2$; and
V are defined in claim 1; and
T and $T^2$ are halogen.

Compound of formula (XI) can be reacted with A1-A-H, where A1 is;

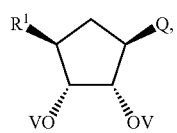

under conventional conditions to provide compound of formula (VIII).

Alternatively, below are routes to enable the efficient preparation of unsymmetrical adenosine $A_{2A}$ receptor ligands:

Either through sequential reaction of a differentially protected diamine linker.

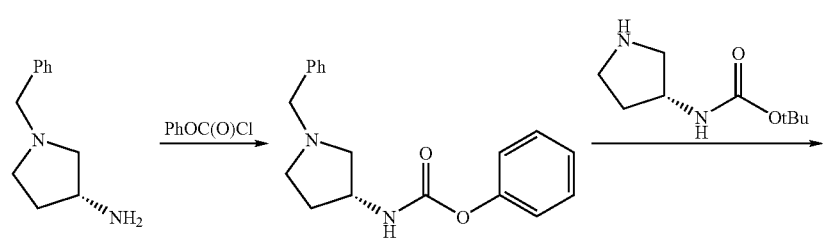

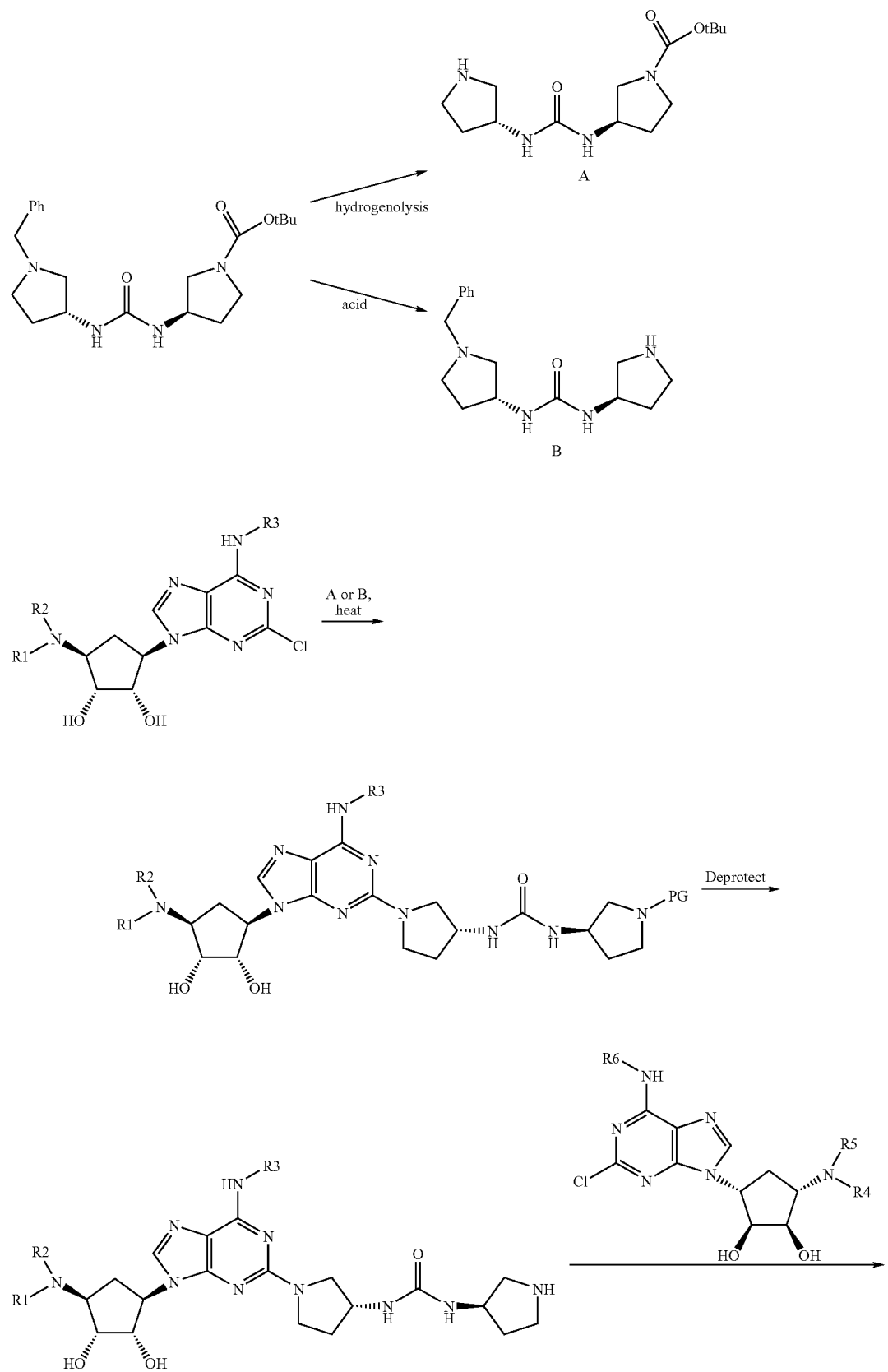

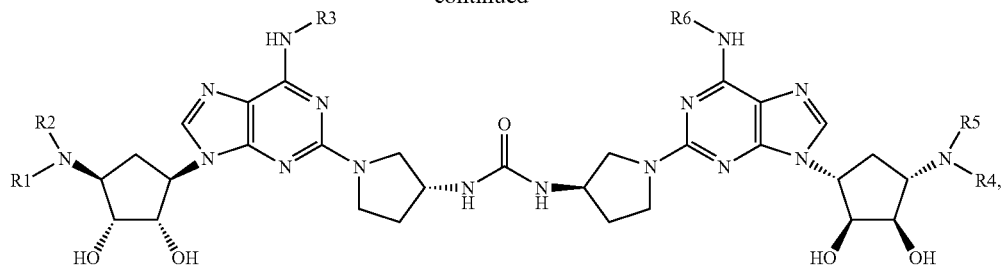
where, PG=the protecting group benzyl or tert-butyloxycarbonyl.
Or alternatively, the central urea linkage can be formed asymmetrically.
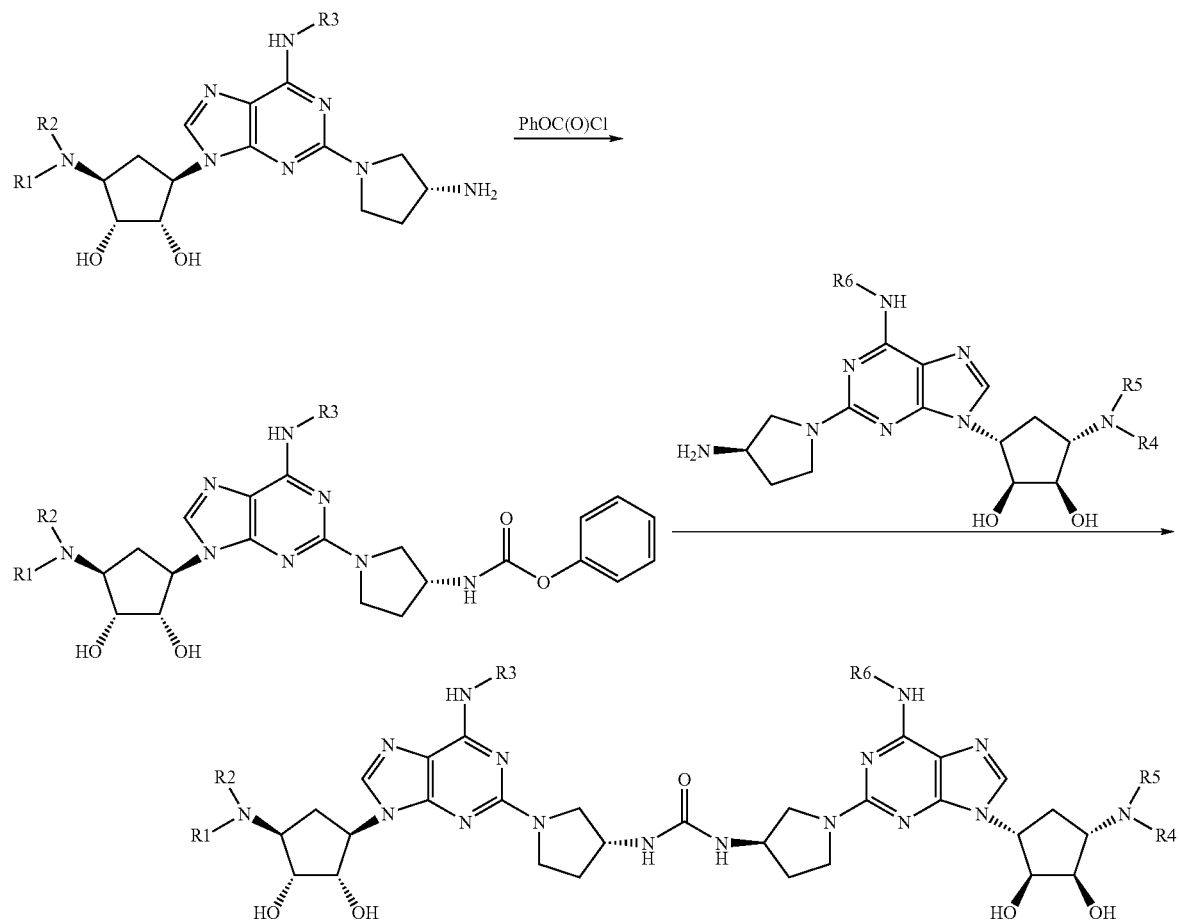
Or the central linkage can be a heterocyclic.
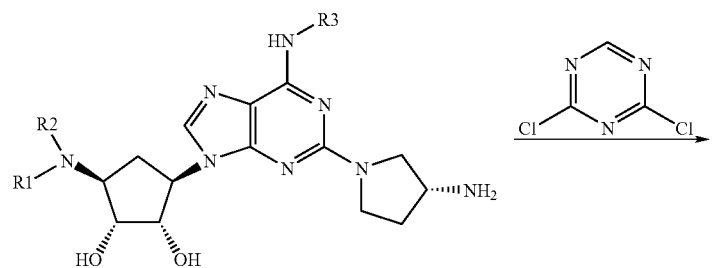

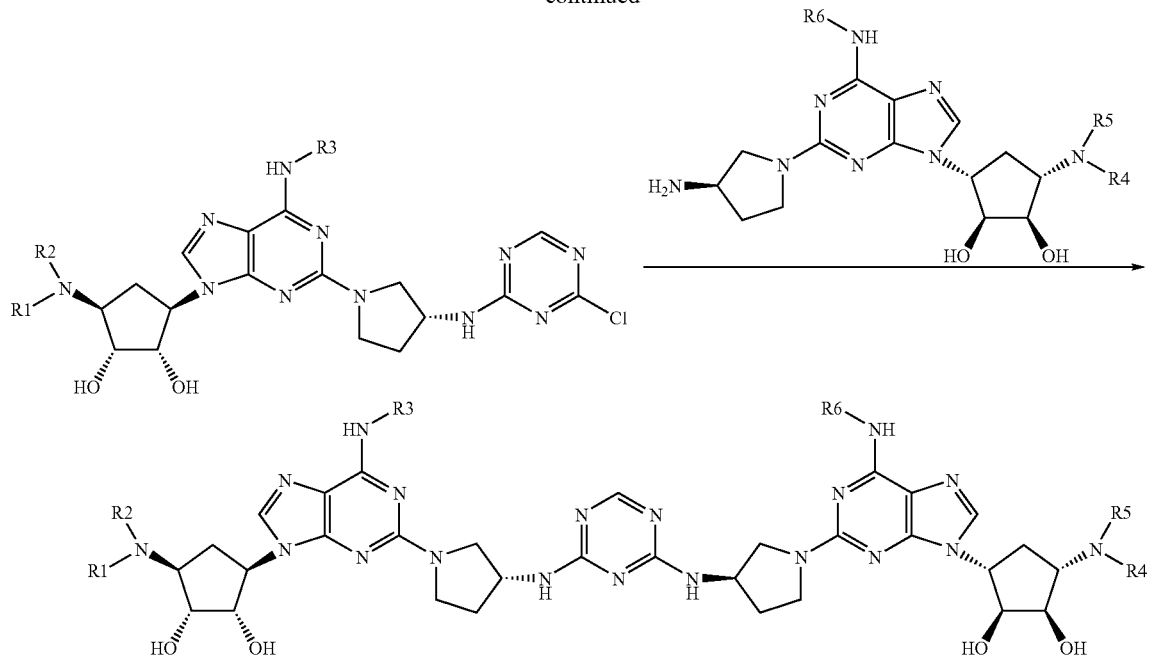

-continued

The compounds of formulae (I) and (II) can be prepared, for example, using the reactions and techniques described below and in the Examples. The compounds of formulae (I) and (II) can be prepared analogously to the preparations described in Applicant's patent applications WO/2006/045552, and WO 2006/074925. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I) or one compound of formula (II) into another compound of formula (II). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5$^{th}$ Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is T. W. Greene and P. G. M. Wuts, *Protective Groups In Organic Synthesis*, Wiley and Sons (1999). It is understood by those skilled in the art that only combinations of substituents that are chemically possible are embodiments of the present invention.

Compounds of formulae (I) and (II), in free form, may be converted into salt form, and vice versa, in a conventional manner. The compounds in free or salt form can be obtained in the form of hydrates or solvates containing a solvent used for crystallisation. Compounds of formula (I) can be recovered from reaction mixtures and purified in a conventional manner. Isomers, such as stereoisomers, may be obtained in a conventional manner, e.g. by fractional crystallisation or asymmetric synthesis from correspondingly asymmetrically substituted, e.g. optically active, starting materials.

Compounds of formulae (I) and (II) and their pharmaceutically acceptable salts are useful as pharmaceuticals. In particular, they activate the adenosine $A_{2A}$ receptor, i.e. they act as $A_{2A}$ receptor agonists. Their properties as $A_{2A}$ agonists may be demonstrated using the method described by L. J. Murphree et al in *Molecular Pharmacology* 61, 455-462 (2002).

Compounds of the Examples hereinbelow have $K_i$ values below 1.0 µM in the above assay. For example, the compounds of Examples 1, 7, 15 and 19 have $K_i$ values of 0.01, 0.01, 0.07 and 0.06 µM, respectively.

Having regard to their activation of the adenosine $A_{2A}$ receptor, compounds of formula (I), in free or pharmaceutically acceptable salt form, hereinafter alternately referred to as "agents of the invention", are useful in the treatment of conditions which respond to the activation of the adenosine $A_{2A}$ receptor, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include bronchiectasis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Other inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. cortico-steroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hyper-eosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunct-ivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Further, agents of the invention may also be used for the treatment of cystic fibrosis, pulmonary hypertension, pulmonary fibrosis, inflammatory bowel syndrome, wound healing, diabetic nephropathy as described in WO 05/107463, reduction of inflammation in transplanted tissue as described in US 2005/182018, inflammatory diseases caused by pathogenic organisms as described in WO 03/086408, and cardiovascular conditions as described in WO 03/029264.

Also, the agents of the invention may be used to assess the severity of coronary artery stenosis as described in WO 00/078774 and useful in conjunction with radioactive imaging agents to image coronary activity and useful in adjunctive therapy with angioplasty as described in WO 00/78779.

Agents of the invention are also useful in combination with a protease inhibitor for prevention of organ ischaemia and reperfusion injury as described in WO 05/003150, and in combination with an integrin antagonist for treating platelet aggregation as described in WO 03/090733.

Agents of the invention are also useful in promoting wound healing in bronchial epithelial cells as described in *AJP-Lung* 290: 849-855.

Other diseases or conditions which may be treated with agents of the invention include diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, conditions characterised by elevated intraocular pressure or secretion of ocular aqueous humor, such as glaucoma, ischemic tissue/organ damage from reperfusion, bedsores and as agents for promoting sleep, as agents for treating demyelinating diseases, eg multiple sclerosis and as neuroprotective agents eg, cerebral haemorrhagic injury and spinal cord ischaemi-reperfusion injury.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* 202:49-57 (1997); Renzi et al, *Am. Rev. Respir. Dis.* 148:932-939 (1993); Tsuyuki et al., *J. Clin. Invest.* 96:2924-2931 (1995); Cemadas et al. *Am. J. Respir. Cell Mol. Biol.* 20:1-8 (1999); and Fozard et al., *Eur. J. Pharmacol.* 438:183-188 (2002).

The agents of the invention are also useful as co-therapeutic agents for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance.

Accordingly, the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 24-5913 and L-648051; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID(TM) CC-10004 (Celgene), VM554/UM565 (Vernalis), T-440 (Tanabe), KW-4490 (Kyowa Hakim Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine $A_{2B}$ receptor antagonists such as those described in WO 02/42298; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 00/75114, which document is incorporated herein by reference, preferably compounds of the Examples thereof, especially a compound of formula:

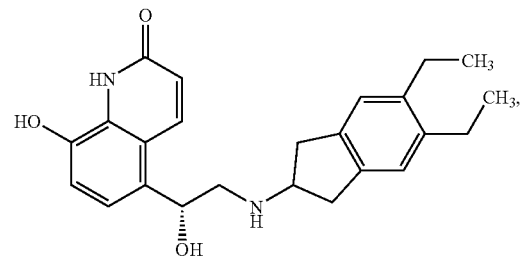

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, US 2005/0133417, US 2005/5159448, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP 1460064, WO 04/087142, WO 04/089892, EP 01477167, US 2004/0242622, US 2004/0229904, WO 04/108675, WO 04/108676, WO 05/033121, WO 05/040103, WO 05/044787, WO 05/058867, WO 05/065650, WO 05/066140 and WO 05/07908.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/018422, WO 04/05285 and WO 05/077361.

Suitable dual anti-inflammatory and bronchodilatory drugs include dual beta-2 adrenoceptor agonist/muscarinic antagonists such as those disclosed in US 2004/0167167, US 2004/0242622, US 2005/182092, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D, Takeda antagonists, such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly Claims 18 and 19), WO 00/66558 (particularly Claim 8), WO 00/66559 (particularly Claim 9), WO 04/018425 and WO 04/026873.

In accordance with the foregoing, the invention also provides a method for the treatment of a condition responsive to activation of the adenosine $A_{2A}$ receptor, for example an inflammatory or allergic condition, particularly an inflammatory or obstructive airways disease, which comprises administering to a subject, particularly a human subject, in need thereof a compound of formula (I) or formula (II), in free form, or in the form of a pharmaceutically acceptable salt. In another aspect the invention provides a compound of formula (I) or formula (II), in free form or in the form of a pharmaceutically acceptable salt, for use in the manufacture of a medicament for the treatment of a condition responsive to activation of the adenosine $A_{2A}$ receptor, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising a compounds of formulae (I) and (II), in free form, or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, for example, the compounds of formula (I) or formula (II) having a particle diameter up to 10 microns, optionally together with a diluent or carrier, such as lactose, of the desired particle size distribution and a compound that helps to protect against product performance deterioration due to moisture e.g. magnesium stearate. When the composition comprises a nebulised formulation, it preferably contains, for example, the compound of formula (I) or formula (II) either dissolved, or suspended, in a vehicle containing water, a co-solvent, such as ethanol or propylene glycol and a stabiliser, which may be a surfactant.

The invention includes:
 (a) a compounds of formula (I) or formula (II) in inhalable form, e.g. in an aerosol or other atomisable composition or in inhalable particulate, e.g. micronised, form,
 (b) an inhalable medicament comprising a compounds of formula (I) or formula (II) in inhalable form;
 (c) a pharmaceutical product comprising a compounds of formula (I) or formula (II) in inhalable form in association with an inhalation device; and
 (d) an inhalation device containing a compounds of formula (I) or formula (II) in inhalable form.

Dosages of compounds of formula (I) or formula (II) employed in practising the present invention will of course vary depending, for example, on the particular condition to be treated, the effect desired and the mode of administration. In general, suitable daily dosages for administration by inhalation are of the order of 0.005-10 mg, while for oral administration suitable daily doses are of the order of 0.05-100 mg.

The invention is illustrated by the following Examples.

Examples 1-25

Compounds of formula (I):

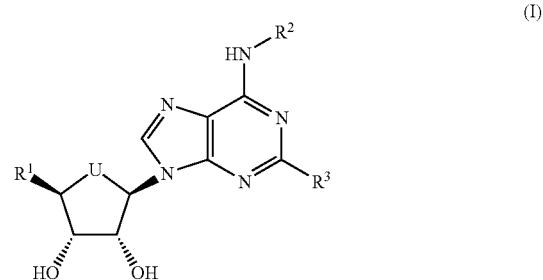

(I)

U is $CH_2$ except in Examples 10, 13 and 20 where U is O, are shown in the following table. Methods for preparing such compounds are described hereinafter. The table also shows mass spectrometry, $MH^+$ {ESMS), data. The Examples are trifluoroacetate salts, except for Example 1, which is in parent form and Examples 20-23 which are hydrochloride salts.

| Ex | Structure |
|---|---|
| 1 | 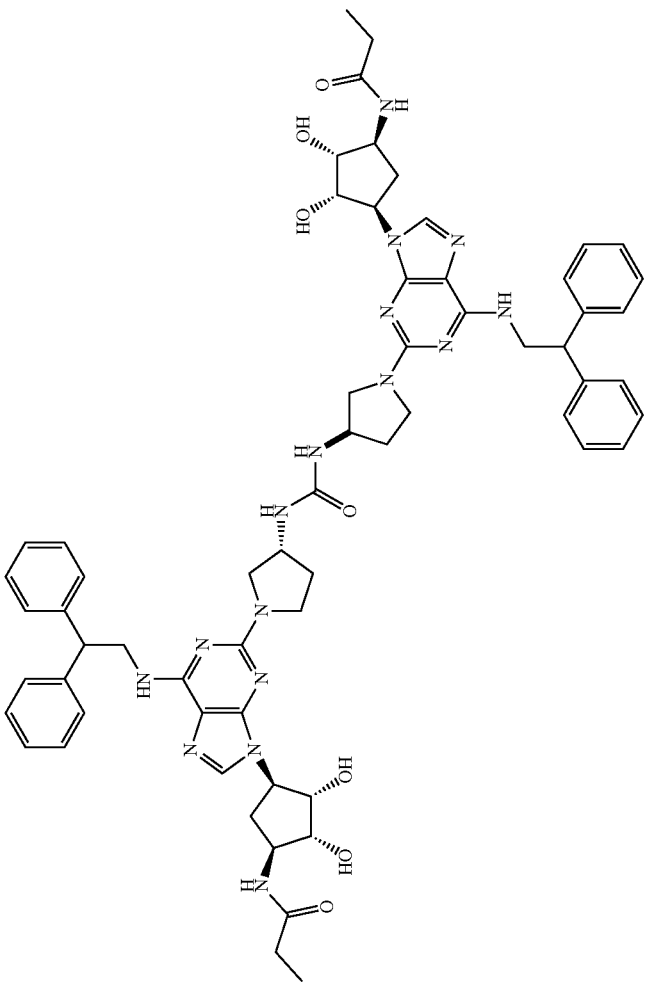 |

-continued
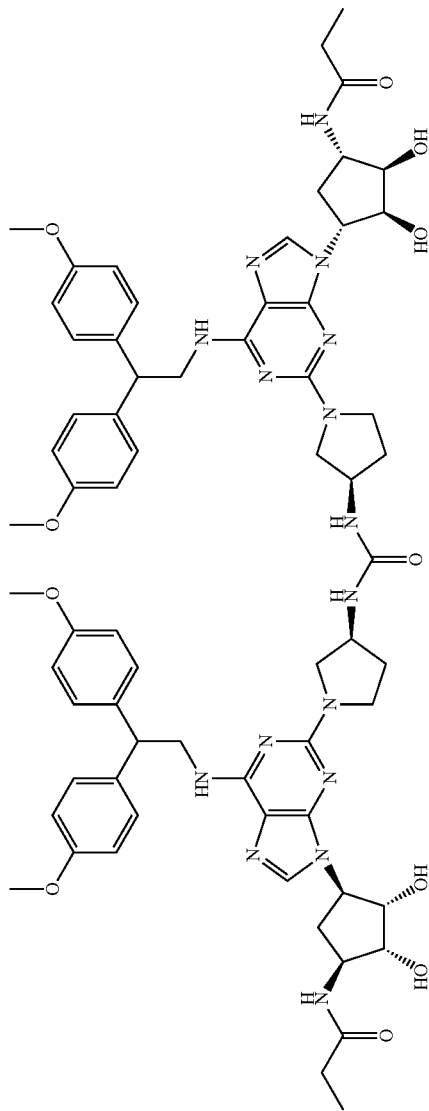
2
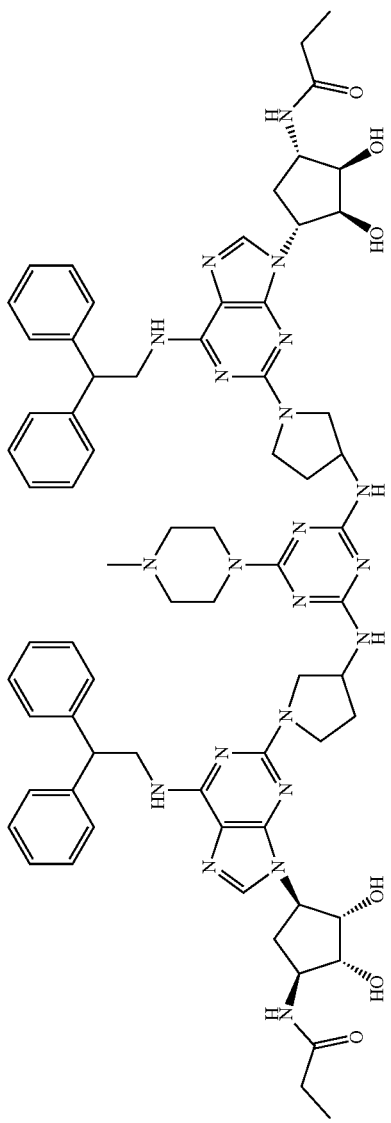
3

-continued
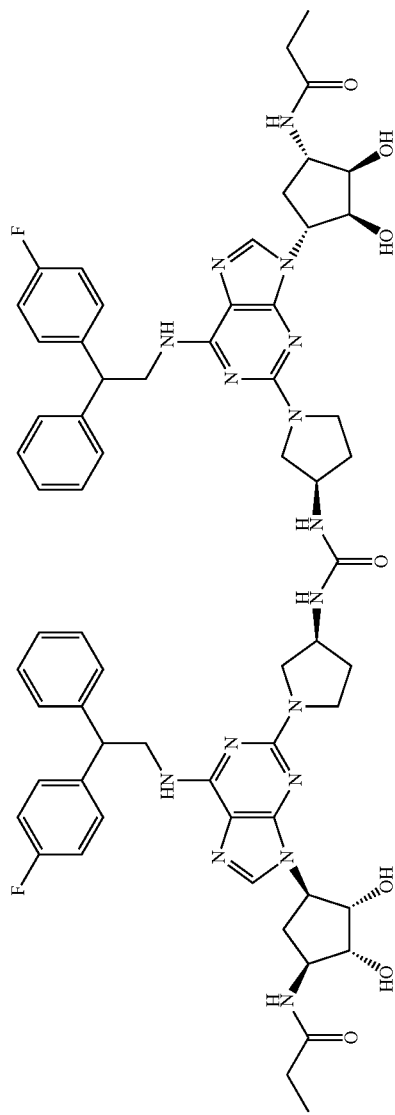
4
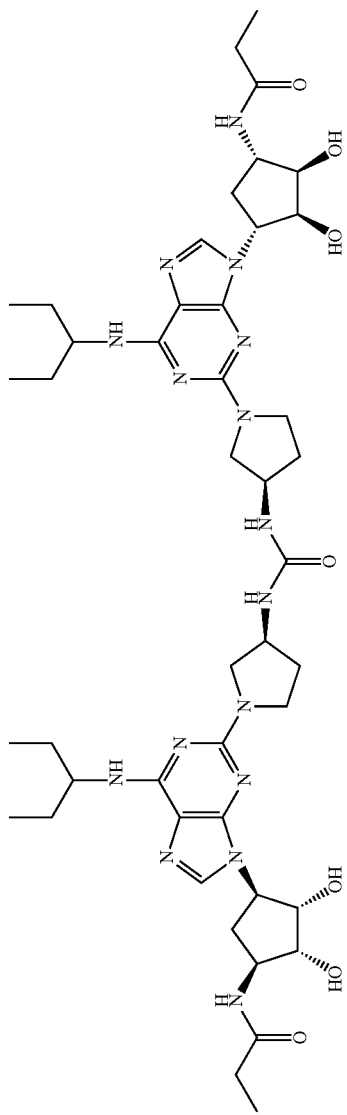
5

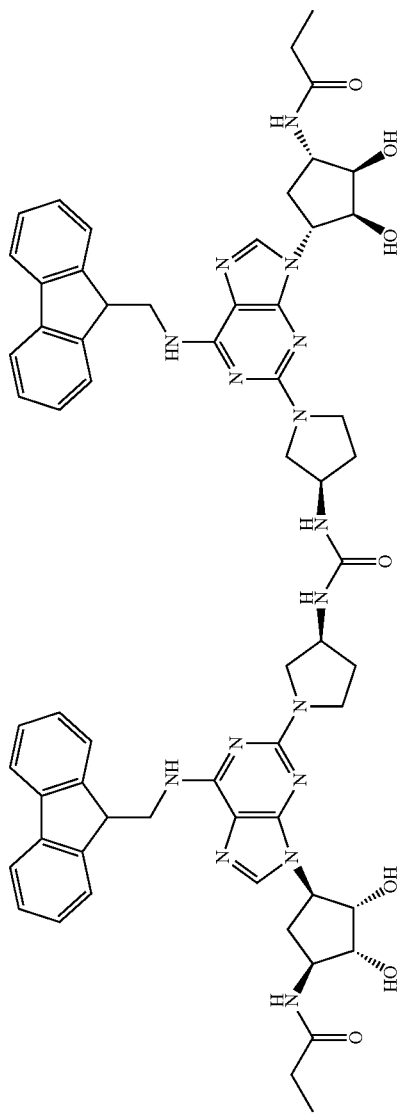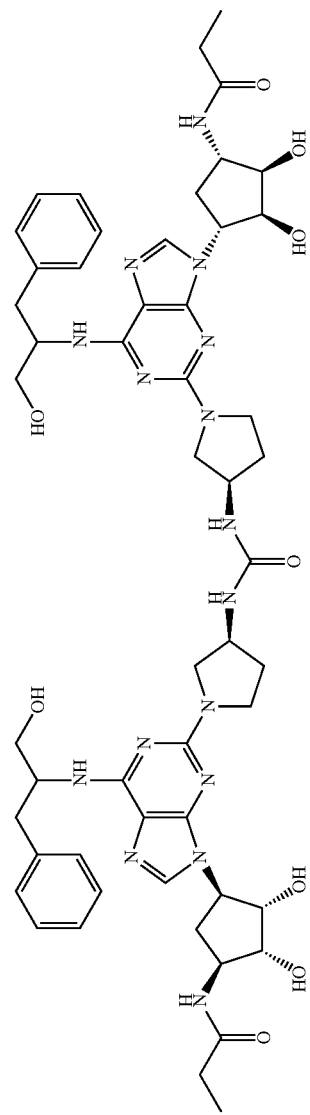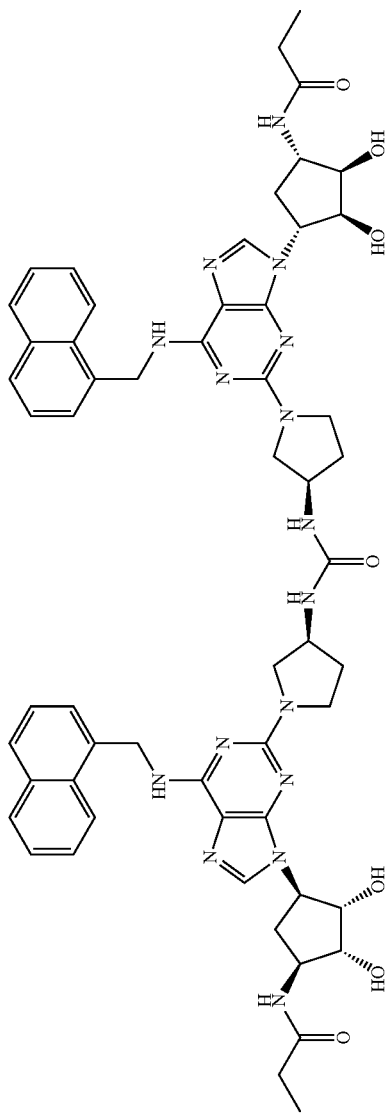

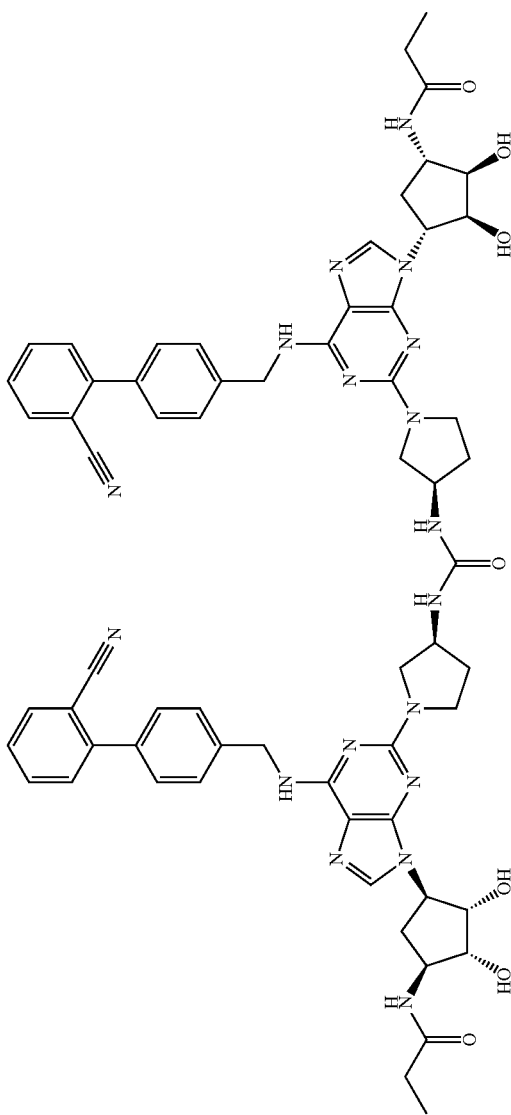
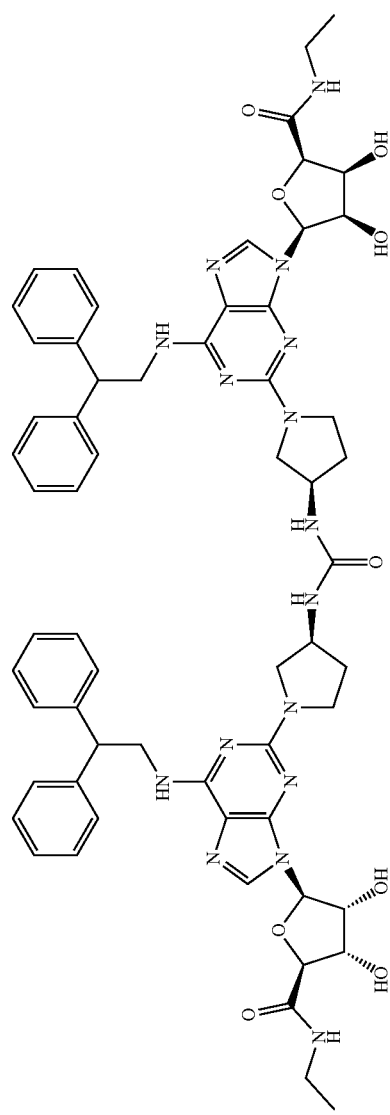

-continued
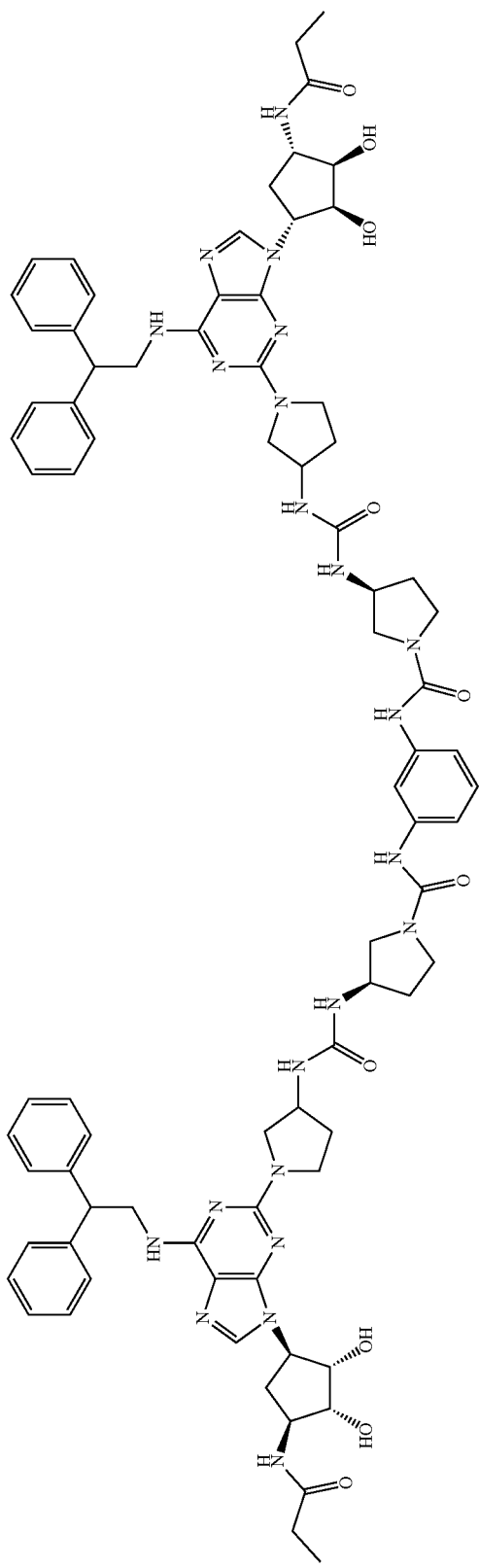
11
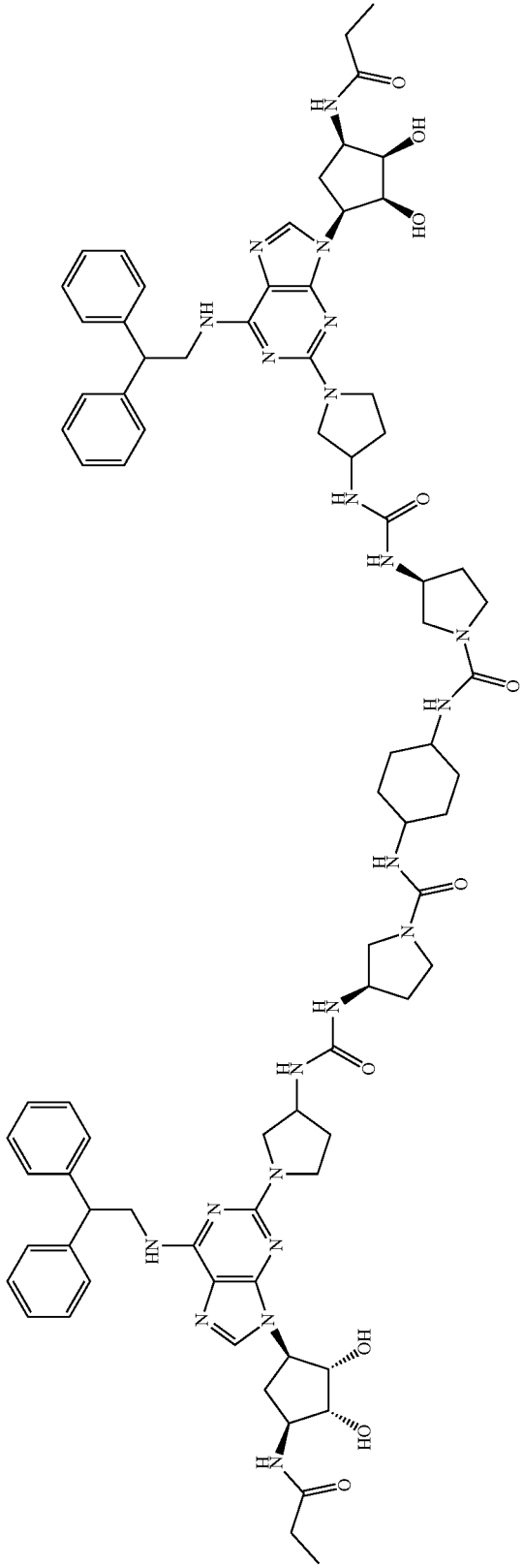
12

-continued
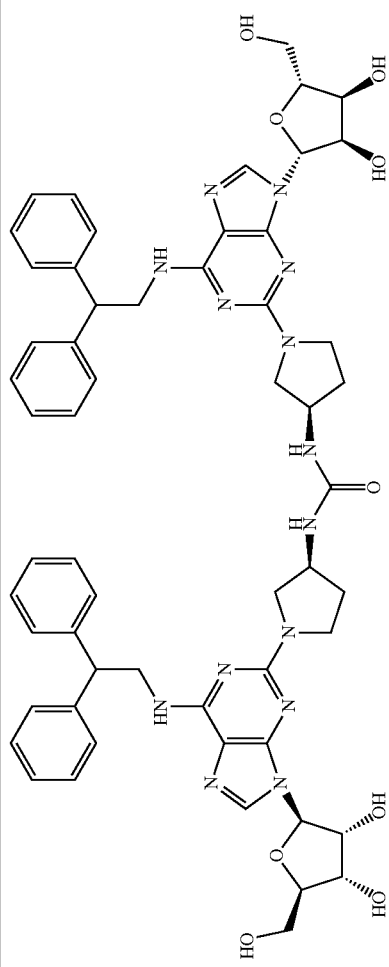
13
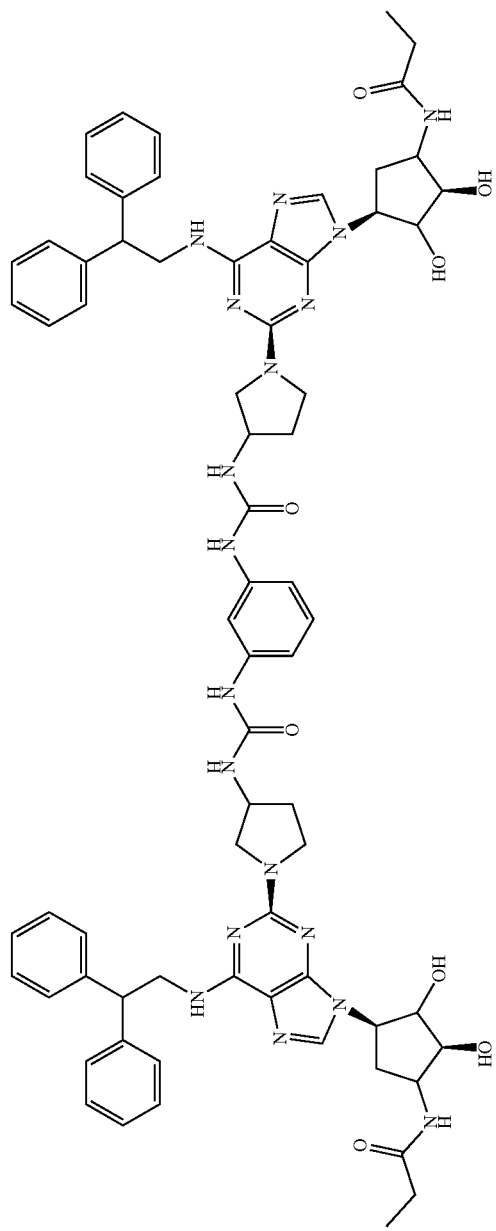
14

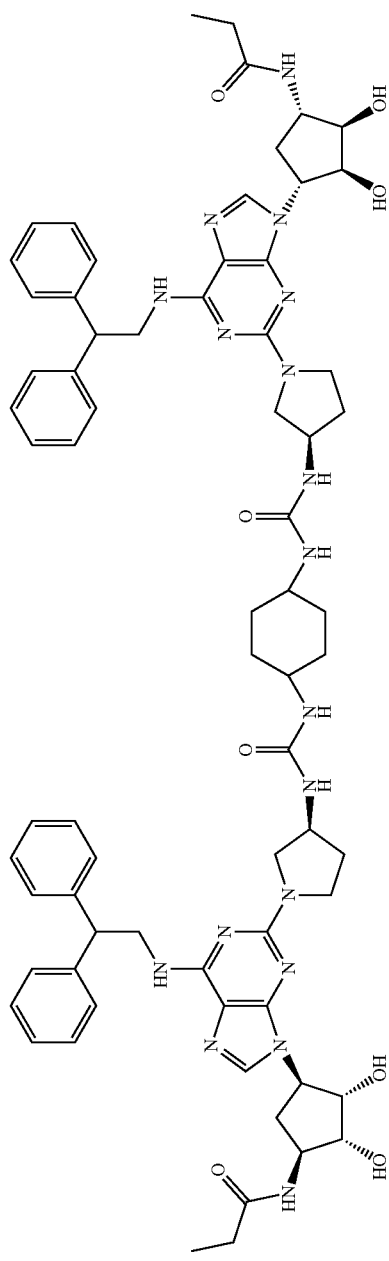
15
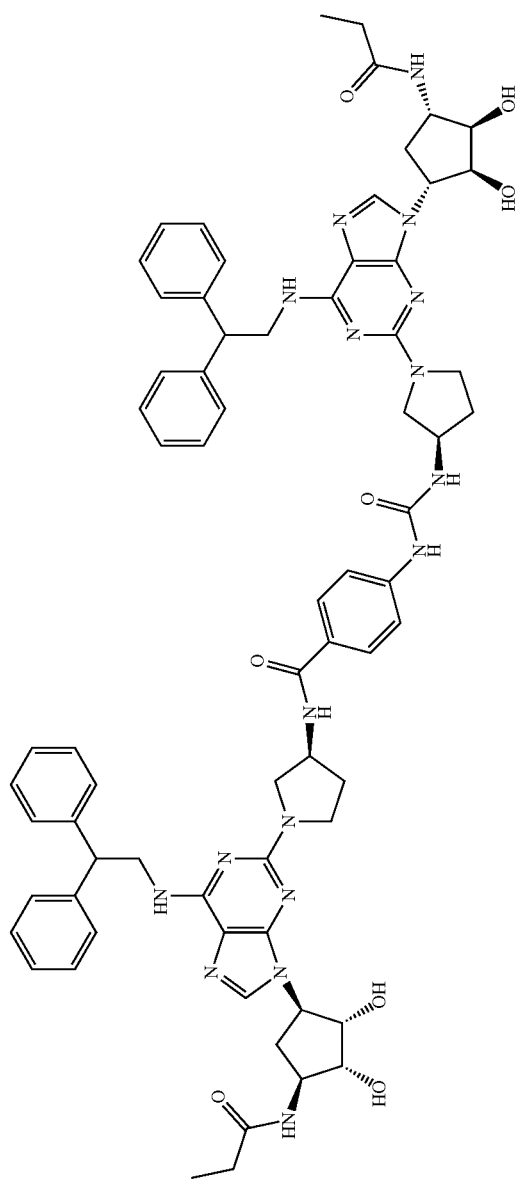
16

-continued
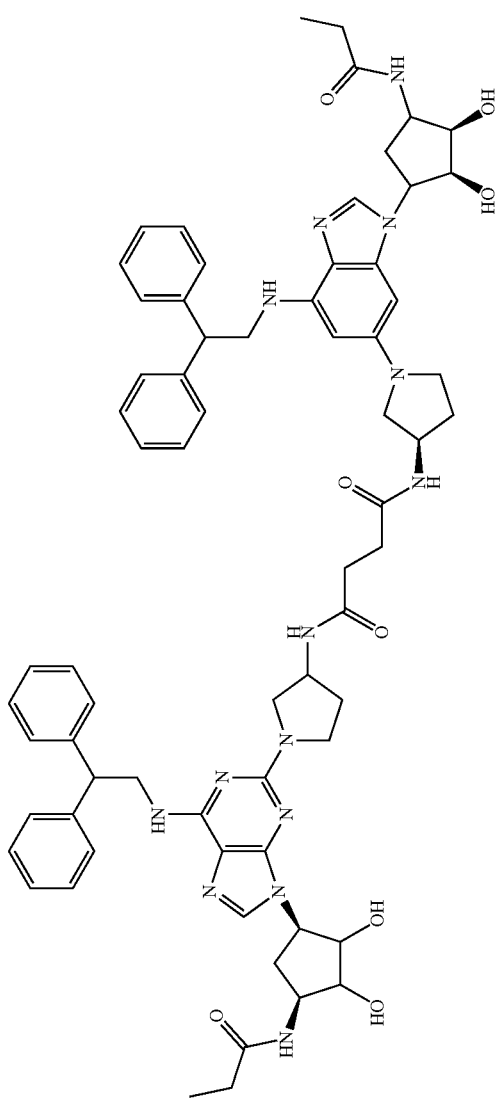
17
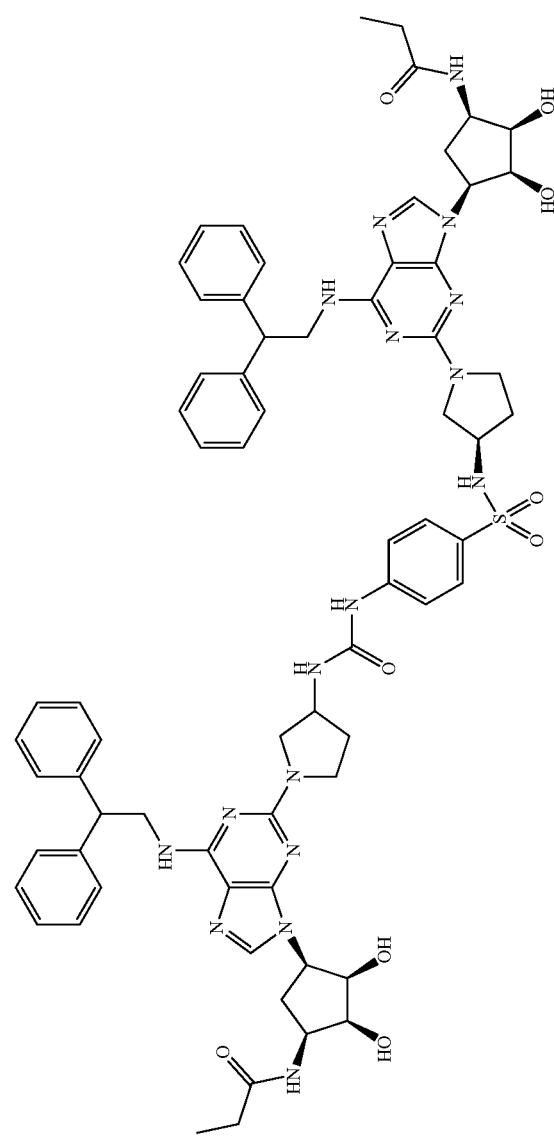
18

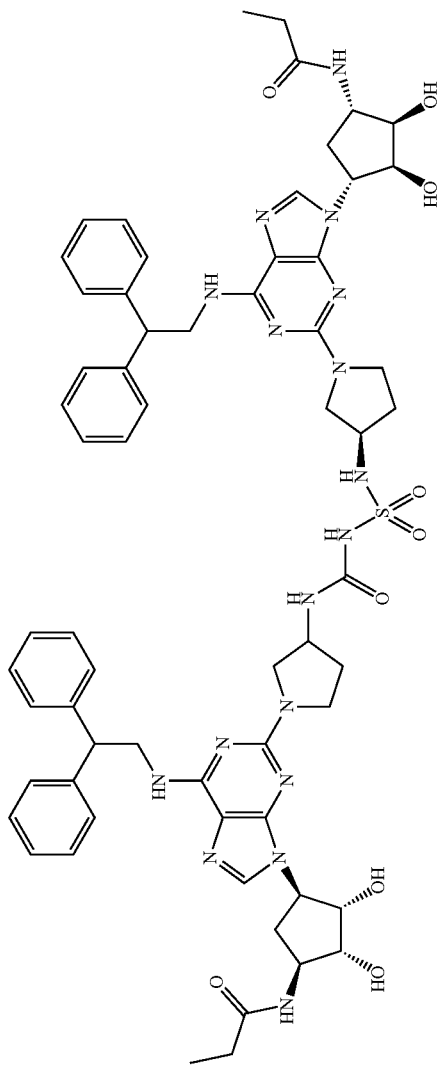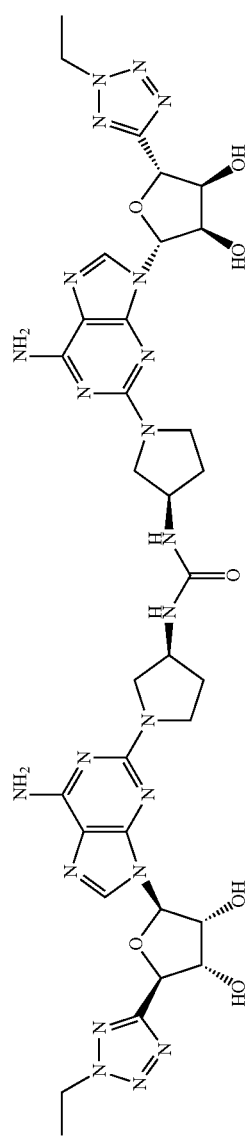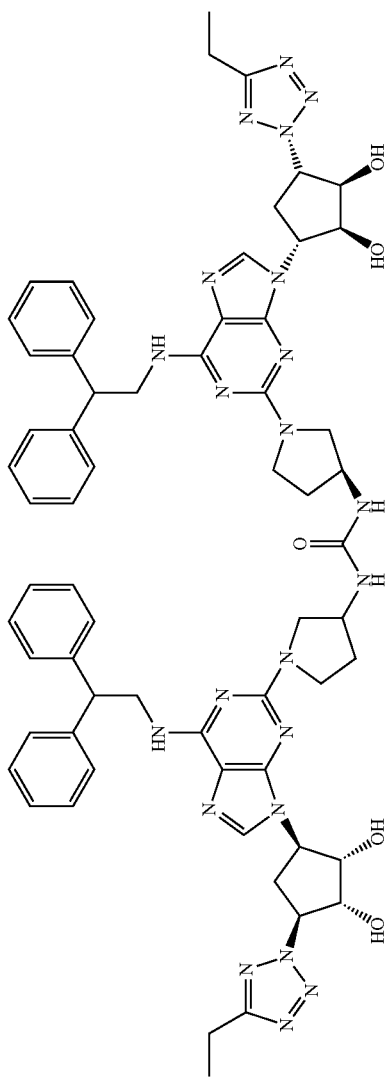

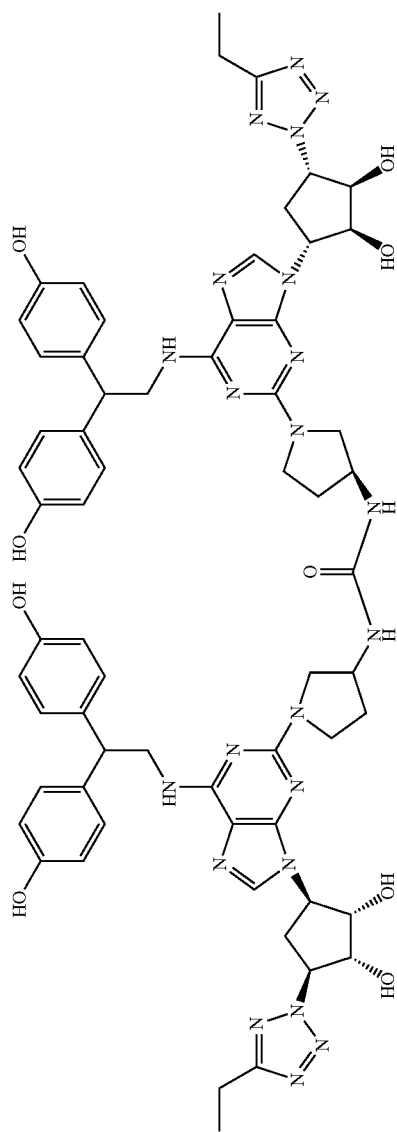
22
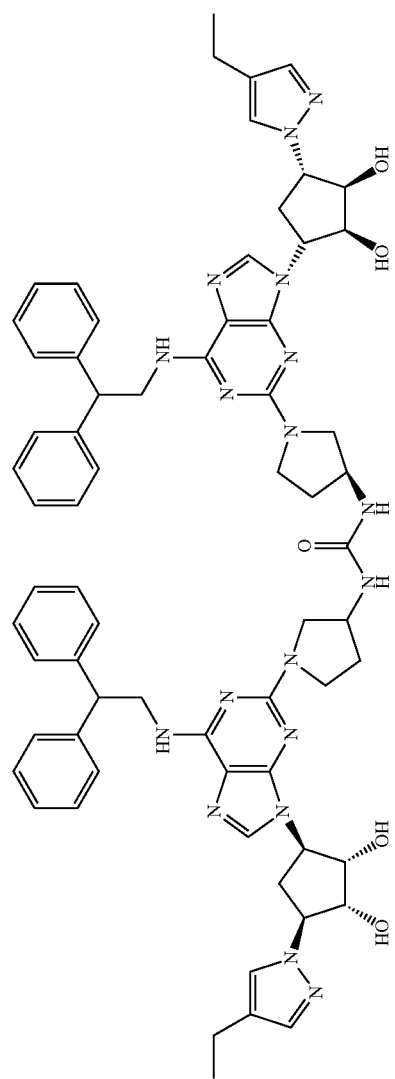
23

-continued
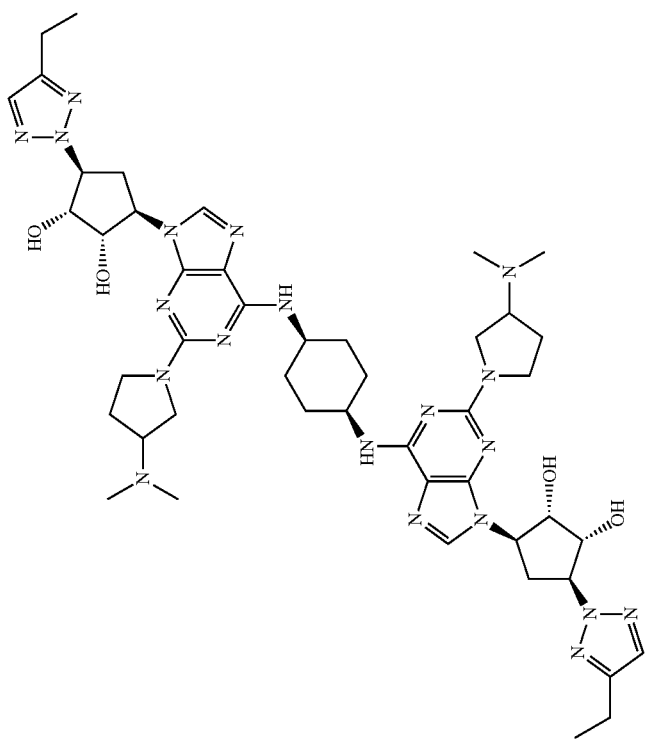
24

-continued
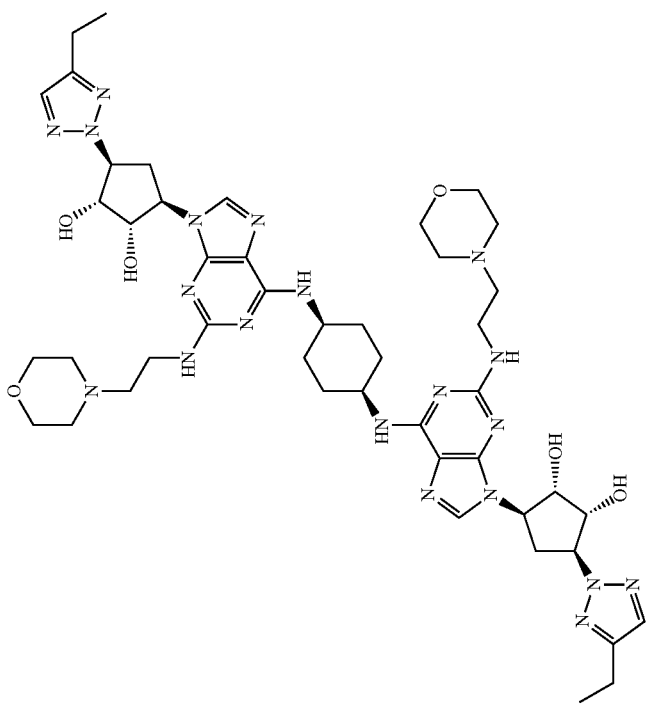

-continued
| Ex | R¹ | R² |
|---|---|---|
| 1 | 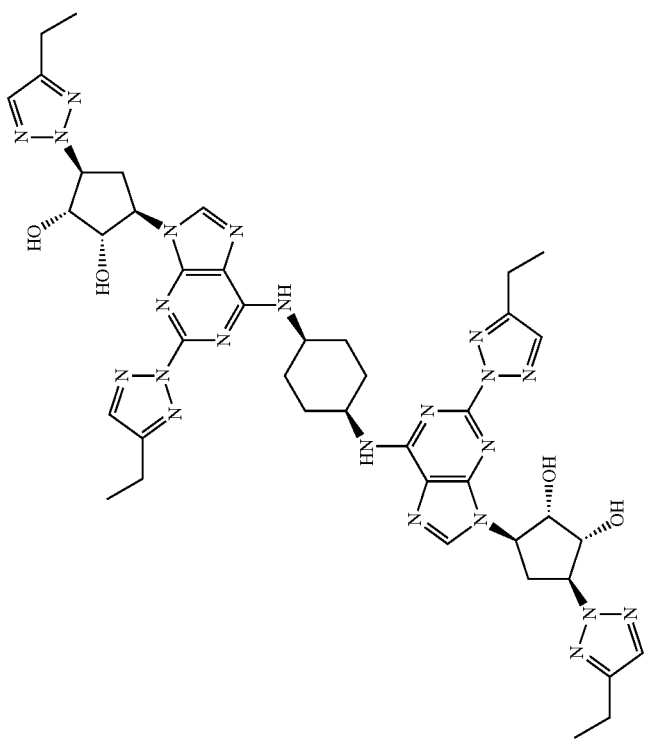 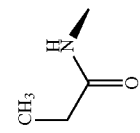 | 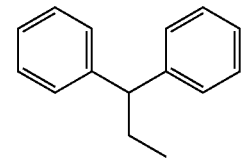 |
26

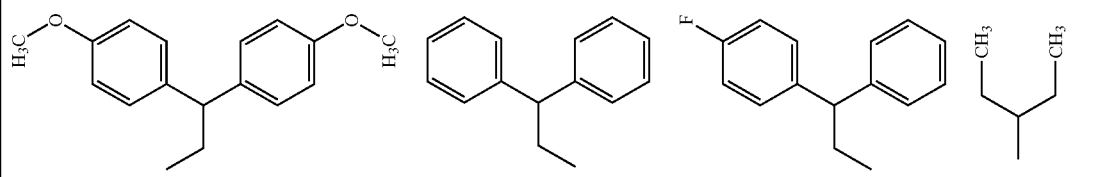
| | | |
|---|---|---|
| 2 | 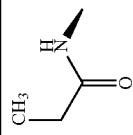 | |
| 3 | 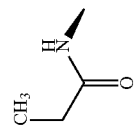 | |
| 4 | 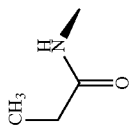 | |
| 5 | 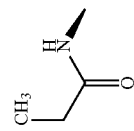 | |

-continued
| 6 | 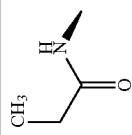 | 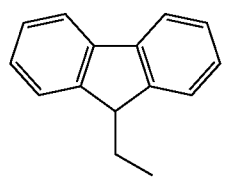 |
| 7 | 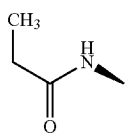 | 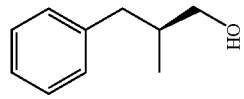 |
| 8 | 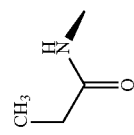 | 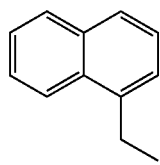 |
| 9 | 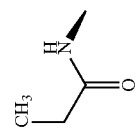 | 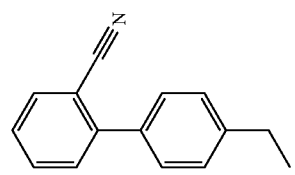 |

-continued
| | | | |
|---|---|---|---|
| 10 | 11 | 12 | 13 |
| 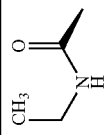 | 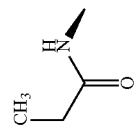 | 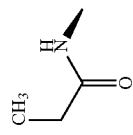 | 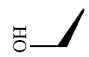 |
| 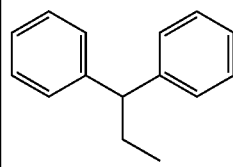 | 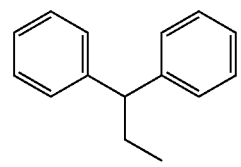 | 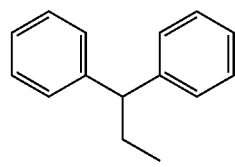 | 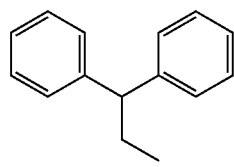 |

| | | |
|---|---|---|
| 14 | 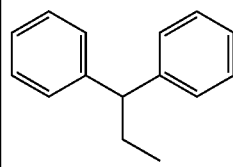 | 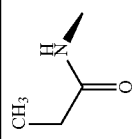 |
| 15 | 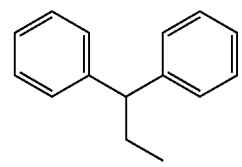 | 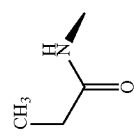 |
| 16 | 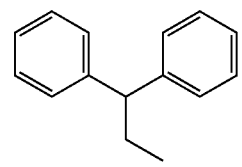 | 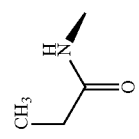 |
| 17 | 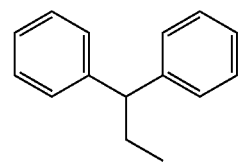 | 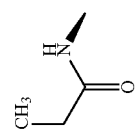 |

-continued
| | | | |
|---|---|---|---|
| 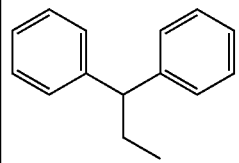 | 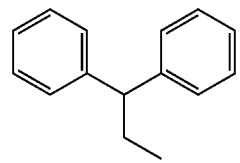 |  | 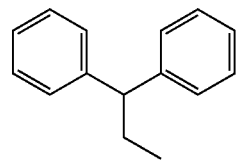 |
| 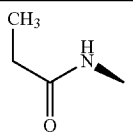 | 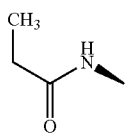 | 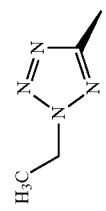 | 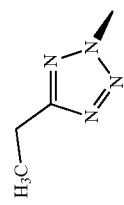 |
| 18 | 19 | 20 | 21 |

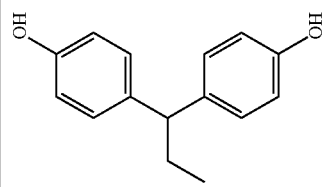
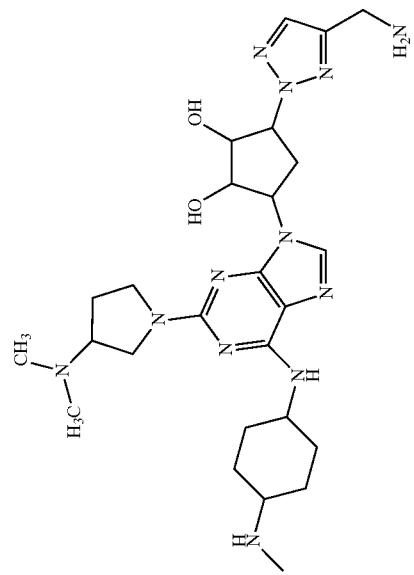
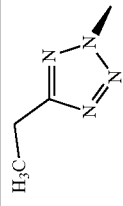
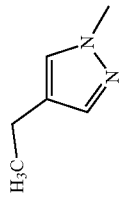
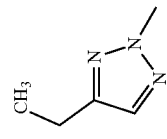

-continued
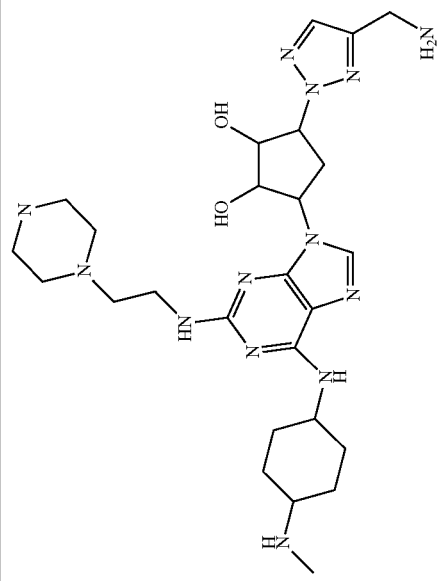
25
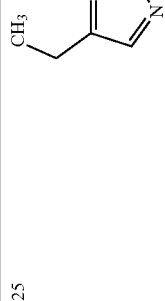
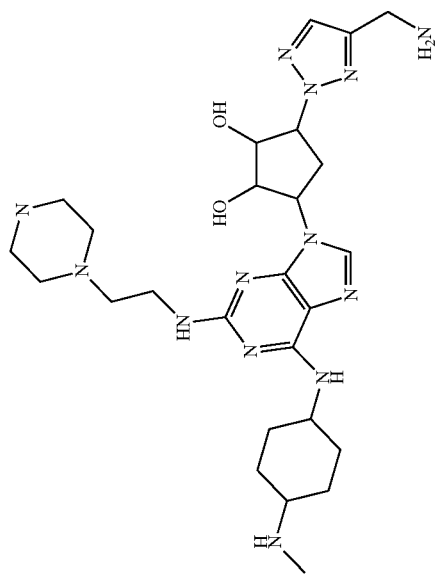
26
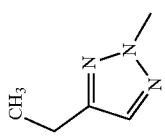

-continued
| Ex | R³ | MH⁺ (unless otherwise described) |
|---|---|---|
| 1 | 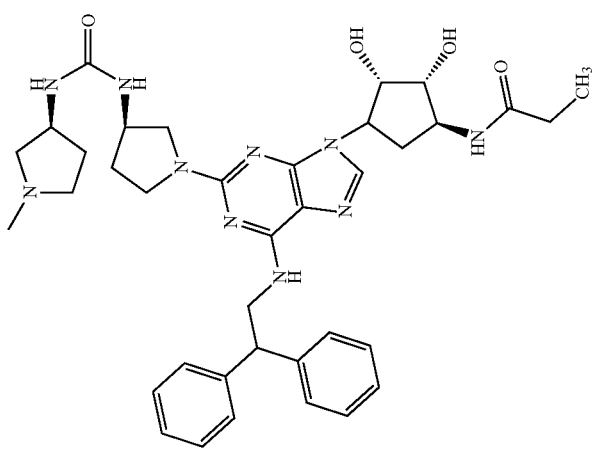 | 585 |
| 2 | 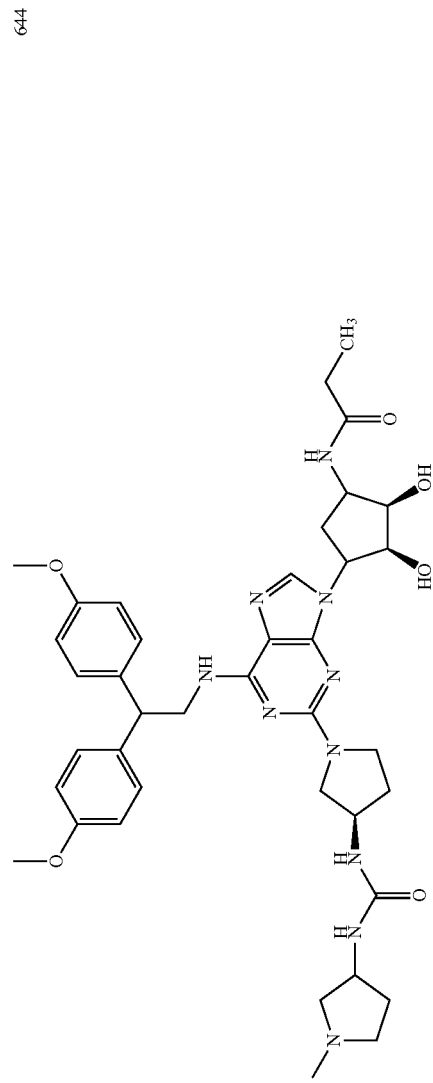 | 644 |

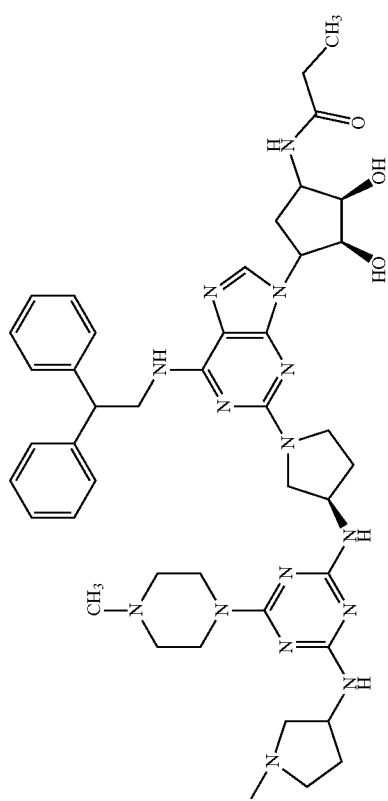
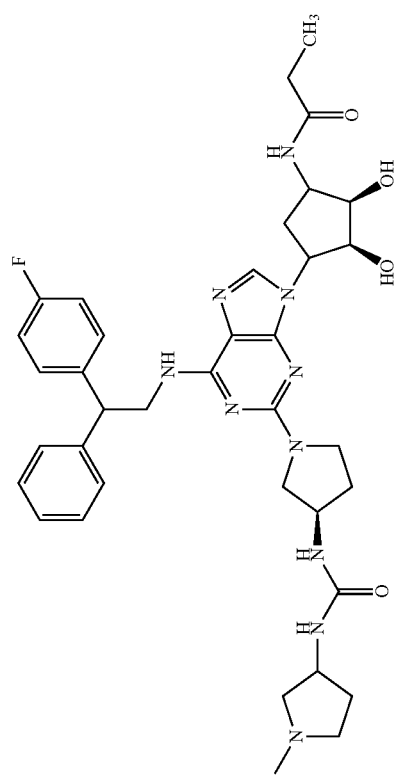

| | | |
|---|---|---|
| 5 | 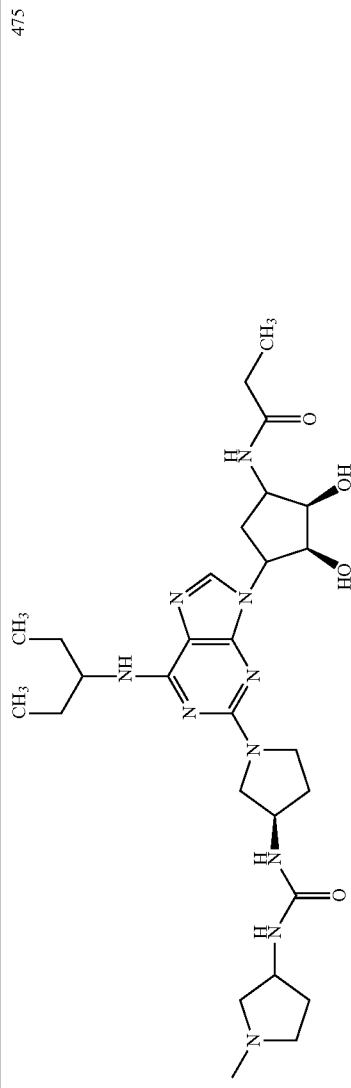 | 475 |
| 6 | 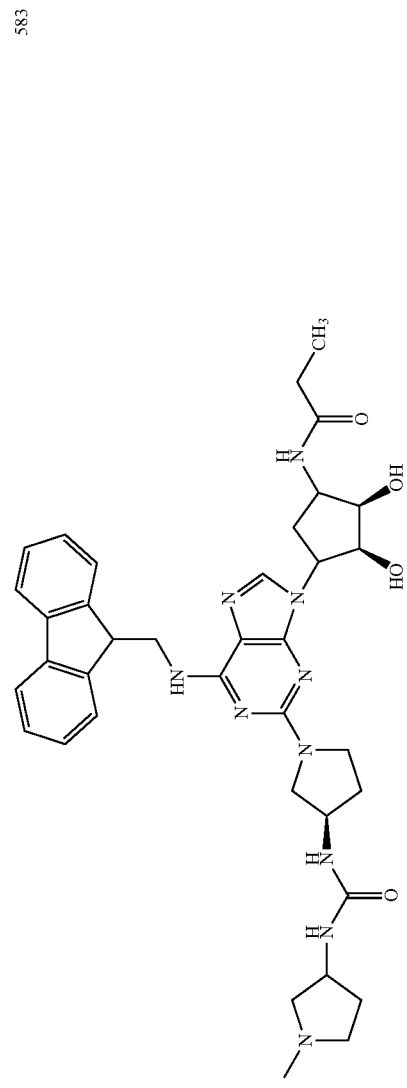 | 583 |
| 7 | 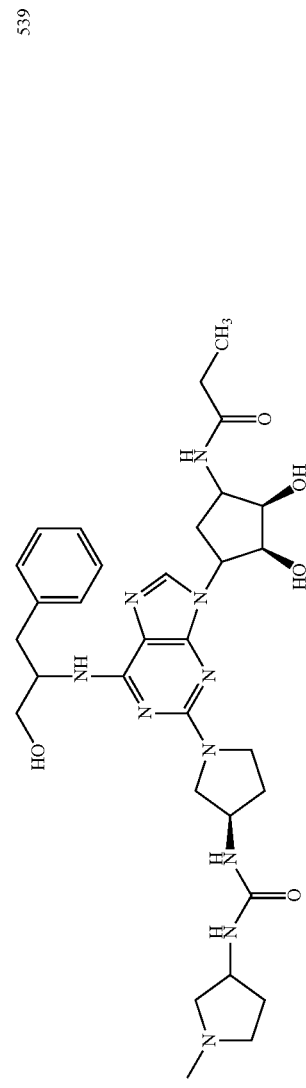 | 539 |

| | | |
|---|---|---|
| 8 | 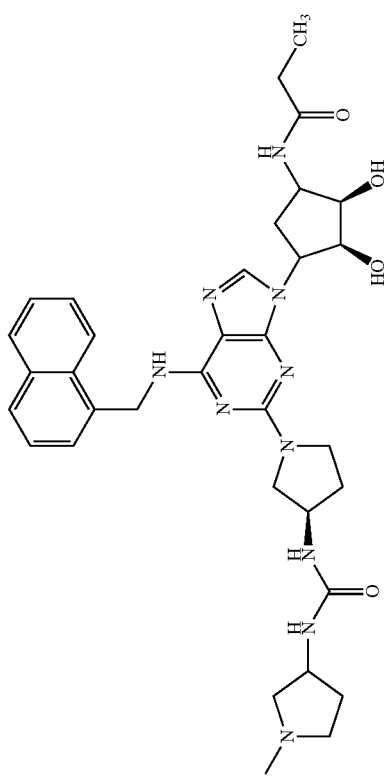 | 544 |
| 9 | 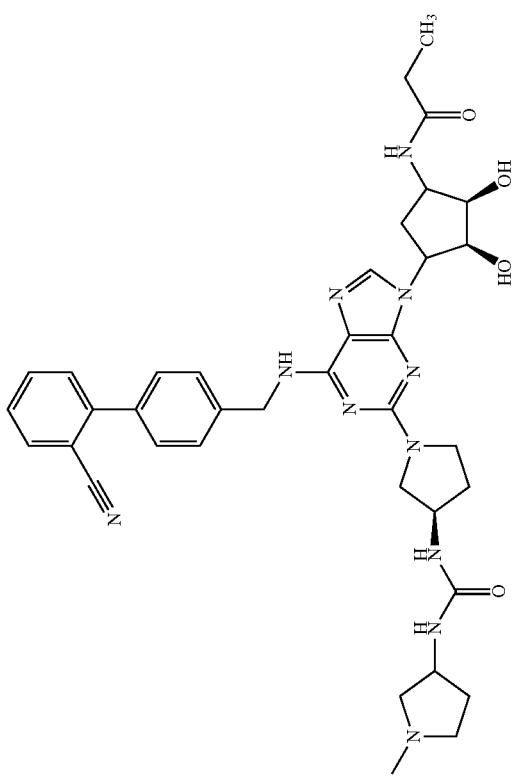 | 596 |

-continued
| 1173 | 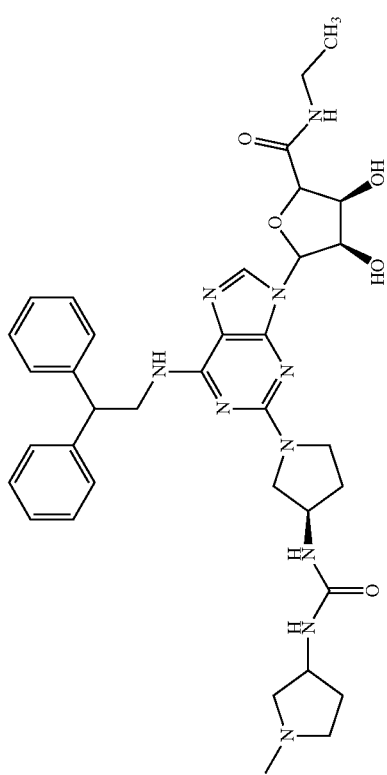 |
| --- | --- |
| 10 | |
| 764 | 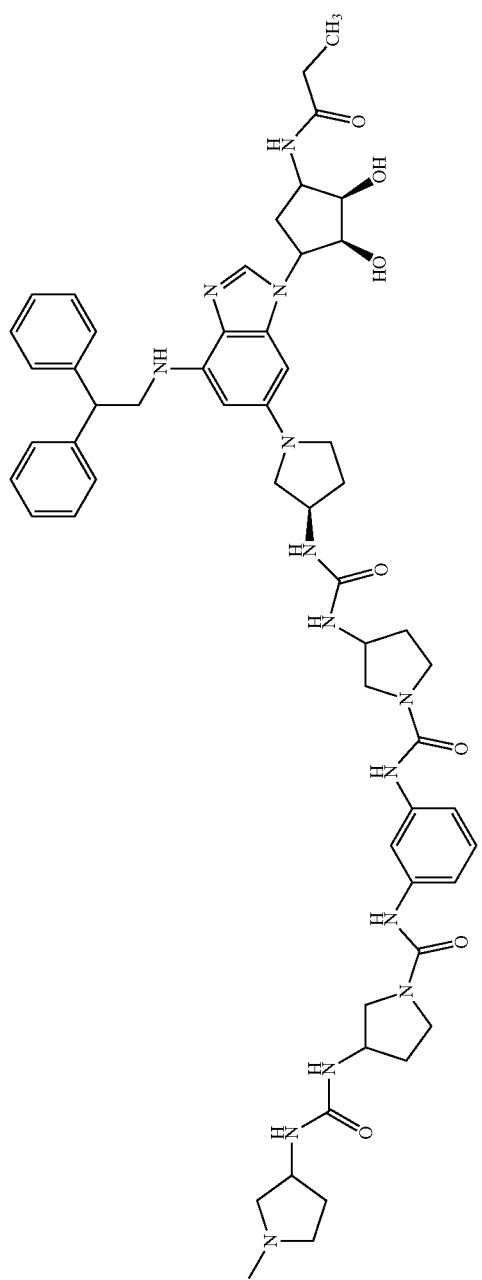 |
| --- | --- |
| 11 | |

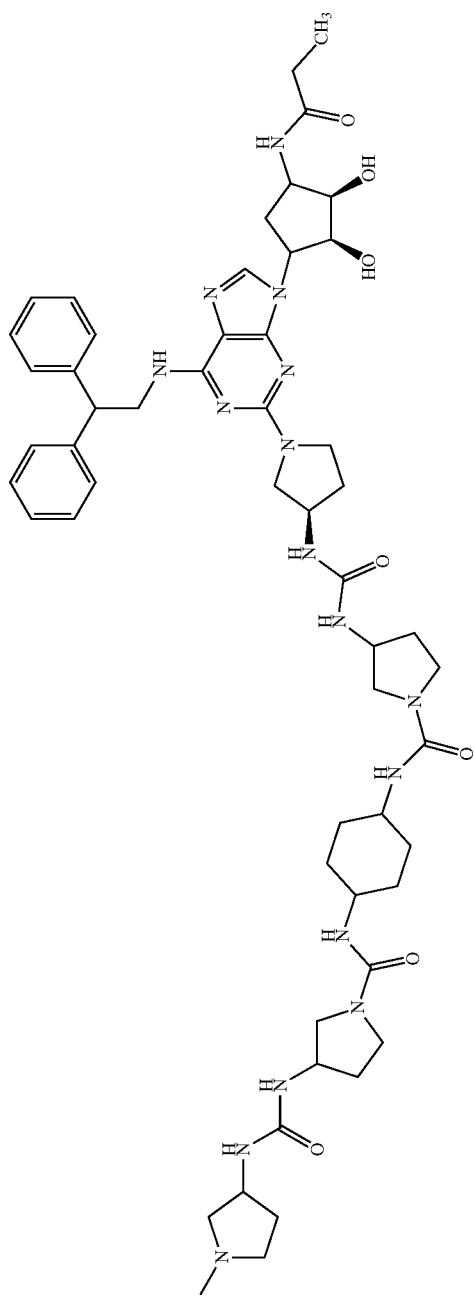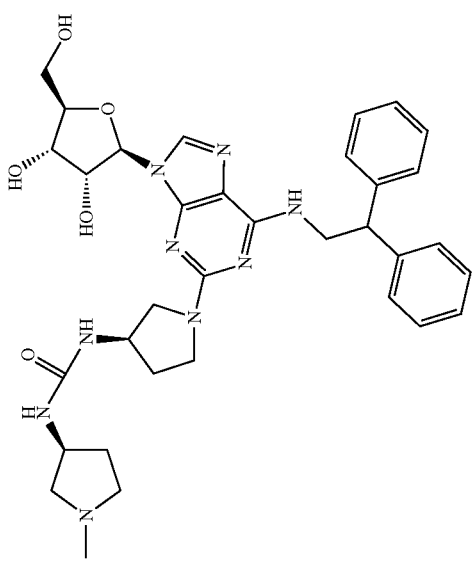

-continued
| 651 | 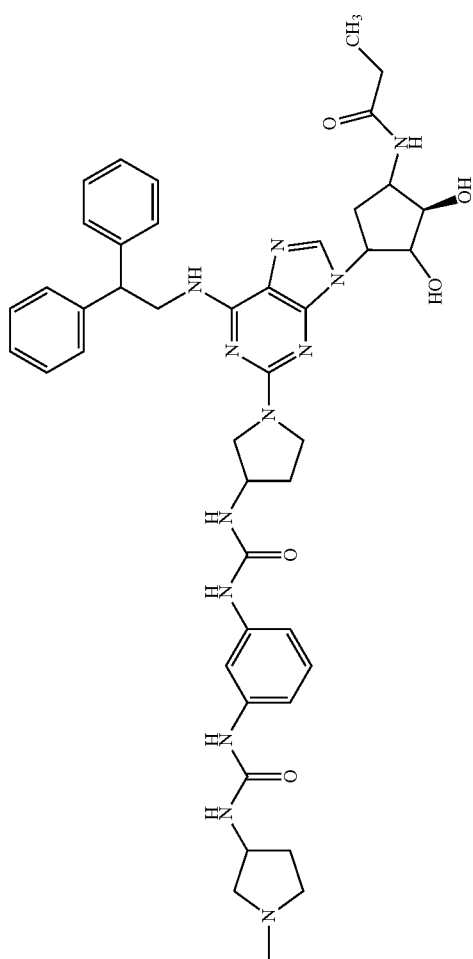 | 14 |
| 655 | 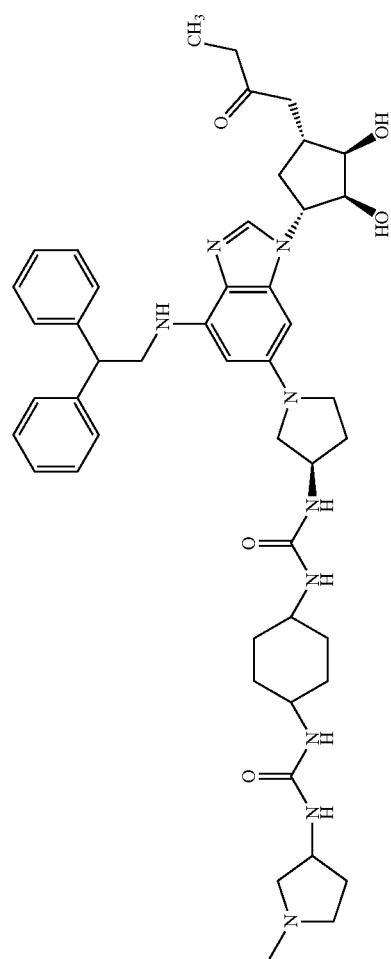 | 15 |

| | |
|---|---|
| 16 | 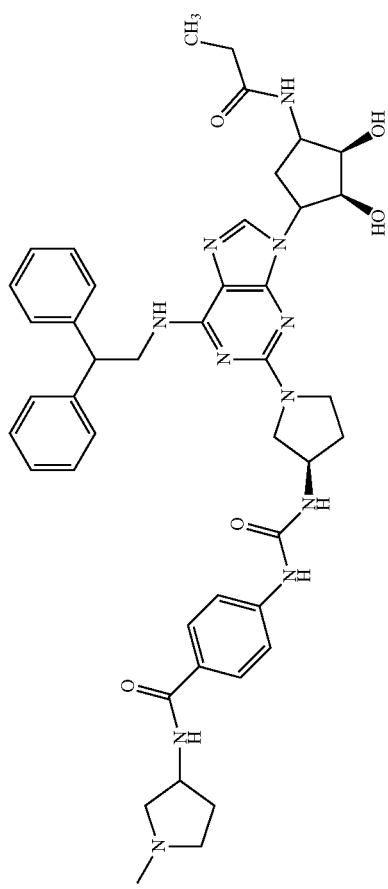 644 |
| 17 | 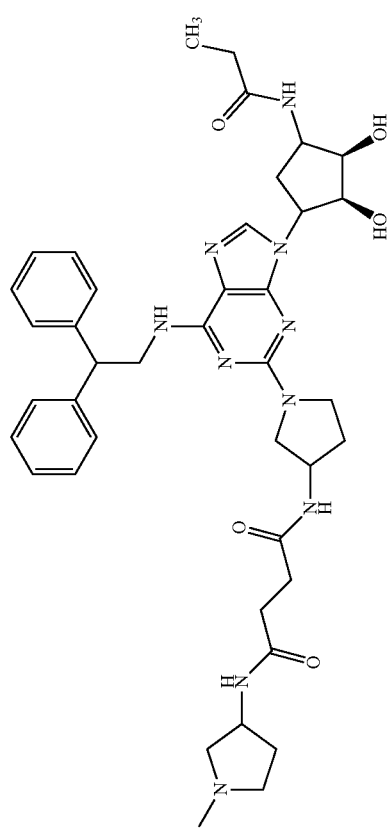 613 |

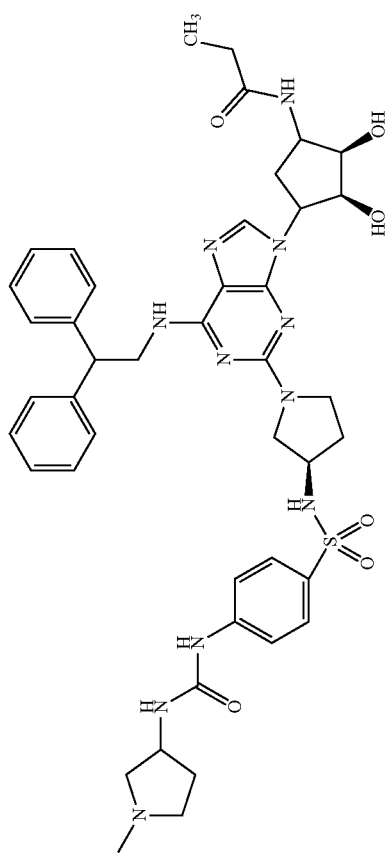
662
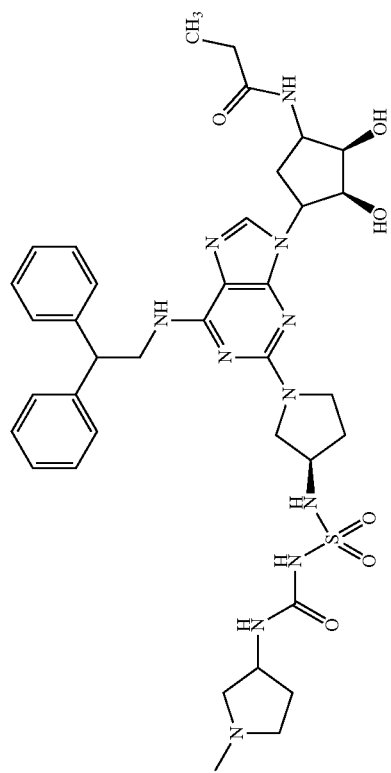
624
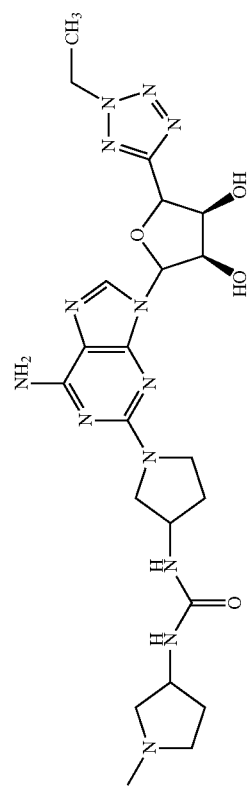
862
(M + 2H)
18
19
20

| 21 | 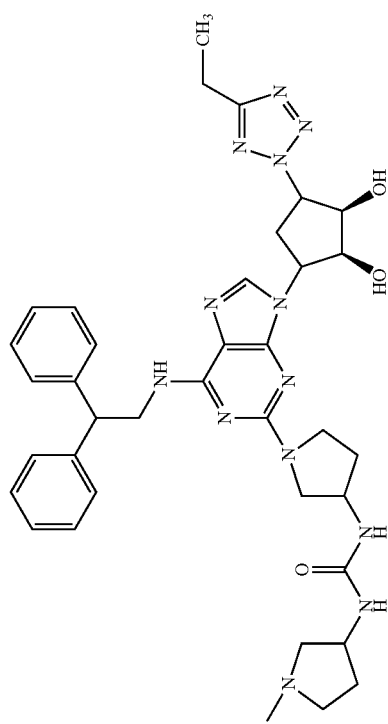 | 406.32 (MH+/3) |
|---|---|---|
| 22 | 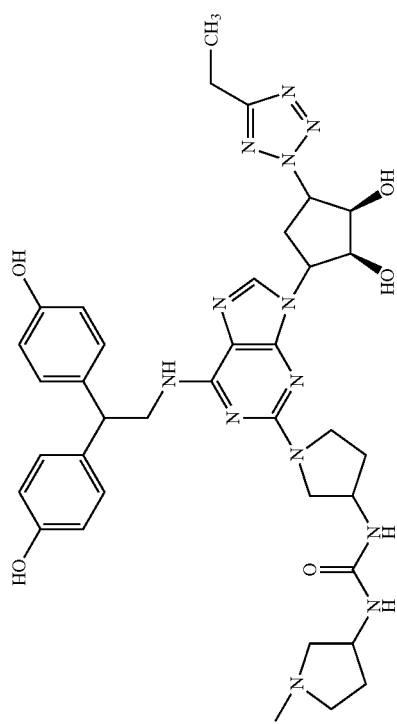 | 641.81 (MH+/2) |

| | | |
|---|---|---|
| 23 | 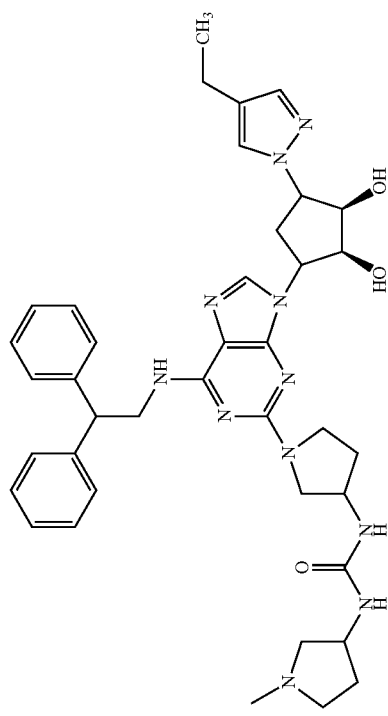 | 607.76 (MH+/2) |
| 24 | 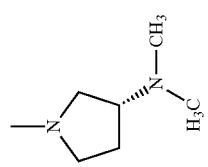 | 483 (MH+/2) |
| 25 | 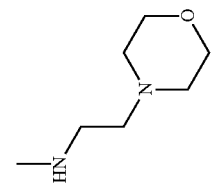 | 499 (MH+/2) |
| 26 | 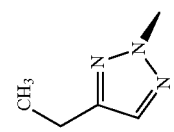 | MH+ 932 |

Preparation of Intermediates

Abbreviations used are as follows:

CDI 1,1'-Carbonyldiimidazole
DCM Dichloromethane
DEAD Diethyl Azodicarboxylate
DIPEA Diisopropylethylamine
DMF Dimethylformamide
DMSO Dimethyl Sulfoxide
EDCI 1-Ethyl-3-(3'-dimethylaminopropyl) carbodiimide
EtOAc Ethyl Acetate
HPLC High Performance Liquid Chromatography
HCl Hydrochloric Acid
LCMS Liquid Chromatographic Mass Spectroscopy
MeOH Methanol
NMO N-Methylmorpholine N-Oxide
NMP n-Methyl Pyrrolidone
RT Room Temperature
TEA Triethylamine
TFA Trifluoroacetic Acid
THF Tetrahydrofuran The following intermediates of formula (A):

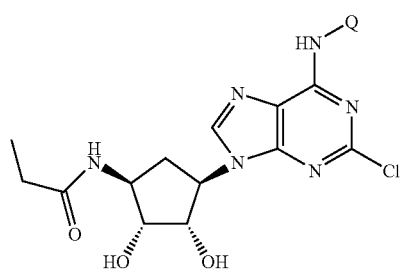

are shown in Table 1 below, their method of preparation being described hereinafter.

TABLE 1

| Intermediate | Q | M/s MH+ |
|---|---|---|
| AA | (diphenylethyl) | 521 |
| AB | (naphthyl-ethyl) | 481 |
| AC | (isobutyl with CH₃ groups) | 411 |
| AD | (1-phenyl-1-(4-fluorophenyl)propyl) | 539 |
| AE | (fluorenyl-ethyl) | 519 |
| AF | (2-methyl-3-phenylpropan-1-ol) | 475 |
| AG | (bis(4-methoxyphenyl)propyl) | 581 |
| AH | (2'-cyano-4-ethyl-biphenyl) | 532 |

Intermediate AA N-{(1S,2R,3S,4R)-4-[2-Chloro-6-(2,2-diphenyl-ethylamino)-purin-9-yl]-2,3-dihydroxy-cyclopentyl}-propionamide Step AA1: (1S,4R)-4-(2,6-Dichloro-purin-9-yl)-cyclopent-2-enol 2,6-Dichloropurine (10 g, 52.90 mmol), (1S,4R)-cis 4-acetoxy-2-cyclopenten-1-ol (10 g, 70.40 mmol), tris(dibenzylideneacetone)dipalladium(0) (3.20 g, 3.50 mmol) and polymer supported triphenylphosphine (3 mmol/g, 11.60 g, 35.00 mmol) are placed in an oven-dried flask under an atmosphere of argon. Dry deoxygenated THF (80 mL) is added and the reaction mixture is stirred gently for 5 minutes. TEA (20 mL) is added and the reaction mixture is stirred at 50° C. The reaction is shown to be complete by LCMS after 1 hour. The reaction mixture is allowed to cool, filtered and the solvent is removed in vacuo. The title compound is obtained after purification by flash column chromatography (silica, DCM:MeOH 25:1).

¹H NMR (CDCl₃, 400 MHz); 8.30 (s, 1H), 6.40 (m, 1H), 5.90 (m, 1H), 5.50 (m, 1H), 4.95 (m, 1H), 3.05 (m, 1H), 2.10 (m, 1H), MS (ES+) m/e 271 (MH⁺).

Step AA2: Carbonic acid (1S,4R)-4-(2,6-dichloro-purin-9-yl)-cyclopent-2-enyl ester ethyl ester (1S,4R)-4-(2,6-Dichloro-purin-9-yl)-cyclopent-2-enol (9.5 g, 35.05 mmol) is placed in an oven-dried flask under an atmosphere of argon. Dry THF (200 mL) is added followed by dry pyridine (5.54 g, 70.1 mmol). Ethyl chloroformate (15.21 g, 140.2 mmol) is added slowly so that the temperature does not rise above 40° C. and the reaction mixture is stirred at RT. The reaction is shown to be complete by LCMS after 1 hour. The solvent is removed in vacuo and the residue is partitioned between DCM (200 mL) and water (200 mL). The organic layer is washed with water (150 mL) and brine (150 mL), dried over MgSO₄, filtered and the solvent is removed in vacuo. The title compound is obtained after crystallisation from methanol.

¹H NMR (CDCl₃, 400 MHz); 8.20 (s, 1H), 6.45 (m, 1H), 6.25 (m, 1H), 5.75 (m, 1H), 5.70 (m, 1H), 4.25 (q, 2H), 3.20 (m, 1H), 2.05 (m, 1H), 1.35 (t, 3H), MS (ES+) m/e 343 (MH⁺).

Step AA3: Di-Boc-[(1S,4R)-4-(2,6-dichloro-purin-9-yl)-cyclopent-2-enyl]-amine

Carbonic acid (1S,4R)-4-(2,6-dichloro-purin-9-yl)-cyclopent-2-enyl ester ethyl ester (2.5 g, 7.29 mmol), di-t-butyl-iminodicarboxylate (1.74 g, 8.02 mmol), and triphenylphosphine (0.29 g, 1.09 mmol) are placed in an oven-dried flask under an atmosphere of argon. Dry deoxygenated THF (30 mL) is added followed by tris(dibenzylideneacetone)dipalladium(0) (0.33 g, 0.36 mmol) and the reaction mixture is stirred at RT. The reaction is shown to be complete by LCMS after 3 hours. The solvent is removed in vacuo and the title compound is obtained after purification by flash column chromatography (silica, EtOAc:iso-hexane 4:1).

¹H NMR (CDCl₃, 400 MHz); 8.70 (s, 1H), 6.20 (m, 1H), 5.85 (m, 1H), 5.80 (m, 1H), 5.40 (m, 1H), 3.20 (m, 1H), 2.15 (m, 1H), 1.55 (s, 18H), MS (ES+) m/e 470 (MH⁺).

Step AA4: (1S,2R,3S,5R)-3-(Di-Boc-amino)-5-(2,6-dichloro-purin-9-yl)-cyclopentane-1,2-diol A mixture comprising di-Boc-[(1S,4R)-4-(2,6-dichloro-purin-9-yl)-cyclopent-2-enyl]-amine (1.30 g, 2.77 mmol) (1.49 g, 3.17 mmol), methane sulphonamide (0.30 g, 3.17 mmol) and AD-mix-α (6.75 g, 1.5 g/mmol) in t-butanol/water (20 mL of a 1:1 mixture) is treated with osmium tetroxide (1.5 mL, 4% w/w in water). After stirring vigorously at RT overnight, the reaction mixture is partitioned between EtOAc and water. The organic portion is separated, washed with water, brine, dried (MgSO₄) and concentrated in vacuo to yield the title compound which is used in the next step without further purification.

¹H NMR (CDCl₃, 400 MHz); 8.35 (s, 1H), 4.80 (m, 1H), 4.70 (m, 1H), 4.50 (m, 1H), 3.85 (m, 1H), 3.75 (m, 1H), 3.10 (m, 1H), 2.75 (m, 1H), 2.55 (m, 1H), 1.55 (s, 18H), MS (ES+) m/e 504 (MH⁺).

Step AA5: (1S,2R,3S,5R)-3-Amino-5-(2,6-dichloro-purin-9-yl)-cyclopentane-1,2-diol trifluoroacetate A solution of (1S,2R,3S,5R)-3-(di-Boc-amino)-5-(2,6-dichloro-purin-9-yl)-cyclopentane-1,2-diol (0.55 g, 1.09 mmol) in DCM (4 mL) is treated with TFA (2 mL) and stirred at RT. After 2 hours, the solvent is removed in vacuo to yield the title compound which is used in the next step without further purification. MS (ES+) m/e 304 (MH⁺).

Step AA6: N-[(1S,2R,3S,4R)-4-(2,6-Dichloro-purin-9-yl)-2,3-dihydroxy-cyclopentyl]-propionamide A solution of (1S,2R,3S,5R)-3-amino-5-(2,6-dichloro-purin-9-yl)-cyclopentane-1,2-diol trifluoroacetate (0.304 g, 1.0 mmol) in THF (10 mL) is treated with DIPEA (0.387 g, 3.0 mmol) followed by propionyl chloride (0.093 g, 1.0 mmol). After stirring at RT for 2 hours, the solvent is removed in vacuo and the title compound is obtained after purification by reverse phase column chromatography (Isolute™ C18, 0-100% acetonitrile in water 0.1% TFA). MS (ES+) m/e 360 (MH⁺).

Step AA7: N-{(1S,2R,3S,4R)-4-[2-Chloro-6-(2,2-diphenyl-ethylamino)-purin-9-yl]-2,3-dihydroxy-cyclopentyl}-propionamide N-[(1S,2R,3S,4R)-4-(2,6-dichloro-purin-9-yl)-2,3-dihydroxy-cyclopentyl]-propionamide (160 mg, 0.44 mmol) is dissolved in THF (5 mL) under an atmosphere of argon. DIPEA (69 mg, 0.53 mmol) is added followed by 2,2-diphenylethylamine (96 mg, 0.49 mmol) and the reaction mixture is stirred at 50° C. The reaction is shown to be complete by LCMS after 2 hours. The solvent is removed in vacuo and the title compound is obtained after purification by reverse phase column chromatography (Isolute™ C18, 0-100% acetonitrile in water—0.1% TFA).

¹H NMR (MeOD, 400 MHz); 8.00 (s, 1H), 7.40-7.15 (m, 10H), 4.75 (m, 1H), 4.60 (m, 1H), 4.50 (m, 1H), 4.20 (m, 3H), 3.95 (m, 1H), 2.85 (m, 1H), 2.40 (q, 2H), 2.10 (m, 1H), 1.20 (t, 3H), MS (ES+) m/e 521 (MH⁺).

Intermediate AA may also be prepared using the following process:

Step AAI1: {2-Chloro-9-[(1R,4S)-4-(di-Boc-amino)-cyclopent-2-enyl]-9H-purin-6-yl}-(2,2-diphenyl-ethyl)-amine (1S,2R,3S,5R)-3-(Di-Boc-amino)-5-(2,6-dichloro-purin-9-yl)-cyclopentane-1,2-diol (13.0 g, 27.66 mmol) is dissolved in THF (250 mL) under an atmosphere of argon. DIPEA (4.28 g, 33.19 mmol) is added followed by 2,2-diphenylethylamine (6.0 g, 30.43 mmol) and the reaction mixture is stirred at 50° C. The reaction is shown to be complete by LCMS after 18 hours. The solvent is removed in vacuo and the reaction mixture is partitioned between DCM (250 mL) and 0.1 M HCl (250 mL). The organic layer is washed with water (200 mL) and brine (200 mL), dried over MgSO₄, filtered and the solvent is removed in vacuo to give the title compound.

¹H NMR (CDCl₃, 400 MHz); 8.05 (s, 1H), 7.30-7.10 (m, 10H), 6.00 (m, 1H), 5.70 (m, 2H), 5.60 (m, 1H), 5.20 (m, 1H), 4.30 (m, 1H), 4.20 (m, 1H), 3.65 (m, 1H), 3.05 (m, 1H), 2.00 (m, 1H), 1.70 (m, 1H), 1.40 (s, 18H), MS (ES+) m/e 631 (MH⁺).

Step AAI2: (1R,2S,3R,5S)-3-[2-Chloro-6-(2,2-diphenyl-ethylamino)-purin-9-yl]-5-(di-Boc-amino)-cyclopentane-1,2-diol The title compound is prepared analogously to (1S,2R,3S,5R)-3-(di-Boc-amino)-5-(2,6-dichloro-purin-9-yl)-cyclopentane-1,2-diol by replacing di-Boc-[(1S,4R)-4-(2,6-dichloro-purin-9-yl)-cyclopent-2-enyl]-amine with {2-chloro-9-[(1R,4S)-4-(di-Boc-amino)-cyclopent-2-enyl]-9H-purin-6-yl}-(2,2-diphenyl-ethyl)-amine.

¹H NMR (MeOD, 400 MHz); 8.05 (s, 1H), 7.35-7.15 (m, 10H), 4.70-4.55 (m, 4H), 4.50 (m, 1H), 4.35 (m, 1H), 4.20 (m, 2H), 2.55 (m, 1H), 2.45 (m, 1H), 1.60 (s, 18H).

Step AAI3: (1S,2R,3S,5R)-3-Amino-5-[2-chloro-6-(2,2-diphenyl-ethylamino)-purin-9-yl]-cyclopentane-1,2-diol trifluoroacetate (1R,2S,3R,5S)-3-[2-Chloro-6-(2,2-diphenyl-ethylamino)-purin-9-yl]-5-(di-Boc-amino)-cyclopentane-1,2-diol (10.3 g, 15.50 mmol) is dissolved in DCM (50 mL). TFA (25 mL) is added and the reaction mixture is stirred at RT. The reaction is shown to be complete by LCMS after 2 hours. The solvent is removed in vacuo to give the title compound.
¹H NMR (MeOD, 400 MHz); 7.90 (s, 1H), 7.30-7.10 (m, 10H), 4.65 (m, 1H), 4.50 (m, 1H), 4.40 (m, 1H), 4.20 (m, 1H), 4.10 (m, 2H), 3.50 (m, 1H), 2.75 (m, 1H), 2.15 (m, 1H), MS (ES+) m/e 465 (MH⁺).

Step AAI4: N-{(1S,2R,3S,4R)-4-[2-Chloro-6-(2,2-diphenyl-ethylamino)-purin-9-yl]-2,3-dihydroxy-cyclopentyl}-propionamide (1S,2R,3S,5R)-3-Amino-5-[2-chloro-6-(2,2-diphenyl-ethylamino)-purin-9-yl]-cyclopentane-1,2-diol trifluoroacetate (9.50 g, 16.42 mmol) and DIPEA (6.36 g, 49.27 mmol) are placed in a flask with dry THF (150 mL). Propionyl chloride (1.52 g, 16.42 mmol) is added dropwise and the reaction mixture is stirred at RT. The reaction is shown to be complete by LCMS after 1 hour. The solvent is removed in vacuo and the residue is partitioned between DCM (250 mL) and water (250 mL). The organic layer is washed with water (200 mL) and brine (200 mL), dried over MgSO₄, filtered and the solvent is removed in vacuo. The solid is re-crystallised from 1,2-dichloroethane to give the title compound.
¹H NMR (MeOD, 400 MHz); 8.00 (s, 1H), 7.40-7.15 (m, 10H), 4.75 (m, 1H), 4.60 (m, 1H), 4.50 (m, 1H), 4.20 (m, 3H), 3.95 (m, 1H), 2.85 (m, 1H), 2.40 (q, 2H), 2.10 (m, 1H), 1.20 (t, 3H), MS (ES+) m/e 521 (MH⁺).

Intermediate AB N-((1S,2R,3S,4R)-4-{2-Chloro-6-[(naphth-1-ylmethyl)-amino]-purin-9-yl}-2,3-dihydroxy-cyclopentyl)-propionamide trifluoroacetate Step AB1: [(1S,4R)-4-(2,6-Dichloro-purin-9-yl)-cyclopent-2-enyl]-propionyl-carbamic acid tert-butyl ester The title compound is prepared analogously to di-Boc-[(1S,4R)-4-(2,6-dichloro-purin-9-yl)-cyclopent-2-enyl]-amine by replacing di-t-butyliminodicarboxylate with propionyl-carbamic acid tert-butyl ester.

Step AB2: [(1S,2R,3S,4R)-4-(2,6-Dichloro-purin-9-yl)-2,3-dihydroxy-cyclopentyl]-propionyl-carbamic acid tert-butyl ester A mixture comprising [(1S,4R)-4-(2,6-dichloro-purin-9-yl)-cyclopent-2-enyl]-propionyl-carbamic acid tert-butyl ester (6.54 g, 15.8 mmol), methane sulphonamide (1.46 g, 15.3 mmol) and AD-mix-α (23 g, 1.5 g/mmol) in t-butanol/water (80 mL of a 1:1 mixture) is treated with osmium tetroxide (3.5 mL, 4% w/w in water). After stirring vigorously at RT for 72 hours, the reaction mixture is partitioned between EtOAc and water. The organic portion is separated, washed with water, brine, dried (MgSO₄) and concentrated in vacuo. The resulting residue is triturated with MeOH to afford the title compound. MS (ES+) m/e 460 (MH⁺).

Step AB3: N-((1S,2R,3S,4R)-4-{2-Chloro-6-[(naphth-1-ylmethyl)-amino]-purin-9-yl}-2,3-dihydroxy-cyclopentyl)-propionamide trifluoroacetate A solution comprising [(1S,2R,3S,4R)-4-(2,6-dichloro-purin-9-yl)-2,3-dihydroxy-cyclopentyl]-propionyl-carbamic acid tert-butyl ester (0.5 g, 1.1 mmol), DIPEA (0.227 mL, 1.3 mmol), 1-napthalenemethylamine (0.175 ml, 1.2 mmol) in 1,2-dichloroethane (3 mL) is heated at 50° C. overnight. 0.1 M HCl (10 mL) is added to the reaction mixture and following agitation, the organic portion is separated and treated with TFA (1 mL). After standing at RT for 2 hours, the solvent is removed in vacuo to yield the title compound.

Intermediate AC N-{(1S,2R,3S,4R)-4-[2-Chloro-6-(1-ethyl-propylamino)-purin-9-yl]-2,3-dihydroxy-cyclopentyl}-propionamide Step AC1: {(1S,4R)-4-[2-Chloro-6-(1-ethyl-propylamino)-purin-9-yl]-cyclopent-2-enyl}-propionyl-carbamic acid tert-butyl ester

[(1S,4R)-4-(2,6-Dichloro-purin-9-yl)-cyclopent-2-enyl]-propionyl-carbamic acid tert-butyl ester (700 mg, 1.64 mmol) is dissolved in THF (15 mL) under an atmosphere of argon. 3-Pentylamine (315 mg, 3.61 mmol) is added and the reaction mixture is stirred at 50° C. The reaction is shown to be complete by LCMS after 18 hours. The reaction mixture is partitioned between DCM (50 mL) and 0.1 M HCl (50 mL). The organic layer is washed with water (20 mL) and brine (20 mL), dried over MgSO₄, filtered and the solvent is removed in vacuo to give the title compound.
¹H NMR (CDCl₃, 400 MHz); 8.10 (s, 1H), 6.00 (m, 1H), 5.70 (m, 1H), 5.60 (m, 2H), 5.45 (m, 1H), 4.20 (m, 1H), 3.65 (m, 1H), 3.00 (m, 1H), 2.65 (m, 3H), 1.95 (m, 1H), 1.60 (m, 3H), 1.45 (s, 9H), 1.10 (m, 4H), 0.85 (t, 6H), MS (ES+) m/e 477 (MH⁺).

Step AC2: {(1S,2R,3S,4R)-4-[2-Chloro-6-(1-ethyl-propylamino)-purin-9-yl]-2,3-dihydroxy-cyclopentyl}-propionyl-carbamic acid tert-butyl ester The title compound is prepared analogously to (1S,2R,3S,5R)-3-(di-Boc-amino)-5-(2,6-dichloro-purin-9-yl)-cyclopentane-1,2-diol by replacing di-Boc-[(1S,4R)-4-(2,6-dichloro-purin-9-yl)-cyclopent-2-enyl]-amine with {(1S,4R)-4-[2-Chloro-6-(1-ethyl-propylamino)-purin-9-yl]-cyclopent-2-enyl}-propionyl-carbamic acid tert-butyl ester. Purification is carried out by reverse phase column chromatography (Isolute™ C18, 0-100% acetonitrile in water—0.1% TFA).
¹H NMR (MeOD, 400 MHz); 8.10 (s, 1H), 4.80 (m, 1H), 4.65 (m, 1H), 4.35 (m, 1H), 4.20 (m, 1H), 2.85 (m, 2H), 2.60 (m, 1H), 2.35 (m, 1H), 1.70 (m, 2H), 1.65 (s, 9H), 1.60 (m, 2H), 1.15 (t, 3H), 0.95 (t, 6H).

Step AC3: N-{(1S,2R,3S,4R)-4-[2-Chloro-6-(1-ethyl-propylamino)-purin-9-yl]-2,3-dihydroxy-cyclopentyl}-propionamide {(1S,2R,3S,4R)-4-[2-Chloro-6-(1-ethyl-propylamino)-purin-9-yl]-2,3-dihydroxy-cyclopentyl}-propionyl-carbamic acid tert-butyl ester (300 mg, 0.59 mmol) is dissolved in DCM (5 mL). TFA (2 mL) is added and the reaction mixture is stirred at RT. The reaction is shown to be complete by LCMS after 1 hour. The solvent is removed in vacuo and the residue is partitioned between DCM (50 mL) and saturated NaHCO₃ (50 mL). The organic layer is washed with water (20 mL) and brine (20 mL), dried over MgSO₄, filtered and the solvent is removed in vacuo to give the title compound.

$^1$H NMR (MeOD, 400 MHz); 8.05 (s, 1H), 4.75 (m, 1H), 4.60 (m, 1H), 4.20 (m, 2H), 4.00 (m, 1H), 2.90 (m, 1H), 2.40 (q, 2H), 2.10 (m, 1H), 1.70 (m, 2H), 1.60 (m, 2H), 1.20 (t, 3H), 0.95 (t, 6H), MS (ES+) m/e 411 (MH⁺).

Intermediate AD-AH

These compounds namely,
N-((1S,2R,3S,4R)-4-{2-chloro-6-[2-(4-fluoro-phenyl)-2-phenyl-ethylamino]-purin-9-yl}-2,3-dihydroxy-cyclopentyl)-propionamide trifluoroacetate (Intermediate AD),
N-((1S,2R,3S,4R)-4-(2-chloro-6-[(9H-fluoren-9-ylmethyl)-amino]-purin-9-yl)-2,3-dihydroxy-cyclopentyl)-propionamide trifluoroacetate (Intermediate AE),
N-{(1S,2R,3S,4R)-4-[2-chloro-6-((S)-1-hydroxymethyl-2-phenyl-ethylamino)-purin-9-yl]-2,3-dihydroxy-cyclopentyl}-propionamide trifluoroacetate (Intermediate AF),
N-((1S,2R,3S,4R)-4-{6-[2,2-bis-(4-methoxy-phenyl)-ethylamino]-2-chloro-purin-9-yl}-2,3-dihydroxy-cyclopentyl)-propionamide trifluoroacetate (Intermediate AG),
N-((1S,2R,3S,4R)-4-{2-Chloro-6-[(2'-cyano-biphenyl-4-ylmethyl)-amino]-purin-9-yl}-2,3-dihydroxy-cyclopentyl)-propionamide trifluoroacetate (Intermediate AH),
are prepared analogously to Intermediate AB by replacing 1-napthalenemethylamine with the appropriate amine.

The following intermediates of formula (B):

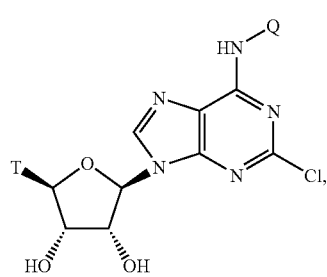

(B)

are shown in Table 2 below, their method of preparation being described hereinafter.

Intermediate BA (2R,3R,4S,5R)-2-[2-Chloro-6-(2,2-diphenyl-ethylamino)-purin-9-yl]-5-hydroxymethyl-tetrahydro-furan-3,4-diol The title compound is prepared by the procedure of Di Ayres, Barry Edward; Gregson, Michael; Ewan, George Blanch; Keeling, Suzanne Elaine; Bell, Richard. 'Preparation of aminopurine-β-D-ribofuranuronamide derivatives as anti-inflammatories.' (WO 96/02553)

Intermediate BB (2S,3S,4R,5R)-5-[2-Chloro-6-(2,2-diphenyl-ethylamino)-purin-9-yl]-3,4-dihydroxy-tetrahydro-furan-2-carboxylic acid ethylamide trifluoroacetate The title compound is prepared by the procedure of Gregson, Michael; Ayres, Barry Edward; Ewan, George Blanch; Ellis, Frank; Knight, John. 'Preparation of diaminopurinylribofuranuronamide derivatives as antiinflammatories.' (WO 94/17090)

Intermediate BC (2R,3R,4S,5R)-2-[2-Chloro-6-(2,2-diphenyl-ethylamino)-purin-9-yl]-5-(2-ethyl-2H-tetrazol-5-yl)-tetrahydro-furan-3,4-diol The title compound is prepared by the procedure of 'Preparation of 2-(purin-9-yl)-tetrahydrofuran-3,4-diol nucleosides as anti-inflammatory agents and agonists against adenosine receptors.' Cox, Brian; Keeling, Suzanne Elaine; Allen, David George; Redgrave, Alison Judith; Barker, Michael David; Hobbs, Heather; Roper, Thomas Davis, N; Geden, Joanna Victoria. (Glaxo Group Ltd., UK). PCT Int. Appl. (1998), 118 pp. WO 98/28319 A1

Intermediate C 1,3-Di-(R)-pyrrolidin-3-yl-urea

Step C1: 1,3-Bis-((R)-1-benzyl-pyrrolidin-3-yl)-urea

A solution comprising (R)-1-benzyl-pyrrolidin-3-ylamine (5.0 g, 28.4 mmol) in DCM (10 mL) is treated with CDI (2.3 g, 14.2 mmol) and the reaction mixture is stirred at RT for 48 hours. The solvent is removed in vacuo and the resulting residue is dissolved in EtOAc. This portion is washed with water followed by brine, dried (MgSO₄) and concentrated in vacuo to yield the title compound as pale orange solid.

TABLE 2

| Intermediate | T | Q | M/s MH+ |
|---|---|---|---|
| BA | OH | (diphenyl-ethyl group) | 482 |
| BB | (N-ethyl acetamide group) | (diphenyl-ethyl group) | 524 |
| BC | (ethyl-methyl-tetrazole group) | H | 368 |

Step C2: 1,3-Di-(R)-pyrrolidin-3-yl-urea

To a solution of 1,3-bis-((R)-1-benzyl-pyrrolidin-3-yl)-urea (5.34 g, 14.1 mmol) in ethanol (80 mL) under an inert atmosphere of argon is added palladium hydroxide on carbon (1.07 g). The reaction mixture is purged with argon and placed under an atmosphere of hydrogen for two days after which time, the mixture is filtered and the catalyst washed with ethanol. The organic portions are combined and concentrated in vacuo to yield the title compound as a white solid.

Intermediate D 6-(4-Methyl-piperazin-1-yl)-N,N'-di-(R)-pyrrolidin-3-yl-[1,3,5]triazine-2,4-diamine trifluoroacetate

Step D1: Intermediate D1

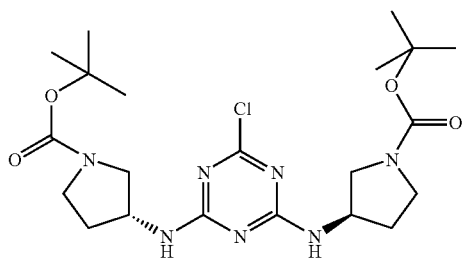

To a cooled (0° C.) solution of cyanuric chloride (0.1 g, 0.54 mmol) in THF (1 mL) and DIPEA (1 mL) is added dropwise, (R)-3-amino-1-N-Boc-pyrrolidine (0.202 g, 1.08 mmol) in THF (1 mL). After stirring at RT for 1 hour, the solvent is removed in vacuo and the product is partitioned between DCM and 2 M HCl. The organic portion is separated, washed with water, brine, dried (MgSO$_4$) and concentrated in vacuo to yield Intermediate D1 which is used in the next step without further purification.

Step D1: Intermediate D2

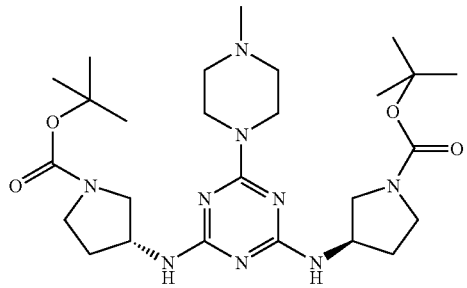

A reaction mixture comprising Intermediate D1 (0.1 g, 0.21 mmol), methylpiperazine (0.104 g, 1.03 mmol), sodium iodide (0.031 g, 0.21 mmol) in NMP (0.25 ml) and acetonitrile (0.25 mL) is heated using microwave radiation in a Personal Chemistry Emrys™ Optimizer microwave reactor at 160° C. for 30 minutes. Intermediate D2 is obtained after purification by reverse phase column chromatography (Isolute™ C18, 0-100% acetonitrile in water—0.1% TFA).

Step D3: 6-(4-Methyl-piperazin-1-yl)-N,N'-di-(R)-pyrrolidin-3-yl-[1,3,5]triazine-2,4-diamine trifluoroacetate A solution of Intermediate D2 (0.1 g, 0.18 mmol) in DCM (2 mL) is treated with TFA (1 mL) and stirred at RT for 2 hours. The solvent is removed in vacuo to yield the title product.

The following intermediates of formula (E):

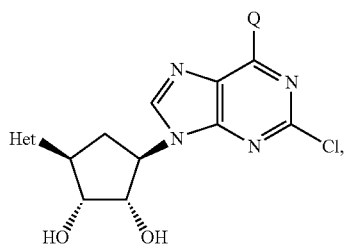

(E)

are shown in table 3 below.

TABLE 3

| Intermediate | Het | Q |
|---|---|---|
| EA | ![tetrazole with ethyl] | diphenylmethyl-CH$_2$-NH-CH$_3$ |
| EB | ![tetrazole with ethyl] | bis(4-hydroxyphenyl)methyl-CH$_2$-NH-CH$_3$ |

TABLE 3-continued

| Intermediate | Het | Q |
|---|---|---|
| EC | 4-ethyl-1-methyl-pyrazole structure | diphenylmethyl-N-methylamine structure |
| ED | 4-ethyl-2-methyl-1,2,3-triazole structure (H₃C-CH₂-) | Cl |

Intermediate EA (1R,2S,3R,5S)-3-[2-Chloro-6-(2,2-diphenyl-ethylamino)-purin-9-yl]-5-(5-ethyl-tetrazol-2-yl)-cyclopentane-1,2-diol Step EA1: 2,6-Dichloro-9-[(1R,4S)-4-(5-ethyl-tetrazol-2-yl)-cyclopent-2-enyl]-9H-purine The title compound is prepared analogously to di-Boc-[(1S,4R)-4-(2,6-dichloro-purin-9-yl)-cyclopent-2-enyl]-amine (AA3) by replacing di-t-butyliminodicarboxylate with 5-ethyltetrazole. MS (ES+) m/e 351.2 (MH$^+$)

Step EA2: {2-Chloro-9-[(1R,4S)-4-(5-ethyl-tetrazol-2-yl)-cyclopent-2-enyl]-9H-purin-6-yl}-(2,2-diphenyl-ethyl)-amine The title compound is prepared analogously to N-{(1S,2R,3S,4R)-4-[2-chloro-6-(2,2-diphenyl-ethylamino)-purin-9-yl]-2,3-dihydroxy-cyclopentyl}-propionamide (AA7) by replacing N-[(1S,2R,3S,4R)-4-(2,6-dichloro-purin-9-yl)-2,3-dihydroxy-cyclopentyl]-propionamide (160 mg, 0.44 mmol) with 2,6-dichloro-9-[(1R,4S)-4-(5-ethyl-tetrazol-2-yl)-cyclopent-2-enyl]-9H-purine (EA1). MS (ES+) m/e 512.2 (MH$^+$)

Step EA3: (1R,2S,3R,5S)-3-[2-Chloro-6-(2,2-diphenyl-ethylamino)-purin-9-yl]-5-(5-ethyl-tetrazol-2-yl)-cyclopentane-1,2-diol The title compound is prepared analogously to (1S,2R,3S,5R)-3-(di-Boc-amino)-5-(2,6-dichloro-purin-9-yl)-cyclopentane-1,2-diol (AA4) by replacing di-Boc-[(1S,4R)-4-(2,6-dichloro-purin-9-yl)-cyclopent-2-enyl]-amine with {2-chloro-9-[(1R,4S)-4-(5-ethyl-tetrazol-2-yl)-cyclopent-2-enyl]-9H-purin-6-yl}-(2,2-diphenyl-ethyl)-amine. MS (ES+) m/e 546.2 (MH$^+$)

Intermediate EB (1R,2S,3R,5S)-3-{6-[2,2-Bis-(4-hydroxy-phenyl)-ethylamino]-2-chloro-purin-9-yl}-5-(5-ethyl-tetrazol-2-yl)-cyclopentane-1,2-diol The title compound is prepared analogously to 1R,2S,3R,5S)-3-[2-chloro-6-(2,2-diphenyl-ethylamino)-purin-9-yl]-5-(5-ethyl-tetrazol-2-yl)-cyclopentane-1,2-diol (Intermediate EA) by replacing 2,2-diphenylethylamine with 4,4'42-aminoethylidene)bisphenol. MS (ES+) m/e 578.34 (MH$^+$)

Intermediate EC (1R,2S,3R,5S)-3-[2-Chloro-6-(2,2-diphenyl-ethylamino)-purin-9-yl]-5-(4-ethyl-pyrazol-1-yl)-cyclopentane-1,2-diol The title compound is prepared analogously to 1R,2S,3R,5S)-3-[2-chloro-6-(2,2-diphenyl-ethylamino)-purin-9-yl]-5-(5-ethyl-tetrazol-2-yl)-cyclopentane-1,2-diol (Intermediate EA) by replacing 5-ethyltetrazole with 4-ethyl-1H-pyrazole. MS (ES+) m/e 544.23 (MH$^+$)

Intermediate ED 3-(2,6-Dichloro-purin-9-yl)-5-(4-ethyl-[1,2,3]triazol-1-yl)-cyclopentane-1,2-diol Step ED1: 2,6-Dichloro-9-[(1R,4S)-4-(4-ethyl-[1,2,3]triazol-1-yl)-cyclopent-2-enyl]-9H-purine A mixture comprising triphenylphosphine (0.299 g, 0.874 mmol) and Pd$_2$(dba)$_3$ (0.267 g, 0.291 mmol) in dry THF (5 mL) under an inert atmosphere of argon is stirred at RT for 10 minutes. This mixture is then added to a pre-stirring mixture of carbonic acid (1S,4R)-4-(2,6-dichloro-purin-9-yl)-cyclopent-2-enyl ester ethyl ester (Intermediate AA2) (2.00 g, 5.83 mmol) and 4-ethyl-2H-[1,2,3]triazole (0.594 g, 6.12 mmol) in THF (15 mL). The resulting mixture is stirred at RT overnight and then concentrated in vacuo. The crude product is purified by chromatography on silica eluting with 0-50% EtOAc in iso-hexane to afford the title compound as a white solid. (MH$^+$ 350).

Step ED2: 3-(2,6-Dichloro-purin-9-yl)-5-(4-ethyl-[1,2,3]triazol-1-yl)-cyclopentane-1,2-diol A solution of 2,6-dichloro-9-[(1R,4S)-4-(4-ethyl-[1,2,3]triazol-1-yl)-cyclopent-2-enyl]-9H-purine (1.442 g, 4.12 mmol) in EtOAc (15 mL) and MeCN (15 mL) is treated with a solution of ruthenium trichloride (0.120 g, 0.58 mmol) and sodium periodate (1.32 g, 6.18 mmol) in water (5 mL). The reaction mixture is stirred vigorously for 6 hours and then treated with sodium metabisulfite (saturated aqueous solution, 25 mL) and then stirred overnight. The resulting mixture is partitioned between water and EtOAc and the aqueous portion is extracted with EtOAc. The combined organic portions are washed with water, dried (MgSO$_4$) and concentrated in vacuo. The crude product is purified by chromatography on silica eluting with 0-100% EtOAc in iso-hexane to afford the title compound as an oil orange solid. (MH$^+$ 350).

Intermediate ED can also be prepared using the following method:

Step ED1': 2,6-Dichloro-9-[(1R,4S)-4-(4-ethyl-[1,2,3]triazol-2-yl)-cyclopent-2-enyl]-9H-purine The title compound is prepared analogously to di-Boc-[(1S,4R)-4-(2,6-dichloro-purin-9-yl)-cyclopent-2-enyl]-amine (AA3) by replacing di-t-butyliminodicarboxylate with 4-ethyl-2H-[1,2,3]triazole.

Step ED2': (1R,2S,3R,5S)-3-(2,6-Dichloro-purin-9-yl)-5-(4-ethyl-[1,2,3]triazol-2-yl)-cyclopentane-1,2-diol The titled compound is prepared analogously to (1S,2R,3S,5R)-3-(di-Boc-amino)-5-(2,6-dichloro-purin-9-yl)-cyclopentane-1,2-diol (AA4) by replacing di-Boc-[(1S,4R)-4-(2,6-dichloro-purin-9-yl)-cyclopent-2-enyl]-amine with 2,6-dichloro-9-[(1R,4S)-4-(4-ethyl-[1,2,3]triazol-2-yl)-cyclopent-2-enyl]-9H-purine (Step 1).

The following intermediates of formula (F):

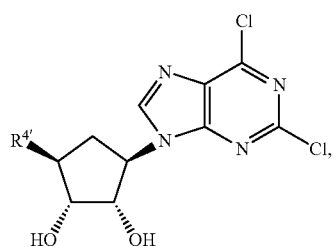

are shown in Table 4 below, their method of preparation being described hereinafter.

TABLE 4

| Intermediate | R⁴' |
|---|---|
| FA | -NH-CH3) |
| FB | |
| FC | |

Intermediate FA Acetic acid [(1S,2R,3S,4R)-4-(2,6-dichloro-purin-9-yl)-2,3-dihydroxy-cyclopentylcarbamoyl]-methyl ester

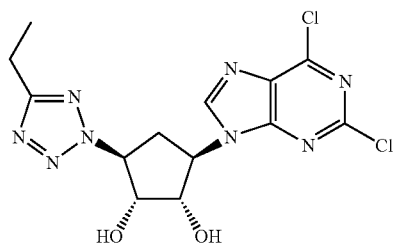

This compound is prepared analogously to Intermediate AA by replacing propionyl chloride in Step AA6 with acetoxyacetyl chloride.

Intermediate FB (1R,2S,3R,5S)-3-(2,6-Dichloro-purin-9-yl)-5-(5-ethyl-tetrazol-2-yl)-cyclopentane-1,2-diol

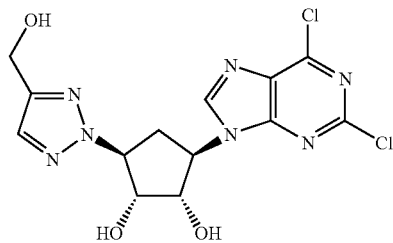

This compound is prepared analogously to (1S,2R,3S,5R)-3-(di-Boc-amino)-5-(2,6-dichloro-purin-9-yl)-cyclopentane-1,2-diol (Step AA4) by replacing di-t-butyliminodicarboxylate (Step AA3) with 5-ethyl-2H-tetrazole.

Intermediate FC (1R,2S,3R,5S)-3-(2,6-Dichloro-purin-9-yl)-5-(4-hydroxymethyl-[1,2,3]triazol-2-yl)-cyclopentane-1,2-diol This compound is prepared analogously to (1S,2R,3S,5R)-3-(di-Boc-amino)-5-(2,6-dichloro-purin-9-yl)-cyclopentane-1,2-diol (Step AA4) by replacing di-t-butyliminodicarboxylate (Step AA3) with (2H-[1,2,3]triazol-4-yl)-methanol.

Intermediate GA Acetic acid {(1S,2R,3S,4R)-4-[2-chloro-6-(2,2-diphenyl-ethylamino)-purin-9-yl]-2,3-dihydroxy-cyclopentylcarbamoyl}-methyl ester Step GA1

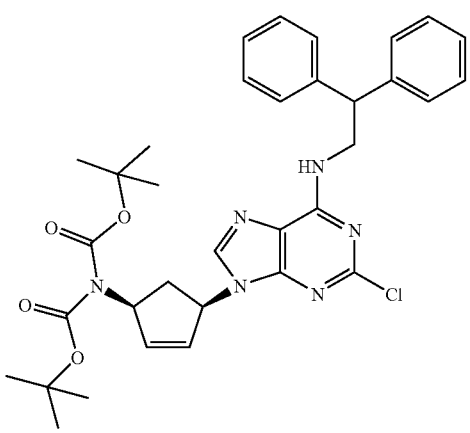

Di-Boc-[(1S,4R)-4-(2,6-dichloro-purin-9-yl)-cyclopent-2-enyl]-amine (Step AA3) (7.0 g, 14.9 mmol), 2,2-diphenyl-ethylamine and DIPEA (2.3 g, 17.9 mmol) are dissolved in dry THF (100 mL) and stirred at 50° C. over night. The reaction mixture is reduced in vacuo and the residue is partitioned between DCM and (0.1 M) HCl$_{(aq)}$. The organic portions are washed with water, brine, dried (MgSO$_4$), filtered and reduced in vacuo to yield title compound.

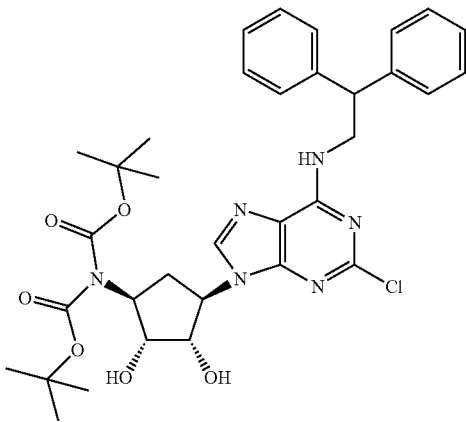

Step GA2

Intermediate GA1 (8.9 g, 14 mmol) and 4-methylmorpholine 4-oxide (3.3 g, 28 mmol) are placed in a flask with THF (75 mL). OsO$_4$ (4% in water) (7.5 mL) is added and the reaction mixture is stirred at RT over night. The reaction mixture is reduced in vacuo and the residue is portioned between DCM and (0.1 M) HCL$_{(aq)}$. The organics are washed with water and brine, dried (MgSO$_4$), filtered and reduced in vacuo. The title compound is precipitated from MeOH.

Step GA3: (1S,2R,3S,5R)-3-Amino-5-[2-chloro-6-(2,2-diphenyl-ethylamino)-purin-9-yl]-cyclopentane-1,2-diol hydrochloride Intermediate GA2 (6.8 g, 10 mmol) is dissolved/suspended in (4 M) HCl in dioxane (10 mL) and MeOH (10 mL). The reaction mixture is stirred at RT over night. The solvent is removed in vacuo to yield title compound.

Step GA4: Acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (1S,2R,3S,5R)-3-Amino-5-[2-chloro-6-(2,2-diphenyl-ethylamino)-purin-9-yl]-cyclopentane-1,2-diol hydrochloride (Intermediate GA3) (3.0 g, 5.6 mmol) is dissolved in dry THF (100 mL) and TEA (2.8 g, 28 mmol). Acetoxyacetylchloride (0.76 g, 5.6 mmol) is dissolved in dry THF (4 mL) and is added to the reaction mixture dropwise.

The solvent is removed in vacuo and the residue is partitioned between DCM and $_{(sat)}$NaHCO$_{3(aq)}$. The organics are washed with water and brine, dried (MgSO$_4$), filtered and reduced in vacuo and the title compound is obtained after purification by flash column chromatography (silica, DCM: MeOH 20:1).

Intermediate GB (1R,2S,3R,5S)-3-[2-Chloro-6-(2,2-diphenyl-ethylamino)-purin-9-yl]-5-(4-hydroxymethyl-[1,2,3]triazol-2-yl)-cyclopentane-1,2-diol (1R,2S,3R,5S)-3-[2-Chloro-6-(2,2-diphenyl-ethylamino)-purin-9-yl]-5-(4-hydroxymethyl-[1,2,3]triazol-2-yl)-cyclopentane-1,2-diol is prepared analogously to N-{(1S,2R,3S,4R)-4-[2-chloro-6-(2,2-diphenyl-ethylamino)-purin-9-yl]-2,3-dihydroxy-cyclopentyl}-propionamide by replacing N-[(1S,2R,3S,4R)-4-(2,6-dichloro-purin-9-yl)-2,3-dihydroxy-cyclopentyl]-propionamide, with (1R,2S,3R,5S)-3-(2,6-dichloro-purin-9-yl)-5-(4-hydroxymethyl-[1,2,3]triazol-2-yl)-cyclopentane-1,2-diol (Intermediate FC).

Intermediate GC N-[(1S,2R,3S,4R)-4-[6-((S)-1-Benzyl-2-hydroxy-ethylamino)-2-chloro-purin-9-yl]-2,3-dihydroxy-cyclopentyl]-2-hydroxy-acetamide N-{(1S,2R,3S,4R)-4-[6-((S)-1-Benzyl-2-hydroxy-ethylamino)-2-chloro-purin-9-yl]-2,3-dihydroxy-cyclopentyl}-2-hydroxy-acetamide is prepared analogously to N-{(1S,2R,3S,4R)-4-[2-chloro-6-(2,2-diphenyl-ethylamino)-purin-9-yl]-2,3-dihydroxy-cyclopentyl}-propionamide by replacing N-[(1S,2R,3S,4R)-4-(2,6-dichloro-purin-9-yl)-2,3-dihydroxy-cyclopentyl]-propionamide, with acetic acid [(1S,2R,3S,4R)-4-(2,6-dichloro-purin-9-yl)-2,3-dihydroxy-cyclopentylcarbamoyl]-methyl ester (Intermediate FA) and replacing 2,2-diphenylethylamine with (4Z,6Z)-(S)-phenylalinol.

The following intermediates of formula (II):

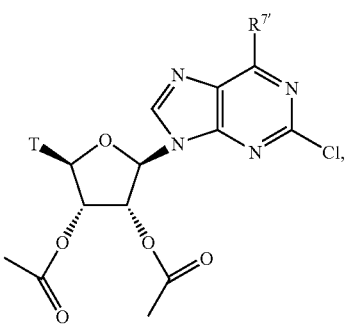

(H)

are shown in Table 5 below, their method of preparation being described hereinafter.

TABLE 5

| Intermediate | T | R<sup>7''</sup> |
|---|---|---|
| HA | H₃C-NH-C(=O)-CH₃ structure | —Cl |
| HB | 2-ethyl-2H-tetrazol-5-yl-methyl | —Cl |
| HC | 2-ethyl-2H-tetrazol-5-yl-methyl | HN-CH₂-CH(Ph)₂ |

Intermediate HA Acetic acid (2S,3S,4R,5R)-4-acetoxy-5-(2,6-dichloro-purin-9-yl)-2-ethylcarbamoyl-tetrahydro-furan-3-yl ester The title compound is prepared by the procedure of Vittori, S.; Costanzi, S.; Lambertucci, C.; Volpini, R.; Cristalli, G. Coupling of 2,6-disubstituted purines to ribose-modified sugars. Nucleosides, Nucleotides & Nucleic Acids (2001), 20(4-7), 771-774.

Intermediate HB Acetic acid (2R,3R,4R,5R)-4-acetoxy-5-(2,6-dichloro-purin-9-yl)-2-(2-ethyl-2H-tetrazol-5-yl)-tetrahydro-furan-3-yl ester The title compound is prepared by the procedure of Cox, Brian; Keeling, Suzanne Elaine; Allen, David George; Redgrave, Alison Judith; Barker, Michael David; Hobbs, Heather; Roper, Thomas Davis, IV; Geden, Joanna Victoria. Preparation of 2-(purin-9-yl)-tetrahydrofuran-3,4-diol nucleosides as antiinflammatory agents and agonists against adenosine receptors. (WO 98/28319 A1)

Intermediate HC Acetic acid (2R,3R,4R,5R)-4-acetoxy-5-[2-chloro-6-(2,2-diphenyl-ethylamino)-purin-9-yl]-2-(2-ethyl-2H-tetrazol-5-yl)-tetrahydro-furan-3-yl ester The title compound is prepared by the procedure of Cox, Brian; Keeling, Suzanne Elaine; Allen, David George; Redgrave, Alison Judith; Barker, Michael David; Hobbs, Heather; Roper, Thomas Davis, IV; Geden, Joanna Victoria. Preparation of 2-(purin-9-yl)-tetrahydrofuran-3,4-diol nucleosides as antiinflammatory agents and agonists against adenosine receptors. (WO 98/28319 A1)

Intermediate IA N,N'-Bis-(4-amino-cyclohexyl)-6-chloro-[1,3,5]triazine-2,4-diamine Step IA1: Intermediate IA1

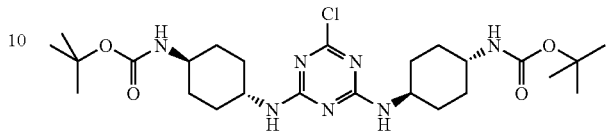

To a cooled (0° C.) solution of cyanuric chloride (1 eq.) in THF and DIPEA is added dropwise, (4-amino-cyclohexyl)-carbamic acid tert-butyl ester (2 eq.) in THF. After stirring at RT for 1 hour, the solvent is removed in vacuo and the product is partitioned between DCM and 2 M HCl. The organic portion is separated, washed with water, brine, dried (MgSO₄) and concentrated in vacuo to yield Intermediate IA1 which is used in the next step without further purification.

Step IA2: N,N'-Bis-(4-amino-cyclohexyl)-6-chloro-[1,3,5]triazine-2,4-diamine trifluoroacetate A solution of Intermediate IA1 in DCM is treated with TFA and stirred at RT for 2 hours. The solvent is removed in vacuo the material is then dissolved in minimal volume of ethanol/saturated aqueous sodium carbonate solution until the pH of the solution is adjusted to pH 9 (ensuring the compound remains in solution). The solution is loaded onto an Isolute™ C18 column and washed through firstly with water and then MeOH. The fractions are combined and concentrated in vacuo to yield the title product.

Intermediate IB N,N'-Bis-(4-amino-cyclohexyl)-[1,3,5]triazine-2,4-diamine

To a solution of N,N'-bis-(4-amino-cyclohexyl)-6-chloro-[1,3,5]triazine-2,4-diamine trifluoroacetate (Intermediate IA) in ethanol under an inert atmosphere of argon is added palladium catalyst on carbon. The reaction mixture is purged with argon and placed under an atmosphere of hydrogen o/n after which time, the mixture is filtered and the catalyst washed with ethanol. The organic portions are combined and concentrated in vacuo to yield the title compound.

N,N'-Bis-(4-amino-cyclohexyl)-[1,3,5]triazine-2,4-diamine (Intermediate IB) may also be prepared using following process:

N,N-Bis-(4-amino-cyclohexyl)-[1,3,5]triazine-2,4-diamine is prepared analogously to N,N'-bis-(4-amino-cyclohexyl)-6-chloro-[1,3,5]triazine-2,4-diamine by replacing cyanuric chloride with 2,4-dichloro-[1,3,5]triazine.

Intermediate IC 1,3-Bis-(4-amino-cyclohexyl)-urea (1,3-Bis-(4-amino-cyclohexyl)-urea is prepared analogously to 1,3-di-(R)-pyrrolidin-3-yl-urea (Intermediate C) by replacing (R)-1-benzyl-pyrrolidin-3-ylamine with (4-amino-cyclohexyl)-carbamic acid benzyl ester.

Intermediate IC may also be prepared using following process:

Step IC1

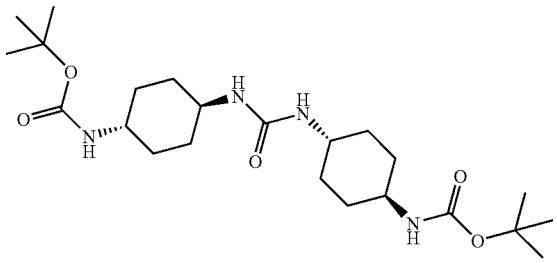

This compound is prepared analogously to Intermediate C by replacing (R)-1-benzyl-pyrrolidin-3-ylamine with (4-amino-cyclohexyl)-carbamic acid tert-butyl ester.

Step IC2: 1,3-Bis-(4-amino-cyclohexyl)-urea

This compound is prepared analogously to N,N'-bis-(4-amino-cyclohexyl)-6-chloro-[1,3,5]triazine-2,4-diamine trifluoroacetate (IA2) by replacing Intermediate IA1, with Intermediate IC1.

Intermediate ID Bis-((R)-3-amino-pyrrolidin-1-yl)-methanone

Bis-((R)-3-amino-pyrrolidin-1-yl)-methanone is prepared analogously to 1,3-bis-(4-amino-cyclohexyl)-urea (Intermediate IC) by replacing 4-amino-cyclohexyl)carbamic acid tert-butyl ester with (R)-pyrrolidin-3-yl-carbamic acid tert-butyl ester.

Intermediate IE
Bis-(4-amino-piperidin-1-yl)-methanone

Bis-(4-amino-piperidin-1-yl)-methanone is prepared analogously to 1,3-bis-(4-amino-cyclohexyl)-urea (Intermediate IC), by replacing 4-amino-cyclohexyl)-carbamic acid tert-butyl ester with piperidin-4-yl-carbamic acid tert-butyl ester.

Intermediate IF (R)-3-Amino-pyrrolidine-1-carboxylic acid (4-amino-cyclohexyl)-amide Step IF1:
(4-tert-Butoxycarbonylamino-cyclohexyl)-carbamic acid phenyl ester Phenyl chloroformate (1 eq.) is added dropwise to a solution of pyridine in DCM. The reaction mixture is cooled to 0° C. and a solution of (4-amino-cyclohexyl)-carbamic acid tert-butyl ester (1 eq.) in DCM is added dropwise. The reaction mixture is stirred at RT for 1 hour. The reaction mixture is partitioned between (0.2 M) HCl$_{(aq)}$ and DCM. The organics are washed with water (×2), $_{(sat)}$NaHCO$_{3(aq)}$ and brine. The organics are dried (MgSO$_4$), filtered and reduced in vacuo to yield the title compound.

Step IF2: [(R)-1-(4-tert-Butoxycarbonylamino-cyclohexylcarbamoyl)-pyrrolidin-3-yl]-carbamic acid tert-butyl ester (4-tert-Butoxycarbonylamino-cyclohexyl)-carbamic acid phenyl ester (1 eq.) and (R)-pyrrolidin-3-yl-carbamic acid tert-butyl ester (1 eq.) are dissolved in NMP and heated at 100° C. for 1 hour.

Step IF3: (R)-3-Amino-pyrrolidine-1-carboxylic acid (4-amino-cyclohexyl)-amide (R)-3-Amino-pyrrolidine-1-carboxylic acid (4-amino-cyclohexyl)-amide is prepared analogously to N,N'-bis-(4-amino-cyclohexyl)-6-chloro-[1,3,5]triazine-2,4-diamine (Intermediate IA) by replacing Intermediate IA1 with [(R)-1-(4-tert-butoxycarbonylamino-cyclohexylcarbamoyl)-pyrrolidin-3-yl]-carbamic acid tert-butyl ester (IF2)

Intermediate IG 4-Amino-piperidine-1-carboxylic acid (4-amino-cyclohexyl)-amide

4-Amino-piperidine-1-carboxylic acid (4-amino-cyclohexyl)-amide is prepared analogously to (R)-3-amino-pyrrolidine-1-carboxylic acid (4-amino-cyclohexyl)-amide (Intermediate IF) by replacing (R)-pyrrolidin-3-yl-carbamic acid tert-butyl ester with piperidin-4-yl-carbamic acid tert-butyl ester.

Intermediate IH (4-Amino-piperidin-1-yl)-((R)-3-amino-pyrrolidin-1-yl)-methanone (4-Amino-piperidin-1-yl)-((R)-3-amino-pyrrolidin-1-yl)-methanone is prepared analogously to (R)-3-amino-pyrrolidine-1-carboxylic acid (4-amino-cyclohexyl)-amide (Intermediate IF) by replacing (4-amino-cyclohexyl)-carbamic acid tert-butyl ester with piperidin-4-yl-carbamic acid tert-butyl ester.

Intermediate II 1-(4-Amino-cyclohexyl)-3-(R)-pyrrolidin-3-yl-urea 1-(4-Amino-cyclohexyl)-3-(R)-pyrrolidin-3-yl-urea is prepared analogously to (R)-3-amino-pyrrolidine-1-carboxylic acid (4-amino-cyclohexyl)-amide (Intermediate IF) by replacing (R)-pyrrolidin-3-yl-carbamic acid tert-butyl ester with (R)-3-amino-pyrrolidine-1-carboxylic acid tert-butyl ester.

Intermediate IJ (R)-3-Amino-pyrrolidine-1-carboxylic acid (R)-pyrrolidin-3-ylamide (R)-3-Amino-pyrrolidine-1-carboxylic acid (R)-pyrrolidin-3-ylamide is prepared analogously to (R)-3-amino-pyrrolidine-1-carboxylic acid (4-amino-cyclohexyl)-amide (Intermediate IF) by replacing (4-amino-cyclohexyl)-carbamic acid tert-butyl ester with (R)-3-amino-pyrrolidine-1-carboxylic acid tert-butyl ester.

Intermediate IK 3,4-Bis-(4-amino-cyclohexylamino)-cyclobut-3-ene-1,2-dione (4-Amino-cyclohexyl)-carbamic acid tert-butyl ester (2 eq.) and 3,4-dimethoxy-3-cyclobutene-1,2-dione (1 eq.) are dissolved in EtOH and heated at 120° C. for 1 hour in the microwave. The solvent is removed in vacuo. The resulting material is dissolved in DCM. TFA is added and the reaction mixture is stirred at RT for 2 hours. The solvent is removed in vacuo the material is then dissolved in minimal volume of ethanol/saturated aqueous sodium carbonate solution until the pH of the solution is adjusted to pH 9 (ensuring the compound remains in solution). The solution is loaded onto an Isolute™ C18 column and washed through firstly with water and then MeOH. The fractions are combined and concentrated in vacuo to yield the title product.

Intermediate JA [4-((R)-3-Pyrrolidin-3-ylureido)-cyclohexyl]-carbamic acid tert-butyl ester

Step JA1: {4-[3-((R)-1-Benzyl-pyrrolidin-3-yl)-ureido]-cyclohexyl}-carbamic acid tert-butyl ester (4-tert-Butoxycarbonylamino-cyclohexyl)-carbamic acid phenyl ester (1 eq.) and (R)-1-benzyl-pyrrolidin-3-ylamine (1 eq.) are dissolved in NMP and heated at 100° C. for 1 hour.

Step JA2: [4-((R)-3-Pyrrolidin-3-ylureido)-cyclohexyl]-carbamic acid tert-butyl ester To a solution of {4-[3-((R)-1-Benzyl-pyrrolidin-3-yl)-ureido]-cyclohexyl}-carbamic acid tert-butyl ester in ethanol under an inert atmosphere of argon is added palladium hydroxide on carbon. The reaction mixture is purged with argon and placed under an atmosphere of hydrogen for over night. The mixture is filtered and the catalyst washed with ethanol. The organic portions are combined and concentrated in vacuo to yield the title compound.

Intermediate JB [(R)-1-((R)-Pyrrolidin-3-ylcarbamoyl)-pyrrolidin-3-yl]-carbamic acid tert-butyl ester

Step JB1: (R)-3-tert-Butoxycarbonylamino-pyrrolidine-1-carboxylic acid phenyl ester Phenyl chloroformate (1 eq.) is added dropwise to a solution of pyridine in DCM. The reaction mixture is cooled to 0° C. and a solution of (R)-pyrrolidin-3-yl-carbamic acid tert-butyl ester (1 eq.) in DCM is added dropwise. The reaction mixture is stirred at RT for 1 hour. The reaction mixture is partitioned between (0.2 M) HCl$_{(aq)}$ and DCM. The organics are washed with water, $_{(sat)}$NaHCO$_{3(aq)}$ and brine. The organics are dried (MgSO$_4$), filtered and reduced in vacuo to yield the title compound.

Step JB2: [(R)-1-((R)-1-Benzyl-pyrrolidin-3-ylcarbamoyl)-pyrrolidin-3-yl]-carbamic acid tert-butyl ester (R)-3-tert-Butoxycarbonylamino-pyrrolidine-1-carboxylic acid phenyl ester (1 eq.) and (R)-1-benzyl-pyrrolidin-3-ylamine (1 eq.) are dissolved in NMP and heated at 100° C. for 1 hour.

Step JB3: [(R)-1-((R)-Pyrrolidin-3-ylcarbamoyl)-pyrrolidin-3-yl]-carbamic acid tert-butyl ester To a solution of [(R)-1-((R)-1-benzyl-pyrrolidin-3-ylcarbamoyl)-pyrrolidin-3-yl]-carbamic acid tert-butyl ester in ethanol under an inert atmosphere of argon is added palladium hydroxide on carbon. The reaction mixture is purged with argon and placed under an atmosphere of hydrogen for over night. The mixture is filtered and the catalyst washed with ethanol. The organic portions are combined and concentrated in vacuo to yield the title compound.

Intermediate JC {4-[3-(4-Amino-cyclohexyl)-ureido]-cyclohexyl}-carbamic acid tert-butyl ester {4-[3-(4-Amino-cyclohexyl)-ureido]-cyclohexyl}-carbamic acid tert-butyl ester is prepared analogously to [44(R)-3-pyrrolidin-3-ylureido)-cyclohexyl]-carbamic acid tert-butyl ester, by replacing (R)-1-benzyl-pyrrolidin-3-ylamine, with (4-amino-cyclohexyl)-carbamic acid benzyl ester.

Intermediate K N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide

Step K1: {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester A reaction mixture comprising N-{(1S,2R,3S,4R)-4-[2-chloro-6-(2,2-diphenyl-ethylamino)-purin-9-yl]-2,3-dihydroxy-cyclopentyl}-propionamide (Intermediate AA) (2.5 g, 4.80 mmol) and (3R)-(+)-(3-Boc-amino)pyrrolidine (2.5 g, 13.6 mmol) in DMSO (8 mL) is heated at 100° C. overnight. Purification of the product by reverse phase column chromatography (Isolute™ C18, 0-20% acetonitrile in water—0.1% TFA) yields the title compound.

Step K2: N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide dihydrochloride {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester (ca 4.80 mmol) is dissolved in 1.25 M HCl in MeOH (60 mL). After stirring at RT for 3 days, the solvent is removed in vacuo to yield the title compound as a brown solid. This is used in the next step without further purification.

Step 3: N-{(1S,2R,3S,4R)-4-[24(R)-3-Amino-pyrrolidin-1-yl)-6-(2,2-diphenyl-ethylamino)-purin-9-yl]-2,3-dihydroxy-cyclopentyl}-propionamide N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide dihydrochloride (ca. 7.7 mmol) is dissolved in minimal volume of a mixture of ethanol/saturated aqueous sodium carbonate solution until the pH of the solution is adjusted to pH 7 (ensuring the compound remains in solution). The solution is loaded onto an Isolute™ C18 column and washed through firstly with water and then MeOH. The fractions are combined and concentrated in vacuo and then further purified by repeating the above process to afford the title compound. LCMS (electrospray): m/z [MH$^+$] 571

Intermediate LA Acetic acid (2R,3R,4S,5S)-4-acetoxy-2-(2,6-dichloro-purin-9-yl)-5-ethylcarbamoyl-tetrahydro-furan-3-yl ester This compound can be prepared by the procedure of Vittori, S.; Costanzi, S.; Lambertucci, C.; Volpini, R.; Cristalli, G. Dipartimento di Scienze Chimiche, University of Camerino, Camerino, Italy. Nucleosides, Nucleotides & Nucleic Acids (2001), 20(4-7), 771-774.

Intermediate LB Acetic acid (2R,3R,4R,5R)-4-acetoxy-2-(2,6-dichloro-purin-9-yl)-5-methoxymethyl-tetrahydro-furan-3-yl ester This compound can be prepared by the procedure of van Tilburg, Erica W.; van der Klein, Pieter A. M.; von Frijtag Drabbe Kuenzel, Jacobien K.; de Groote, Miriam; Starmek, Christina; Lorenzen, Anna; IJzerman, Ad P. Division of Medicinal Chemistry, Leiden/Amsterdam Center for Drug Research, Leiden, Neth. Journal of Medicinal Chemistry (2001), 44(18), 2966-2975.

Intermediate LC Acetic acid (2R,3R,4R,5S)-4-acetoxy-2-(2,6-dichloro-purin-9-yl)-5-(3-ethyl-isoxazol-5-yl)-tetrahydro-furan-3-yl ester This compound can be prepared by the procedure of Chan, Chuen; Cousins, Richard Peter Charles; Cox, Brian. Preparation and antiinflammatory activity of 2-(purin-9-yl)-tetrahydrofuran-3,4-diol derivatives. (WO 99/38877)

Intermediate LD Acetic acid (2R,3R,4R,5R)-4-acetoxy-2-(2,6-dichloro-purin-9-yl)-5-(2-ethyl-2,1-tetrazol-5-yl)-tetrahydro-furan-3-yl ester This compound can be prepared by the procedure of Cox, Brian; Keeling, Suzanne Elaine; Allen, David George; Redgrave, Alison Judith; Barker, Michael David; Hobbs, Heather; Roper, Thomas Davis, I V; Geden, Joanna Victoria. (Glaxo Group Ltd., UK). (WO 98/28319)

Intermediate LE Acetic acid (2R,3R,4R,5R)-4-acetoxy-5-acetoxymethyl-2-(2,6-dichloro-purin-9-A-tetrahydro-furan-3-yl ester This compound can be prepared by the procedure of Francom, Paula; Robins, Morris J. Nucleic Acid Related Compounds. 118. Nonaqueous Diazotization of Aminopurine Derivatives. Convenient Access to 6-Halo- and 2,6-Dihalopurine Nucleosides and 2'-Deoxynucleosides with Acyl or Silyl Halides. Journal of Organic Chemistry (2003), 68(2), 666-669.

Intermediates NA-NC

These compounds namely,
[(1S,2R,3S,4R)-4-(2,6-Dichloro-purin-9-yl)-2,3-dihydroxy-cyclopentyl]-carbamic acid methyl ester,
N-[(1S,2R,3S,4R)-4-(2,6-Dichloro-purin-9-yl)-2,3-dihydroxy-cyclopentyl]-2-hydroxy-acetamide,
Cyclobutanecarboxylic acid [(1S,2R,3S,4R)-4-(2,6-dichloro-purin-9-yl)-2,3-dihydroxy-cyclopentyl]-amide,
can be prepared analogously to N-[(1S,2R,3S,4R)-4-(2,6-dichloro-purin-9-yl)-2,3-dihydroxy-cyclopentyl]-propionamide (Intermediate AA6) by replacing propionyl chloride with the appropriate acid chloride or chloroformate.

Intermediates ND-NE

These compounds namely,
(1R,2S,3R,5S)-3-(2,6-Dichloro-purin-9-yl)-5-(5-ethyl-tetrazol-2-yl)-cyclopentane-1,2-diol and
(1R,2S,3R,5S)-3-(2,6-Dichloro-purin-9-yl)-5-(4-ethyl-pyrazol-1-yl)-cyclopentane-1,2-diol,
can be prepared analogously to Intermediate ED by replacing 4-ethyl-2H-[1,2,3]triazole (Step ED1') with 5-ethyl-2H-tetrazole and 4-ethyl-1H-pyrazole, respectively.

Intermediate MA Sodium Nitromalonaldehyde

Sodium nitromalonaldehyde can be prepared as described by Fanta P. E. Org. Syntheses, Coll. Vol. 4 (1963), pp 844-845.

Intermediate QA {(1S,2R,3S,4R)-4-[2-Chloro-6-(2,2-diphenyl-ethylamino)-purin-9-yl]-2,3-dihydroxy-cyclopentyl}-2-hydroxy-acetamide The title compound can be prepared by dissolving acetic acid {(1S,2R,3S,4R)-4-[2-chloro-6-(2,2-diphenyl-ethylamino)-purin-9-yl]-2,3-dihydroxy-cyclopentyl-carbamoyl}-methyl ester (Intermediate GA) in 1.25 M HCl in methanol, stirring at RT until complete, and removing the volatile components under reduced pressure.

Intermediate QB N-{(1S,2R,3S,4R)-4-[6-(2,2-Diphenylethylamino)-2-hydrazino-purin-9-yl]-2,3-dihydroxy-cyclopentyl}-2-hydroxy-acetamide The title compound can be prepared by dissolving {(1S,2R,3S,4R)-4-[2-chloro-6-(2,2-diphenyl-ethylamino)-purin-9-yl]-2,3-dihydroxy-cyclopentyl}-2-hydroxy-acetamide (Intermediate QA) in hydrazine monohydrate, and stirring at RT for 72 hours. Sufficient isopropyl alcohol is added to give a final ratio of 20% isopropyl alcohol in hydrazine monohydrate, before the volatile components are removed under reduced pressure, to leave a gummy solid. This is triturated with water, and stirred for 12 hours. The resulting suspension can be filtered, washed with water, and dried, to give a colourless solid, to be used without further purification.

Intermediate QC N-{(1S,2R,3S,4R)-4-[2-Hydrazino-6-((S)-1-hydroxymethyl-2-phenyl-ethylamino)-purin-9-yl]-2,3-dihydroxy-cyclopentyl}-2-hydroxy-acetamide The title compound can be prepared from N-{(1S,2R,3S,4R)-4-[2-chloro-6-((S)-1-hydroxymethyl-2-phenylethylamino)-purin-9-yl]-2,3-dihydroxy-cyclopentyl}-2-hydroxy-acetamide (Intermediate GC), as described for N-{(1S,2R,3S,4R)-4-[6-(2,2-diphenylethylamino)-2-hydrazino-purin-9-yl]-2,3-dihydroxy-cyclopentyl}-2-hydroxy-acetamide (Intermediate QB).

Intermediate QD N-{(1S,2R,3S,4R)-4-[6-(2,2-Diphenyl-ethylamino)-2-(4-nitro-pyrazol-1-yl)-purin-9-yl]-2,3-dihydroxy-cyclopentyl}-2-hydroxy-acetamide Route A
The title compound can be prepared by dissolving N-{(1S,2R,3S,4R)-4-[6-(2,2-diphenylethylamino)-2-hydrazino-purin-9-yl]-2,3-dihydroxy-cyclopentyl}-2-hydroxy-acetamide (Intermediate QB) in ethanol, adding 1.2 eq. of sodium nitromalonaldehyde (Intermediate MA), and stirring the resulting solution at reflux for 3 hours. Concentration of the solution under reduced pressure, dilution with hexane to give a suspension and filtration would give the product as a colourless solid.

Route B

The title compound can be prepared by dissolving {(1S,2R,3S,4R)-4-[2-chloro-6-(2,2-diphenyl-ethylamino)-purin-9-yl]-2,3-dihydroxy-cyclopentyl}-2-hydroxy-acetamide (Intermediate QA) in N-methyl-2-pyrrolidinone, followed by potassium carbonate (5 eq.) and 4-nitropyrazole (10 eq.). The mixture is heated by microwave irradiation to 150° C. for 2 hours, then diluted with ethyl acetate and washed consecutively with water (×2) and brine, before drying over magnesium sulphate. Filtration, removal of the volatile components under reduced pressure and purification by flash column chromatography/crystallisation would give the desired product.

Intermediate QE N-{(1S,2R,3S,4R)-2,3-Dihydroxy-4-[6-((S)-1-hydroxymethyl-2-phenyl-ethylamino)-2-(4-nitro-pyrazol-1-yl)-purin-9-yl]-cyclopentyl}-2-hydroxy-acetamide The title compound can be prepared from N-{(1S,2R,3S,4R)-4-[2-hydrazino-6-((S)-1-hydroxymethyl-2-phenyl-ethylamino)-purin-9-yl]-2,3-dihydroxy-cyclopentyl}-2-hydroxy-acetamide (Intermediate QC), as described for N-{(1S,2R,3S,4R)-4-[6-(2,2-diphenyl-ethylamino)-2-(4-nitro-pyrazol-1-yl)-purin-9-yl]-2,3-dihydroxy-cyclopentyl}-2-hydroxy-acetamide (Routes A & B) (Intermediate QD).

Intermediate QF N-{(1S,2R,3S,4R)-4-[2-(4-Amino-pyrazol-1-yl)-6-(2,2-diphenyl-ethylamino)-purin-9-yl]-2,3-dihydroxy-cyclopentyl}-2-hydroxy-acetamide The title compound can be prepared by dissolving N-{(1S,2R,3S,4R)-4-[6-(2,2-diphenylethylamino)-2-(4-nitro-pyrazol-1-yl)-purin-9-yl]-2,3-dihydroxy-cyclopentyl}-2-hydroxy-acetamide (Intermediate QD) in methanol and adding a 2:1 by mass mixture of activated carbon and iron (III) chloride (40 mol % with respect to the substrate), followed by a large excess (100-fold with respect to the substrate) of hydrazine monohydrate. The resulting mixture is stirred at 65° C. for 3 hours, then filtered, before being concentrated under reduced pressure. Trituration of the residue with petroleum ether and subsequent filtration would give the desired product as a colourless solid.

Intermediate QG N-{(1S,2R,3S,4R)-4-[2-(4-Amino-pyrazol-1-yl)-6-((S)-1-hydroxymethyl-2-phenyl-ethylamino)-purin-9-yl]-2,3-dihydroxy-cyclopentyl}-2-hydroxy-acetamide The title compound can be prepared from N-{(1S,2R,3S,4R)-2,3-dihydroxy-4-[6-((S)-1-hydroxymethyl-2-phenyl-ethylamino)-2-(4-nitro-pyrazol-1-yl)-purin-9-yl]-cyclopentyl}-2-hydroxy-acetamide (Intermediate QE), as described for N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate QF).

Intermediate QH {1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester The title compound can be synthesised from N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate QF) by suspending in sufficient DCM and adding to a solution of phenyl chloroformate (1.1 eq.) in 2:1 pyridine to dichloromethane on ice, to give a final ratio of 1:1 pyridine to DCM. After 1 hour, the volatile components can be removed under reduced pressure; the residue is taken up in EtOAc and washed with 0.1 M HCl (×2) before drying over magnesium sulphate. Filtration and removal of the solvent under reduced pressure gives the desired product.

Intermediate QI {1-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-1H-pyrazol-4-yl}-carbamic acid phenyl ester The title compound can be prepared from N-{(1S,2R,3S,4R)-4-[2-(4-amino-pyrazol-1-yl)-6-((S)-1-hydroxymethyl-2-Phenyl-ethylamino)-purin-9-yl]-2,3-dihydroxy-cyclopentyl}-2-hydroxy-acetamide (Intermediate QG), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate RA N-[(1S,2R,3S,4R)-4-(6-{[Bis-(4-methoxy-phenyl)-methyl]-amino}-2-chloro-purin-9-yl)-2,3-dihydroxy-cyclopentyl]-propionamide To a solution of N-[(1S,2R,3S,4R)-4-(2,6-dichloro-purin-9-yl)-2,3-dihydroxy-cyclopentyl]-propionamide (Intermediate AA6) (2.6 g, 7.22 mmol) in dry THF (26 mL) was added bis-(4-methoxy-phenyl)-methylamine (3.5 g, 14.44 mmol). The mixture was stirred at 50° C. for 12 hours, then cooled and solvent was removed under reduced pressure. The residue was taken up in chloroform and washed sequentially with 1.5 N HCl, water and saturated aqueous brine solution. The organic phase was dried over anhydrous sodium sulphate and concentrated to give the crude title compound. Purification by flash column chromatography over silica gel (60-120 mesh) using 2% MeOH in chloroform as eluant, gave the pure title compound (2.2 g, 54%). LC-MS (0.1% formic acid, acetonitrile): 567 ($M^+$)

Intermediate RB Acetic acid [(1S,2R,3S,4R)-4-(6-{[bis-(4-methoxy-phenyl)-methyl]-amino}-2-chloro-purin-9-yl)-2,3-dihydroxy-cyclopentylcarbamoyl]-methyl ester The title compound can be synthesised analogously to N-[(1S,2R,3S,4R)-4-(6-{[bis-(4-methoxy-phenyl)-methyl]-amino}-2-chloro-purin-9-yl)-2,3-dihydroxy-cyclopentyl]-propionamide (Intermediate RA) by replacing N-[(1S,2R,3S,4R)-4-(2,6-dichloro-purin-9-yl)-2,3-dihydroxy-cyclopentyl]-propionamide (Intermediate AA6) with acetic acid [(1S,2R,3S,4R)-4-(2,6-dichloro-purin-9-yl)-2,3-dihydroxy-cyclopentylcarbamoyl]-methyl ester (Intermediate FA).

Intermediate RC (1R,2S,3R,5S)-3-(6-{[Bis-(4-methoxy-phenyl)-methyl]-amino}-2-chloro-purin-9-yl)-5-(4-hydroxymethyl-[1,2,3]triazol-2-yl)-cyclopentane-1,2-diol The title compound can be synthesised analogously to N-[(1S,2R,3S,4R)-4-(6-{[bis-(4-methoxy-phenyl)-methyl]-amino}-2-chloro-purin-9-yl)-2,3-dihydroxy-cyclopentyl]-propionamide (Intermediate RA) by replacing N-[(1S,2R,3S, 4R)-4-(2,6-dichloro-purin-9-yl)-2,3-dihydroxy-cyclopentyl]-propionamide (Intermediate AA6) with (1R,2S,3R,5S)-3-(2,6-dichloro-purin-9-yl)-5-(4-hydroxymethyl-[1,2,3]triazol-2-yl)-cyclopentane-1,2-diol (Intermediate FC).

Intermediate SA N-{(1S,2R,3S,4R)-2,3-Dihydroxy-4-[6-((S)-1-hydroxymethyl-2-phenyl-ethylamino)-2-(4-nitro-imidazol-1-yl)-purin-9-yl]-cyclopentyl}-2-hydroxy-acetamide The title compound can be prepared from N-{(1S,2R,3S,4R)-4-[6-((S)-1-benzyl-2-hydroxy-ethylamino)-2-chloro-purin-9-yl]-2,3-dihydroxy-cyclopentyl}-2-hydroxy-acetamide (Intermediate GC) and 4-nitro-imidazole, as described for N-{(1S,2R,3S,4R)-4-[6-(2,2-diphenyl-ethylamino)-2-(4-nitro-pyrazol-1-yl)-purin-9-yl]-2,3-dihydroxy-cyclopentyl}-2-hydroxy-acetamide (Intermediate QD).

Intermediate SB N-{(1S,2R,3S,4R)-2,3-Dihydroxy-4-[6-((S)-1-hydroxymethyl-2-phenyl-ethylamino)-2-(3-nitro-[1,2,4]triazol-1-yl)-purin-9-yl]-cyclopentyl}-2-hydroxy-acetamide The title compound can be prepared from N-{(1S,2R,3S,4R)-4-[6-((S)-1-benzyl-2-hydroxy-ethylamino)-2-chloro-purin-9-yl]-2,3-dihydroxy-cyclopentyl}-2-hydroxy-acetamide (Intermediate GC) and 3-nitro-1,2,4-triazole, as described for N-{(1S,2R,3S,4R)-4-[6-(2,2-diphenyl-ethylamino)-2-(4-nitro-pyrazol-1-yl)-purin-9-yl]-2,3-dihydroxy-cyclopentyl}-2-hydroxy-acetamide (Intermediate QD).

Intermediate SC N-{(1S,2R,3S,4R)-4-[2-(4-Amino-imidazol-1-yl)-6-((S)-1-hydroxymethyl-2-phenyl-ethylamino)-purin-9-yl]-2,3-dihydroxy-cyclopentyl}-2-hydroxy-acetamide The title compound can be prepared from N-{(1S,2R,3S,4R)-2,3-dihydroxy-4-[6-((S)-1-hydroxymethyl-2-phenyl-ethylamino)-2-(4-nitro-imidazol-1-yl)-purin-9-yl]-cyclopentyl}-2-hydroxy-acetamide (Intermediate SA), as described for N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate QF).

Intermediate SD N-{(1S,2R,3S,4R)-4-[2-(3-Amino-[1,2,4]triazol-1-yl)-6-((S)-1-hydroxymethyl-2-phenyl-ethylamino)-purin-9-yl]-2,3-dihydroxy-cyclopentyl}-2-hydroxy-acetamide The title compound can be prepared from N-{(1S,2R,3S,4R)-2,3-dihydroxy-4-[6-((S)-1-hydroxymethyl-2-phenyl-ethylamino)-2-(3-nitro-[1,2,4]triazol-1-yl)-purin-9-yl]-cyclopentyl}-2-hydroxy-acetamide (intermediate SB), as described for N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate QF).

Intermediate SE N-{(1S,2R,3S,4R)-4-[6-{[Bis-(4-methoxy-phenyl)-methyl]-amino}-2-(3-nitro-[1,2,4]triazol-1-A-purin-9-yl]-2,3-dihydroxy-cyclopentyl}-2-hydroxy-acetamide The title compound can be prepared from acetic acid [(1S,2R,3S,4R)-4-(6-{[bis-(4-methoxy-phenyl)-methyl]-amino}-2-chloro-purin-9-yl)-2,3-dihydroxy-cyclopentylcarbamoyl]-methyl ester (Intermediate RB) and 3-nitro-1,2,4-triazole, as described for N-{(1S,2R,3S,4R)-4-[6-(2,2-diphenyl-ethylamino)-2-(4-nitro-pyrazol-1-yl)-purin-9-yl]-2,3-dihydroxy-cyclopentyl}-2-hydroxy-acetamide (Intermediate QD).

Intermediate SF {1-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-1H-imidazol-4-yl}-carbamic acid phenyl ester The title compound can be prepared from N-{(1S,2R,3S,4R)-4-[2-(4-amino-imidazol-1-yl)-6-((S)-1-hydroxymethyl-2-phenyl-ethylamino)-purin-9-yl]-2,3-dihydroxy-cyclopentyl}-2-hydroxy-acetamide (Intermediate SC), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate SG {1-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-1H-[1,2,4]triazol-3-yl}-carbamic acid phenyl ester The title compound can be prepared from N-{(1S,2R,3S,4R)-4-[2-(3-amino-[1,2,4]triazol-1-yl)-6-((S)-1-hydroxymethyl-2-phenyl-ethylamino)-purin-9-yl]-2,3-dihydroxy-cyclopentyl}-2-hydroxy-acetamide (Intermediate SD), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate SH (1-{6-{[Bis-(4-methoxy-phenyl)-methyl]-amino}-9-[(1R,2S,3R,4S)-2,3-dihydroxy-4-(2-hydroxy-acetylamino)-cyclopentyl]-9H-purin-2-yl}-1H-[1,2,4]triazol-3-yl)-carbamic acid phenyl ester The title compound can be prepared from N-{(1S,2R,3S,4R)-4-[6-{[bis-(4-methoxy-phenyl)-methyl]-amino}-2-(3-nitro-[1,2,4]triazol-1-yl)-purin-9-yl]-2,3-dihydroxy-cyclopentyl}-2-hydroxy-acetamide (Intermediate SE), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate TA (1S,2R,3S,5R)-3-Amino-5-[2-chloro-6-((S)-1-hydroxymethyl-2-phenyl-ethylamino)-purin-9-yl]-cyclopentane-1,2-diol Step TA1: {2-Chloro-9-[(1R,4S)-4-(di-Boc-amino)-cyclopent-2-enyl]-9H-purin-6-yl}-((S)-1-hydroxymethyl-2-phenyl-ethylamino)

{2-Chloro-9-[(1R,4S)-4-(di-Boc-amino)-cyclopent-2-enyl]-9H-purin-6-yl}-((S)-1-hydroxymethyl-2-phenyl-ethylamino) is prepared analogously to {2-chloro-9-[(1R,4S)-4-(di-Boc-amino)-cyclopent-2-enyl]-9H-purin-6-yl}-(2,2-diphenyl-ethyl)-amine (Step AAI1) by replacing 2,2-diphenyl ethylamine with (S)-phenylalinol.

Step TA2: (1R,2S,3R,5S)-3-[2-Chloro-6-((S)-1-hydroxymethyl-2-phenyl-ethylamino)-purin-9-yl]-5-(di-Boc-amino)-cyclopentane-1,2-diol (1R,2S,3R,5S)-3-[2-Chloro-6-((S)-1-hydroxymethyl-2-phenyl-ethylamino)-purin-9-yl]-5-(di-Boc-amino)-cyclopentane-1,2-diol is prepared analogously to (1R,2S,3R,5S)-3-[2-chloro-6-(2,2-diphenyl-ethylamino)-purin-9-yl]-5-(di-Boc-amino)-cyclopentane-1,2-diol (Step AAI2) by replacing {2-chloro-9-[(1R,4S)-4-(di-Boc-amino)-cyclopent-2-enyl]-9H-purin-6-yl}-(2,2-diphenyl-ethyl)-amine (Step AAI1) with (2-chloro-9-[(1R,4S)-4-(di-Boc-amino)-cyclopent-2-enyl]-9H-purin-6-yl)-((S)-1-hydroxymethyl-2-phenyl-ethylamino) (Step TA1).

Step TA3: (1S,2R,3S,5R)-3-Amino-5-[2-chloro-6-((S)-1-hydroxymethyl-2-phenyl-ethylamino)-purin-9-yl]-cyclopentane-1,2-diol (1S,2R,3S,5R)-3-Amino-5-[2-chloro-6-((S)-1-hydroxymethyl-2-phenyl-ethylamino)-purin-9-yl]-cyclopentane-1,2-diol is prepared analogously to (1S,2R,3S,5R)-3-amino-5-[2-chloro-6-(2,2-diphenyl-ethylamino)-purin-9-yl]-cyclopentane-1,2-diol trifluoroacetate (Step AAI3) by replacing 1R,2S,3R,5S)-3-[2-chloro-6-(2,2-diphenyl-ethylamino)-purin-9-yl]-5-(di-Boc-amino)-cyclopentane-1,2-diol (Step AAI2) with (1R,2S,3R,5S)-3-[2-chloro-6-((S)-1-hydroxymethyl-2-phenyl-ethylamino)-purin-9-yl]-5-(di-Boc-amino)-cyclopentane-1,2-diol (Step TA2).

Intermediate UA ({1S,2R,3S,4R)-4-[2-Chloro-6-(2,2-diphenyl-ethylamino)-purin-9-yl]-2,3-dihydroxy-cyclopentylcarbamoyl}-methyl)-carbamic acid benzyl ester (1S,2R,3S,5R)-3-Amino-5-[2-chloro-6-(2,2-diphenyl-ethylamino)-purin-9-yl]-cyclopentane-1,2-diol trifluoroacetate (Step AAI3) is dissolved in THF. Z-Glycine-N-succinimidyl ester is added and the reaction mixture is stirred at RT over night. The reaction mixture is reduced to yield the title compound.

Intermediate UB ({(1S,2R,3S,4R)-4-[2-Chloro-6-((S)-1-hydroxymethyl-2-phenyl-ethylamino)-purin-9-yl]-2,3-dihydroxy-cyclopentylcarbamoyl}-methyl)-carbamic acid benzyl ester ({(1S,2R,3S,4R)-4-[2-Chloro-6-((S)-1-hydroxymethyl-2-phenyl-ethylamino)-purin-9-yl]-2,3-dihydroxy-cyclopentylcarbamoyl}-methyl)-carbamic acid benzyl ester is prepared analogues to ({(1S,2R,3S,4R)-4-[2-chloro-6-(2,2-diphenyl-ethylamino)-purin-9-yl]-2,3-dihydroxy-cyclopentylcarbamoyl}-methyl)-carbamic acid benzyl ester (Intermediate UA) by replacing (1S,2R,3S,5R)-3-amino-5-[2-chloro-6-(2,2-diphenyl-ethylamino)-purin-9-yl]-cyclopentane-1,2-diol trifluoroacetate (Step AAI3) with (1S,2R,3S,5R)-3-amino-5-[2-chloro-64(S)-1-hydroxymethyl-2-phenyl-ethylamino)-purin-9-yl]-cyclopentane-1,2-diol (Intermediate TA).

These compounds namely,
({(1S,2R,3S,4R)-4-[2-Chloro-6-((S)-1-hydroxymethyl-2-phenyl-ethylamino)-purin-9-yl]-2,3-dihydroxy-cyclopentylcarbamoyl}-methyl)-ethyl-carbamic acid benzyl ester (Intermediate UC),
((S)-1-{(1S,2R,3S,4R)-4-[2-Chloro-6-((S)-1-hydroxymethyl-2-phenyl-ethylamino)-purin-9-yl]-2,3-dihydroxy-cyclopentylcarbamoyl}-2-hydroxy-ethyl)-carbamic acid benzyl ester (Intermediate UD),
((R)-1-{(1S,2R,3S,4R)-4-[2-Chloro-6-((S)-1-hydroxymethyl-2-phenyl-ethylamino)-purin-9-yl]-2,3-dihydroxy-cyclopentylcarbamoyl}-2-hydroxy-ethyl)-carbamic acid benzyl ester (Intermediate UE),
are prepared analogously to ({(1S,2R,3S,4R)-4-[2-chloro-6-((S)-1-hydroxymethyl-2-phenyl-ethylamino)-purin-9-yl]-2,3-dihydroxy-cyclopentylcarbamoyl}-methyl)-carbamic acid benzyl ester (Intermediate UB) by replacing Z-glycine-N-succinimidyl ester with the appropriate succinimidyl ester.

Intermediate VA 3-{(1S,2R,3S,4R)-4-[2-Chloro-6-(2,2-diphenyl-ethylamino)-purin-9-yl]-2,3-dihydroxy-cyclopentyl}-imidazolidine-2,4-dione ({(1S,2R,3S,4R)-4-[2-Chloro-6-(2,2-diphenyl-ethylamino)-purin-9-yl]-2,3-dihydroxy-cyclopentylcarbamoyl}-methyl)-carbamic acid benzyl ester (Intermediate UA) is dissolved in EtOH and purged with argon and Pd/C is added. The reaction mixture is placed under a positive pressure of $H_{2(g)}$ (0.35 Barr) at RT over night. The reaction mixture is filtered through celite and reduced in vacuo. Intermediate VA is obtained after purification by reverse phase column chromatography (Isolute™ C18, 0-100% acetonitrile in water—0.1% TFA).

These compounds namely,
3-{(1S,2R,3S,4R)-4-[2-Chloro-6-((S)-1-hydroxymethyl-2-phenyl-ethylamino)-purin-9-yl]-2,3-dihydroxy-cyclopentyl}-imidazolidine-2,4-dione (Intermediate VB),
3-{(1S,2R,3S,4R)-4-[2-Chloro-6-((S)-1-hydroxymethyl-2-phenyl-ethylamino)-purin-9-yl]-2,3-dihydroxy-cyclopentyl}-1-ethyl-imidazolidine-2,4-dione (Intermediate VC),
(S)-3-{(1S,2R,3S,4R)-4-[2-Chloro-6-((S)-1-hydroxymethyl-2-phenyl-ethylamino)-purin-9-yl]-2,3-dihydroxy-cyclopentyl}-5-hydroxymethyl-imidazolidine-2,4-dione (Intermediate VD),
(R)-3-{(1S,2R,3S,4R)-4-[2-Chloro-6-((S)-1-hydroxymethyl-2-phenyl-ethylamino)-purin-9-yl]-2,3-dihydroxy-cyclopentyl}-5-hydroxymethyl-imidazolidine-2,4-dione (Intermediate VE),
are prepared analogously to Intermediate VA by replacing Intermediate UA with the appropriate U Intermediates.

Intermediate VF 3-{(1S,2R,3S,4R)-2,3-Dihydroxy-4-[6-((S)-1-hydroxymethyl-2-phenyl-ethylamino)-2-(4-nitro-imidazol-1-yl)-purin-9-yl]-cyclopentyl}-imidazolidine-2,4-dione 3-{(1S,2R,3S,4R)-4-[2-Chloro-6-((S)-1-hydroxymethyl-2-phenyl-ethylamino)-purin-9-yl]-2,3-dihydroxy-cyclopentyl}-imidazolidine-2,4-dione (Intermediate VB) and 4-nitro-imidazole, as described for N-{(1S,2R,3S,4R)-4-[6-(2,2-diphenyl-ethylamino)-2-(4-nitro-pyrazol-1-yl)-purin-9-yl]-2,3-dihydroxy-cyclopentyl}-2-hydroxy-acetamide (Intermediate QD).

Intermediate VG 3-{(1S,2R,3S,4R)-4-[2-(4-Amino-imidazol-1-yl)-6-((S)-1-hydroxymethyl-2-phenyl-ethylamino)-purin-9-yl]-2,3-dihydroxy-cyclopentyl}-imidazolidine-2,4-dione The title compound can be prepared from 3-{(1S,2R,3S,4R)-2,3-dihydroxy-4-[6-((S)-1-hydroxymethyl-2-phenyl-ethylamino)-2-(4-nitro-imidazol-1-yl)-purin-9-yl]-cyclopentyl}-imidazolidine-2,4-dione (Intermediate VF), as described for N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate QF).

Intermediate WA 9-((1R,4S)-4-Hydroxy-cyclopent-2-enyl)-6-((S)-1-hydroxymethyl-2-phenyl-ethylamino)-9H-purine-2-carboxylic acid methyl ester 6-((S)-1-Hydroxymethyl-2-phenyl-ethylamino)-9H-purine-2-carboxylic acid methyl ester (1.05 eq.) is suspended in THF (deoxygenated & dry). NaH (1.05 eq.) is added over 5 minutes and the reaction mixture is stirred at RT over 30 minutes. A solution of acetic acid (1S,3R)-3-hydroxy-cyclopentyl ester (1 eq.), triphenylphosphane (0.15 eq.) and tris (dibenzylideneacetone)dipalladium(0) in THF (deoxygenated & dry) is added to reaction. The reaction mixture is reflux for 6 hours. The reaction mixture is reduce in vacuo and columned to give the title compound.

Intermediate WB 9-((1R,4S)-4-Ethoxycarbonyloxy-cyclopent-2-enyl)-6-((S)-1-hydroxymethyl-2-phenyl-ethylamino)-9H-purine-2-carboxylic acid methyl ester 9-((1R,4S)-4-Hydroxy-cyclopent-2-enyl)-6-((S)-1-hydroxymethyl-2-phenyl-ethylamino)-9H-purine-2-carboxylic acid methyl ester (Intermediate WA) is dissolved in THF (dry). Pyridine is added and the reaction mixture is cooled to 0° C. Ethyl chloroformate is added dropwise keeping the temperature below 10° C. The reaction mixture is warmed to RT and stirred for 2 hours. The reaction mixture is reduced in vacuo and portioned between EtOAc and (1 M) HCl$_{(aq)}$. The organics are washed with water, brine, dried (MgSO$_4$) and reduced in vacuo. The resulting residue is columned to give the title compound.

Intermediate WC 9-((1R,4S)-4-(Di-Boc-amino)-cyclopent-2-enyl)-6-((S)-1-hydroxymethyl-2-phenyl-ethylamino)-9H-purine-2-carboxylic acid methyl ester 9-((1R,4S)-4-Ethoxycarbonyloxy-cyclopent-2-enyl)-6-((S)-1-hydroxymethyl-2-phenyl-ethylamino)-9H-purine-2-carboxylic acid methyl ester (Intermediate WB) (1 eq.), di-tert-butyl iminodicarboxylate (1.1 eq.), triphenylphosphane (0.15 eq.) and TEA are dissolved in THF (deoxygenated & dry).) Tris(dibenzylideneacetone)dipalladium$^{(O)}$ (0.05 eq.) is added and the reaction mixture is stirred at 50° C. for 1 hour. The reaction mixture is removed in vacuo and the title compound is obtained by column chromatography.

Intermediate WD 9-((1R,2S,3R,4S)-4-(Di-Boc-amino)-2,3-dihydroxy-cyclopentyl)-6-((S)-1-hydroxymethyl-2-phenyl-ethylamino)-9H-purine-2-carboxylic acid methyl ester The title compound is made analogous to (1S,2R,3S,5R)-3-(di-Boc-amino)-5-(2,6-dichloro-purin-9-yl)-cyclopentane-1,2-diol (Step AA4), by replacing di-Boc-[(1S,4R)-4-(2,6-dichloro-purin-9-yl)-cyclopent-2-enyl]-amine (Step AA3) with 9-01R,4S)-4-(di-Boc-amino)-cyclopent-2-enyl)-6-((S)-1-hydroxymethyl-2-phenyl-ethylamino)-9H-purine-2-carboxylic acid methyl ester (Intermediate WC).

Intermediate WE 9-((1R,2S,3R,4S)-4-Amino-2,3-dihydroxy-cyclopentyl)-6-((S)-1-hydroxymethyl-2-phenyl-ethylamino)-9H-purine-2-carboxylic acid methyl ester The title compound is made analogous to (1S,2R,3S,5R)-3-amino-5-(2,6-dichloro-purin-9-yl)-cyclopentane-1,2-diol trifluoroacetate (Step AA5), by replacing (1S,2R,3S,5R)-3-(di-Boc-amino)-5-(2,6-dichloro-purin-9-yl)-cyclopentane-1,2-diol with 9-((1R,2S,3R,4S)-4-(di-Boc-amino)-2,3-dihydroxy-cyclopentyl)-6-((S)-1-hydroxymethyl-2-phenyl-ethylamino)-9H-purine-2-carboxylic acid methyl ester (Intermediate WD).

Intermediate WF 9-[(1R,2S,3R,4S)-4-(2-Acetoxy-acetylamino)-2,3-dihydroxy-cyclopentyl]-6-((S)-1-hydroxymethyl-2-phenyl-ethylamino)-9H-purine-2-carboxylic acid methyl ester The title compound is made analogous to N-{(1S,2R,3S,4R)-4-[2-chloro-6-(2,2-diphenyl-ethylamino)-purin-9-yl]-2,3-dihydroxy-cyclopentyl}-propionamide (Step AAI4), by replacing (1S,2R,3S,5R)-3-amino-5-[2-chloro-6-(2,2-diphenyl-ethylamino)-purin-9-yl]-cyclopentane-1,2-diol trifluoroacetate with 9-((1R,2S,3R,4S)-4-amino-2,3-dihydroxy-cyclopentyl)-6-((S)-1-hydroxymethyl-2-phenyl-ethylamino)-9H-purine-2-carboxylic acid methyl ester (Intermediate WE) and replacing propionyl chloride with acetoxyacteyl chloride.

Intermediate WG 9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purine-2-carboxylic acid (2-amino-ethyl)-amide 9-[(1R,2S,3R,4S)-4-(2-Acetoxy-acetylamino)-2,3-dihydroxy-cyclopentyl]-6-((S)-1-hydroxymethyl-2-phenyl-ethylamino)-9H-purine-2-carboxylic acid methyl ester (Intermediate WF) is dissolved in ethylenediamine (>10 eq.). The reaction mixture is stirred at 90° C. for 1 hour. The reaction mixture is cooled and reduced in vacuo. The title compound is obtained by column chromatography.

Intermediate XA {3-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-prop-2-ynyl}-carbamic acid tert-butyl ester N-{(1S,2R,3S,4R)-4-[6-((S)-1-Benzyl-2-hydroxy-ethylamino)-2-chloro-purin-9-yl]-2,3-dihydroxy-cyclopentyl}-2-hydroxy-acetamide (Intermediate GC) (1 eq.), prop-2-ynyl-carbamic acid tert-butyl ester (10 eq.), CuI (0.25 eq.), bis(triphenylphosphine)-palladium(II) chloride (0.25 eq.) and triphenylphosphine (0.5 eq.) are dissolved in diethylamine and DMF. The reaction mixture is heated in a microwave for 1 hour at 120° C. The title compound is obtained by column chromatography.

Intermediate XB 4-{3-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-prop-2-ynyl}-piperidine-1-carboxylic acid tert-butyl ester The title compound is made analogously to {3-[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purin-2-yl]-prop-2-ynyl}-carbamic acid tert-butyl ester (Intermediate XA), by replacing prop-2-ynyl-carbamic acid tert-butyl ester with 4-prop-2-ynyl-piperidine-1-carboxylic acid tert-butyl ester.

Intermediate XC ((R)-1-{3-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-prop-2-ynyl}-pyrrolidin-3-yl)-carbamic acid tert-butyl ester The title compound is made analogously to {3-[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purin-2-yl]-prop-2-ynyl}-carbamic acid tert-butyl ester (Intermediate XA), by replacing prop-2-ynyl-carbamic acid tert-butyl ester with ((R)-1-But-2-ynyl-pyrrolidin-3-yl)-carbamic acid tert-butyl ester.

Intermediate YA N-{(1S,2R,3S,4R)-4-[2-(3-Amino-prop-1-ynyl)-6-((S)-1-hydroxymethyl-2-phenyl-ethylamino)-purin-9-yl]-2,3-dihydroxy-cyclopentyl}-2-hydroxy-acetamide {3-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-prop-2-ynyl}-carbamic acid tert-butyl ester (Intermediate XA) is dissolved in 1.25 M HCl in MeOH. After stirring at RT for 3 days, the solvent is removed in vacuo to yield the title compound. This is used in the next step without further purification.

Intermediate YB N-{(1S,2R,3S,4R)-2,3-Dihydroxy-4-[6-((S)-1-hydroxymethyl-2-phenyl-ethylamino)-2-(3-piperidin-4-yl-prop-1-ynyl)-purin-9-yl]-cyclopentyl}-2-hydroxy-acetamide 4-{3-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-prop-2-ynyl}-piperidine-1-carboxylic acid tert-butyl ester (Intermediate XB) is dissolved in 1.25 M HCl in MeOH. After stirring at RT for 3 days, the solvent is removed in vacuo to yield the title compound. This is used in the next step without further purification.

Intermediate YC N-{(1S,2R,3S,4R)-4-[2-[3-((R)-3-Amino-pyrrolidin-1-yl)-prop-1-ynyl]-6-((S)-1-hydroxymethyl-2-phenyl-ethylamino)-purin-9-yl]-2,3-dihydroxy-cyclopentyl}-2-hydroxy-acetamide ((R)-1-{3-[9-[(1R,2S,3R,4S)-2,3-Dihydroxy-4-(2-hydroxy-acetylamino)-cyclopentyl}-6-((S)-1-hydroxymethyl-2-phenyl-ethylamino)-9H-purin-2-yl]-prop-2-ynyl]-pyrrolidin-3-yl)-carbamic acid tert-butyl ester (Intermediate XC) is dissolved in 1.25 M HCl in MeOH. After stirring at RT for 3 days, the solvent is removed in vacuo to yield the title compound. This is used in the next step without further purification.

Intermediate ZA (2-{[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purine-2-carbonyl]-amino}-ethyl)-carbamic acid phenyl ester The title compound can be prepared from 9-[(1R,2S,3R,4S)-2,3-dihydroxy-4-(2-hydroxy-acetylamino)-cyclopentyl]-64S)-1-hydroxymethyl-2-phenyl-ethylamino)-9H-purine-2-carboxylic acid (2-amino-ethyl)-amide (Intermediate WG), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate ZB {3-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-prop-2-ynyl}-carbamic acid phenyl ester The title compound can be prepared from N-{(1S,2R,3S,4R)-4-[2-(3-amino-prop-1-ynyl)-6-((S)-1-hydroxymethyl-2-phenyl-ethylamino}-purin-9-yl]-2,3-dihydroxy-cyclopentyl-2-hydroxy-acetamide (Intermediate YA), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate ZC 4-{3-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-prop-2-ynyl}-piperidine-1-carboxylic acid phenyl ester The title compound can be prepared from N-{(1S,2R,3S,4R)-2,3-dihydroxy-4-[6-((S)-1-hydroxymethyl-2-phenyl-ethylamino)-2-(3-piperidin-4-yl-prop-1-ynyl)-purin-9-yl]-cyclopentyl}-2-hydroxy-acetamide (Intermediate YB), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate ZD ((R)-1-{3-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-prop-2-ynyl}-pyrrolidin-3-yl)-carbamic acid phenyl ester The title compound can be prepared from N-{(1S,2R,3S,4R)-4-[2-[3-((R)-3-amino-pyrrolidin-1-yl)-prop-1-ynyl]-6-((S)-1-hydroxymethyl-2-phenyl-ethylamino)-purin-9-yl]-2,3-dihydroxy-cyclopentyl}-2-hydroxy-acetamide (Intermediate YC), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate ZE {1-[9-[(1R,2S,3R,4S)-4-(2,5-Di-oxo-imidazolidin-1-yl)-2,3-dihydroxy-cyclopentyl]-6-((S)-1-hydroxymethyl-2-phenyl-ethylamino)-9H-purin-2-yl]-1H-imidazol-4-yl}-carbamic acid phenyl ester The title compound can be prepared from 3-{(1S,2R,3S,4R)-4-[2-(4-amino-imidazol-1-yl)-6-((S)-1-hydroxymethyl-2-phenyl-ethylamino)-purin-9-yl]-2,3-dihydroxy-cyclopentyl}-imidazolidine-2,4-dione (Intermediate VG), as described for {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH).

Intermediate ZF N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-hydroxy-acetamide trifluoroacetate Step 1: 2-Benzyloxy-N-{(1S,2R,3S,4R)-4-[2-chloro-6-(2,2-diphenyl-ethylamino)-purin-9-yl]-2,3-dihydroxy-cyclopentyl}-acetamide The title compound is prepared analogously to N-{(1S,2R,3S,4R)-4-[2-chloro-6-(2,2-diphenyl-ethylamino)-purin-9-yl]-2,3-dihydroxy-cyclopentyl}-propionamide (Intermediate AA) by replacing cyclopropanecarboxylic acid propionyl chloride with benzyloxy-acetyl chloride.

Step 2: N-{(1S,2R,3S,4R)-4-[24(R)-3-Amino-pyrrolidin-1-yl)-6-(2,2-diphenyl-ethylamino)-purin-9-yl]-2,3-dihydroxy-cyclopentyl}-2-benzyloxy-acetamide trifluoroacetate A solution of 2-benzyloxy-N-{(1S,2R,3S,4R)-4-[2-chloro-6-(2,2-diphenyl-ethylamino)-purin-9-yl]-2,3-dihydroxy-cyclopentyl}-acetamide (80 mg, 0.13 mmol) in NMP:MeCN (1 mL of a 1:1 mixture) is treated with sodium iodide (6 mg, 0.04 mmol) followed by (3R)-3-aminopyrrolidine (34 mg, 0.4 mmol). The reaction mixture is heated using microwave radiation in a Personal Chemistry Emrys™ Optimizer microwave reactor at 200° C. The reaction is shown to be complete by LCMS after 30 minutes. The title compound is obtained after purification by reverse phase column chromatography (Isolute™ C18, 0-100% acetonitrile in water—0.1% TFA).

Step 3: N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-hydroxy-acetamide trifluoroacetate A solution of N-{(1S,2R,3S,4R)-4-[24(R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (0.022 g, 0.03 mmol) in ethanol (2 mL) under an atmosphere of argon is treated with palladium hydroxide on carbon (0.05 g, 20% w/w carbon). The reaction mixture is placed under an atmosphere of hydrogen and stirred at RT for 30 hours and then filtered through Celite™. The filtrate is concentrated in vacuo and purification of the crude by reverse phase column chromatography (Isolute™ C18, 0-100% acetonitrile in water—0.1% TFA) yields the title product.

PREPARATION OF SPECIFIC EXAMPLES

Example 1

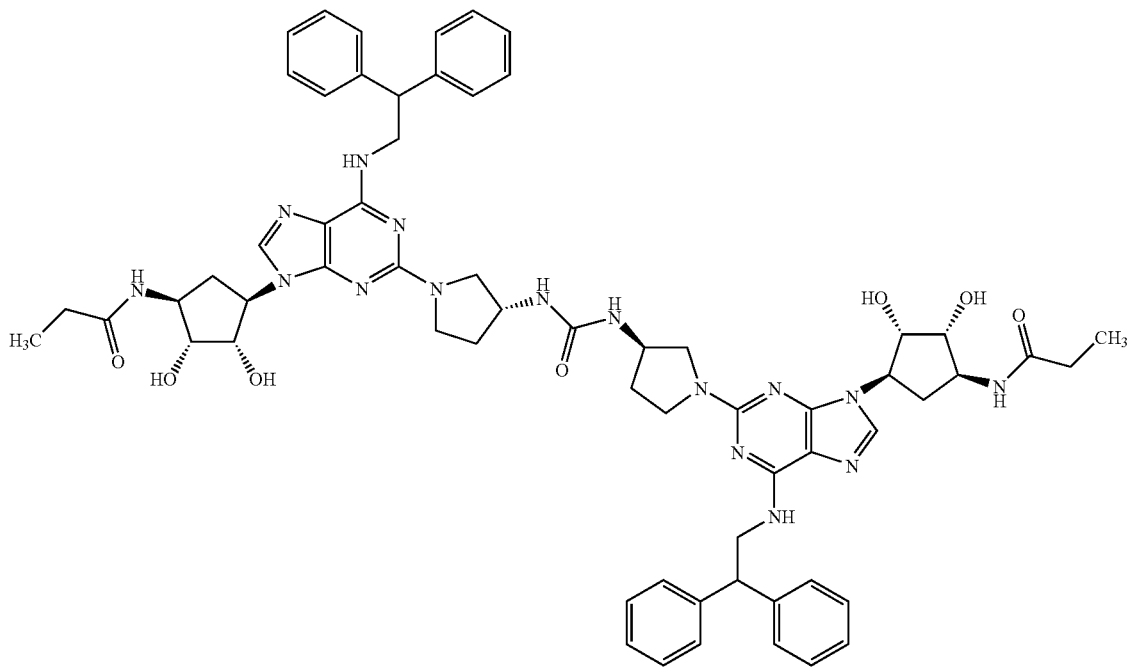

A solution comprising N-{(1S,2R,3S,4R)-4-[2-chloro-6-(2,2-diphenyl-ethylamino)-purin-9-yl]-2,3-dihydroxy-cyclopentyl}-propionamide (Intermediate AA) (0.25 g, 0.48 mmol) and 1,3-di(R)-pyrrolidin-3-yl-urea (Intermediate C) (0.105 g, 0.53 mmol) in DMSO (0.4 mL) is heated at 110° C. for 3 hours. Purification of the product by reverse phase column chromatography (Isolute™ C18, 0-100% acetonitrile in water—0.1% TFA) yields Example 1 and N-((1S,2R,3S,4R)-4-{6-(2,2-diphenyl-ethylamino)-2-[(R)-34(R)-3-pyrrolidin-3-ylureido)-pyrrolidin-1-yl]-purin-9-yl}-2,3-dihydroxy-cyclopentyl)-propionamide.

Example 2

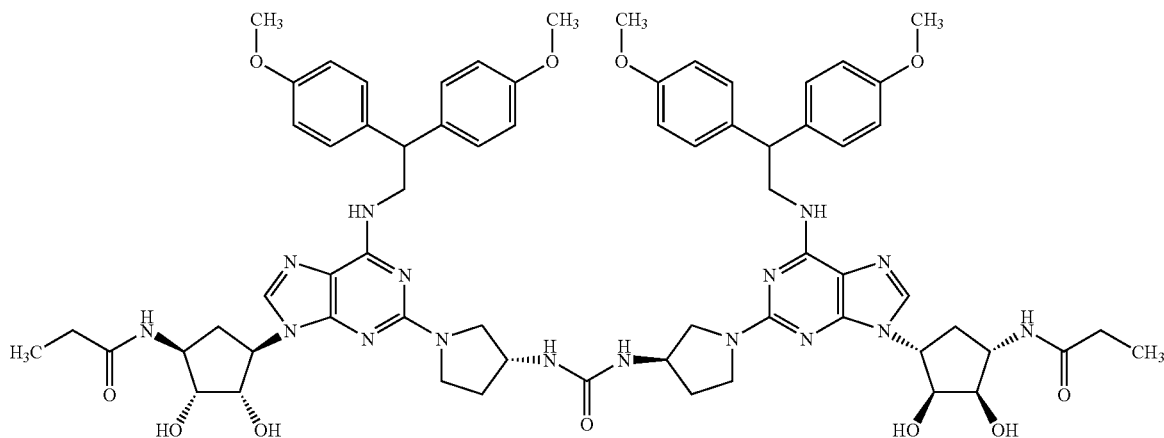

Example 2 is prepared analogously to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate AA) with N-((1S,2R,3S,4R)-4-{6-[2,2-bis-(4-methoxy-phenyl)-ethylamino]-2-chloro-purin-9-yl}-2,3-dihydroxy-cyclopentyl)-propionamide trifluoroacetate (Intermediate AG).

Example 3

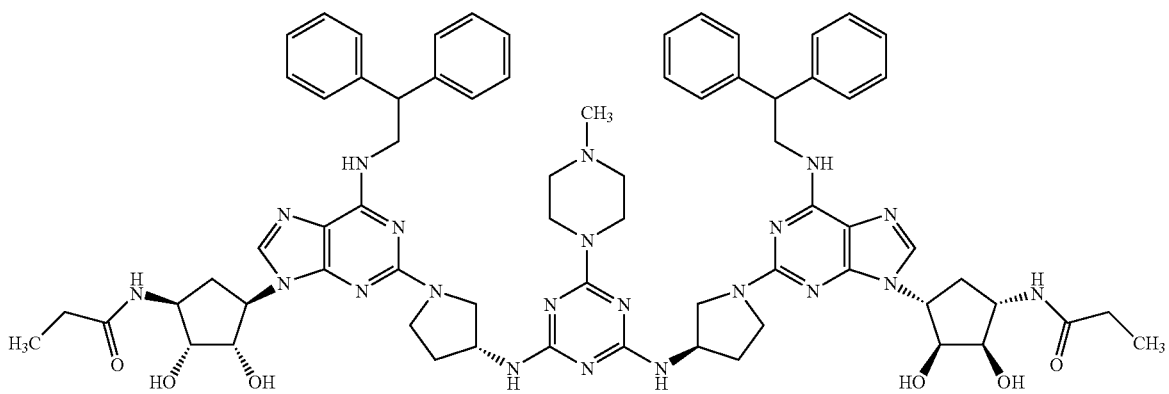

Example 3 is prepared analogously to Example 1 by replacing 1,3-di-(R)-pyrrolidin-3-yl-urea (Intermediate C) with 6-(4-methyl-piperazin-1-yl)-N,N'-di-(R)-pyrrolidin-3-yl-[1,3,5]triazine-2,4-diamine trifluoroacetate (Intermediate D).

Example 4

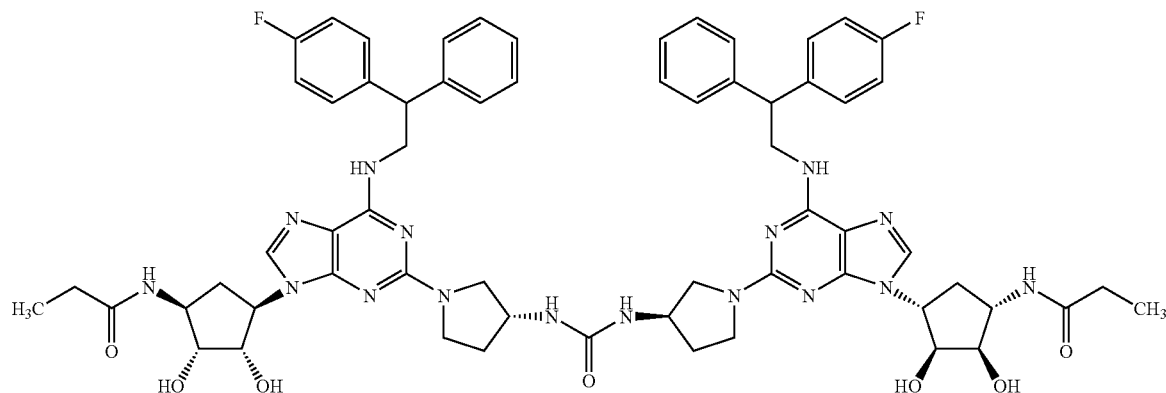

A reaction mixture comprising N-((1S,2R,3S,4R)-4-{2-chloro-6-[2-(4-fluoro-phenyl)-2-phenyl-ethylamino]-purin-9-yl}-2,3-dihydroxy-cyclopentyl)-propionamide trifluoroacetate (Intermediate AD) (50 mg, 0.08 mmol), 1,3-di-(R)-pyrrolidin-3-yl-urea (Intermediate C) (16 mg, 0.08 mmol), sodium hydrogen carbonate (7 mg, 0.08 mmol) in DMSO (0.1 mL) is heated at 100° C. over night. Purification of the product by reverse phase column chromatography (Isolute™ C18, 0-100% acetonitrile in water—0.1% TFA) yields Example 4.

Examples 5-10

These compounds,

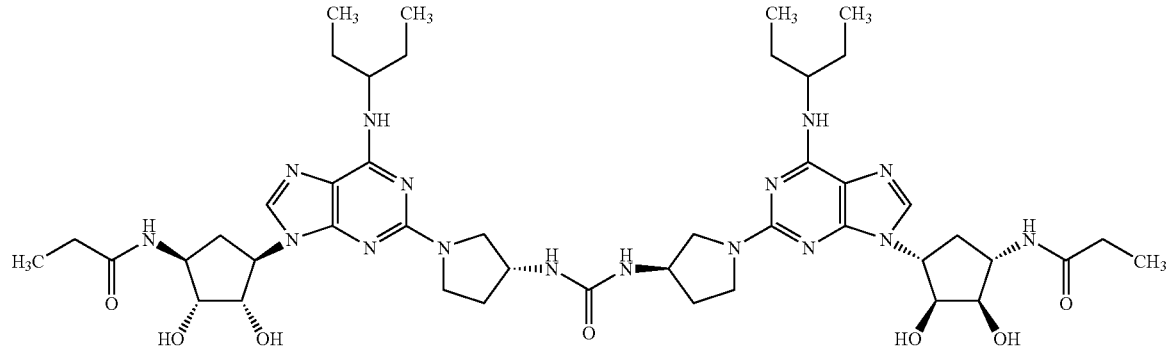

(Example 5),

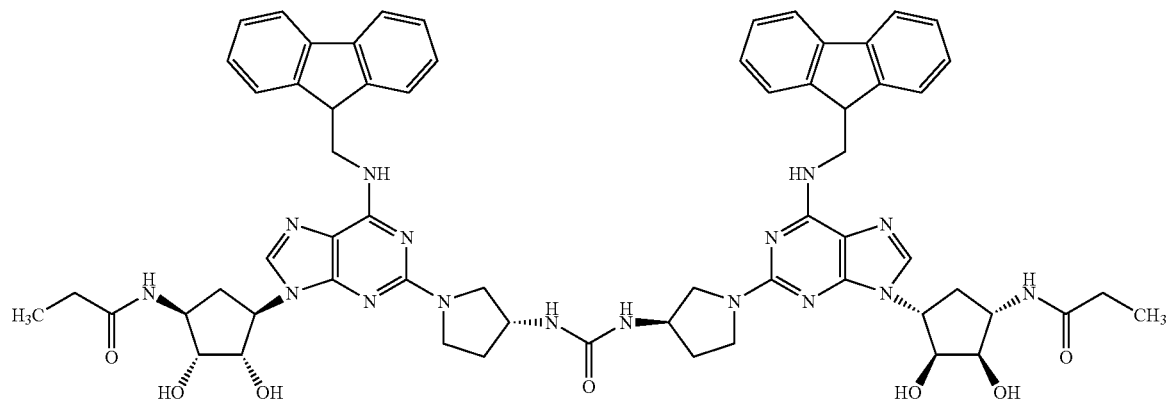

(Example 6),
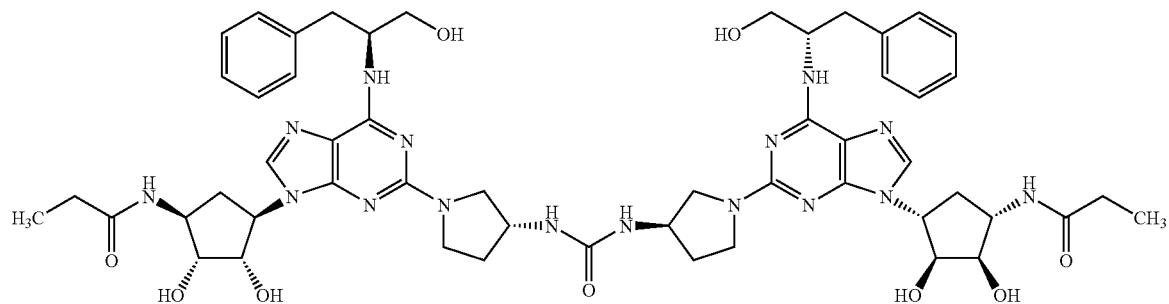
(Example 7),
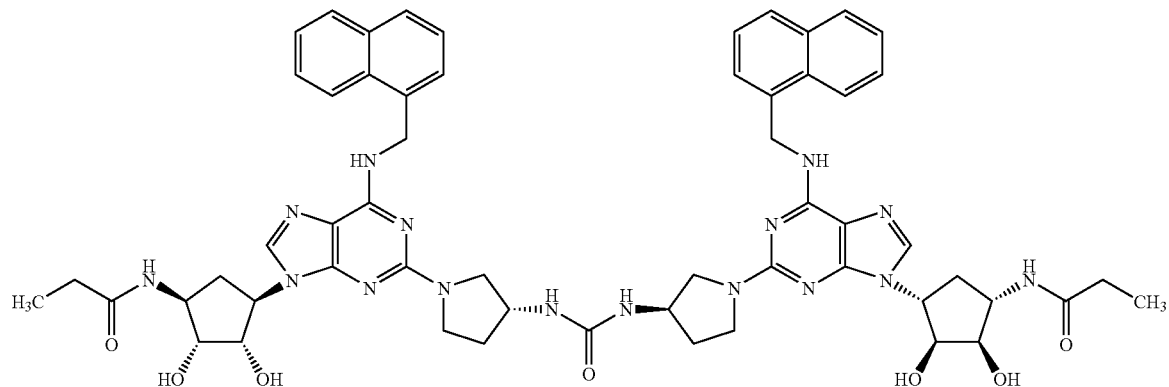
(Example 8),
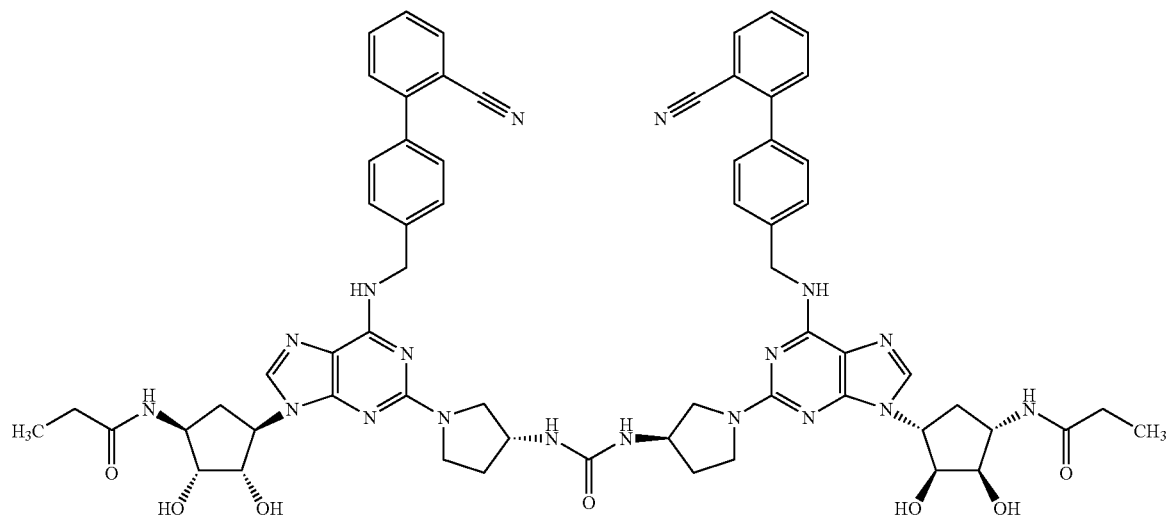

(Example 9),
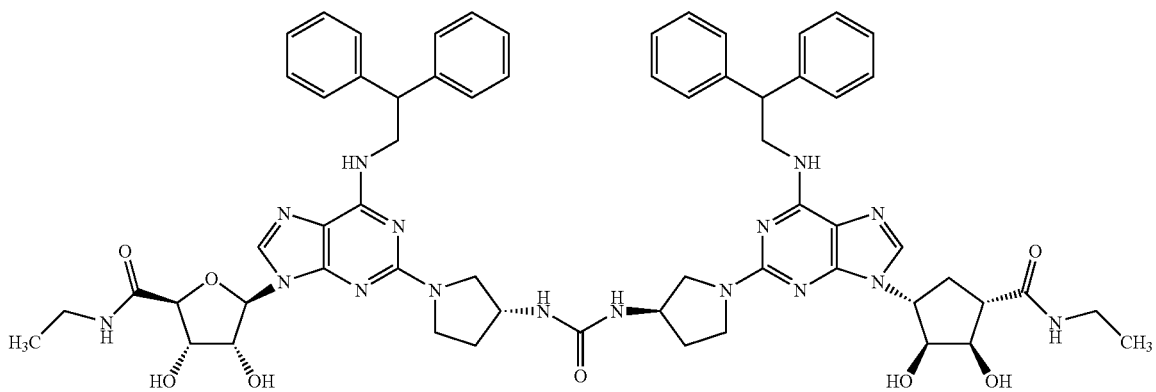
(Example 10), are prepared analogously to Example 4 by replacing N-((1S,2R,3S,4R)-4-{2-chloro-6-[2-(4-fluorophenyl)-2-phenyl-ethylamino]-purin-9-yl}-2,3-dihydroxycyclopentyl)-propionamide trifluoroacetate (Intermediate AD) with the appropriate intermediate the preparations of which are described herein.
Example 11
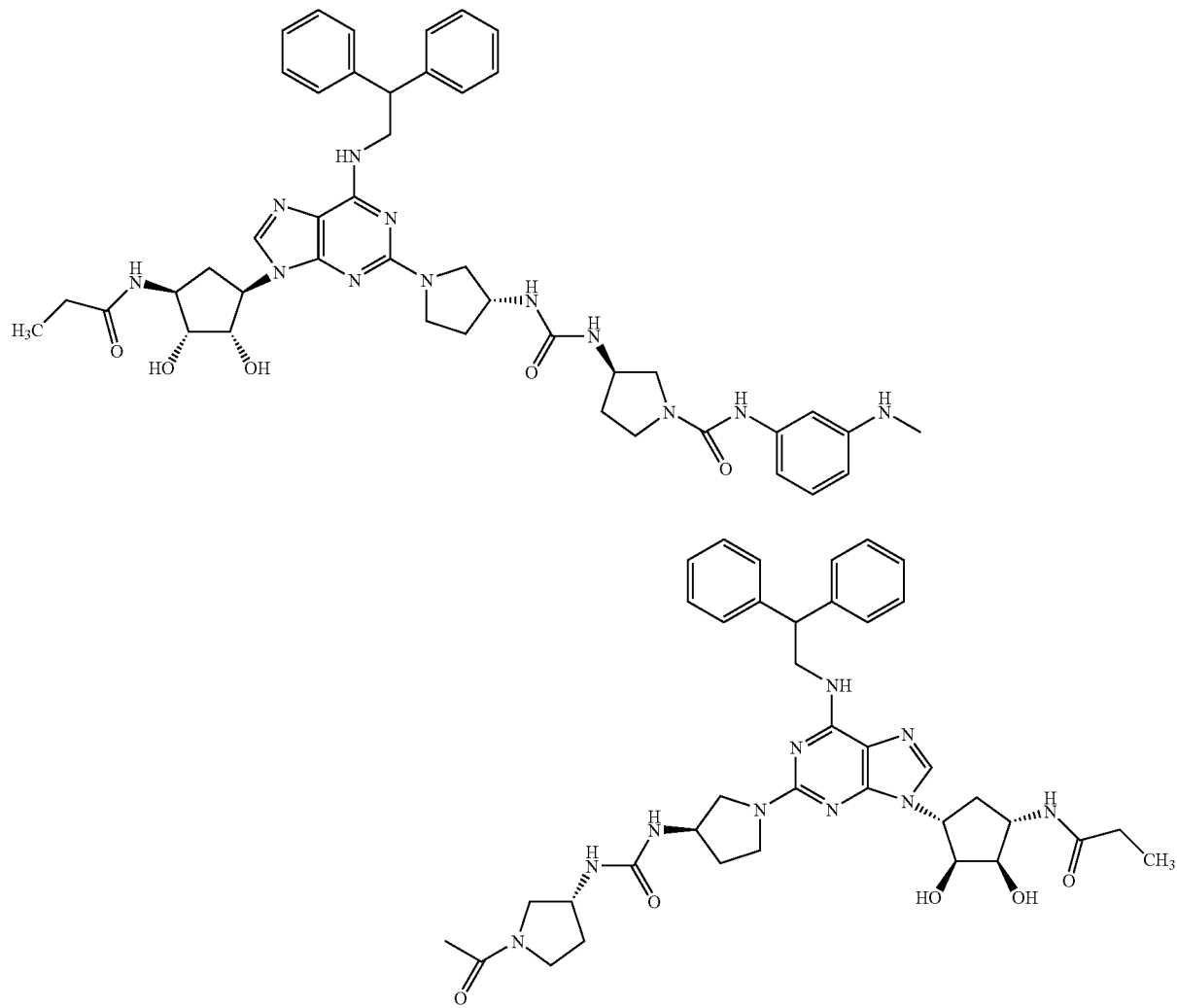

A solution comprising N-((1S,2R,3S,4R)-4-{6-(2,2-diphenyl-ethylamino)-2-[(R)-3-((R)-3-pyrrolidin-3-ylureido)-pyrrolidin-1-yl]-purin-9-yl}-2,3-dihydroxy-cyclopentyl)-propionamide (10 mg, 14.5 μmol) in NMP (0.3 mL) is treated with a solution of 1,3-phenylenediisocyanate (1.2 mg, 7.3 μmol) in NMP (0.2 mL). After 1 hour at RT, the product is purified by reverse phase column chromatography (Isolute™ C18, 0-100% acetonitrile in water—0.1% TFA) to yield Example 11.

Example 12

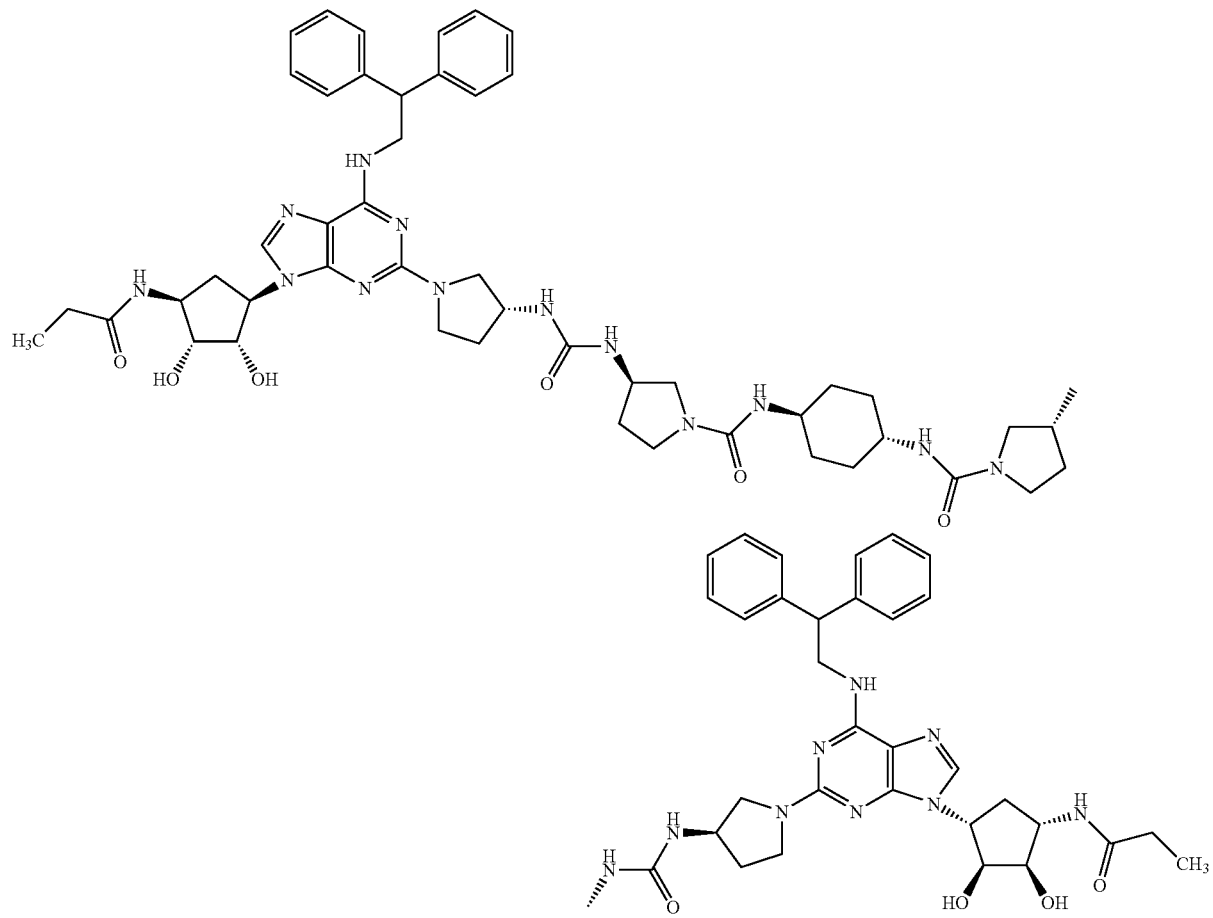

Example 12 is prepared analogously to Example 11 by replacing 1,3-phenylenediisocyanate with trans-1,4-cyclohexylenediisocyanate.

Example 13

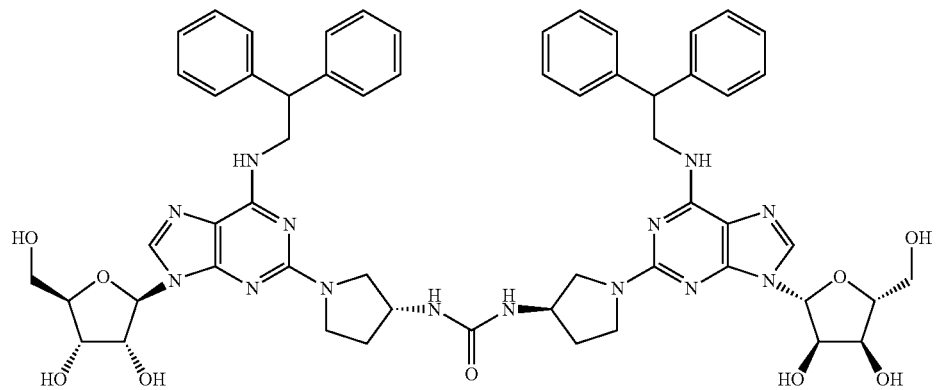

To a stirred solution of (2R,3R,4S,5R)-2-[2-chloro-6-(2,2-diphenyl-ethylamino)-purin-9-yl]-5-hydroxymethyl-tetrahydro-furan-3,4-diol (Intermediate BA) (0.05 g, 0.1 mmol) and sodium iodide (0.016 g, 0.1 mmol) in acetonitrile: NMP (1.0 mL of a 1:1 solution) is added 1,3-di-(R)-pyrrolidin-3-yl-urea (Intermediate C) (0.041 g, 0.2 mmol) and DIPEA (0.05 ml, 0.26 mmol). The reaction mixture is heated to 160° C. for 30 minutes in a microwave. Purification by reverse phase column chromatography (Isolute™ C18, 0-100% acetonitrile in water—0.1% TFA) affords Example 13 and 1-{(R)-1-[9-((2R,3R,4S,5R)-3,4-dihydroxy-5-hydroxymethyl-tetrahydro-furan-2-yl)-6-(2,2-diphenyl-ethylamino)-9H-purin-2-yl]-pyrrolidin-3-yl}-3-(R)-pyrrolidin-3-yl-urea trifluoroacetate.

Example 14

Step 2: N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide dihydrochloride {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester (ca 4.80 mmol) is dissolved in 1.25 M HCl in MeOH (60 mL). After stirring at RT for 3 days, the solvent is removed in vacuo to yield the title compound as a brown solid. This is used in the next step without further purification.

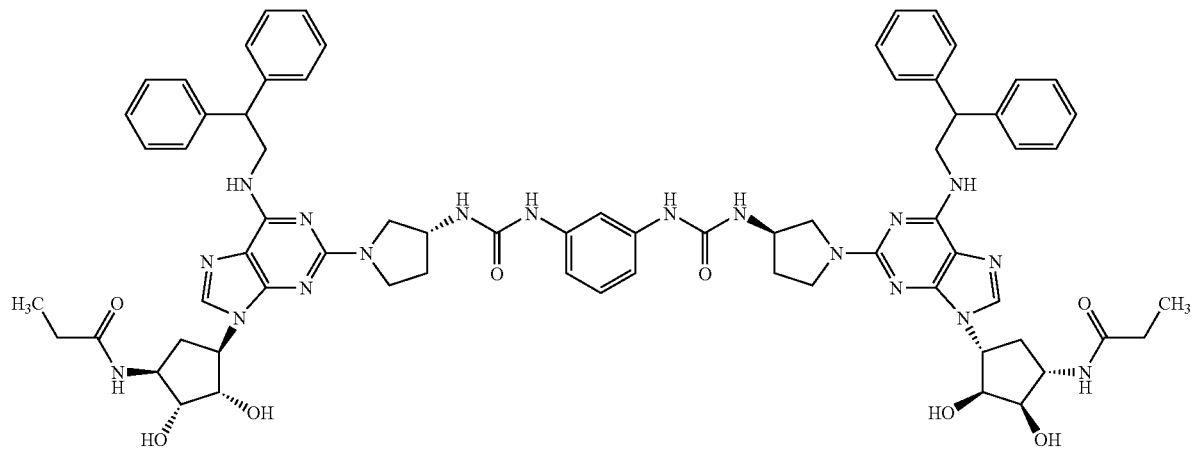

Step 1: {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester A reaction mixture comprising N-{(1S,2R,3S,4R)-4-[2-chloro-6-(2,2-diphenyl-ethylamino)-purin-9-yl]-2,3-dihydroxy-cyclopentyl}-propionamide (Intermediate AA) (2.5 g, 4.80 mmol) and (3R)-(+)-(3-Boc-amino)pyrrolidine (2.5 g, 13.6 mmol) in DMSO (8 mL) is heated at 100° C. over night. Purification of the product by reverse phase column chromatography (Isolute™ C18, 0-20% acetonitrile in water—0.1% TFA) yields the title compound.

Step 3: N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide dihydrochloride (ca. 7.7 mmol) is dissolved in minimal volume of a mixture of ethanol/saturated aqueous sodium carbonate solution until the pH of the solution is adjusted to pH 7 (ensuring the compound remains in solution). The solution is loaded onto an Isolute™ C18 column and washed through firstly with water and then MeOH. The fractions are combined and concentrated in vacuo and then further purified by repeating the above process to afford the title compound. LCMS (electrospray): m/z [MH$^+$] 571

Step 4

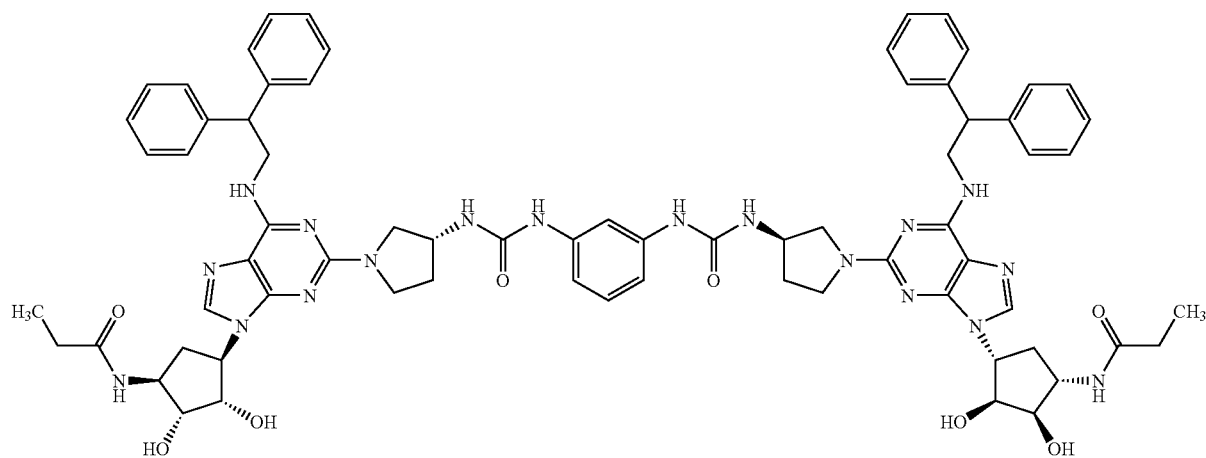

A solution comprising N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (10 mg, 17.5 μmol) in dry THF (0.3 mL) is treated with 1,3-diisocyanatobenzene (1.4 mg, 8.8 mop and stirred at RT for 3 days. Purification of the product by reverse phase column chromatography (Isolute™ C18, 0-100% acetonitrile in water—0.1% TFA) affords Example 14.

Examples 15 and 16

These compounds,

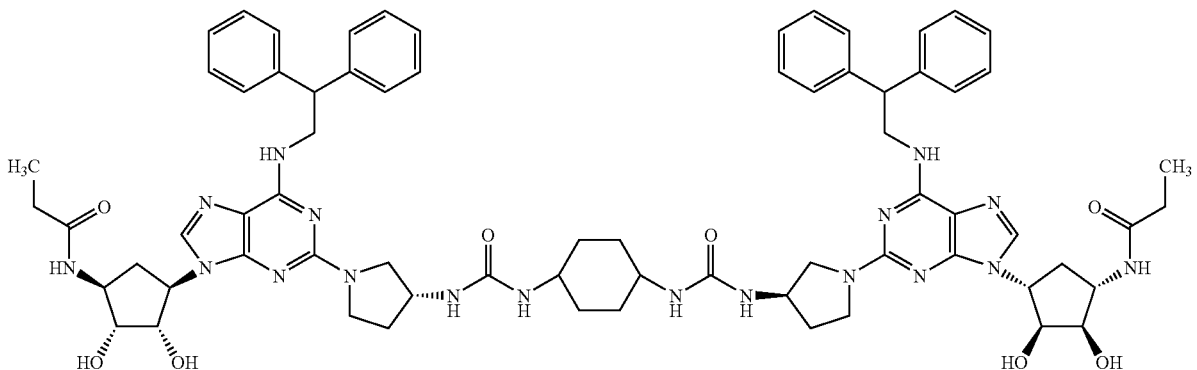

(Example 15) and

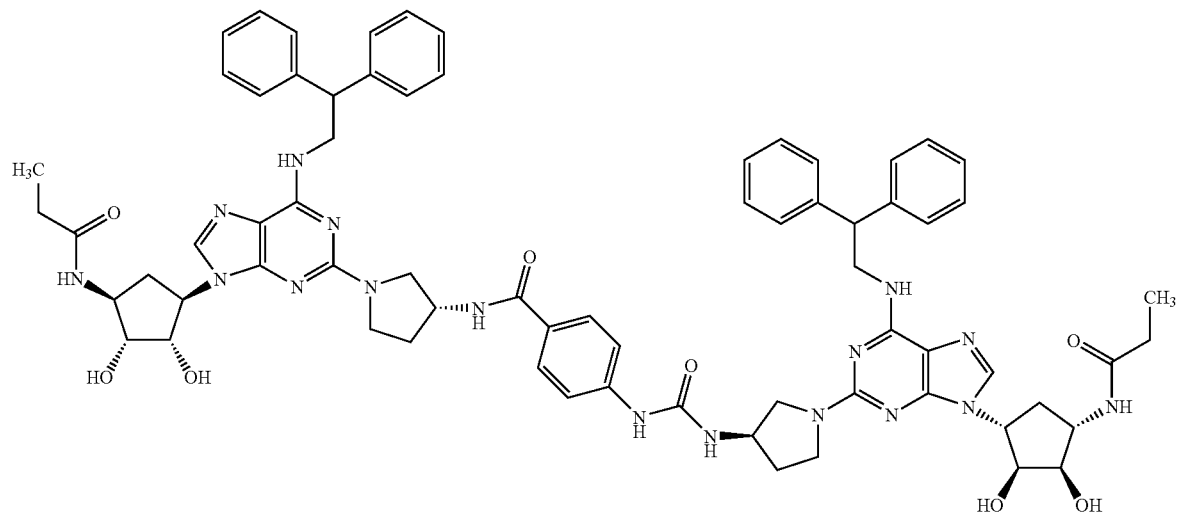

are prepared analogously to Example 14 by replacing 1,3-diisocyanatobenzene with the appropriate acid chloride/isocyanate.

Example 17

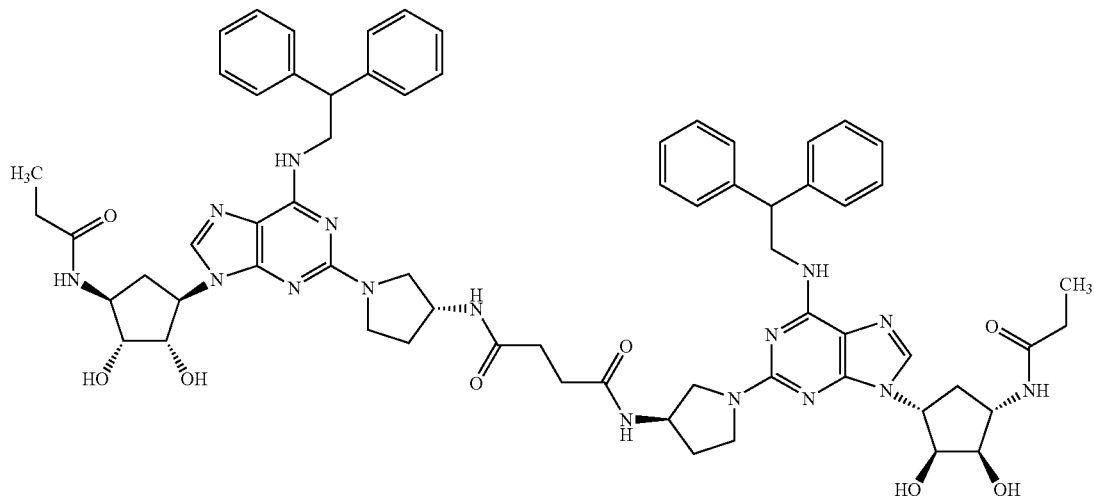

To a solution of {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (10 mg, 17.5 µmol) and TEA (7 mg, 0.07 mmol) in dry THF (0.3 mL) is added butanedioyl chloride (1.93 µL, 0.018 mmol) and the reaction mixture is allowed to stand at RT for 18 hours. The solvent is removed in vacuo and purification of the crude product by reverse phase column chromatography (Isolute™ C18, 0-100% acetonitrile in water—0.1% TFA) affords Example 17.

Examples 18 and 19

These compounds,

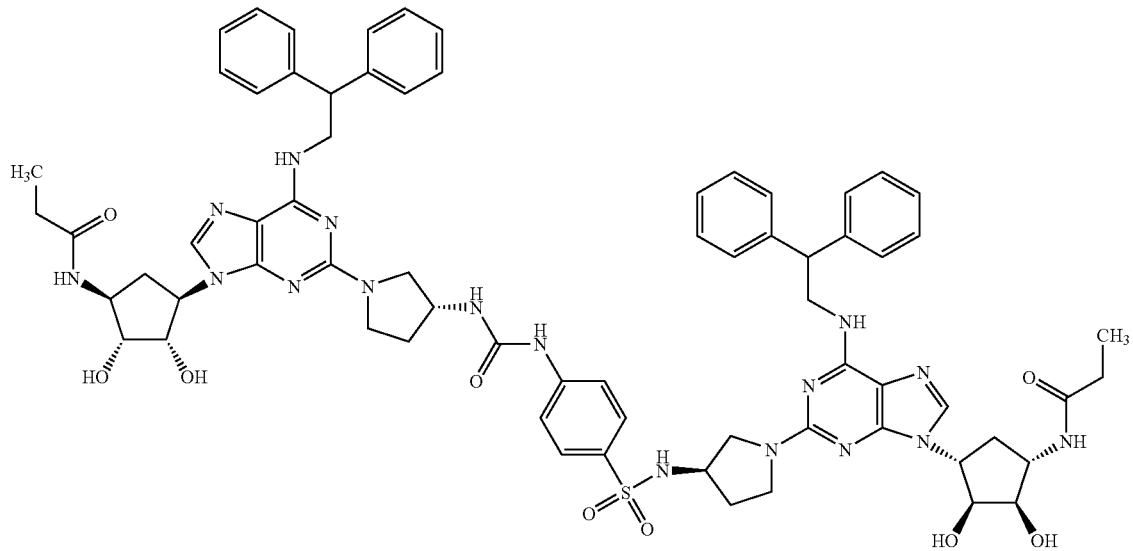

(Example 18) and
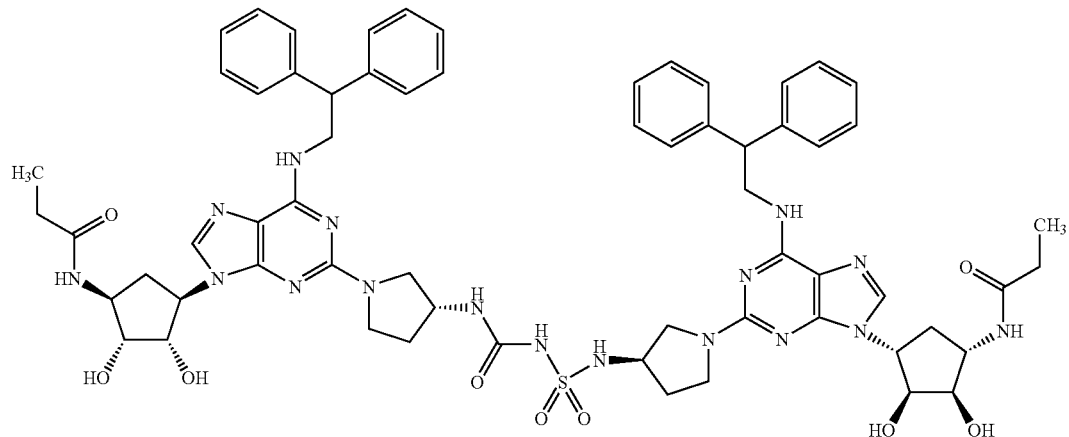
(Example 19), are prepared analogously to Example 17 by replacing butanedioyl chloride with the appropriate sulphonyl chloride isocyanate.
Examples 20 and 23
These compounds,
(Example 20),
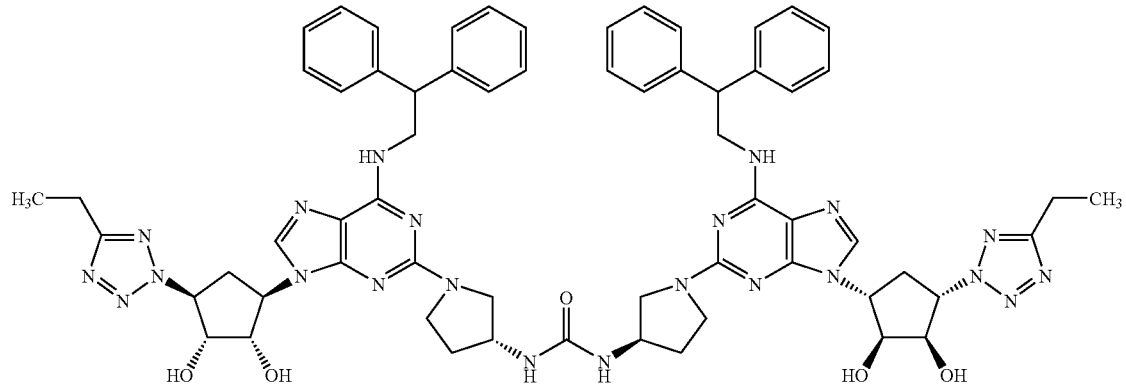

(Example 21),

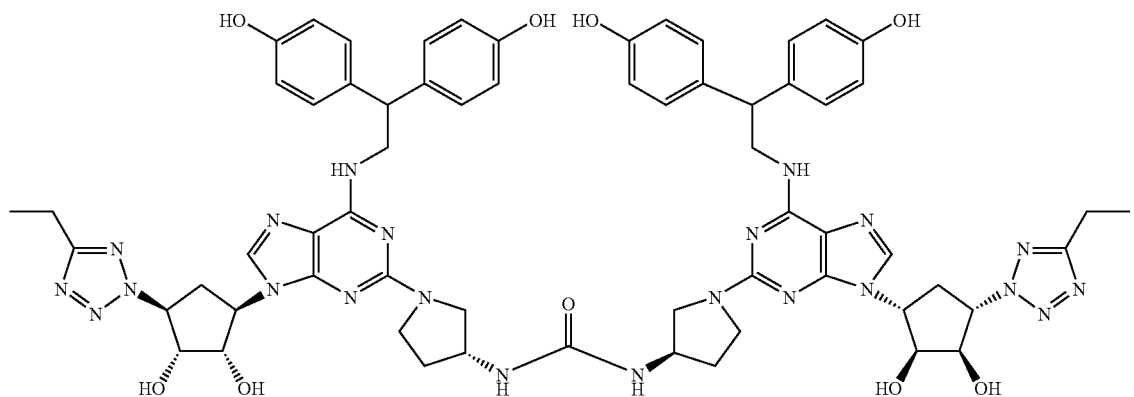

(Example 22) and

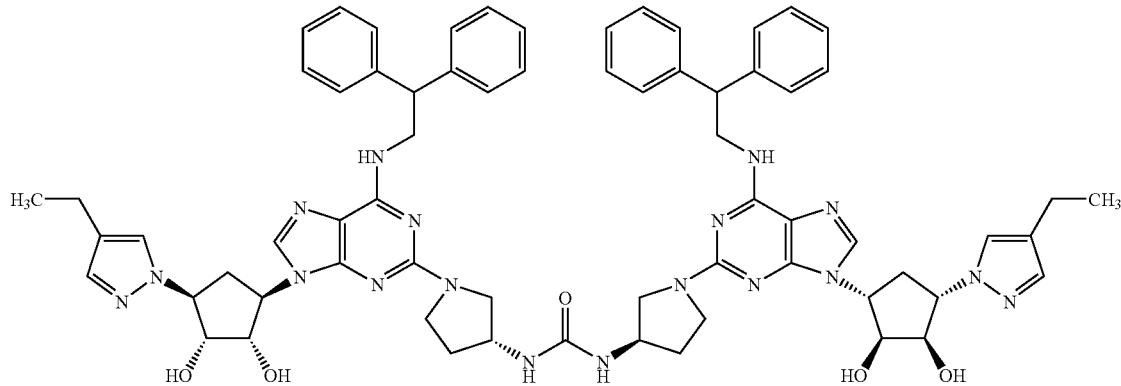

(Example 23), are prepared analogously to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate A) with the appropriate intermediate, the preparations of which are described herein.

Example 24

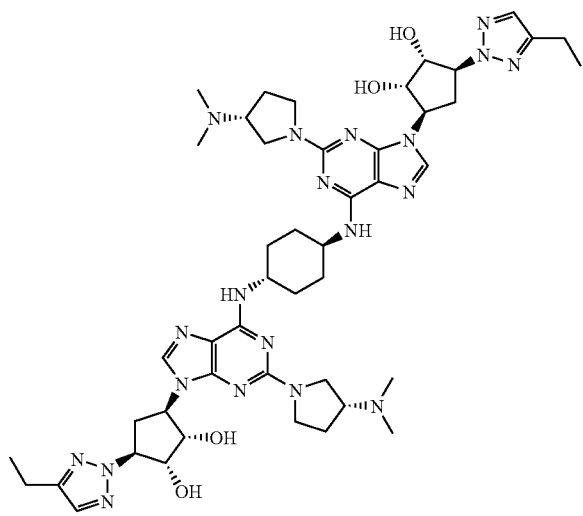

Step 1

3-(2,6-Dichloro-purin-9-yl)-5-(4-ethyl-[1,2,3]triazol-1-yl)-cyclopentane-1,2-diol (Intermediate BD) (0.612 g, 1.59 mmol) and diamino(trans-1,4)cyclohexane (0.091 g, 0.796 mmol) in iso-propanol (6 mL) are treated with DIPEA (0.694 mL, 3.98 mmol) and the resulting mixture is heated to 83° C. over night. After cooling to RT, the solvent is removed in vacuo and the resulting solid is purified by reverse phase column chromatography (Isolute™ C18, 0-100% acetonitrile in water—0.1% TFA). The fractions are combined, treated with saturated sodium bicarbonate solution (to pH 8) purified again by reverse phase column chromatography (Isolute™ C18, 0-100% MeOH in water) to afford the title product.

Step 2

A mixture comprising the product from Step 1 (0.05 g, 0.0617 mmol), (3R)-(+)-3-dimethylaminopyrrolidine (0.078 ml, 0.617 mmol) and potassium carbonate (43 mg, 0.309 mmol in NMP (0.5 mL) is heated using microwave radiation in a Personal Chemistry Emrys™ Optimizer microwave reactor at 170° C. for 30 minutes. The product is obtained after purification by reverse phase column chromatography (Isolute™ C18, 0-30% acetonitrile in water—0.1% TFA).

Example 25

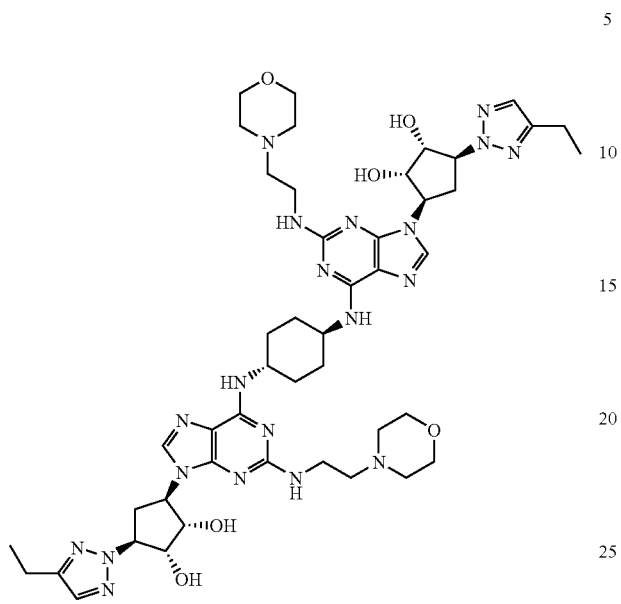

This compound is prepared analogously to Example 24 by replacing (3R)-(+)-3-dimethylaminopyrrolidine (Step 2) with 2-(4-morpholinyl)ethylamine.

Example 26

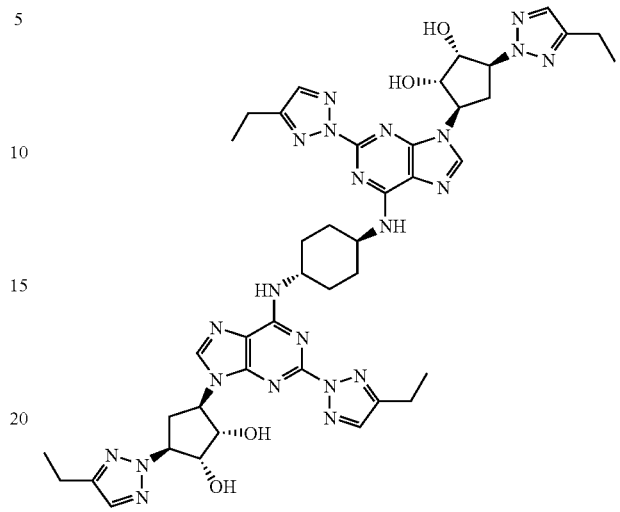

This compound is prepared analogously to Example 24 by replacing (3R)-(+)-3-dimethylaminopyrrolidine (Step 2) with 4-ethyl-2H-[1,2,3]triazole.

Examples 27-55

The compounds of formula (X) are shown in the following table. Methods of preparing such compounds are described hereinafter.

| Ex | Structure | R[11] | R[12] |
|---|---|---|---|
| | (X) structure with two purine-sugar systems linked via cyclohexyl-NH bridges; M is CH$_2$ except in Examples 27 to 36 where M is O | | |
| 27 | [structure] | CH$_3$CH$_2$NHC(O)– | (3R)-1-methyl-3-(dimethylamino)pyrrolidinyl |

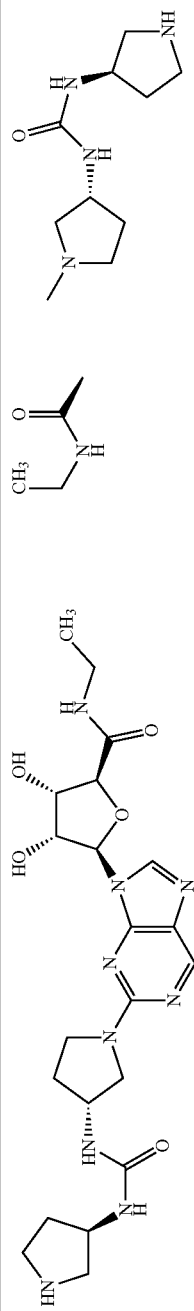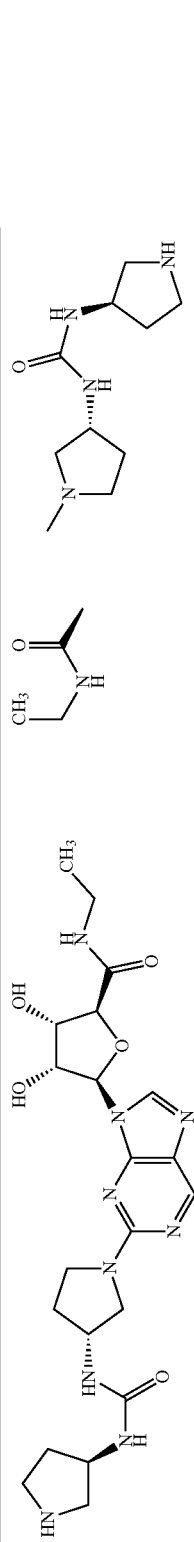

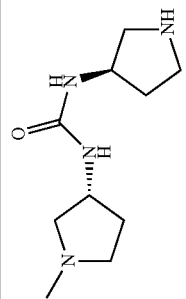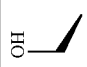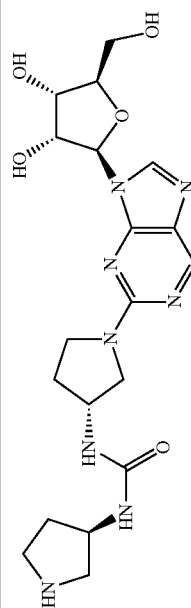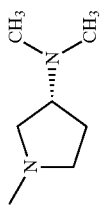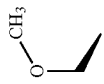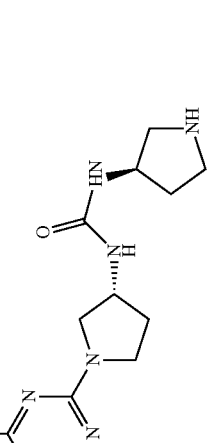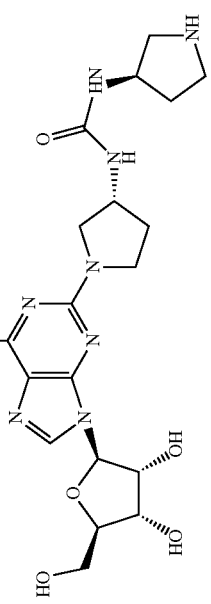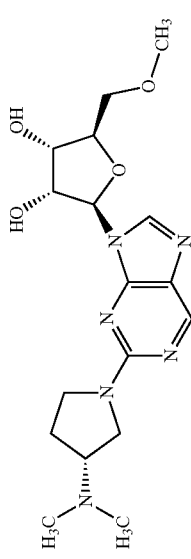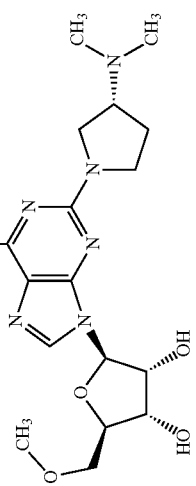

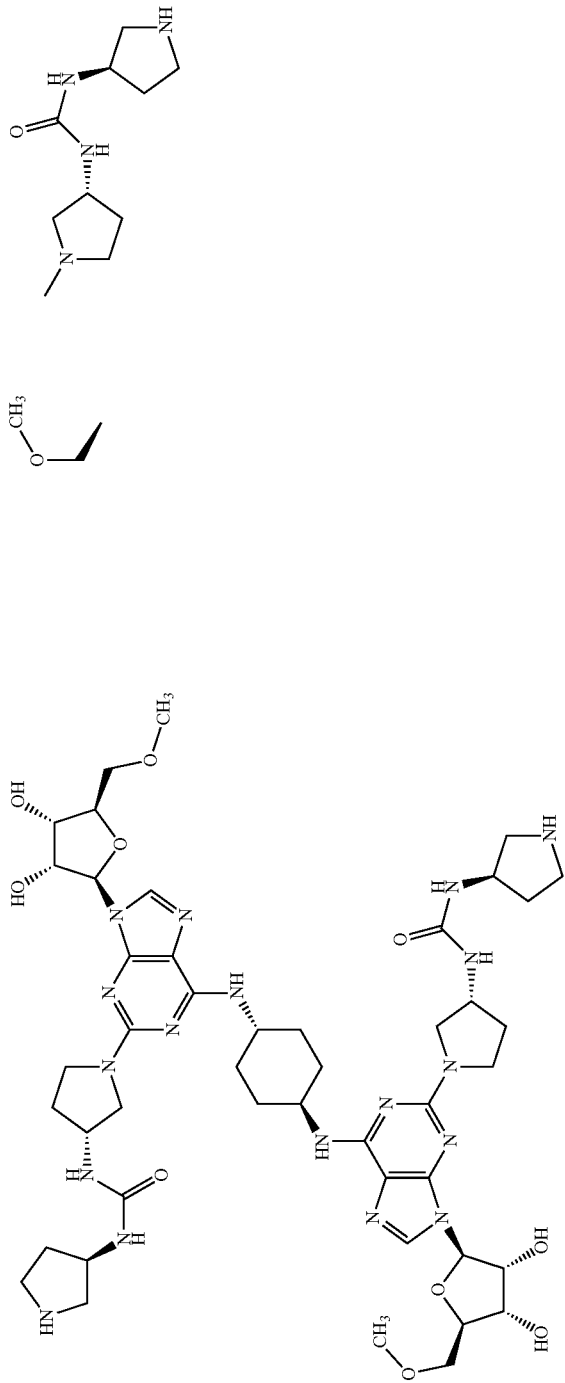
32

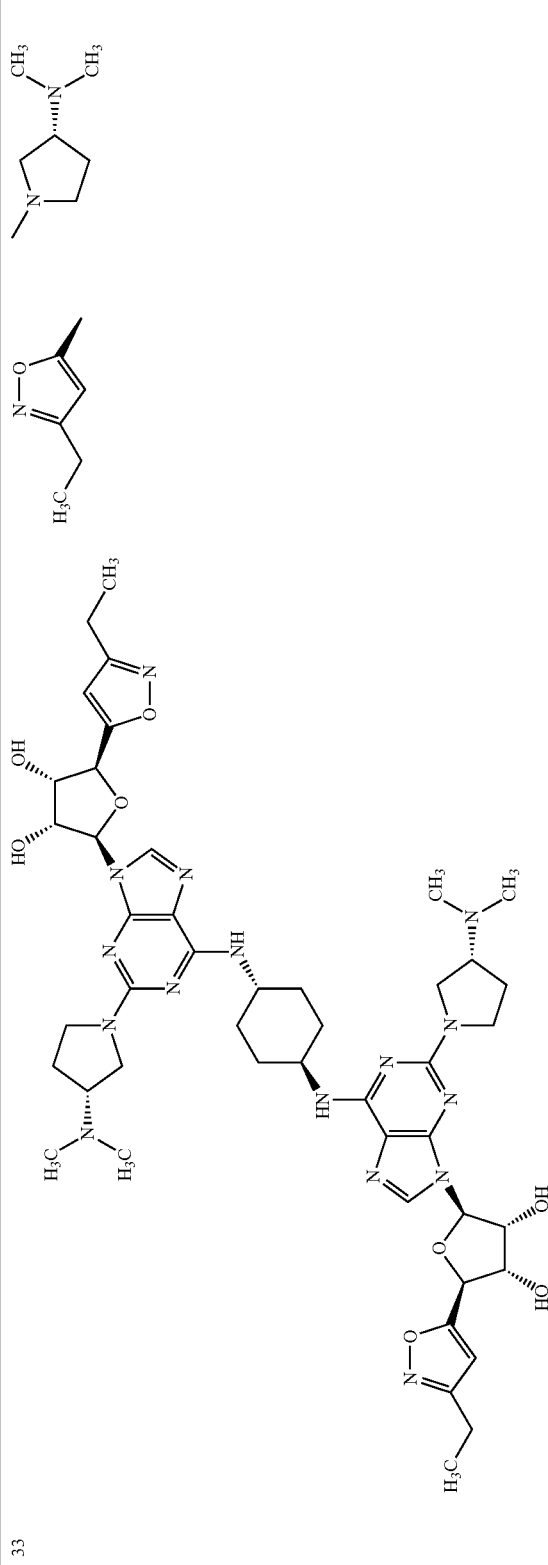
33
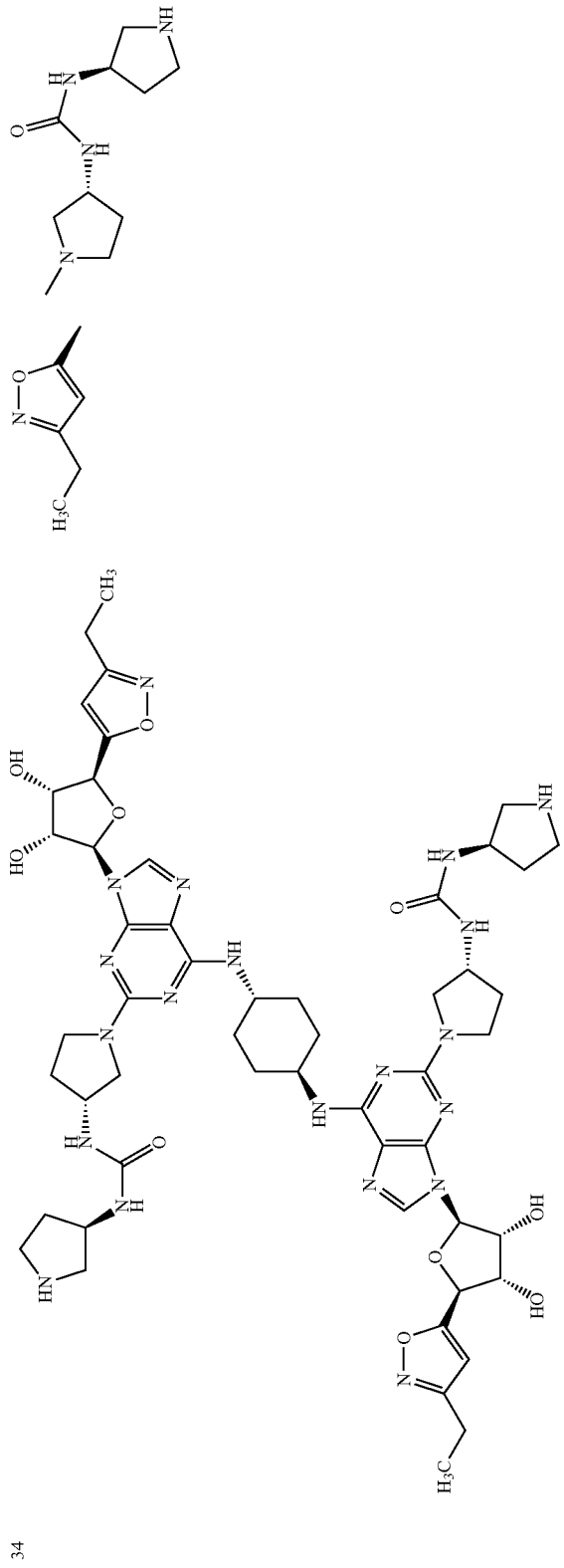
34

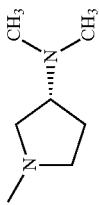
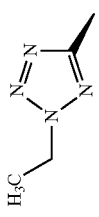
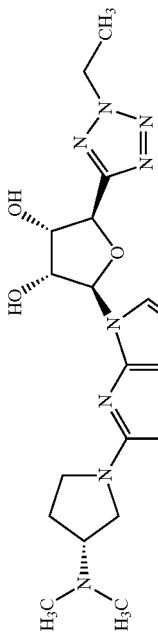
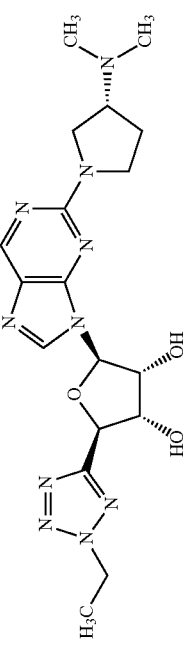

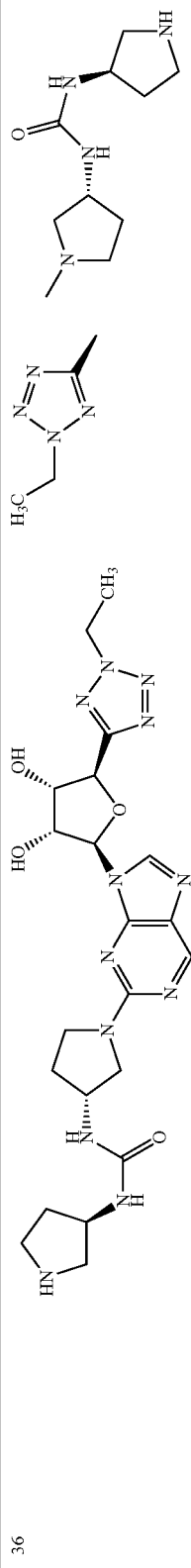
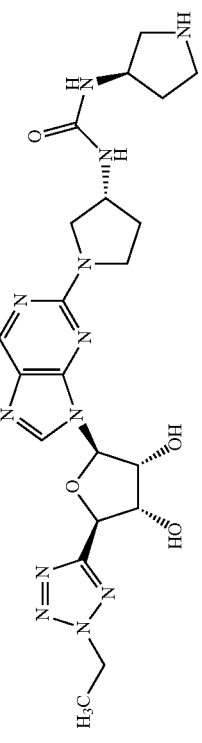
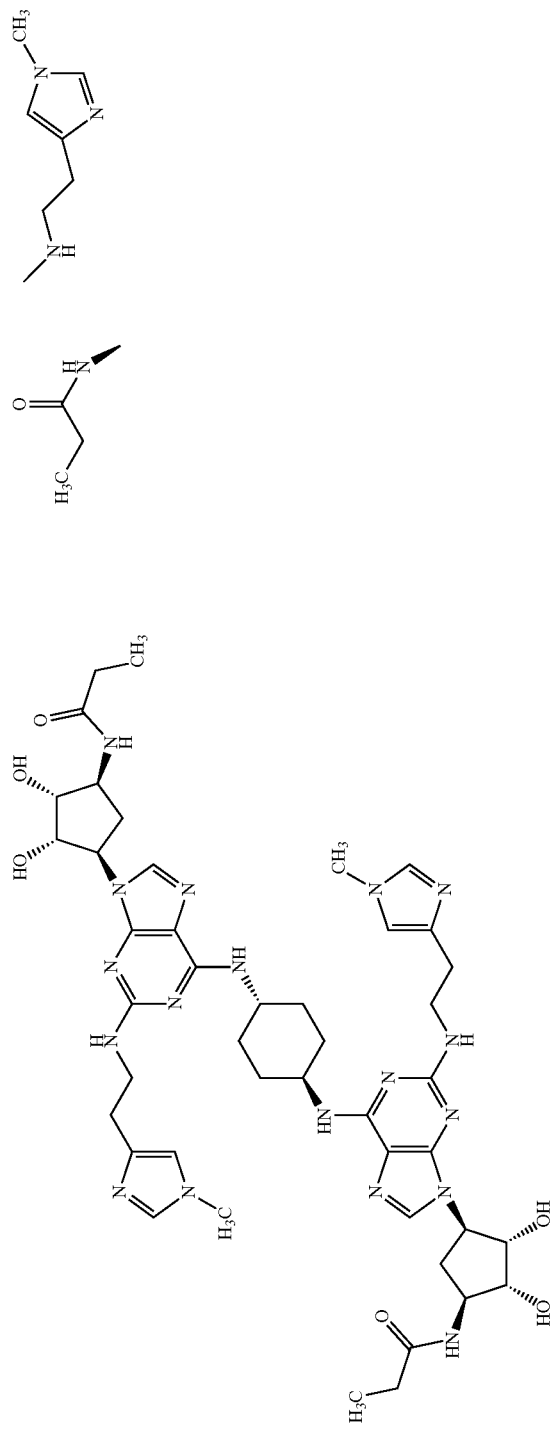

| 38 | 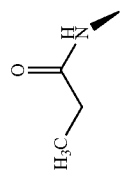 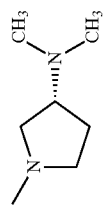 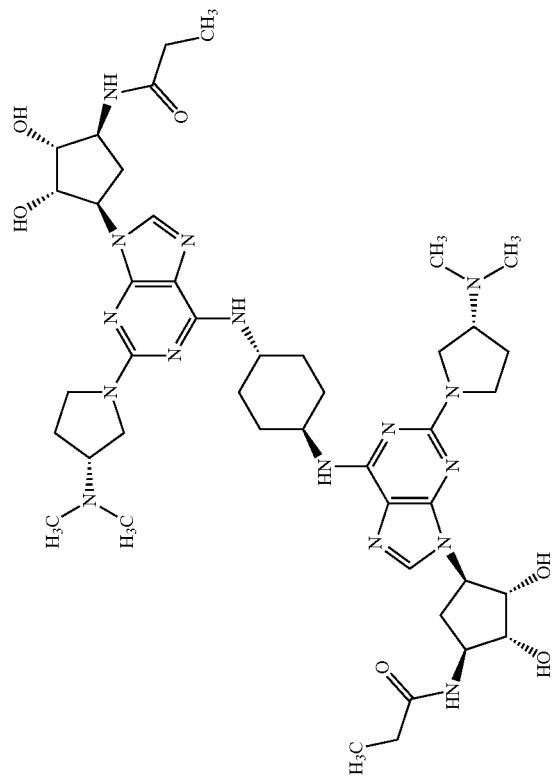 |
| 39 | 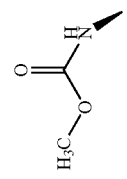 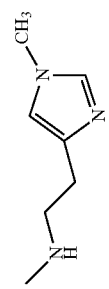 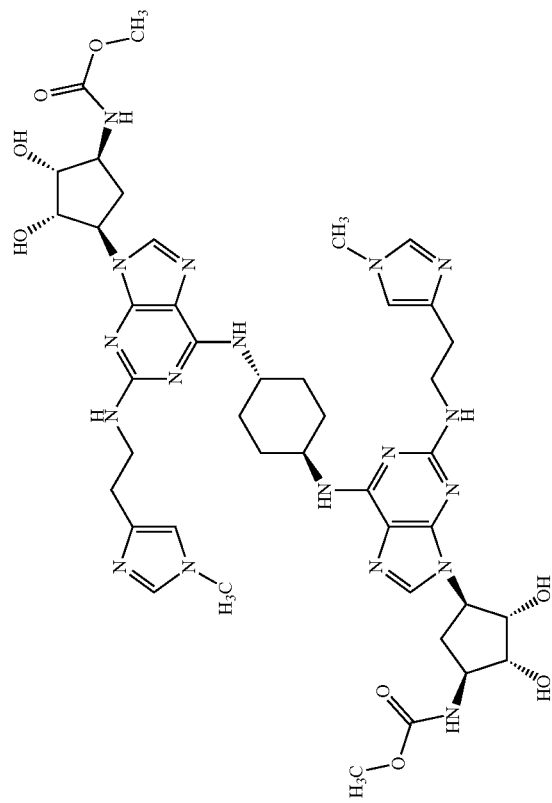 |

| 40 | 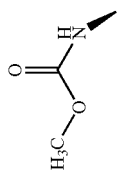 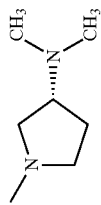 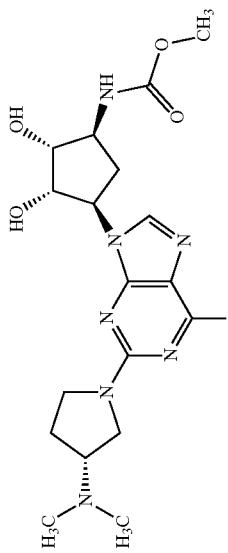 |
| --- | --- |
| 41 | 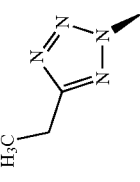 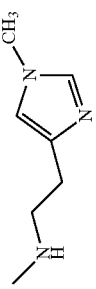 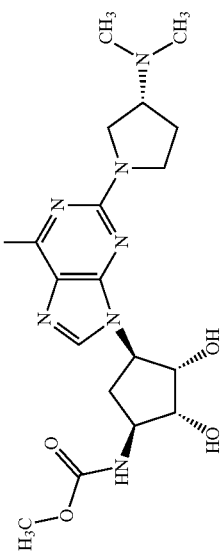 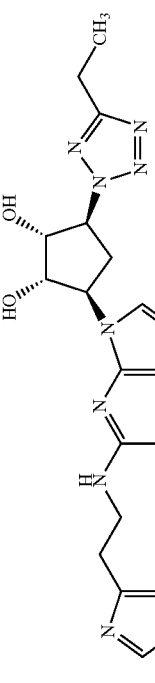 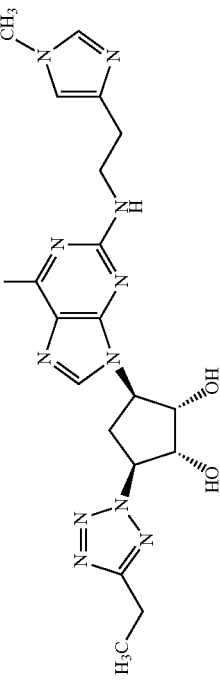 |

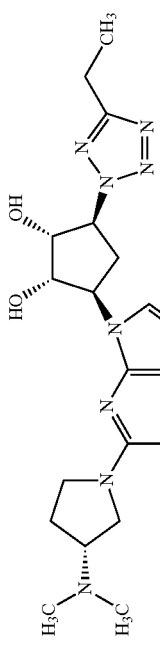
42
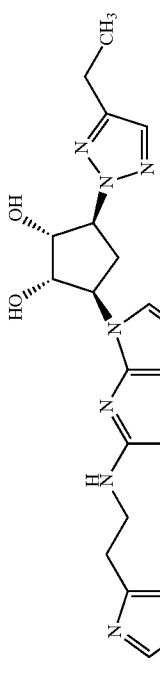
43

| | | | |
|---|---|---|---|
| 44 | 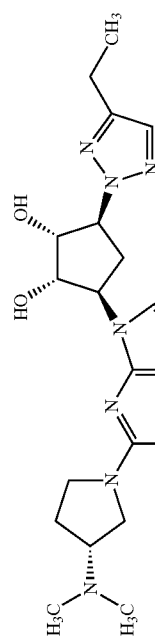 | 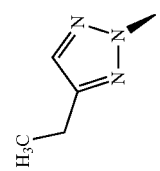 | 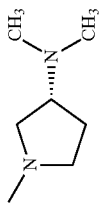 |
| 45 | 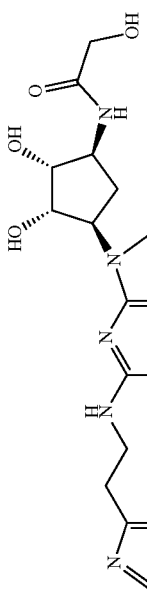 | 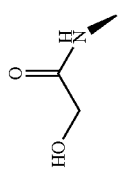 | 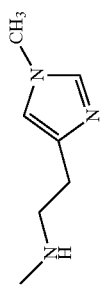 |

| 46 | 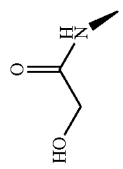 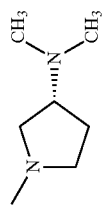 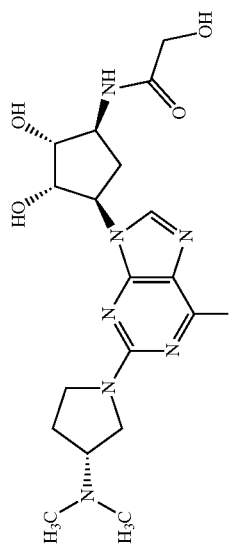 |
| 47 | 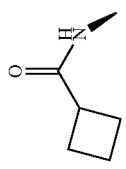  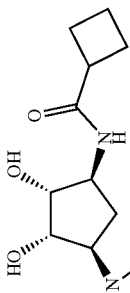 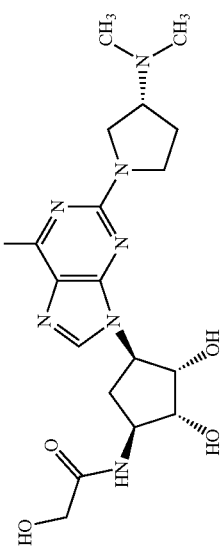 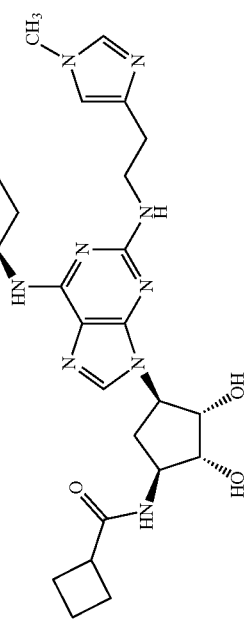 |

| 48 | 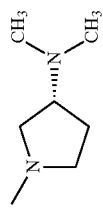 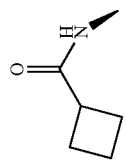 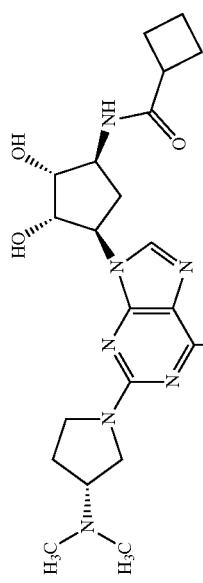 |
| --- | --- |
| 49 | 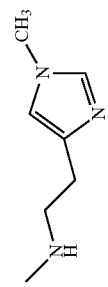 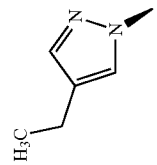 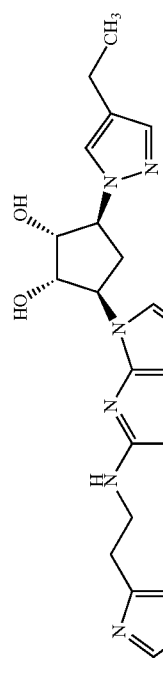 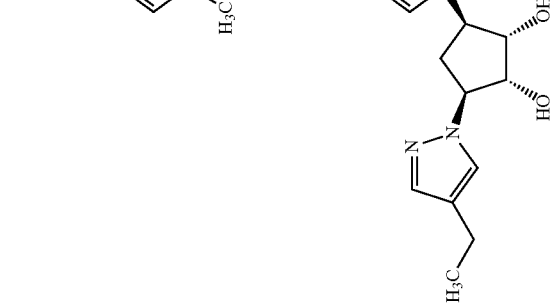 |

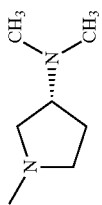
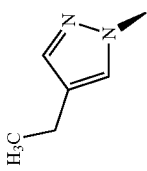
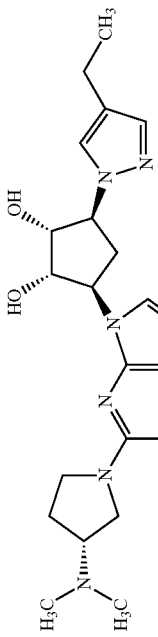
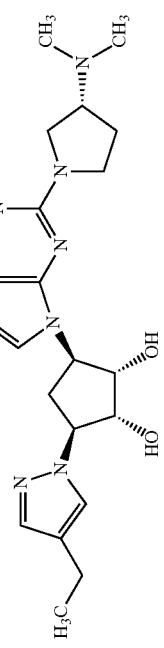

Examples 51-90

The compounds of formula (X1) are shown in the following table. Methods of preparing such compounds are described hereinafter.

| Ex | Structure | R11 | A |
|---|---|---|---|
| | (X1) M is CH2 except in Example 51-66 where M is O | | |
| 51 | 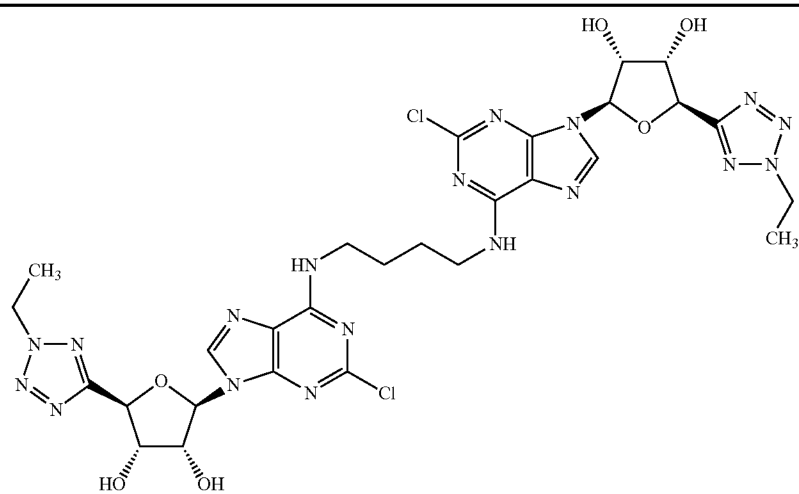 | 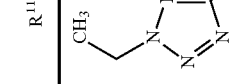 | 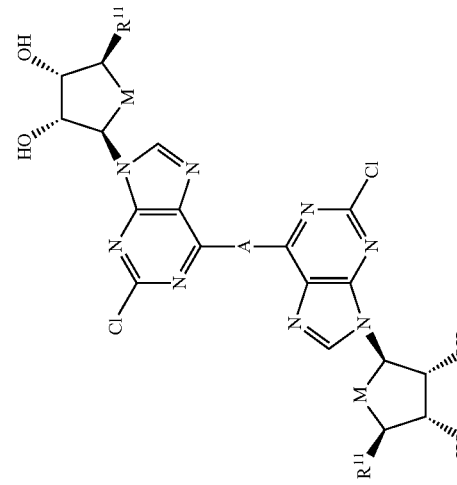 |

| | | | |
|---|---|---|---|
| 52 | 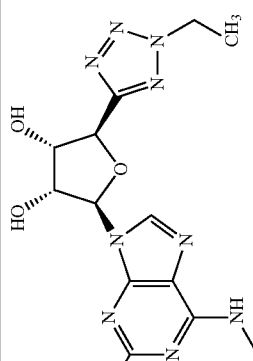 | 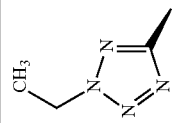 | 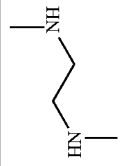 |
| 53 | 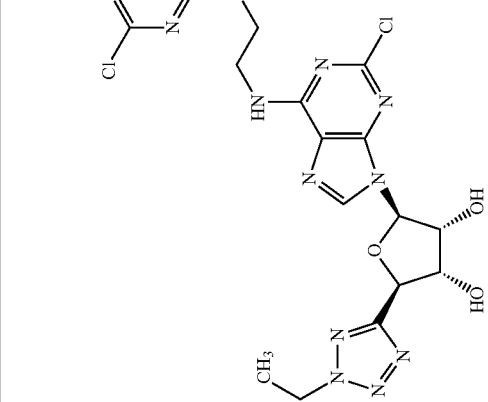 | 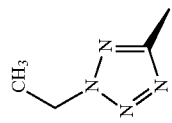 | 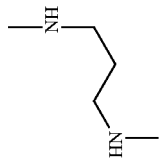 |
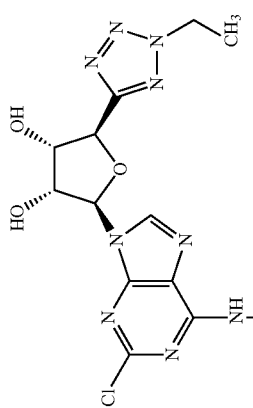
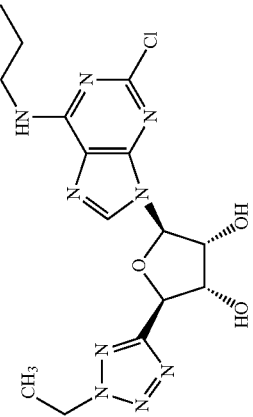

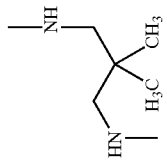
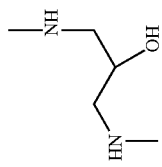
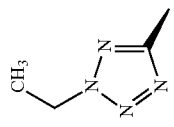
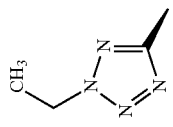
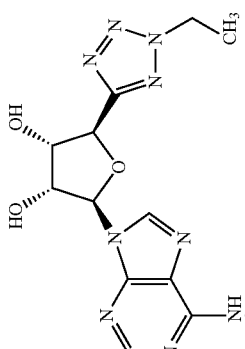
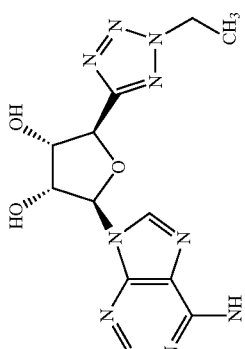
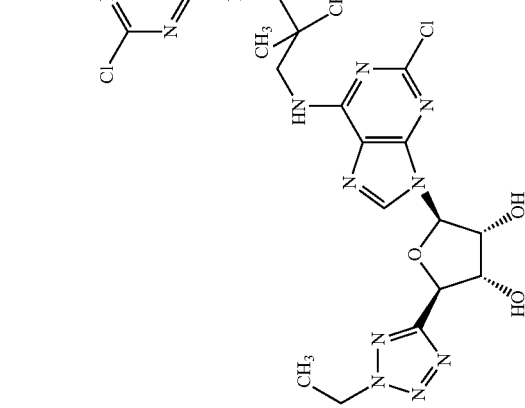
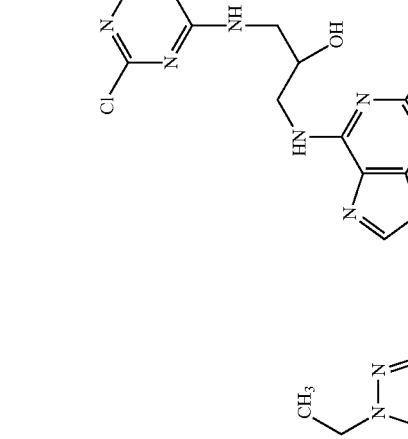

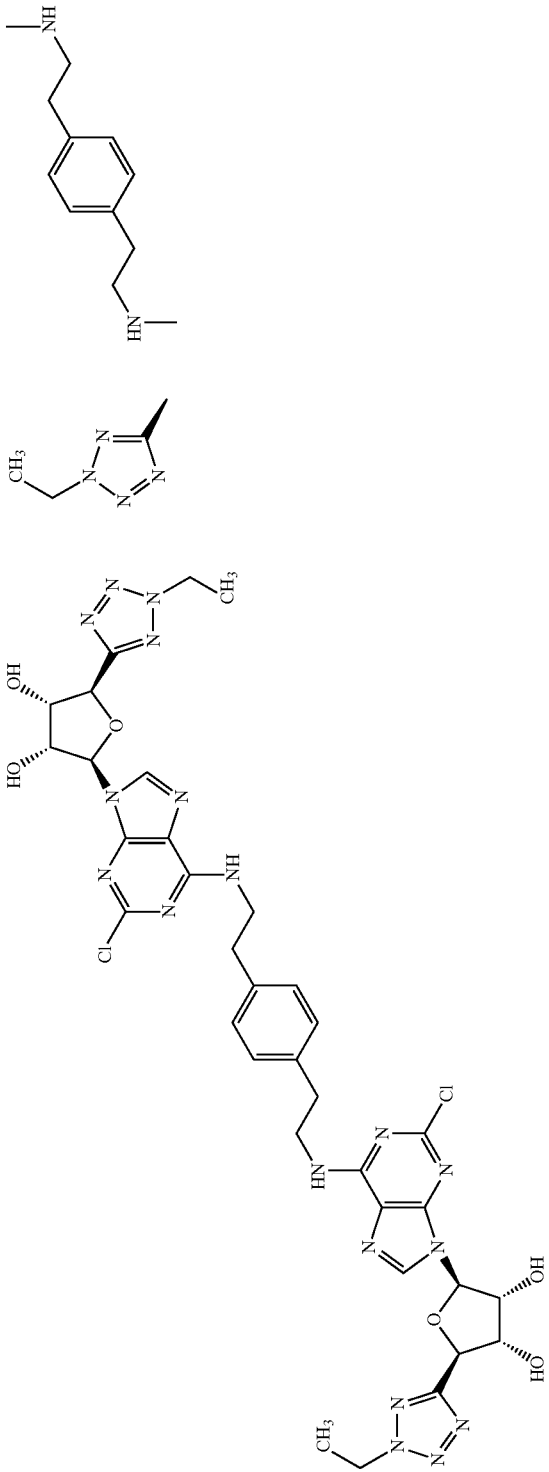

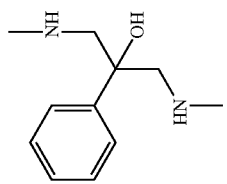
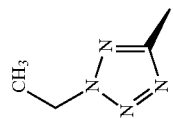
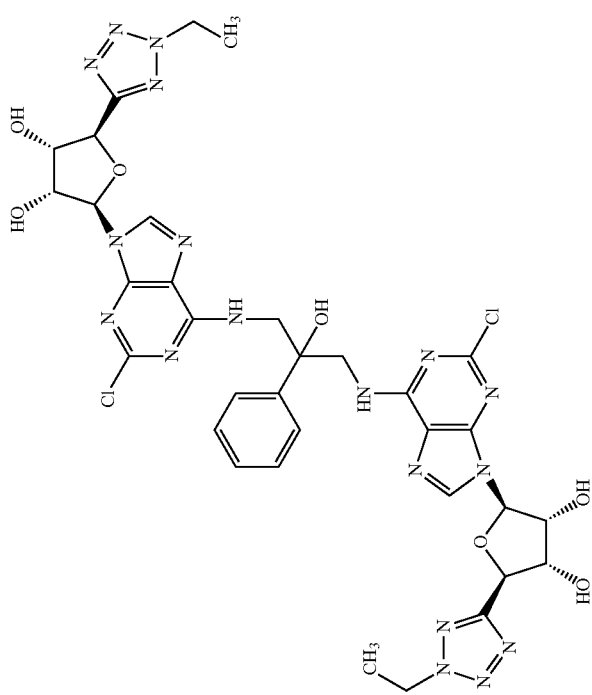

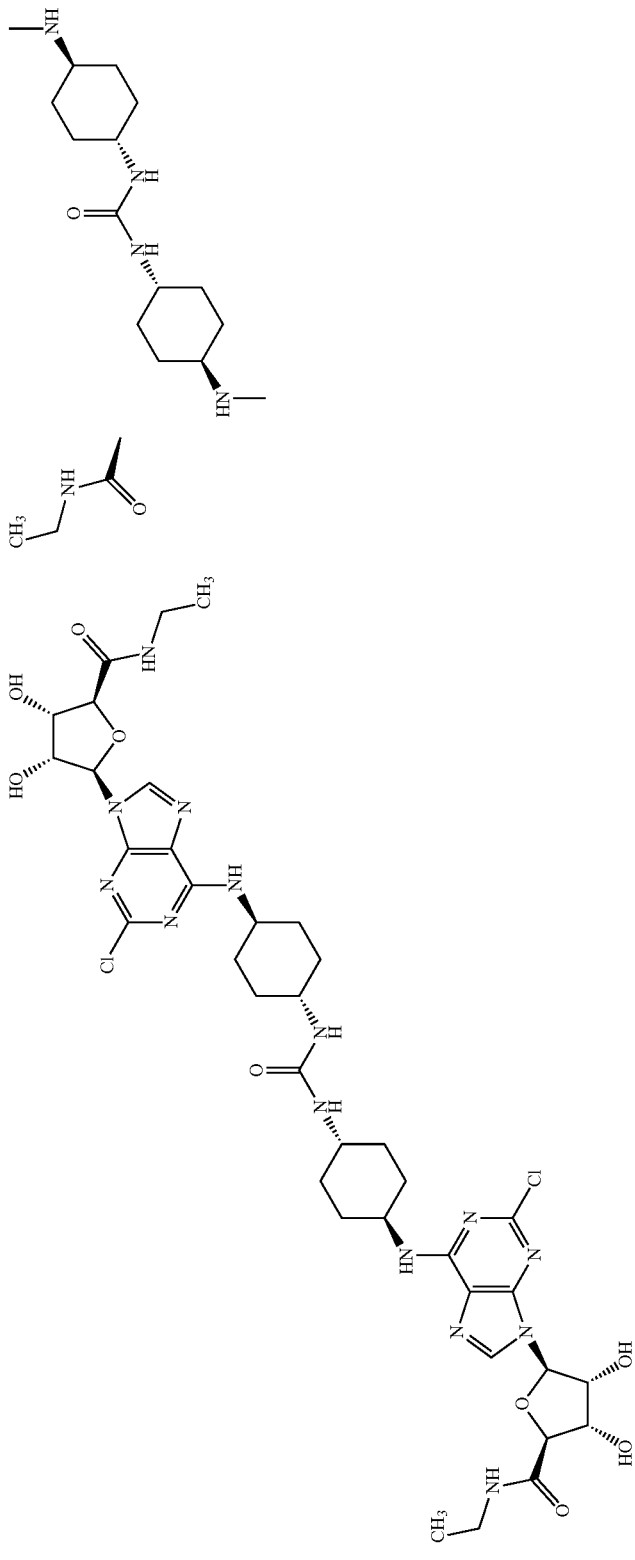
58

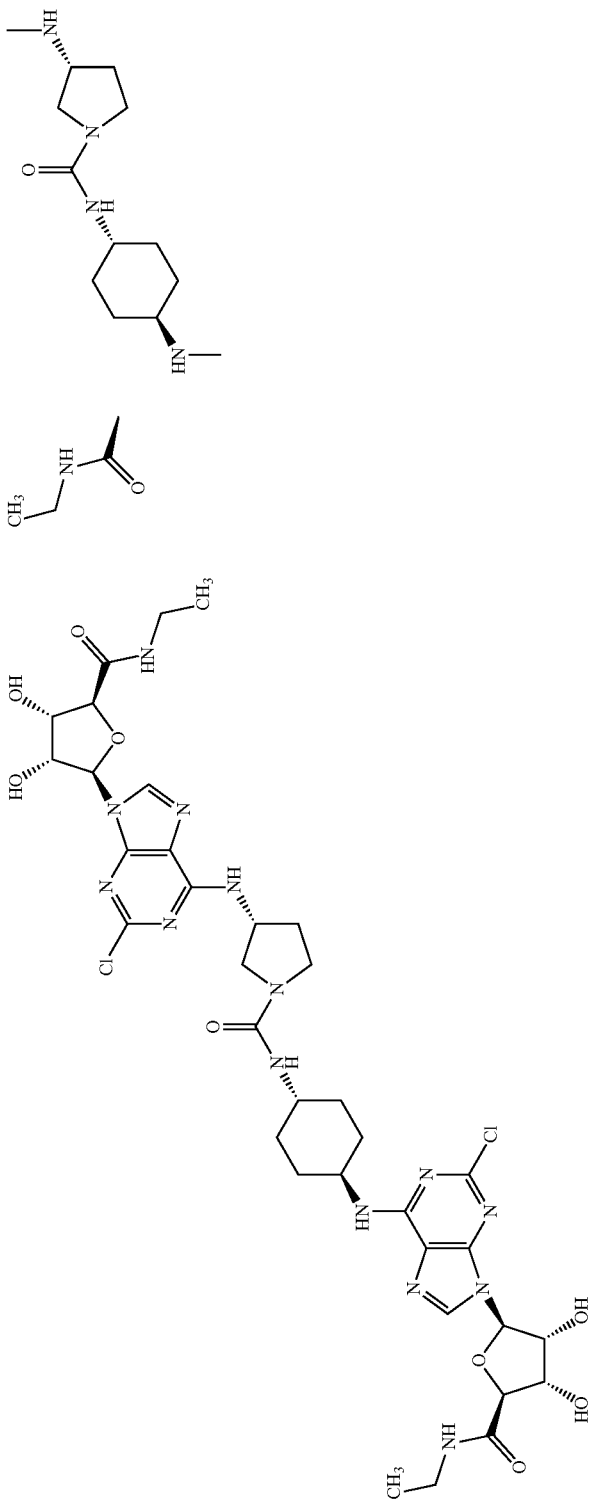

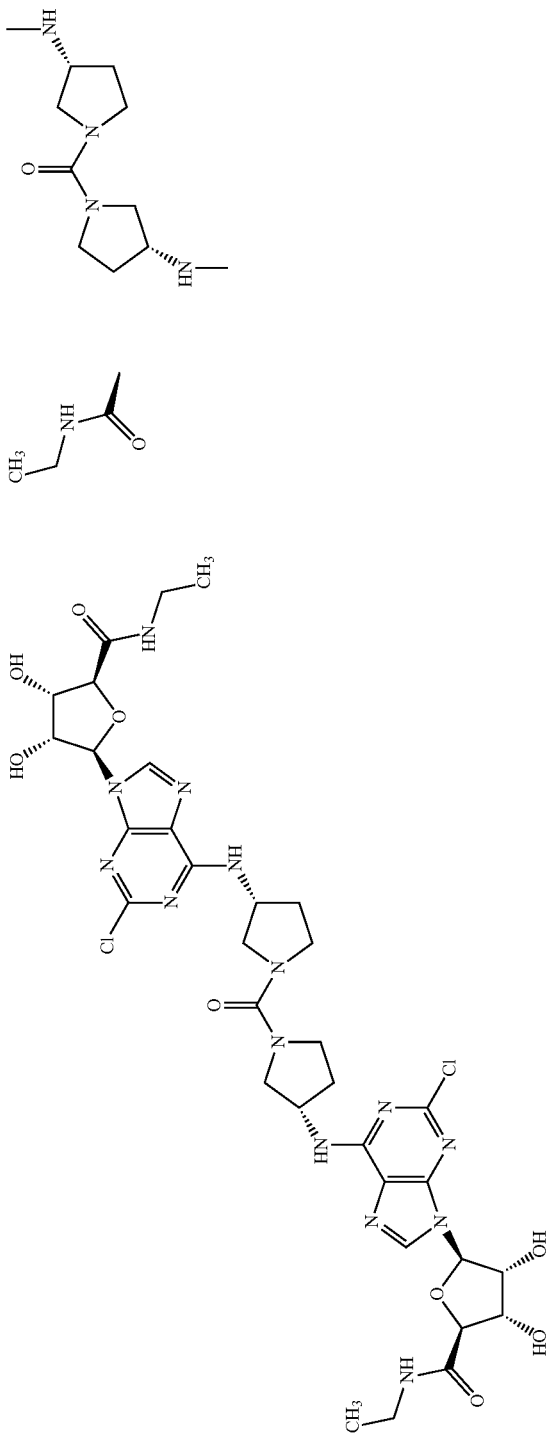

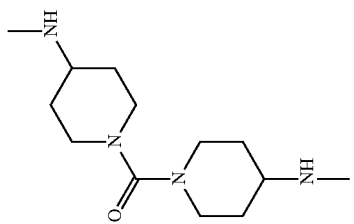
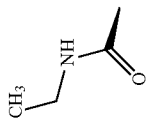
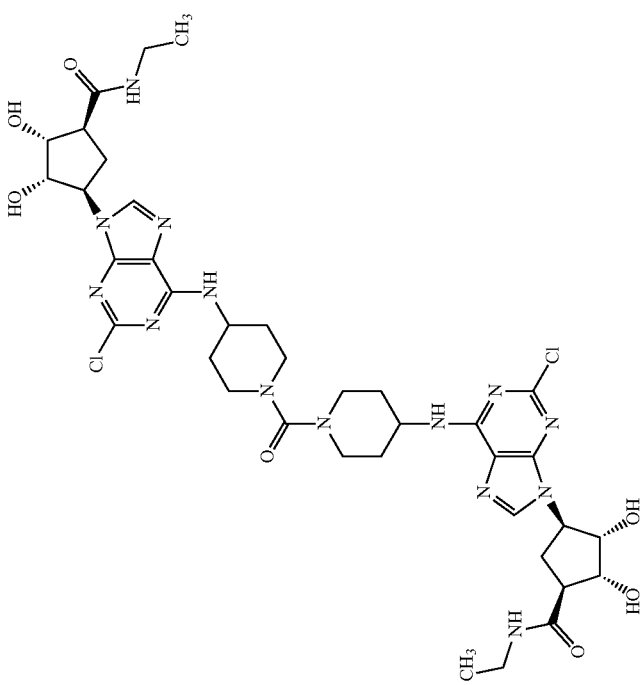

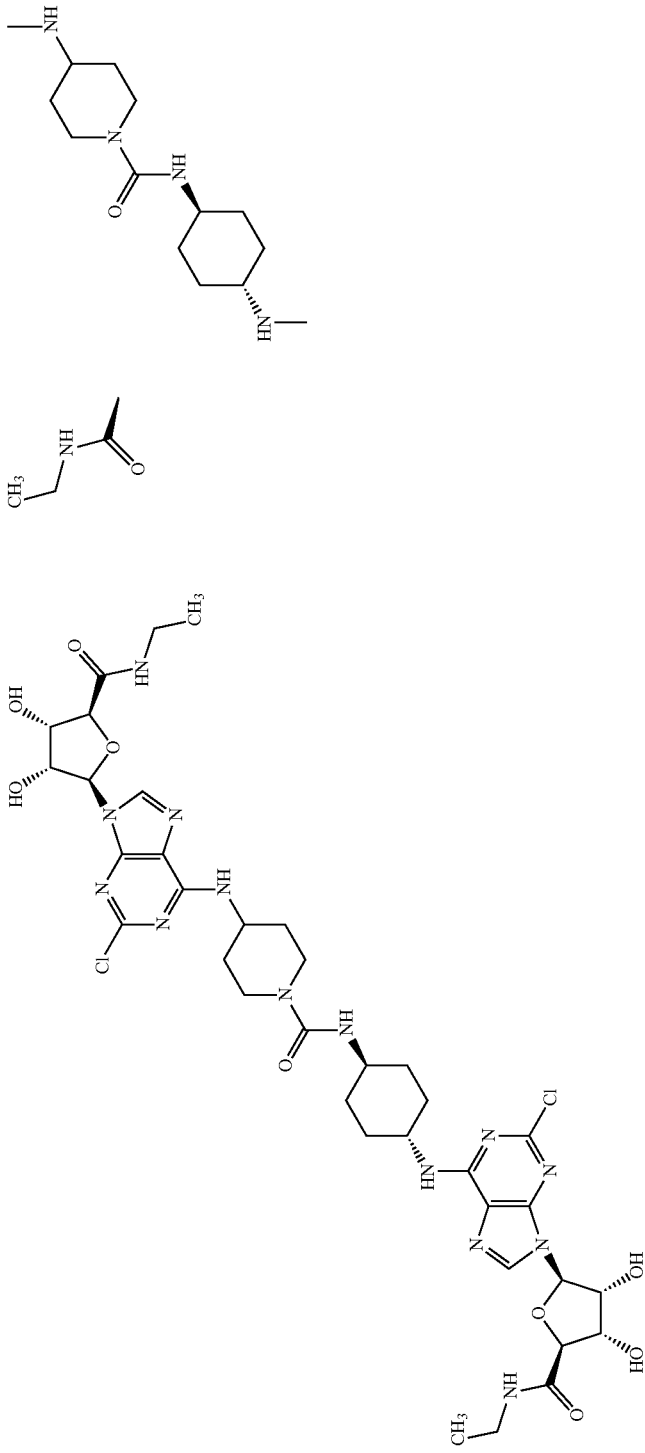

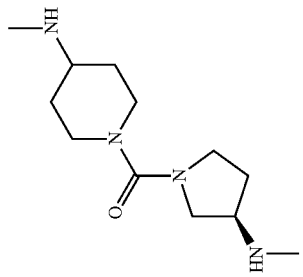
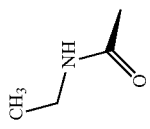
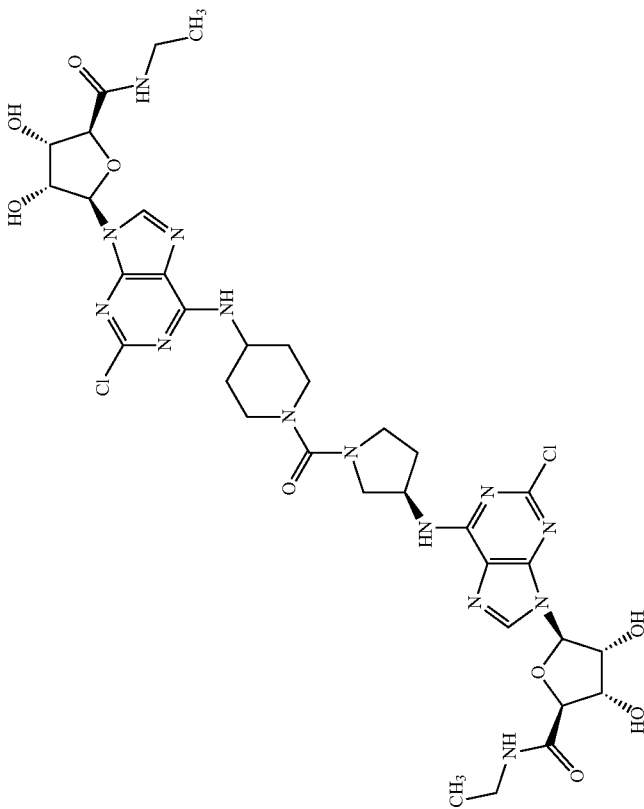
63

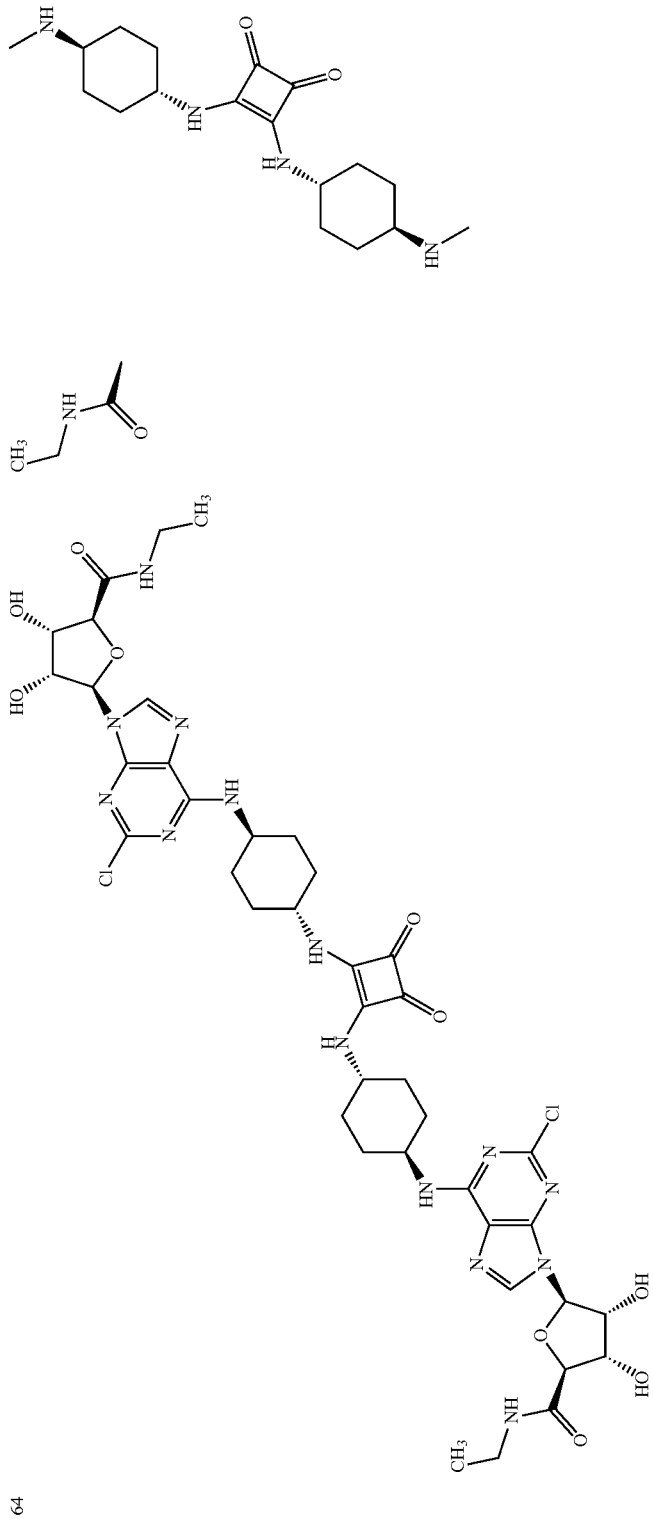

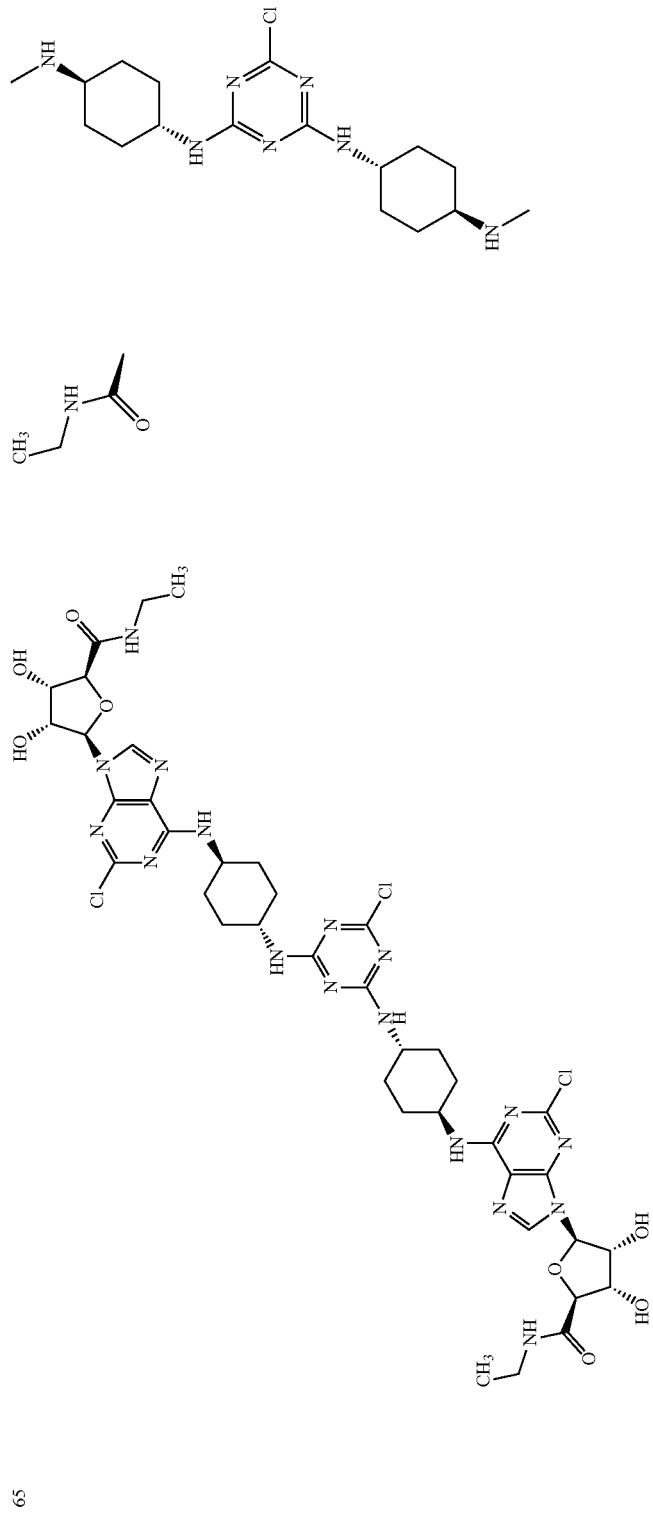

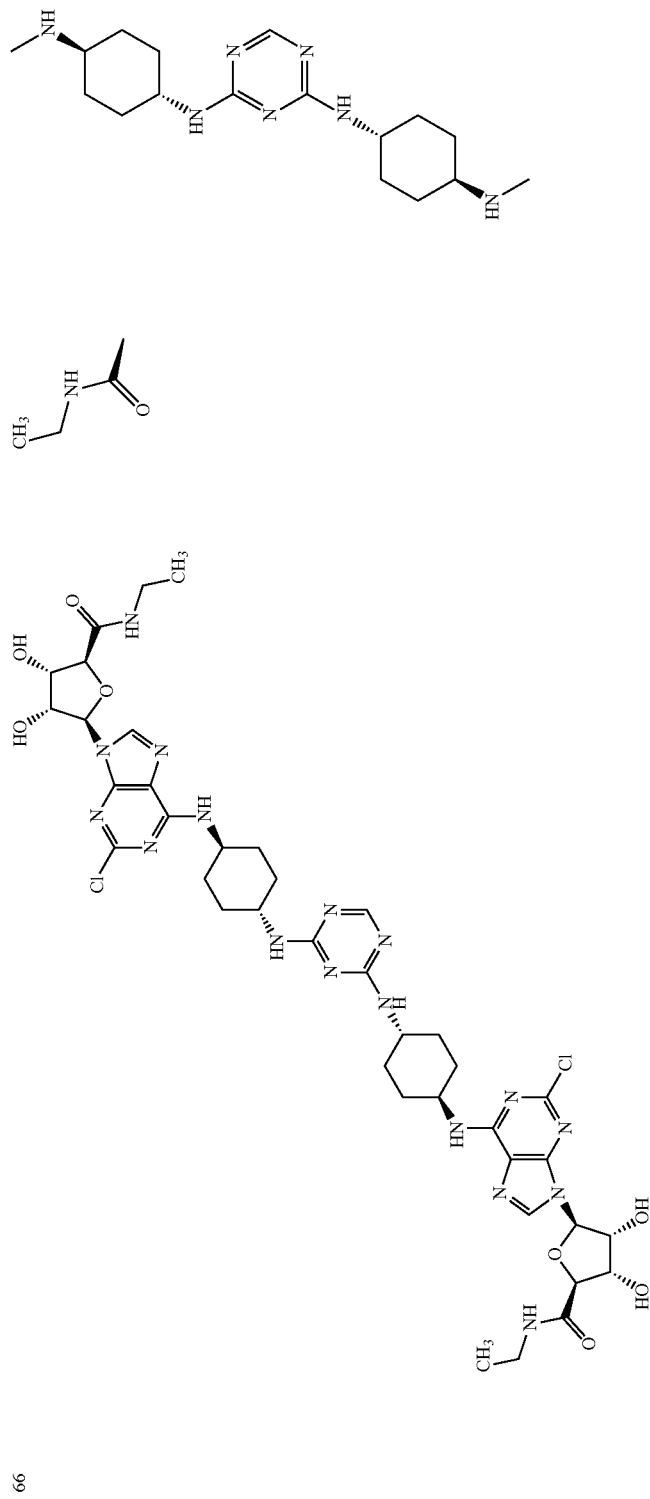

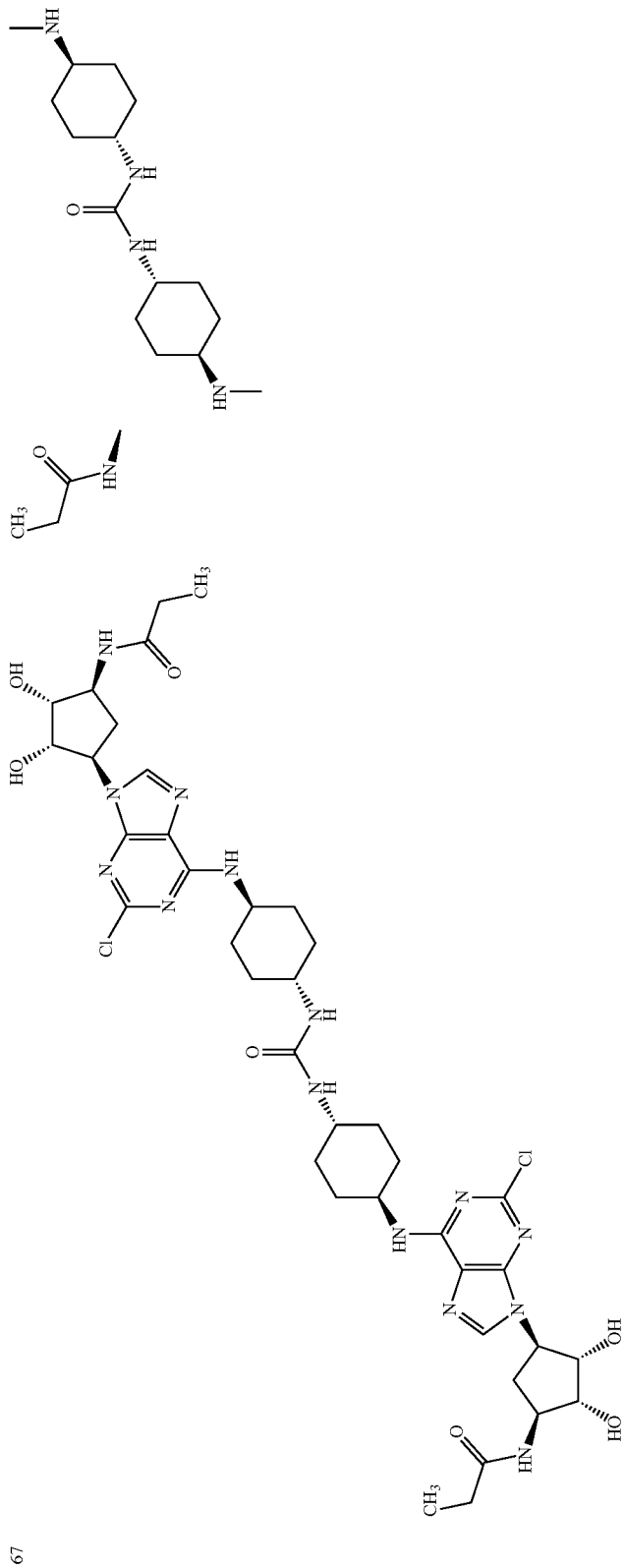

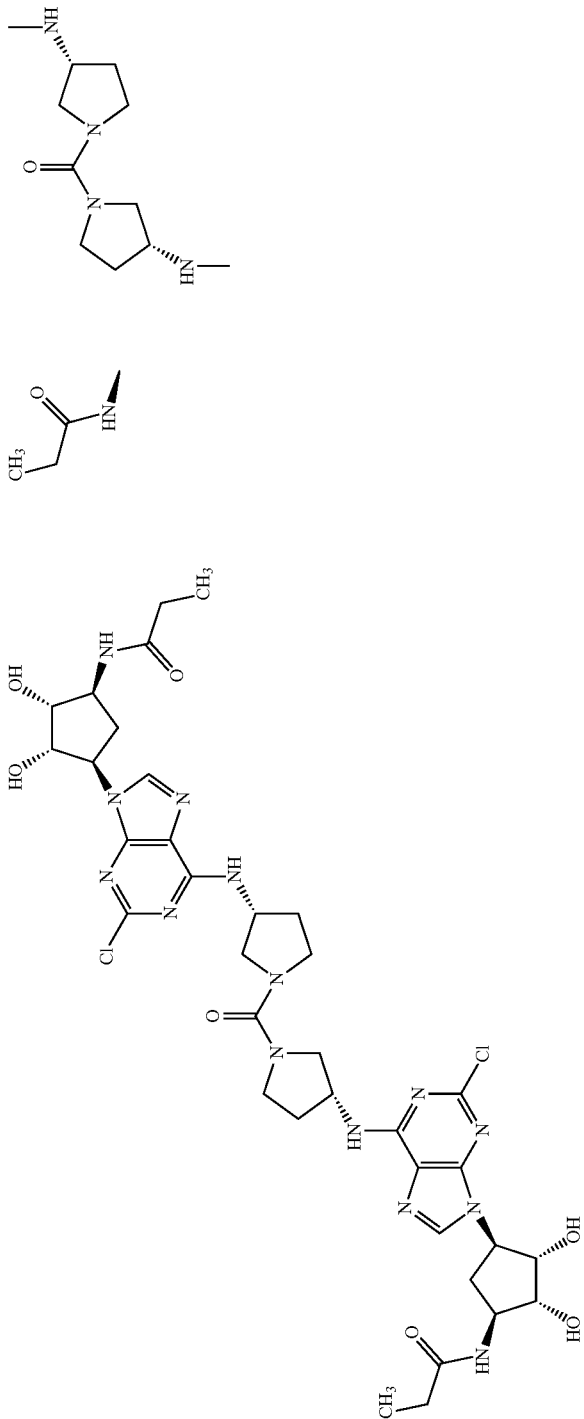

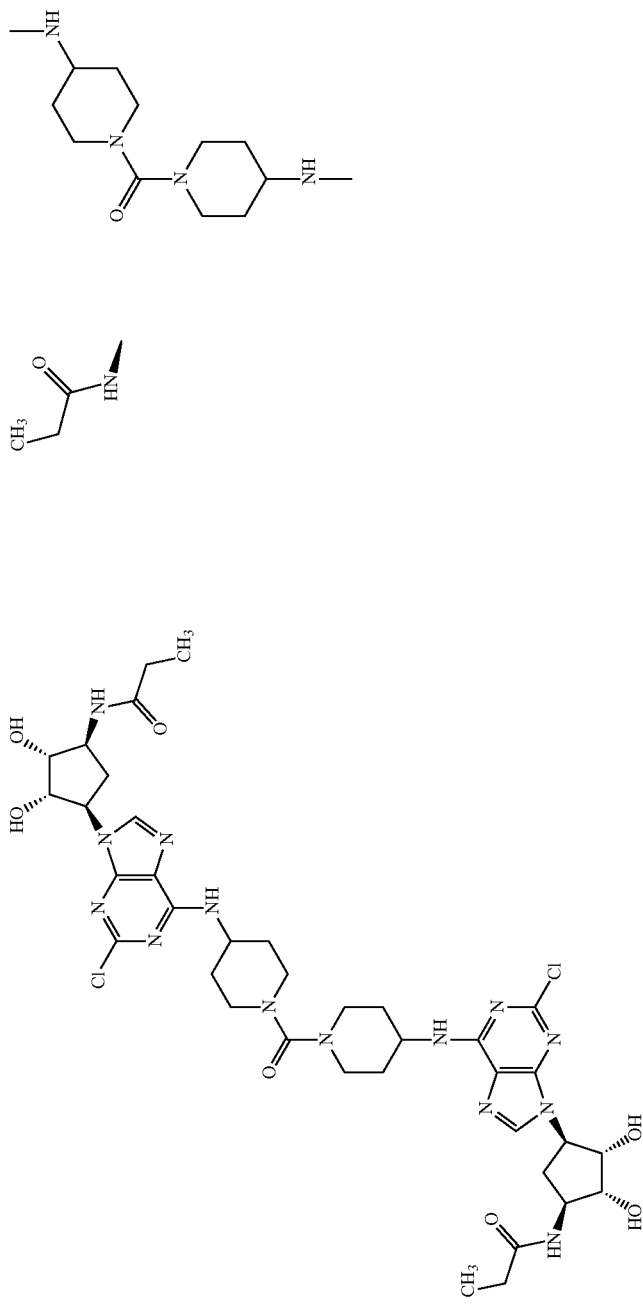

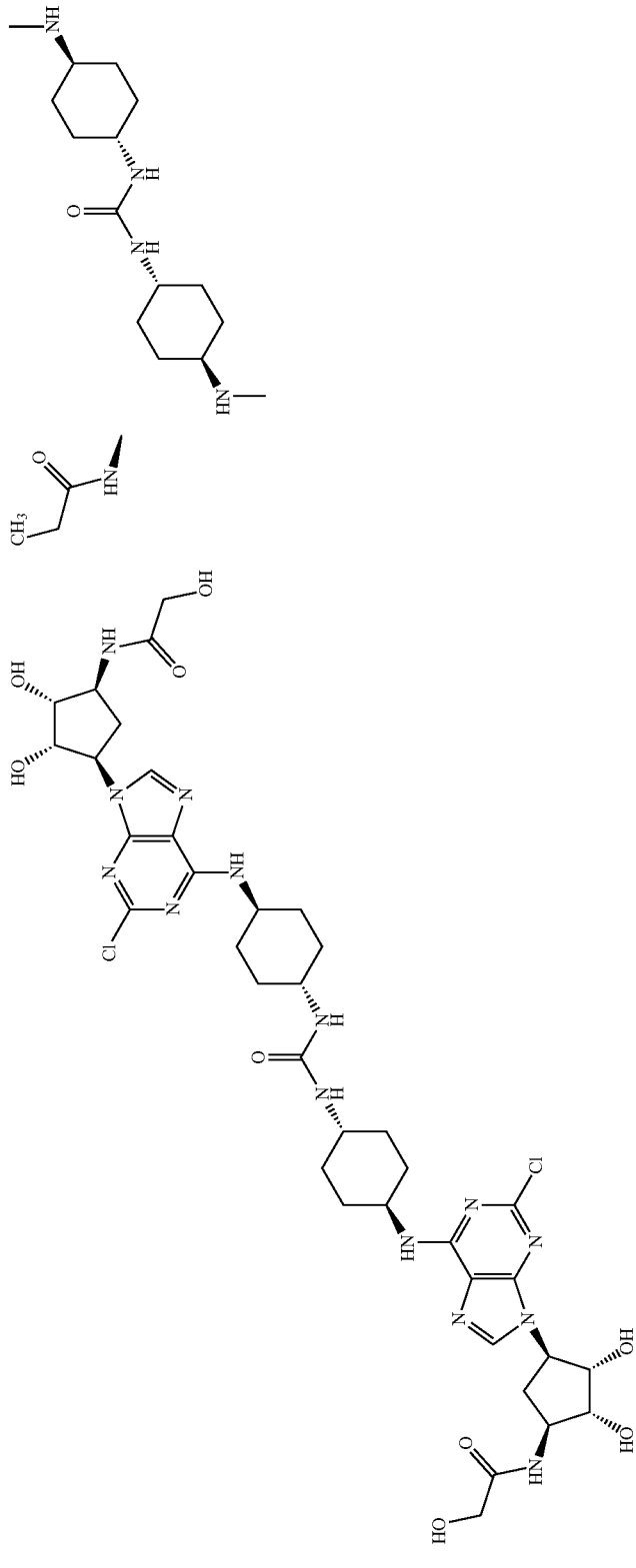
70

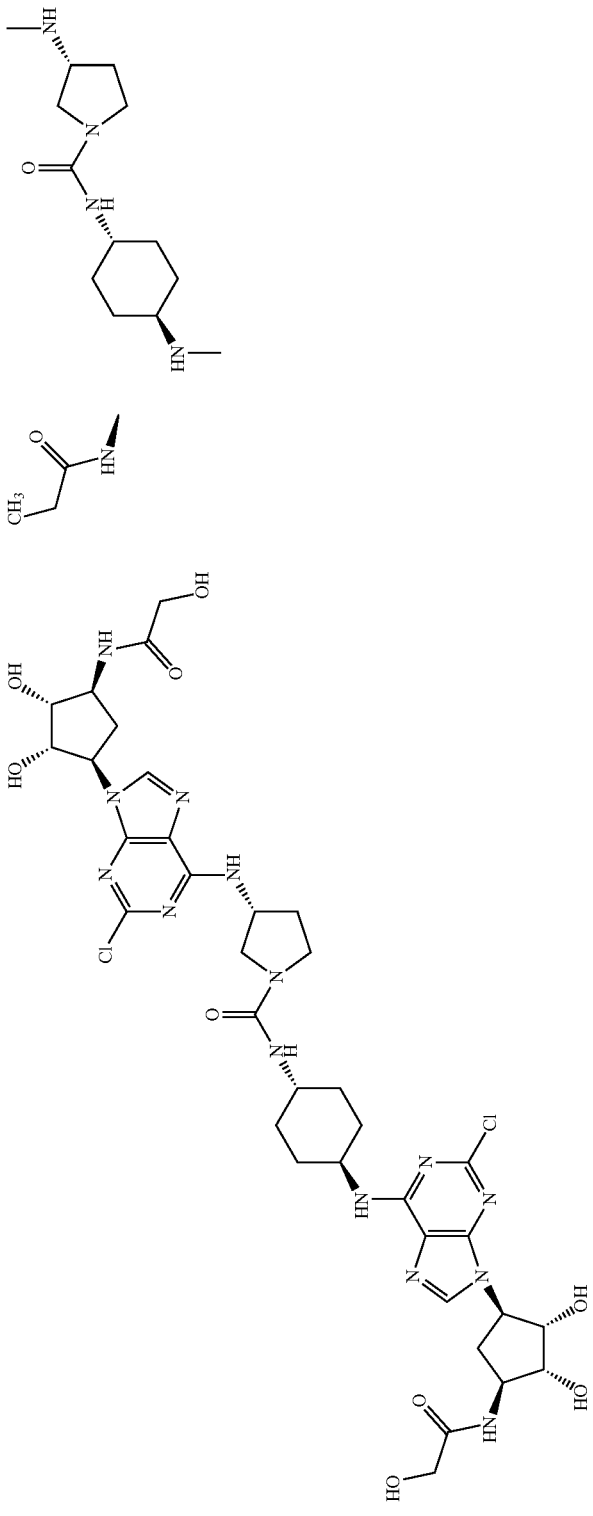
71

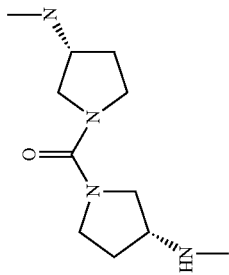
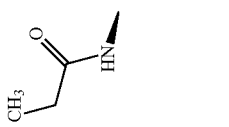
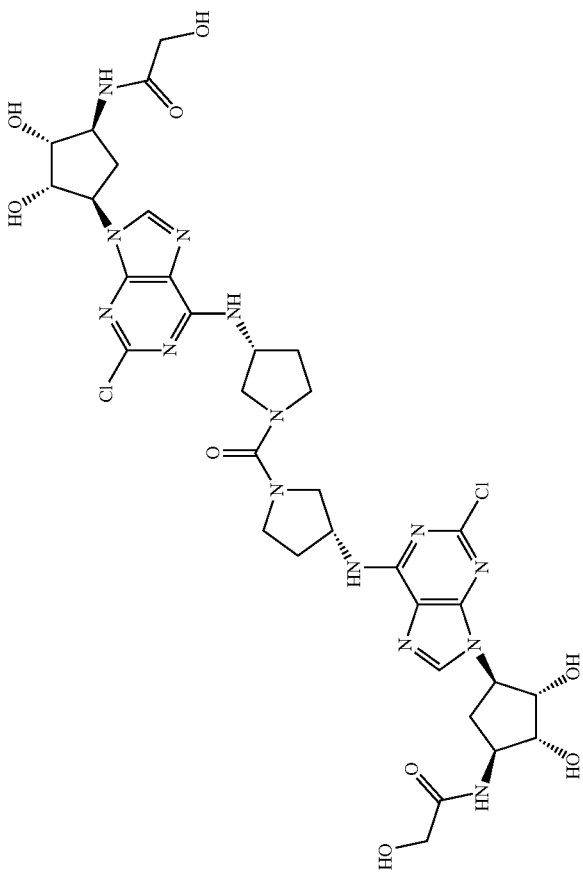

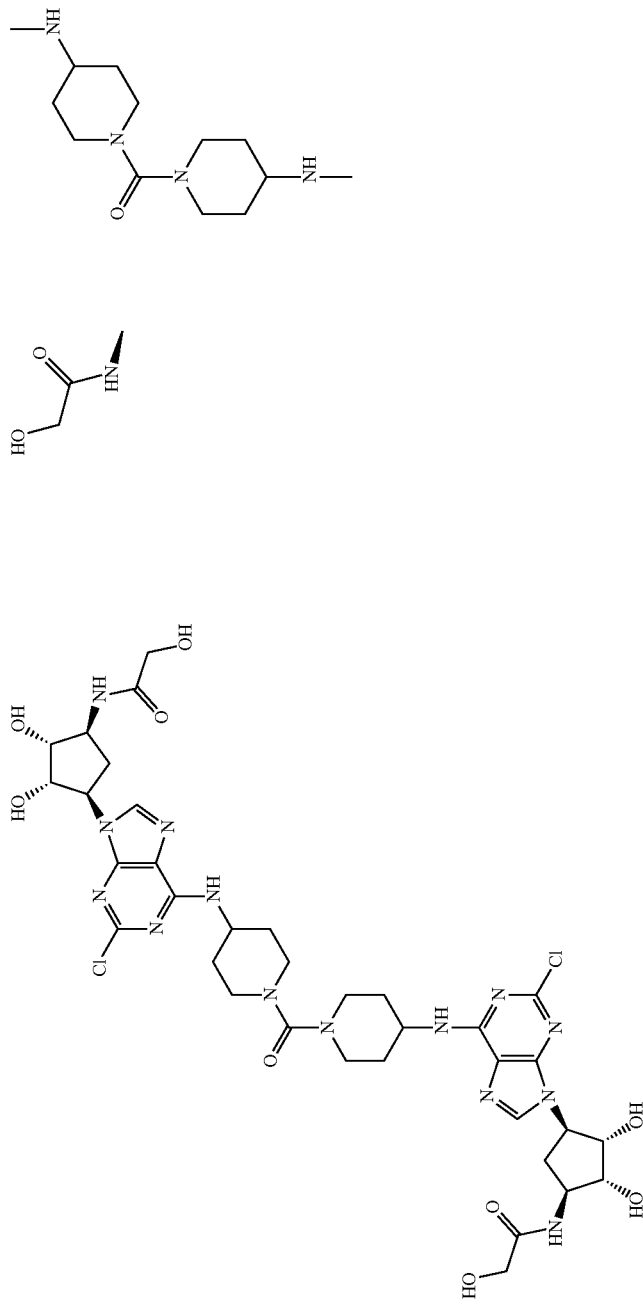

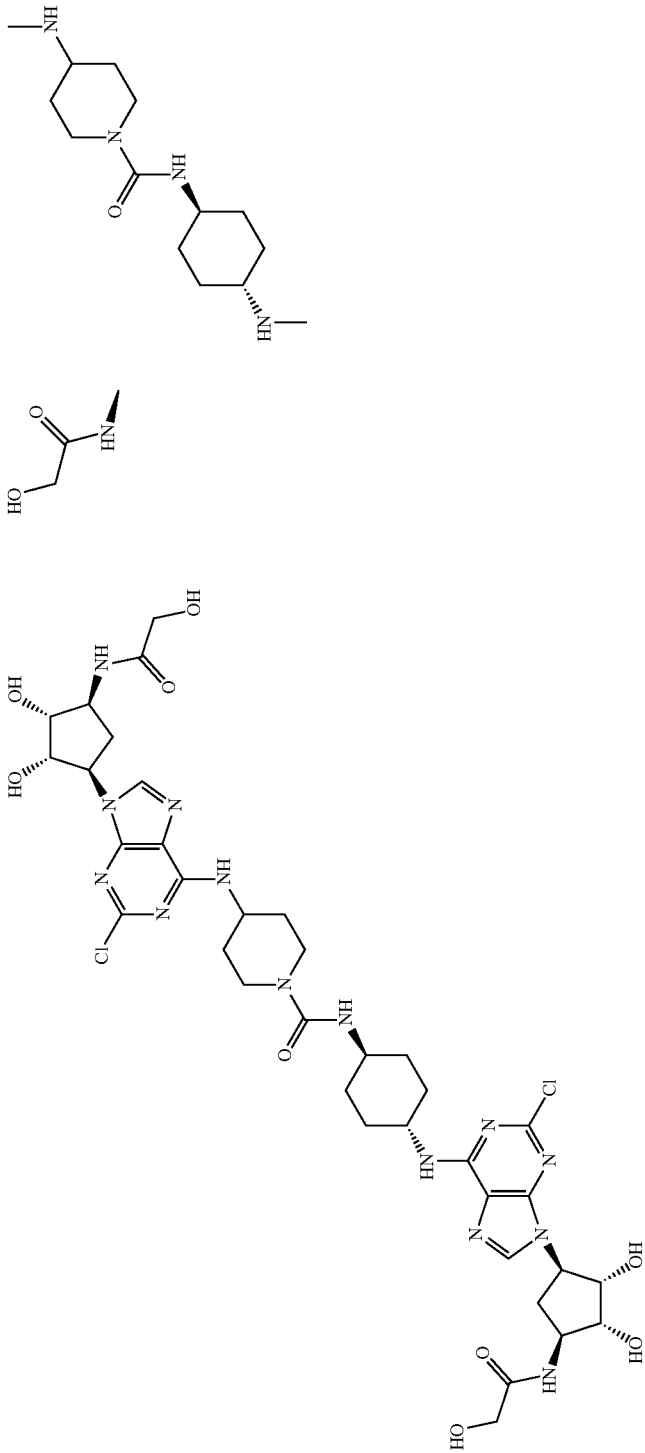

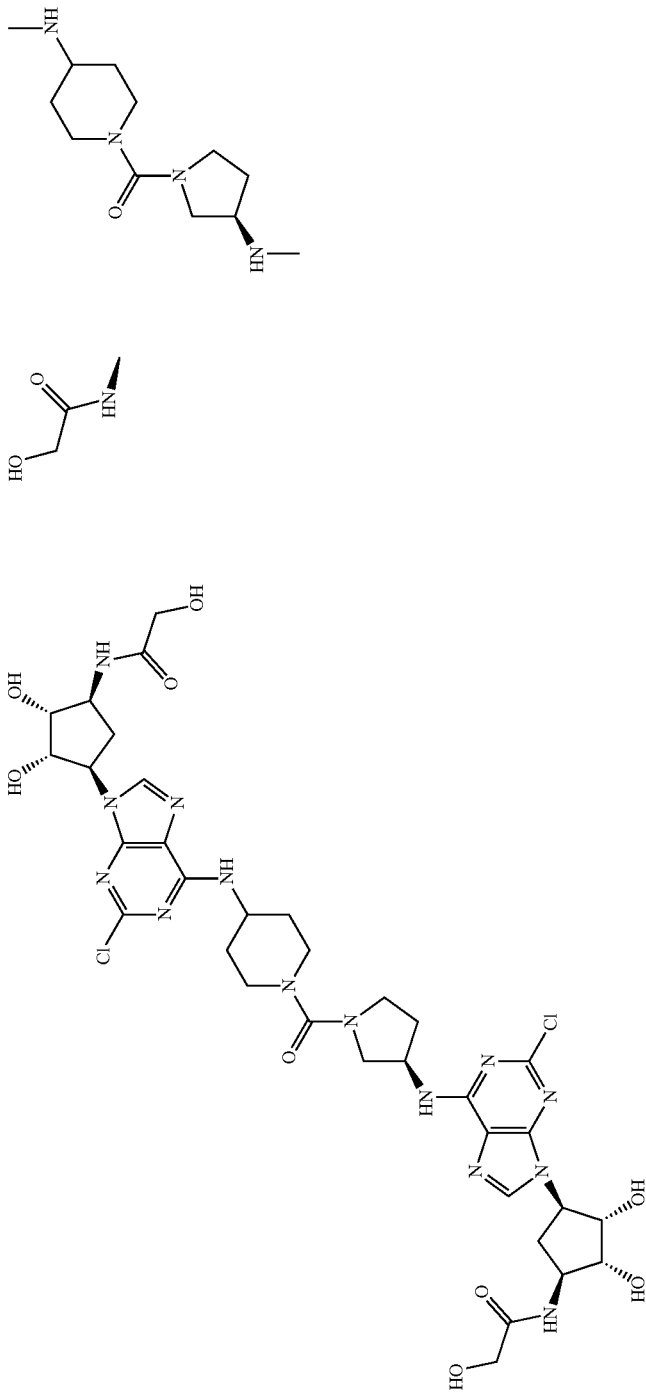

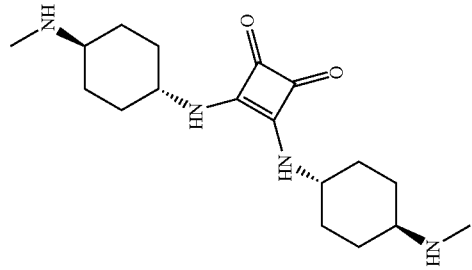
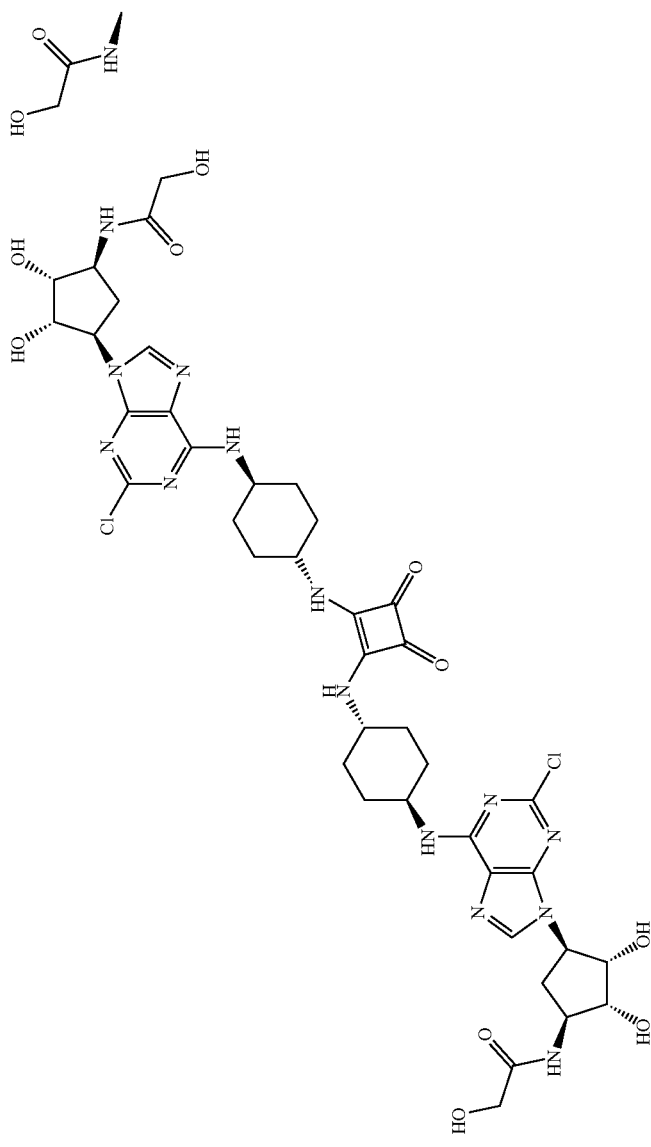
76

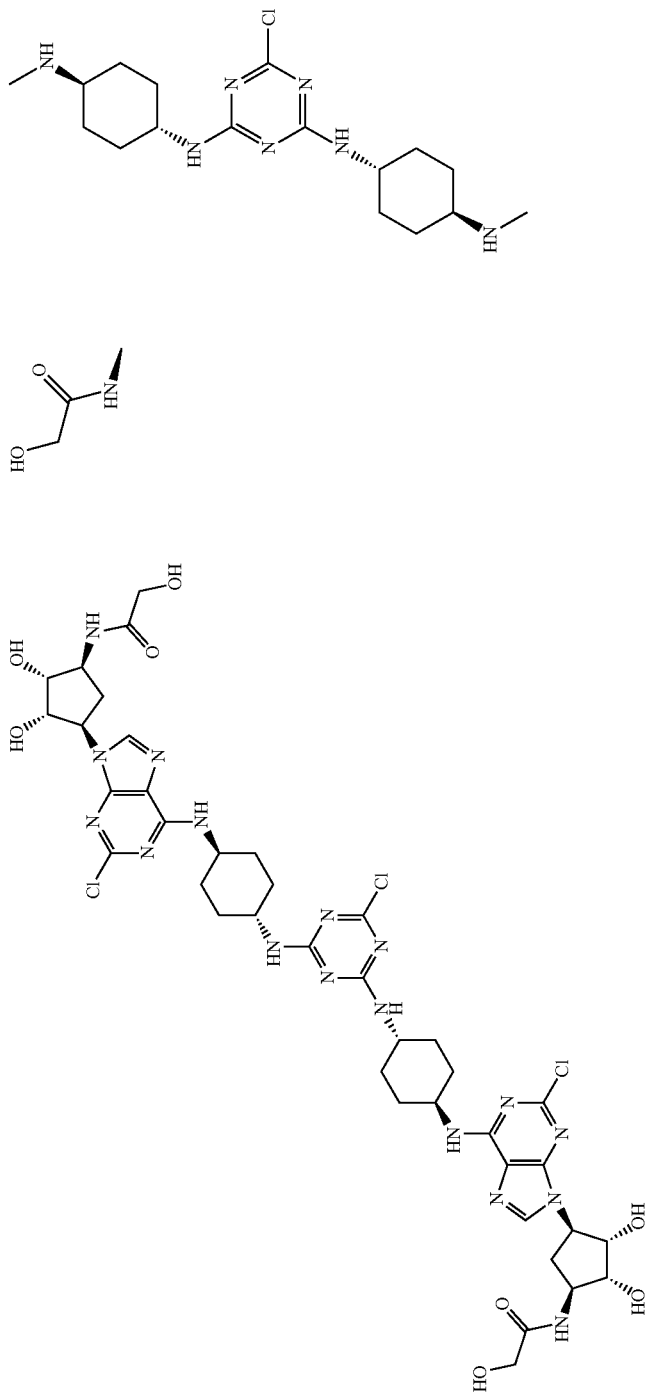

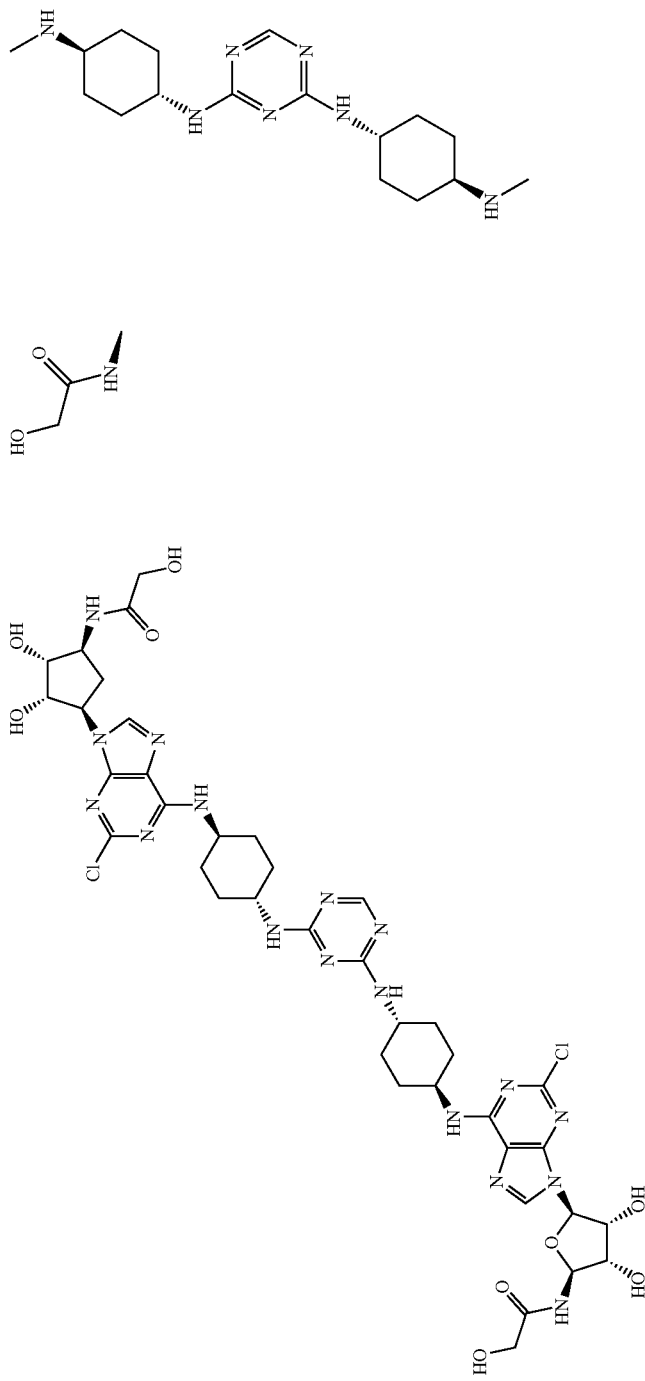

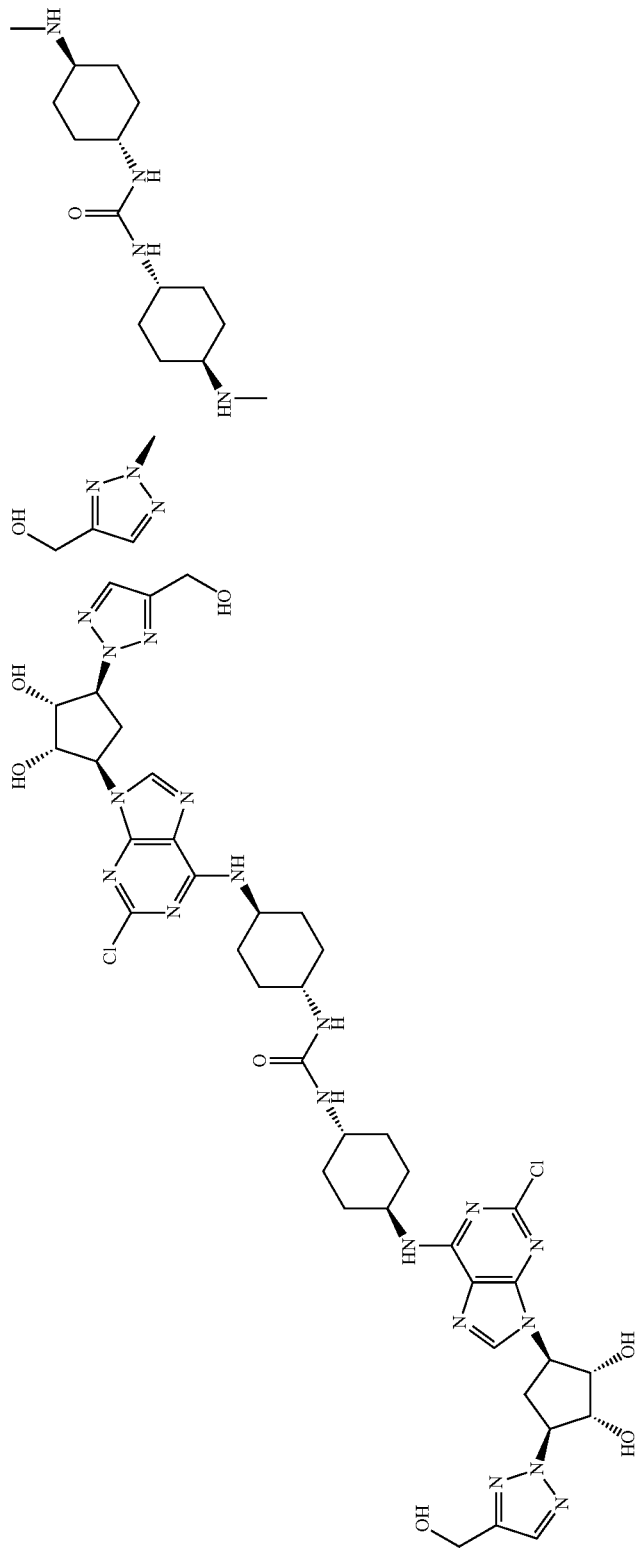

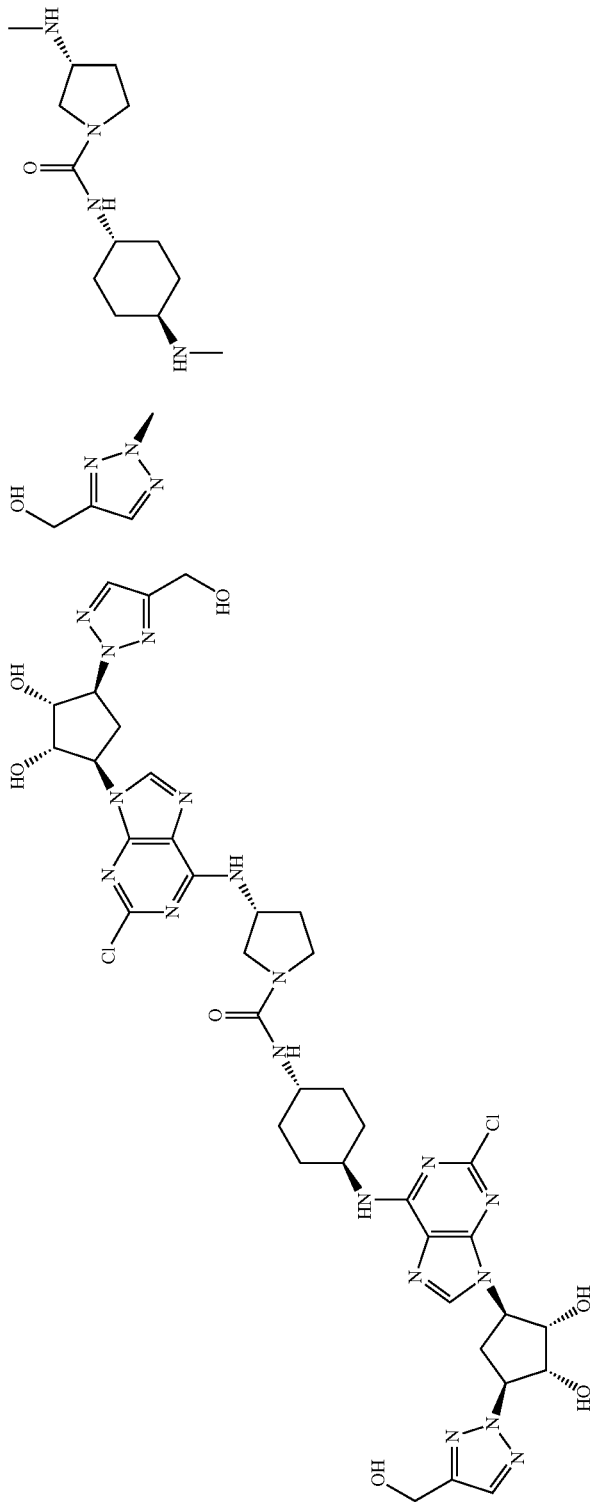
80

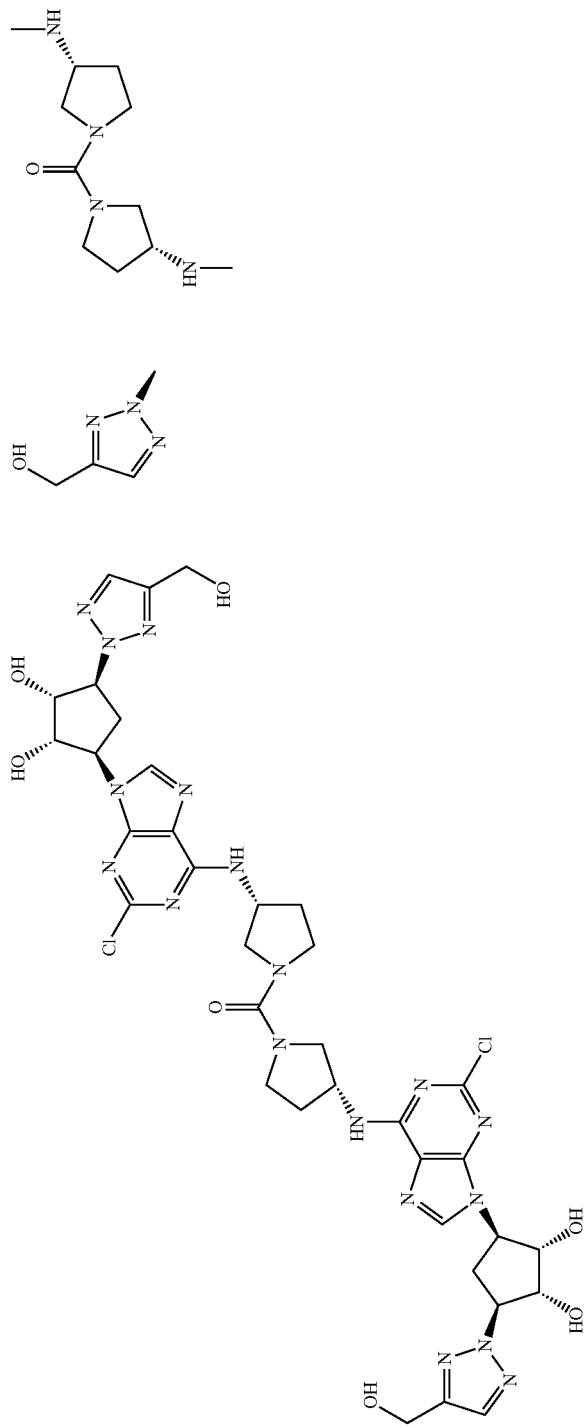

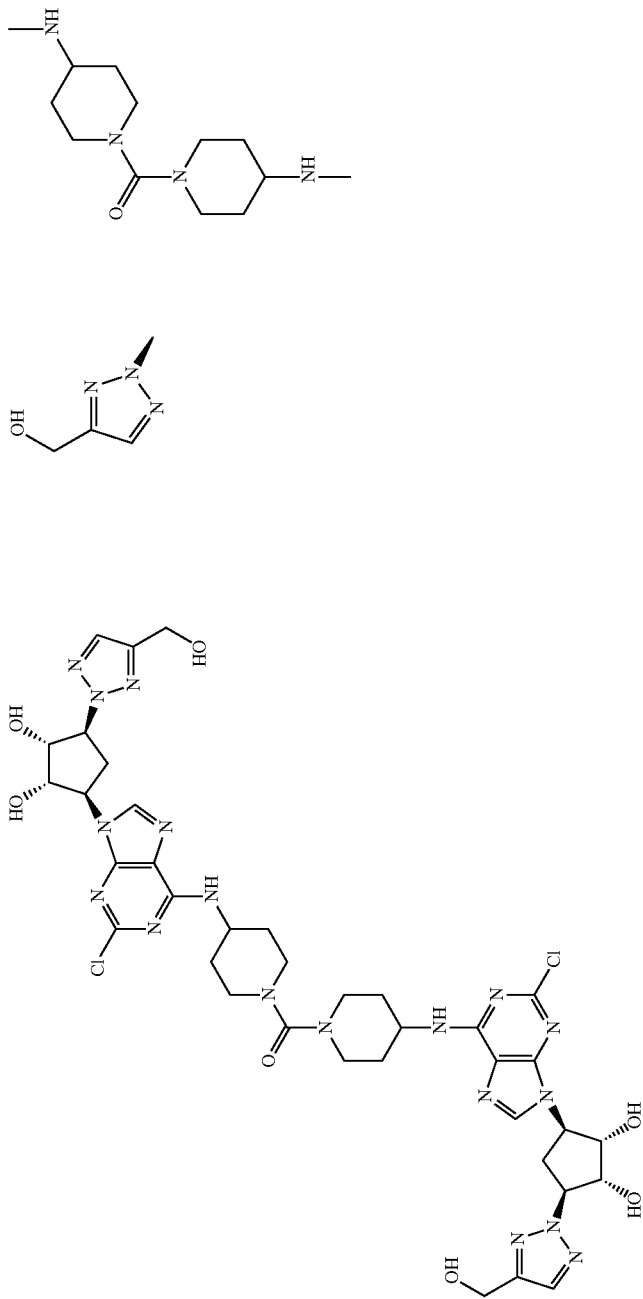

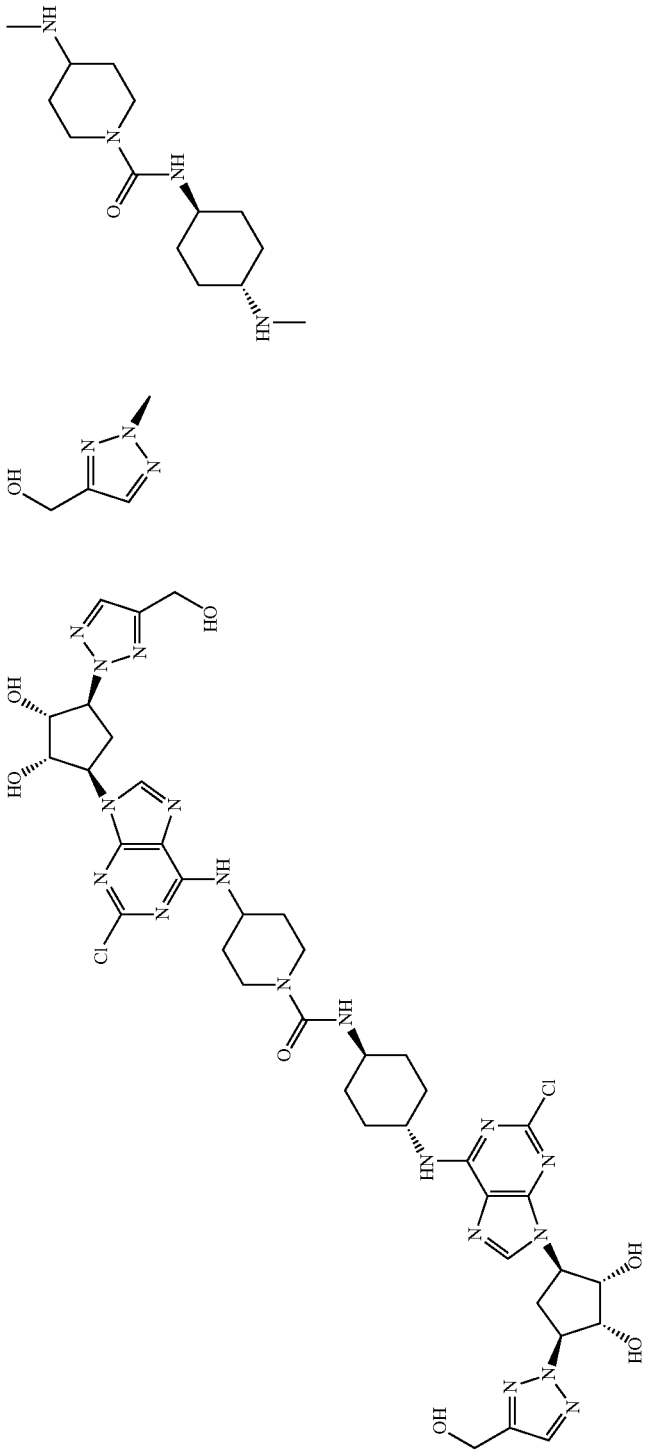

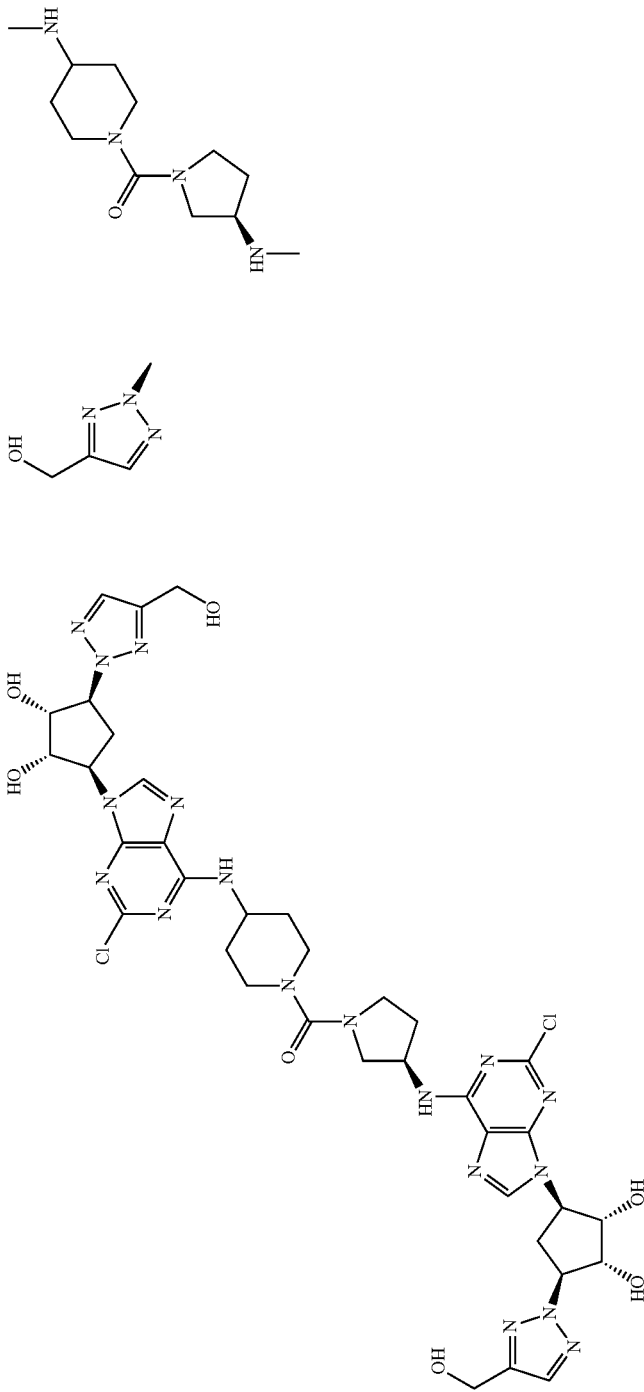

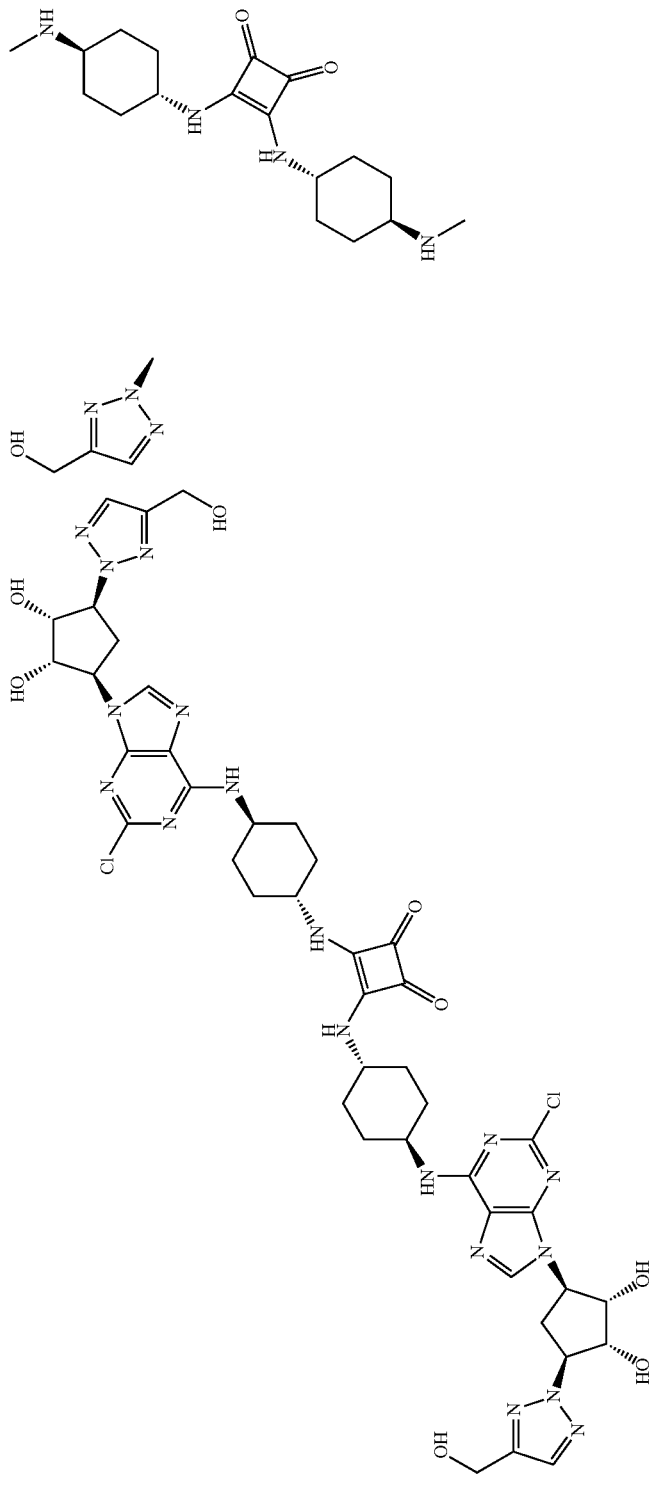

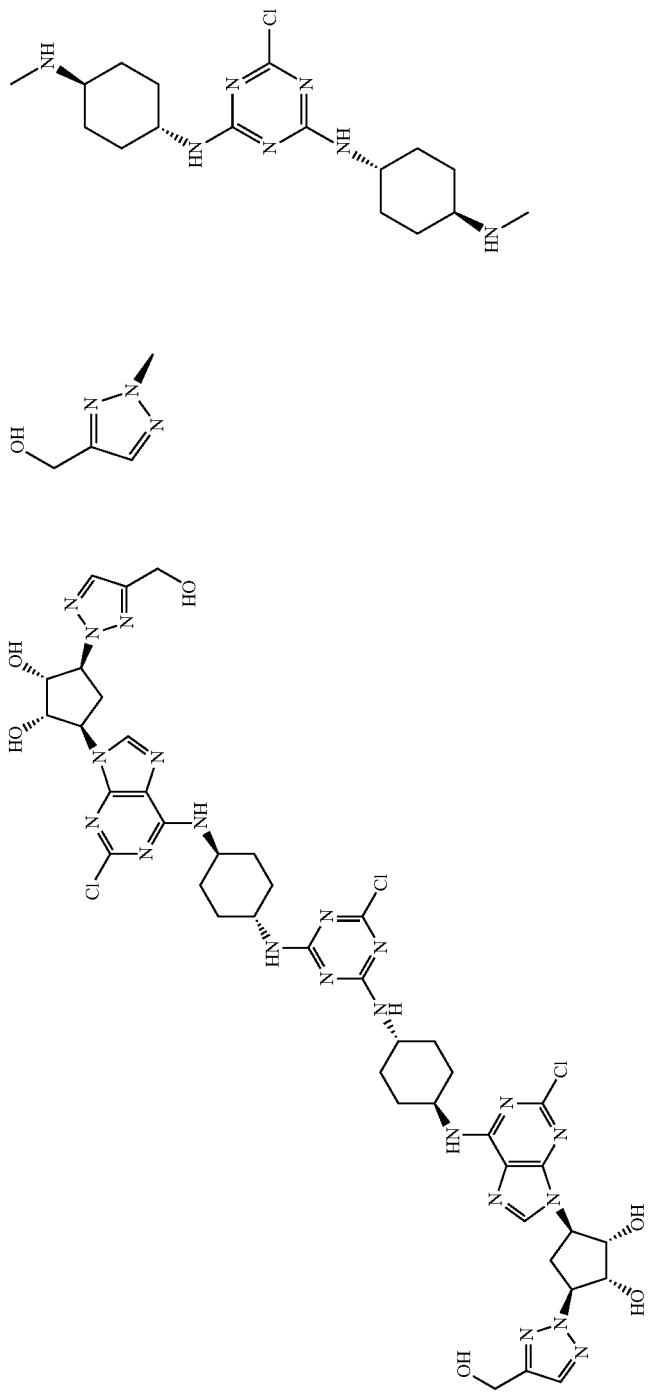

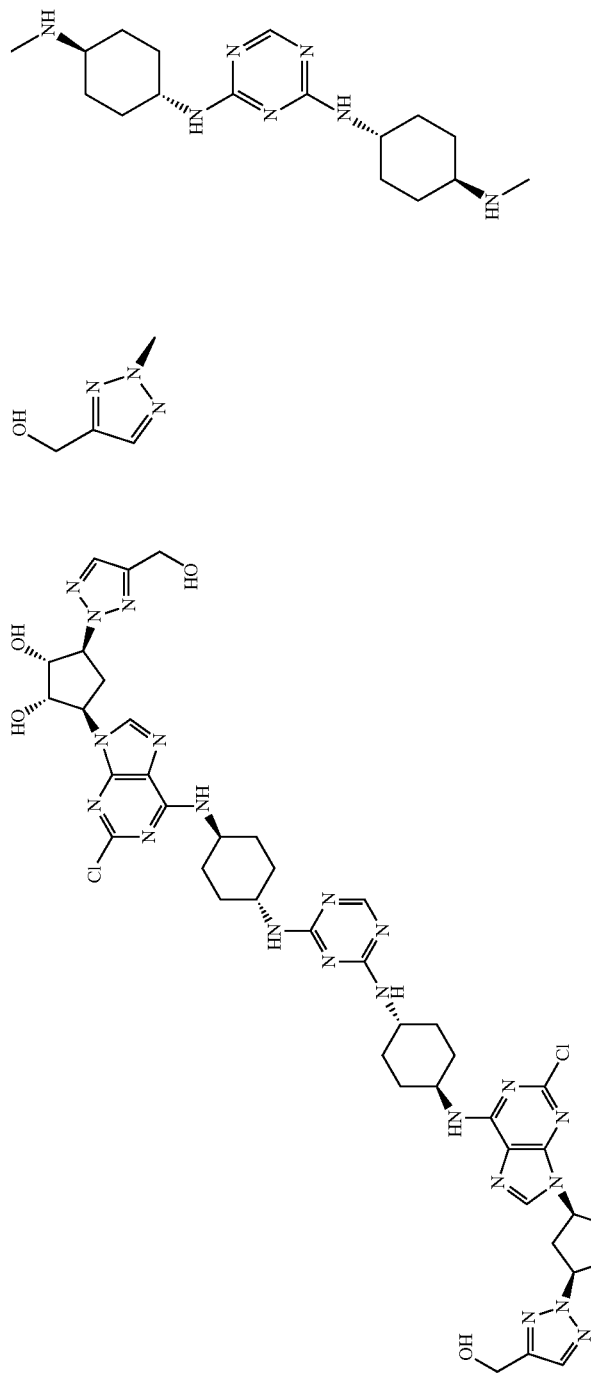

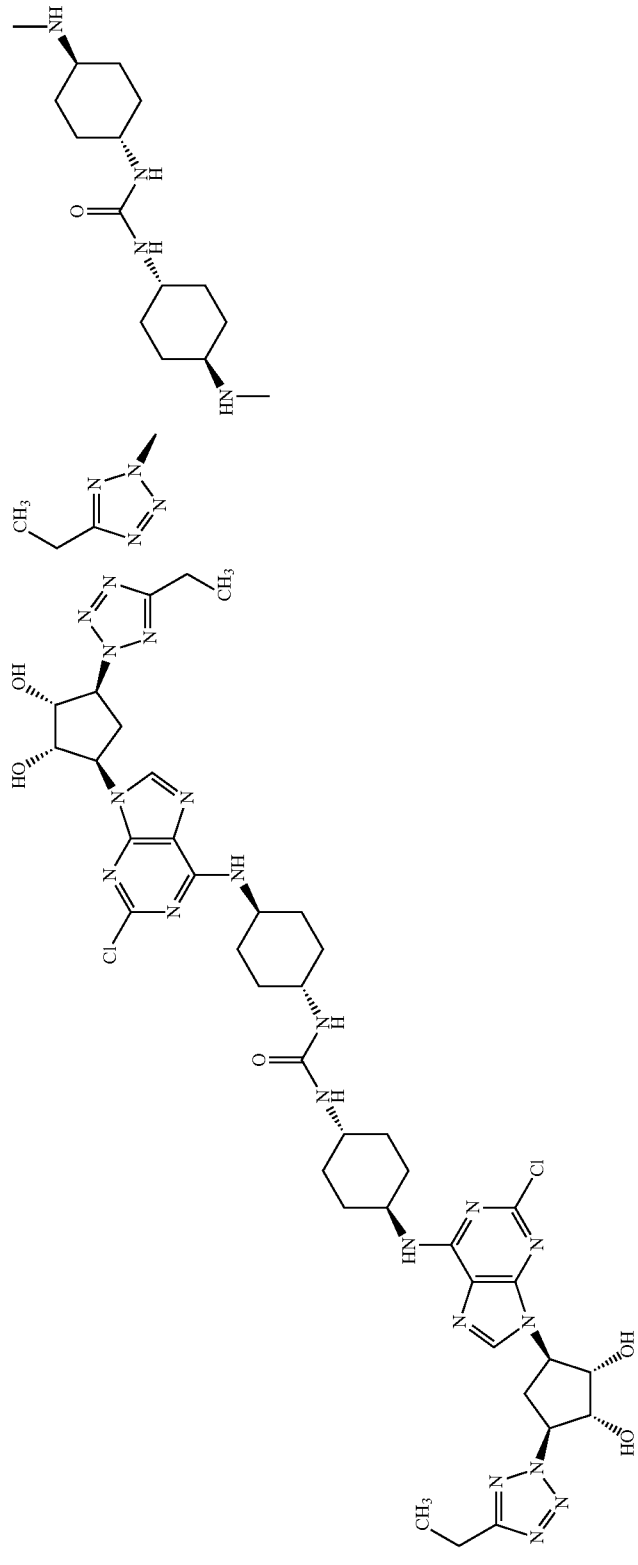
88

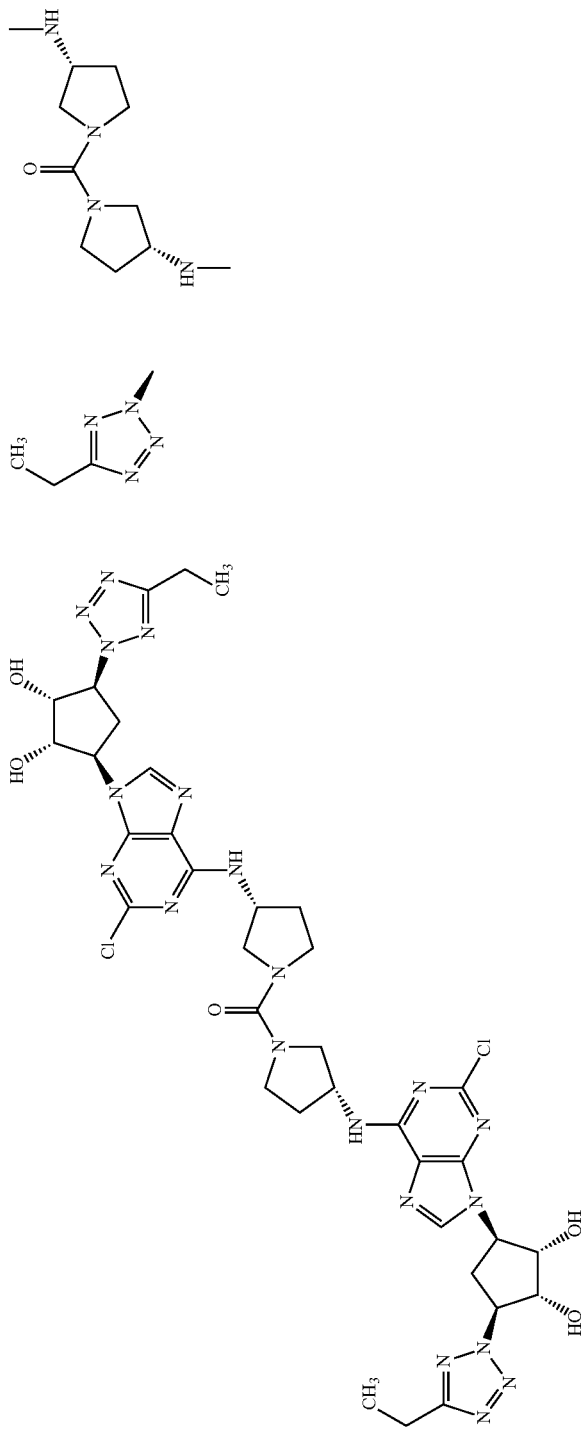

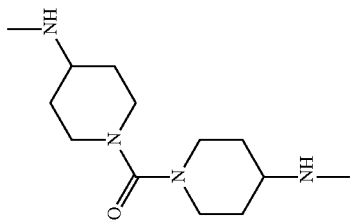
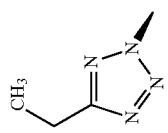
90
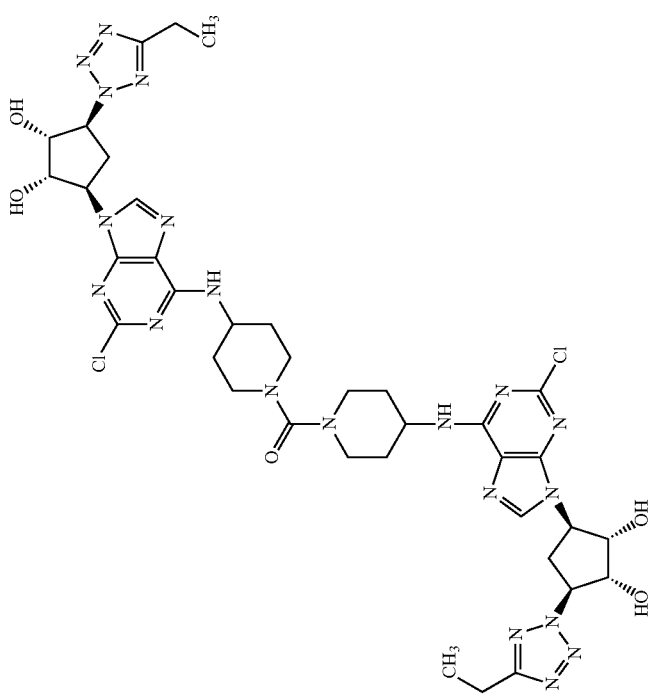

Examples 91-163
The compounds of formula (X2) are shown in the following table. Methods of preparing such compounds are described hereinafter.
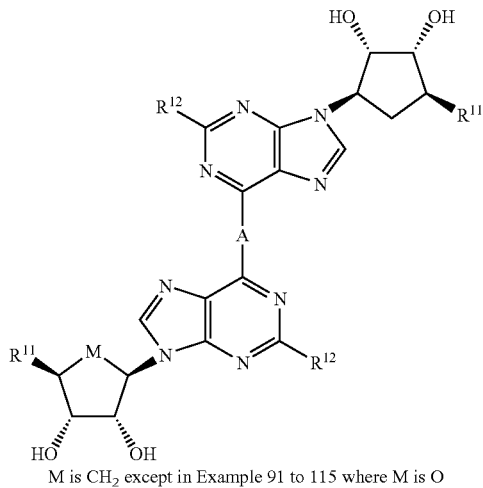
M is CH$_2$ except in Example 91 to 115 where M is O
| Ex | Structure |
|---|---|
| 91 | 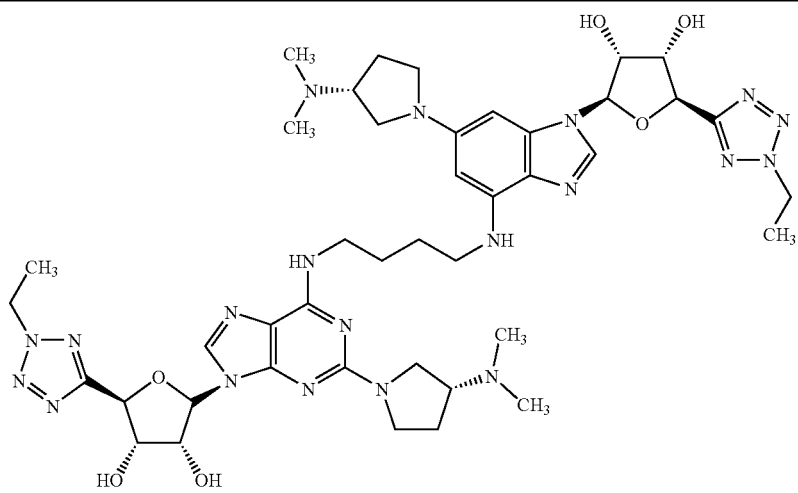 |
| 92 | 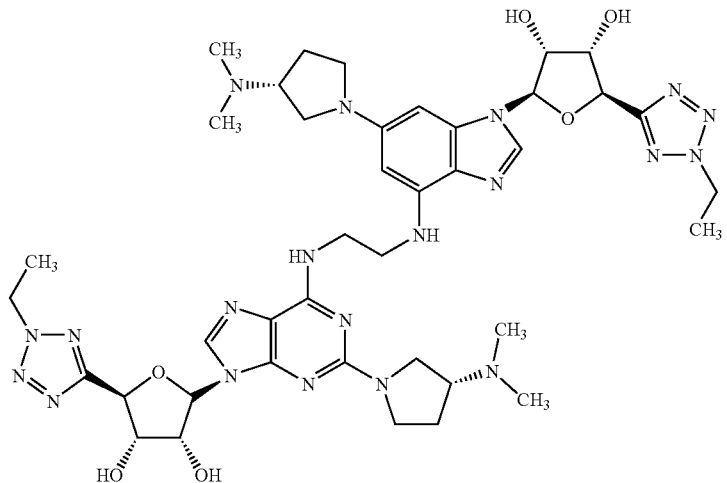 |

93
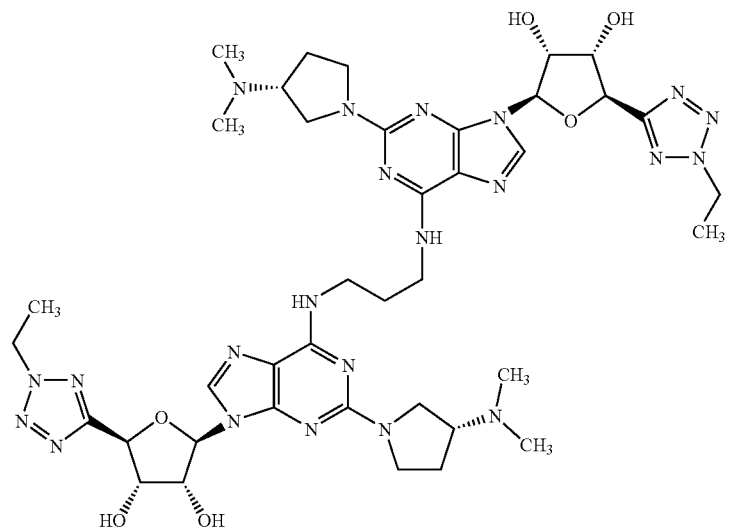
94
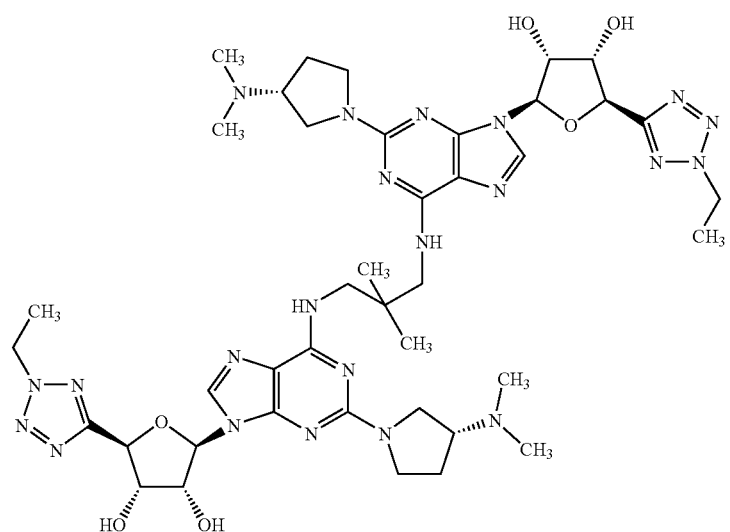
95
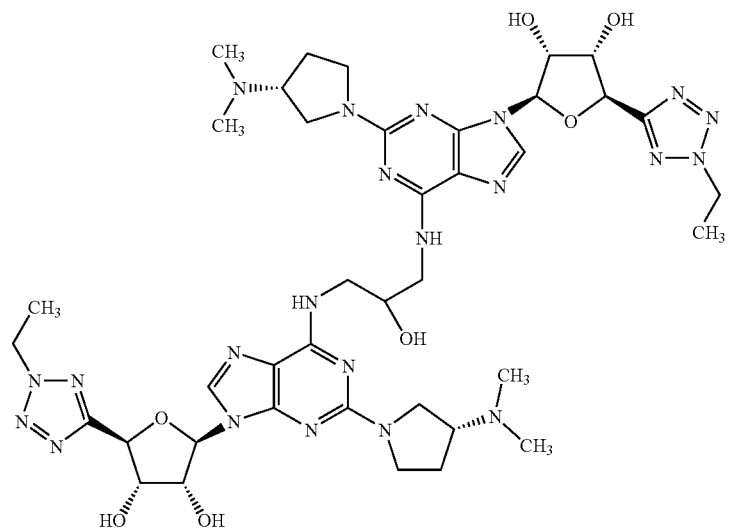

96
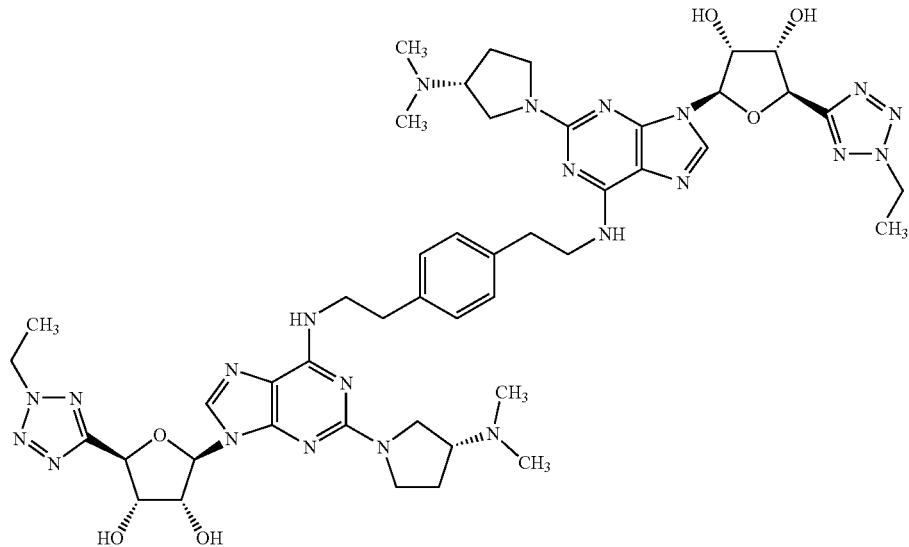
97
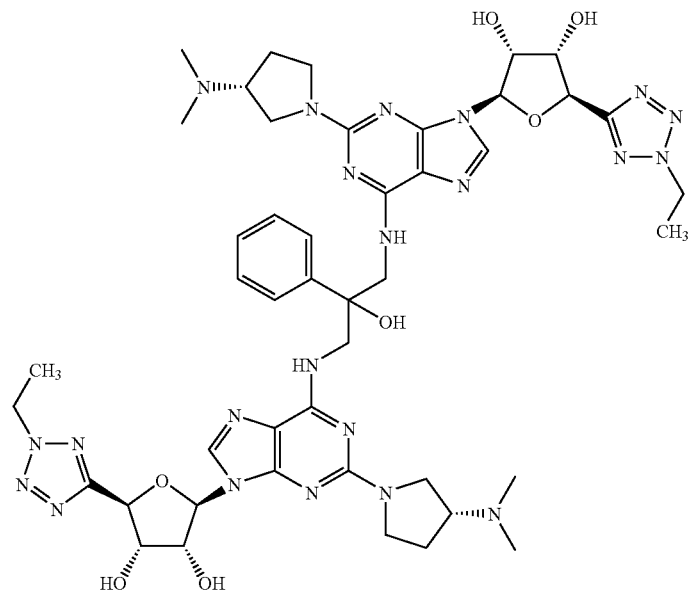

98
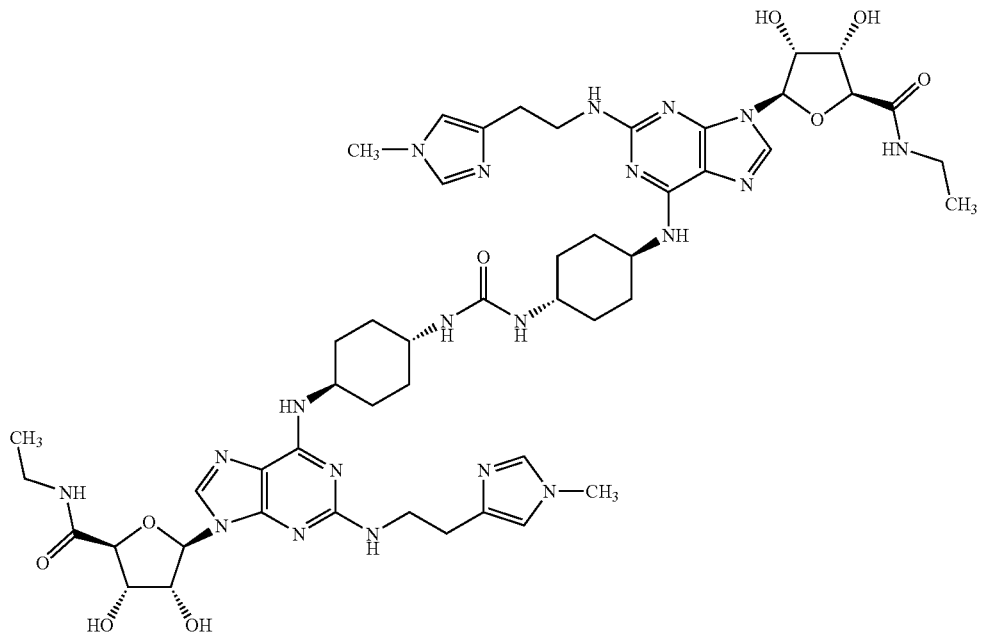
99
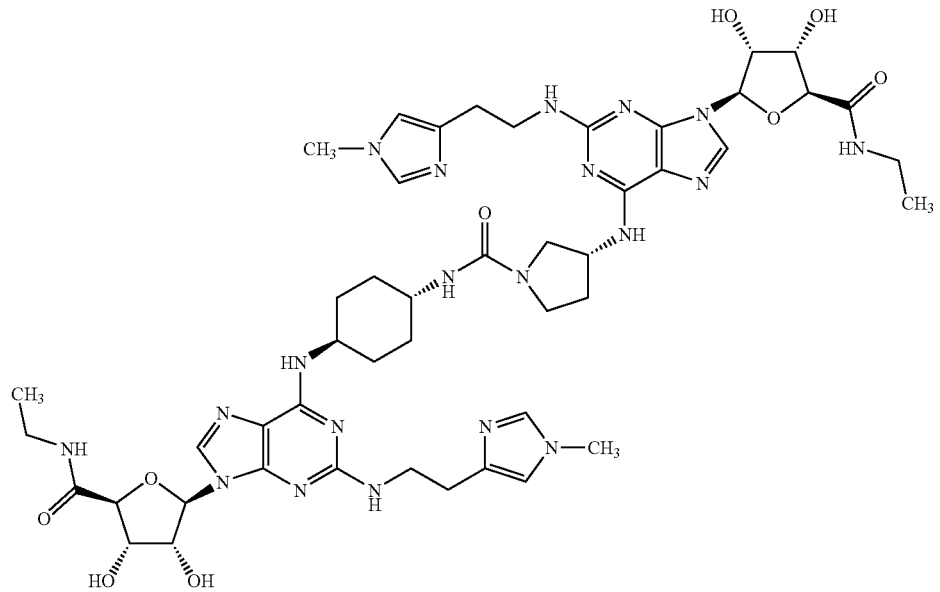

100
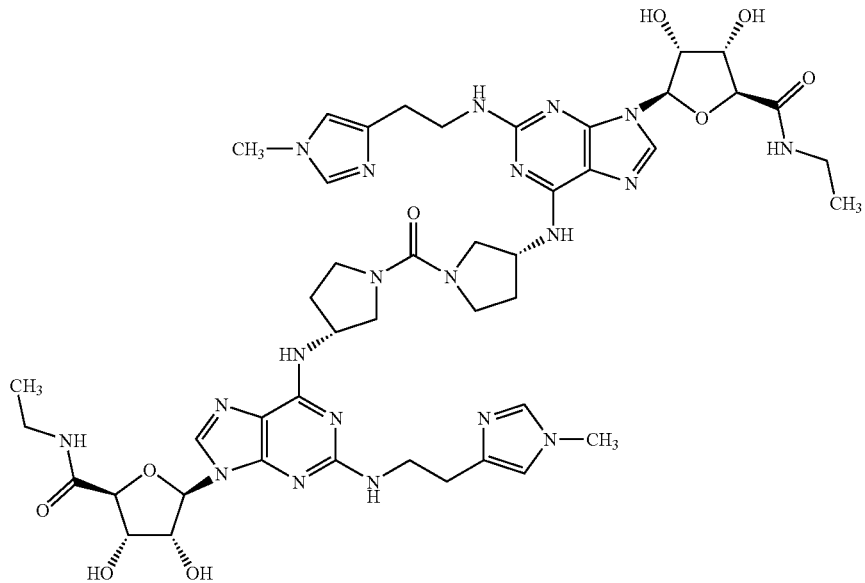
101
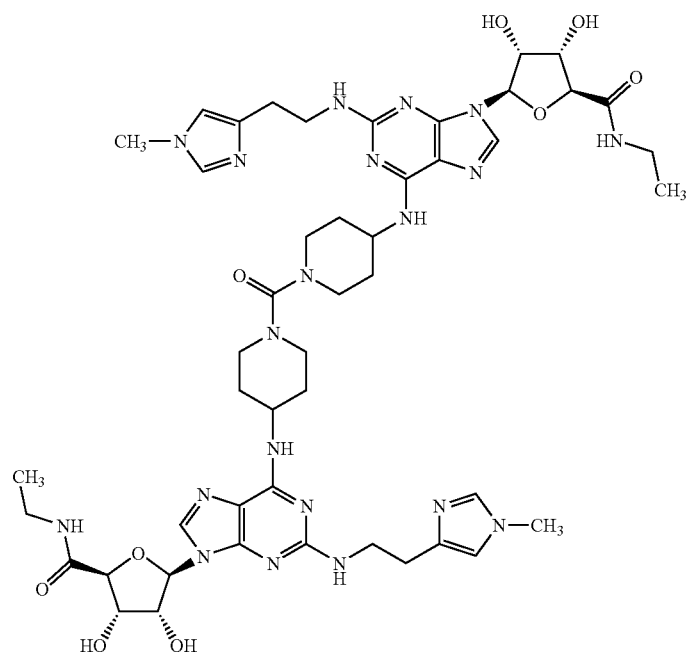

102
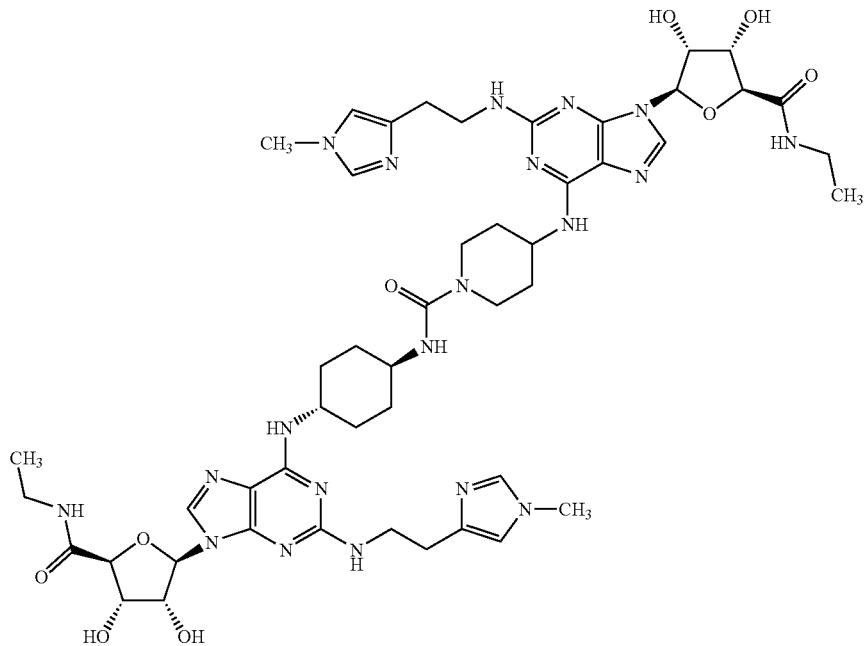
103
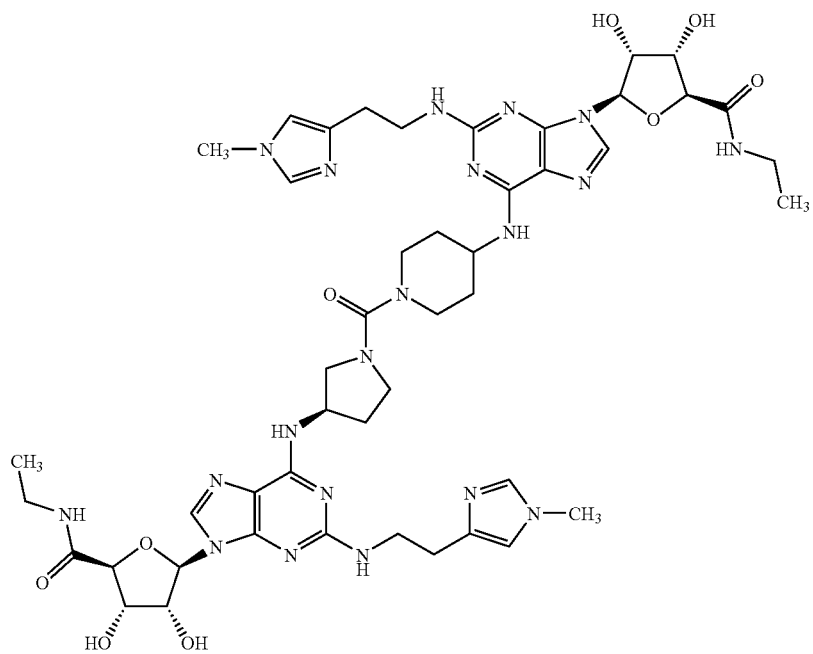

104
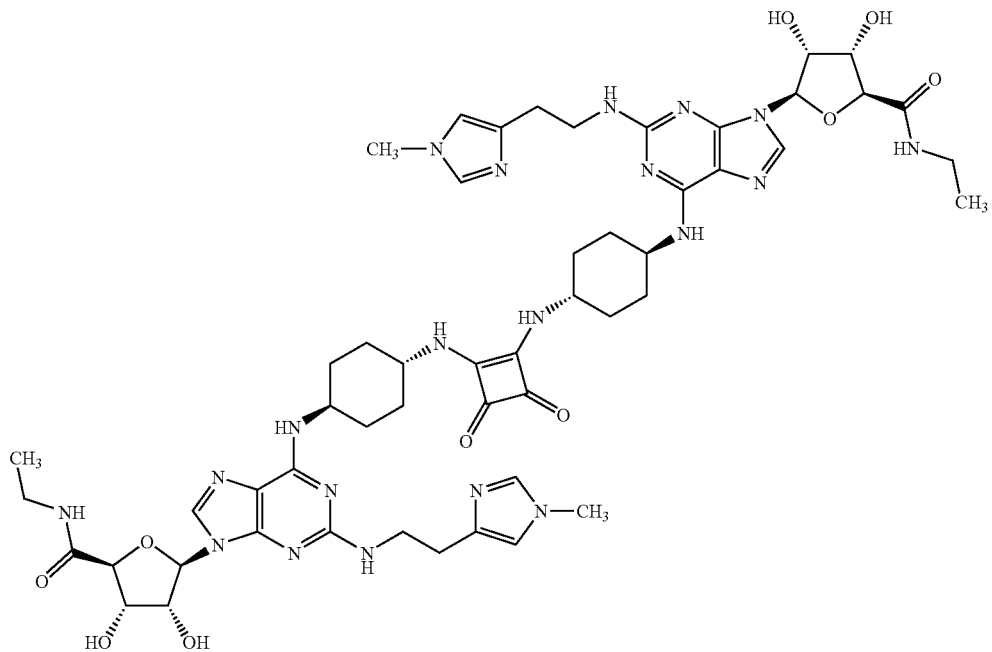
105
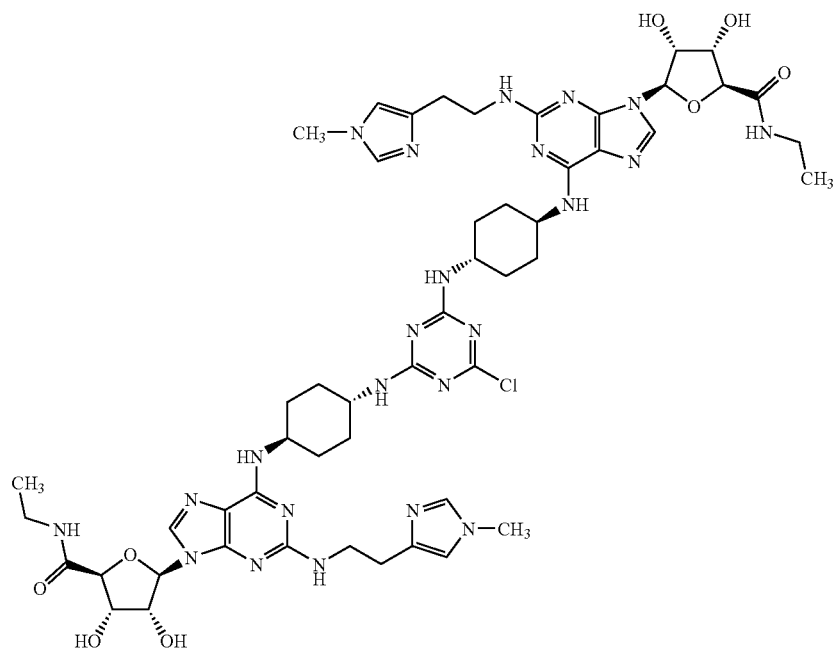

106
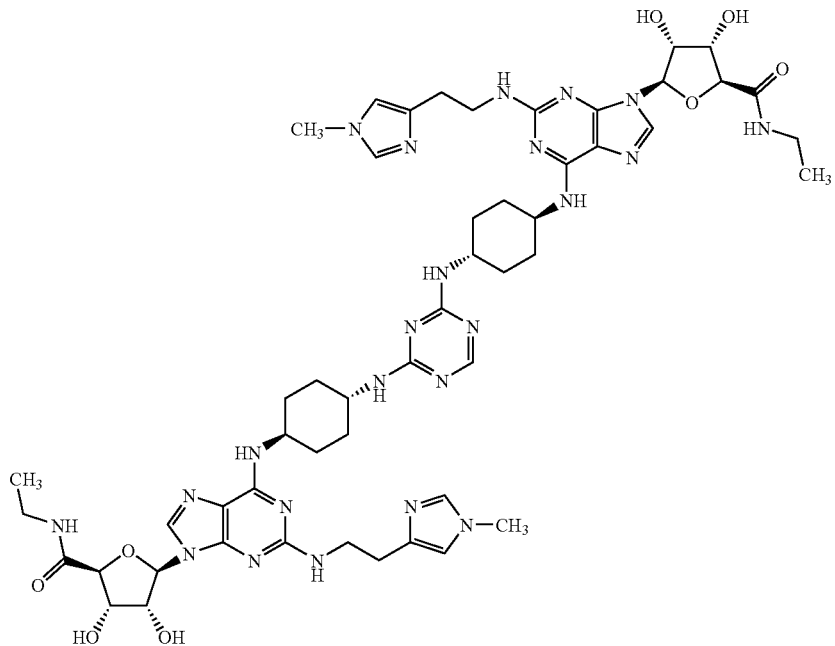
107
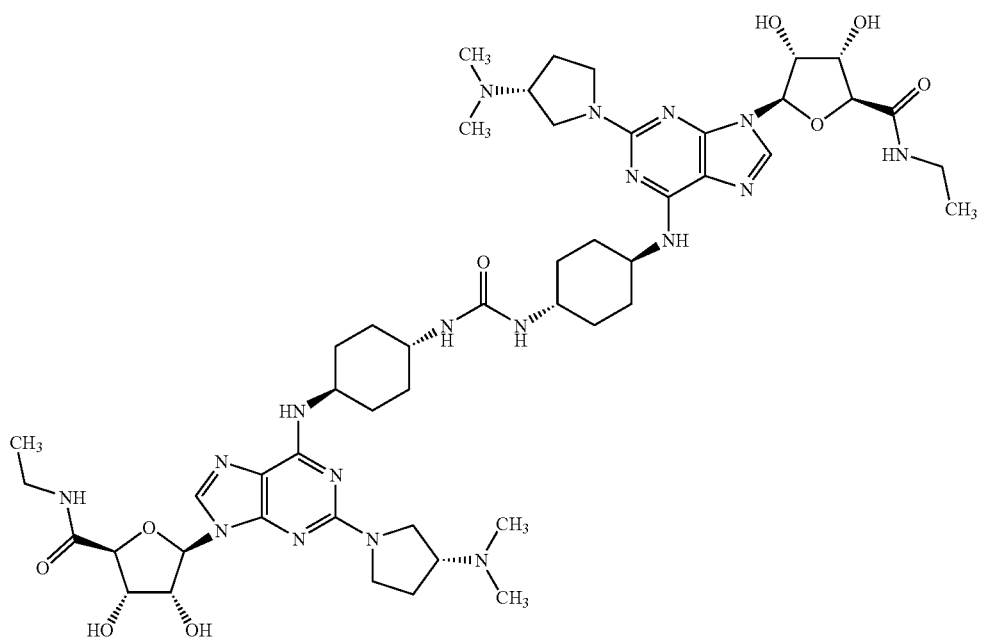

108
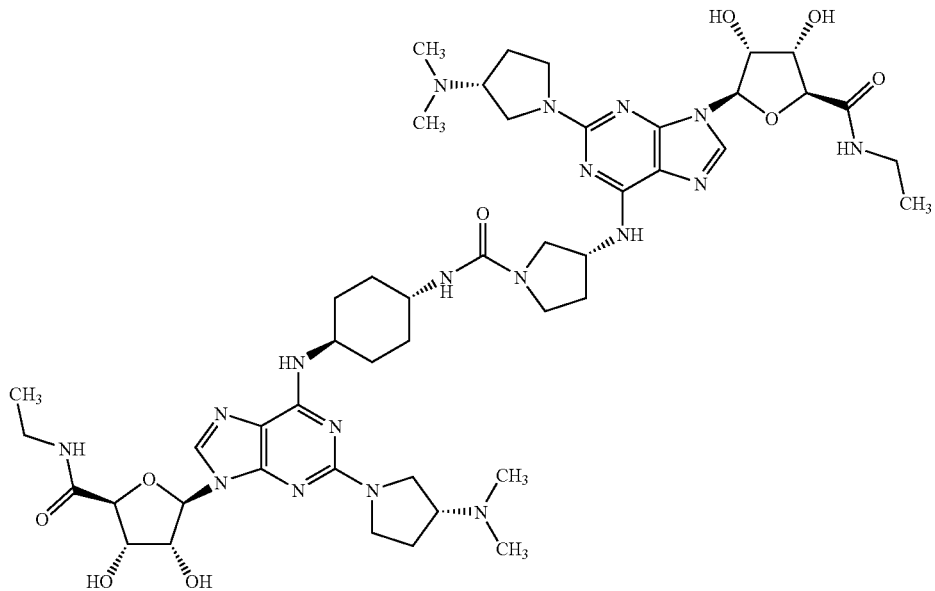
109
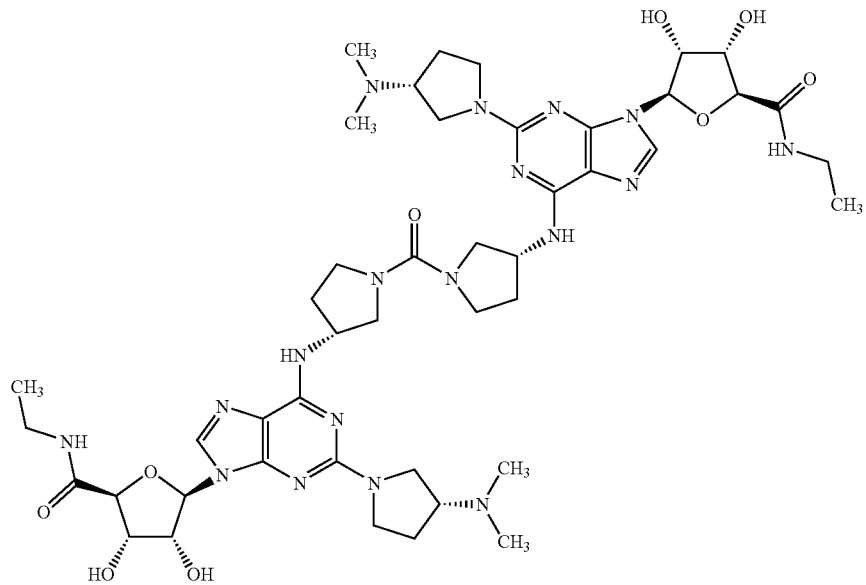

110
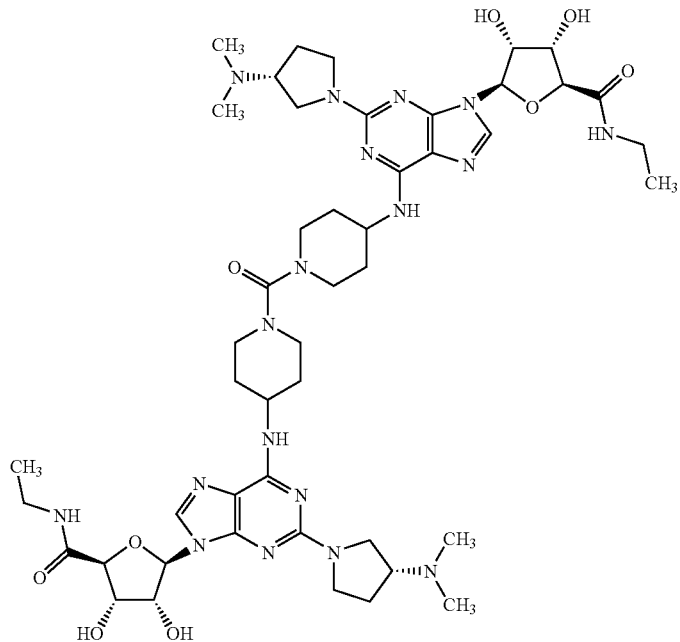
111
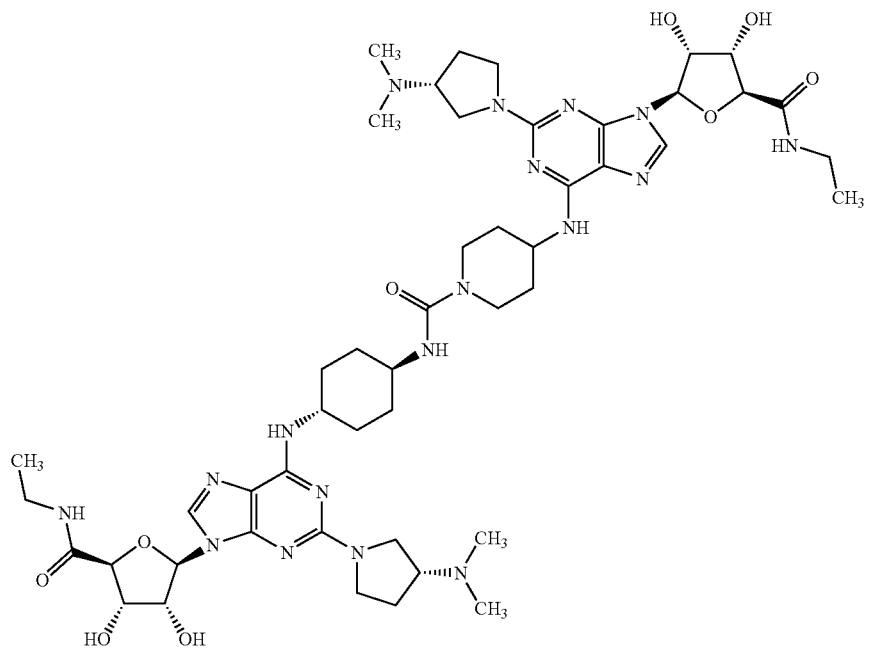

112
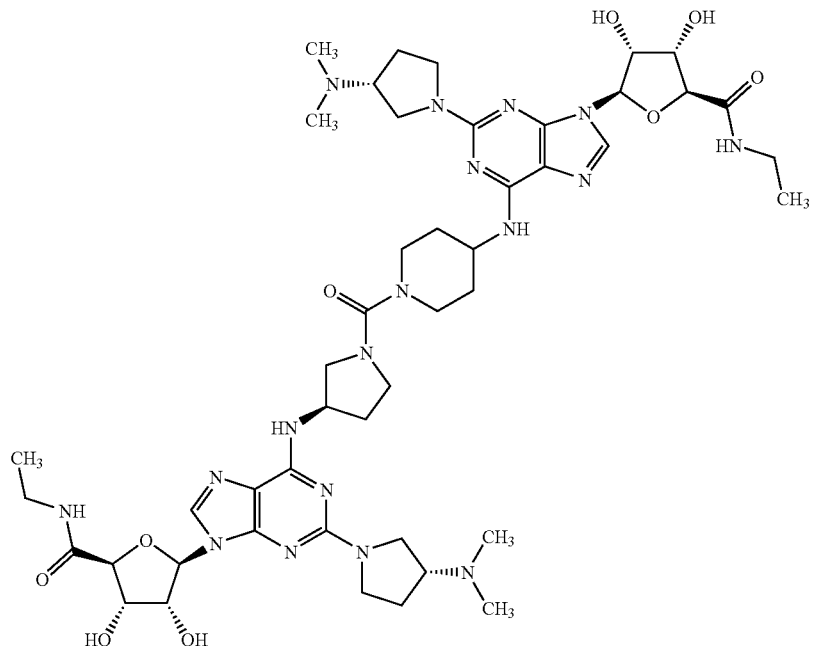
113
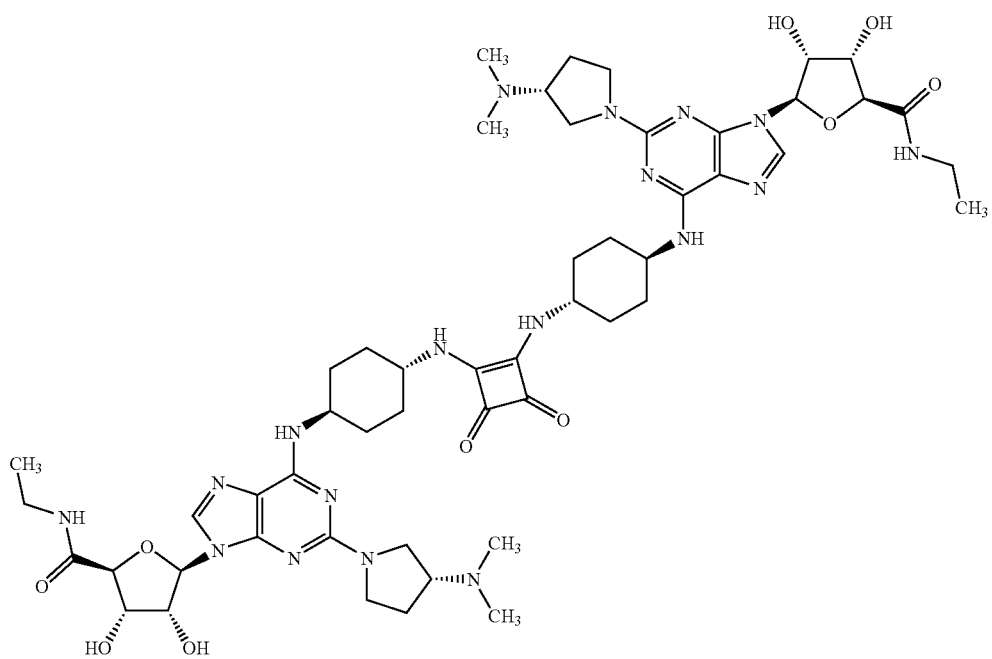

114
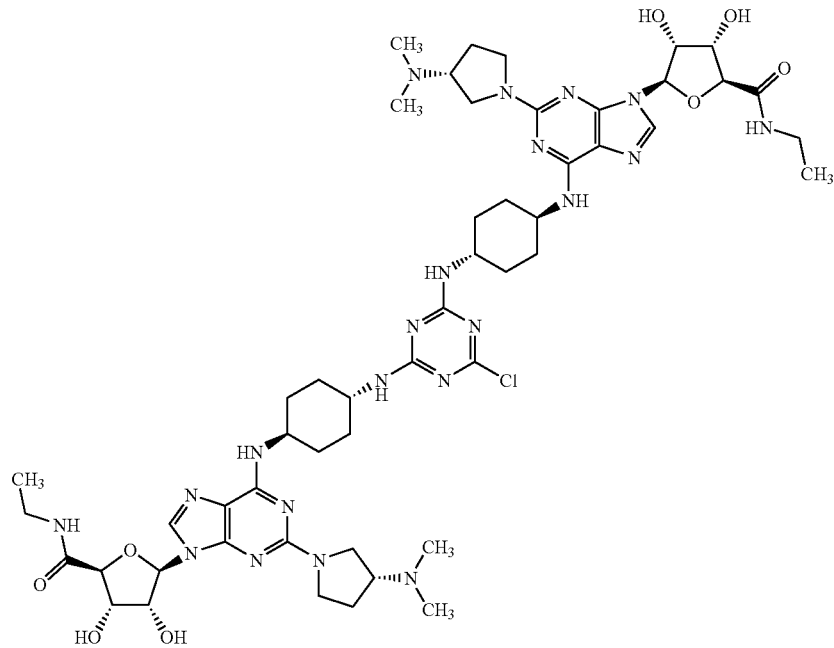
115
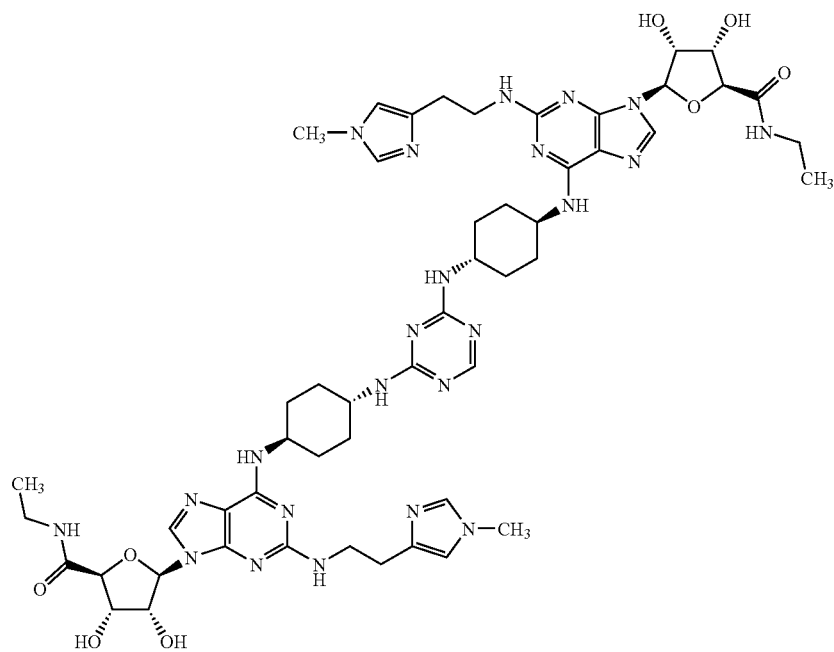

116
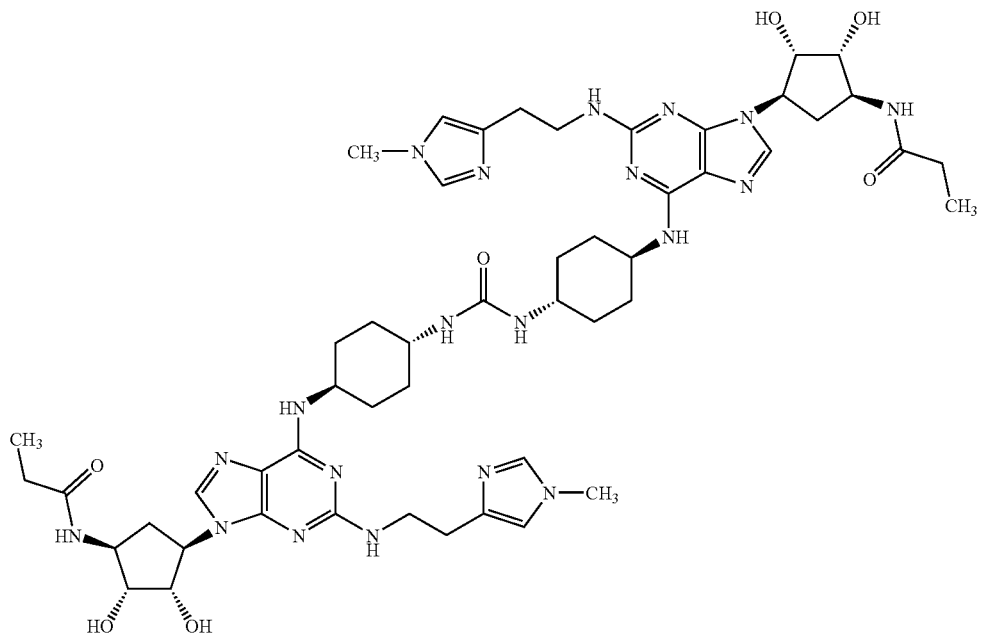
117
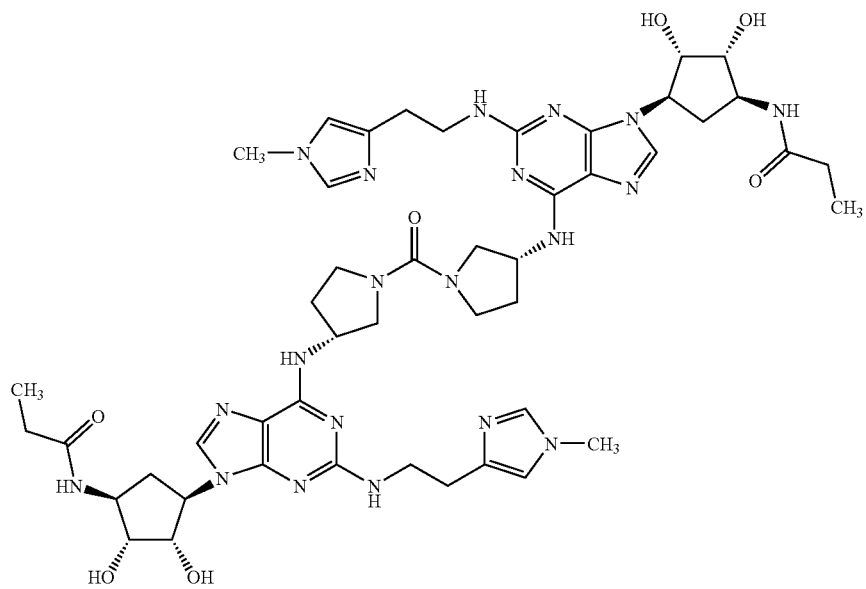

118
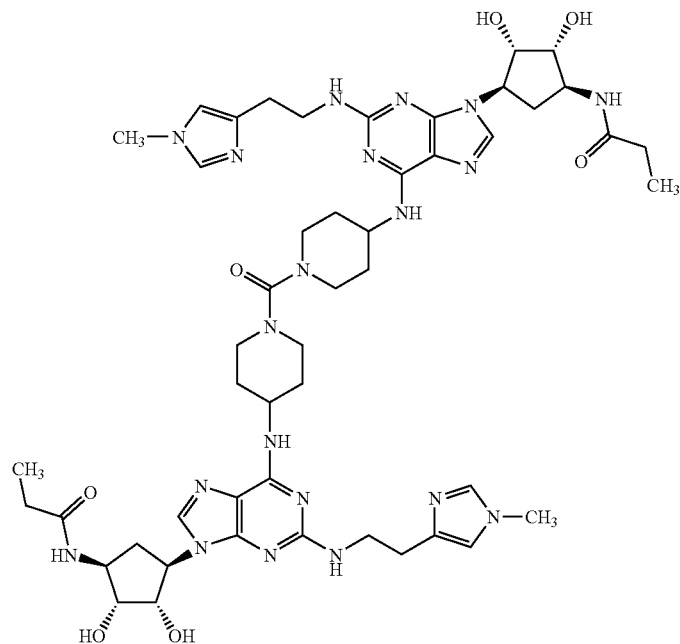
119
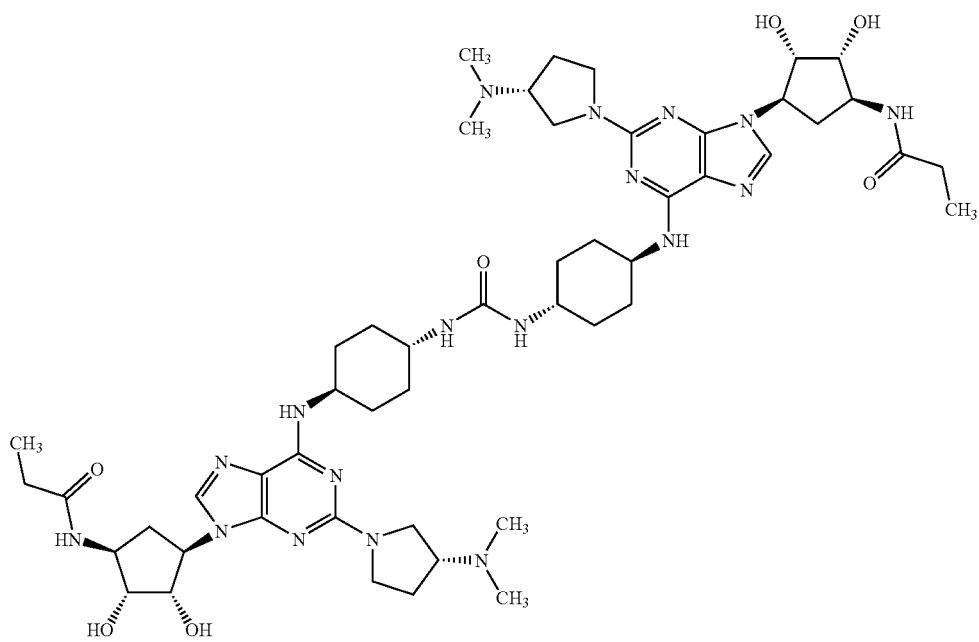

120
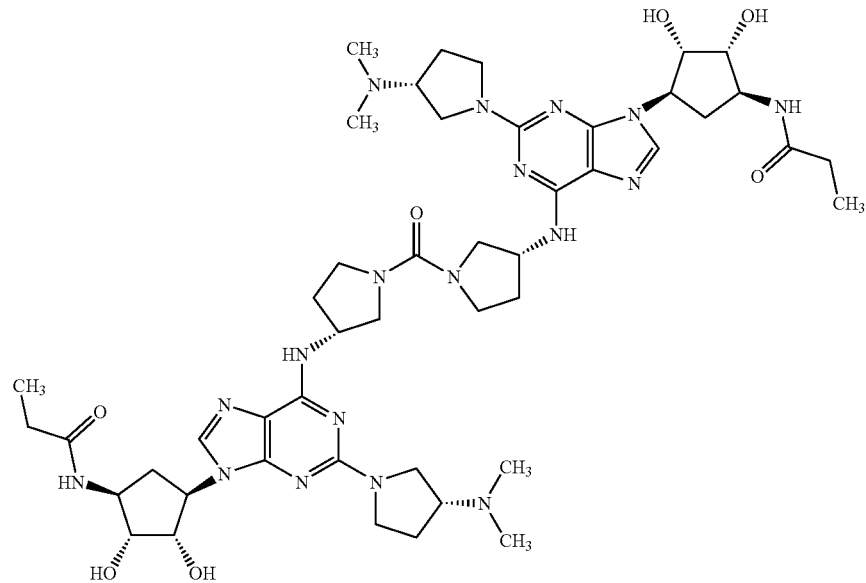
121
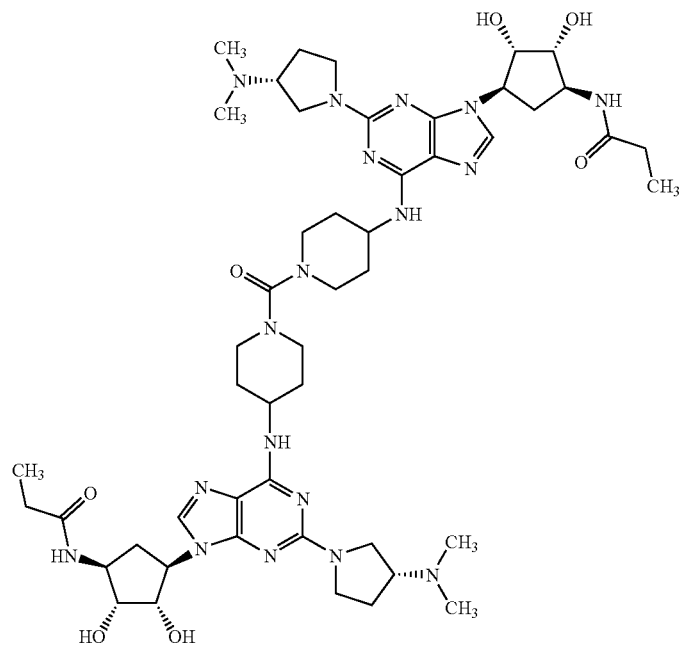

122
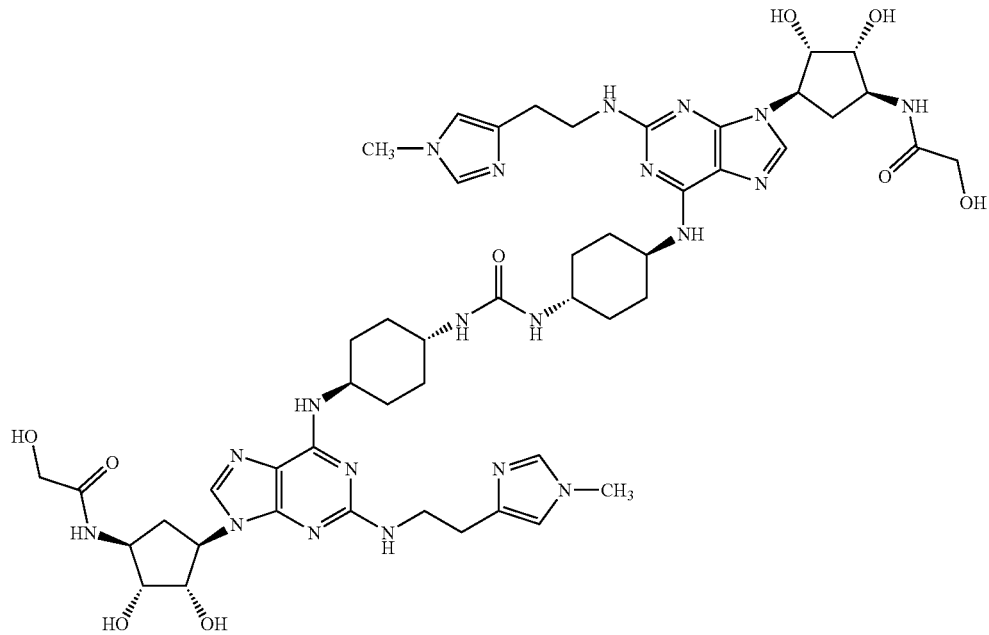
123
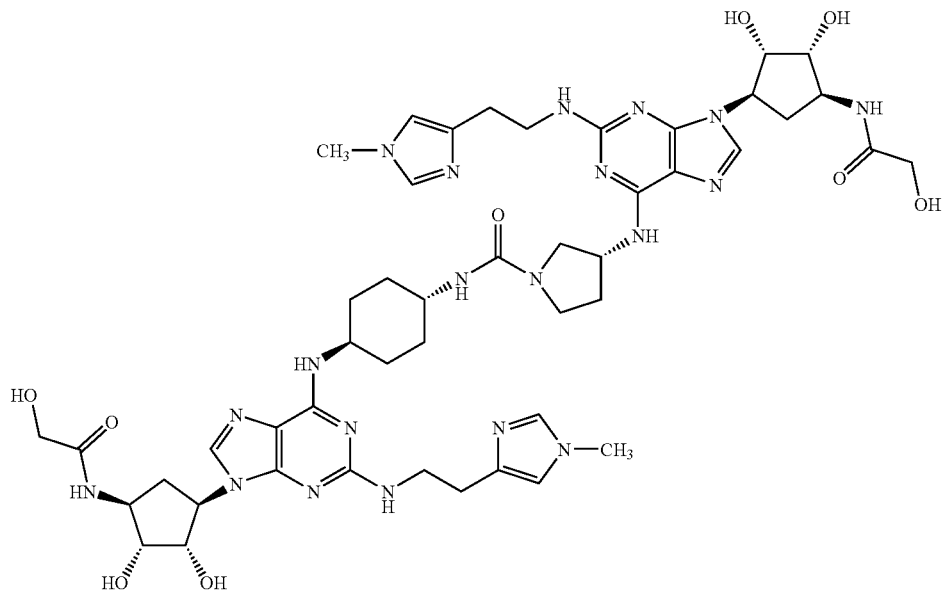

124
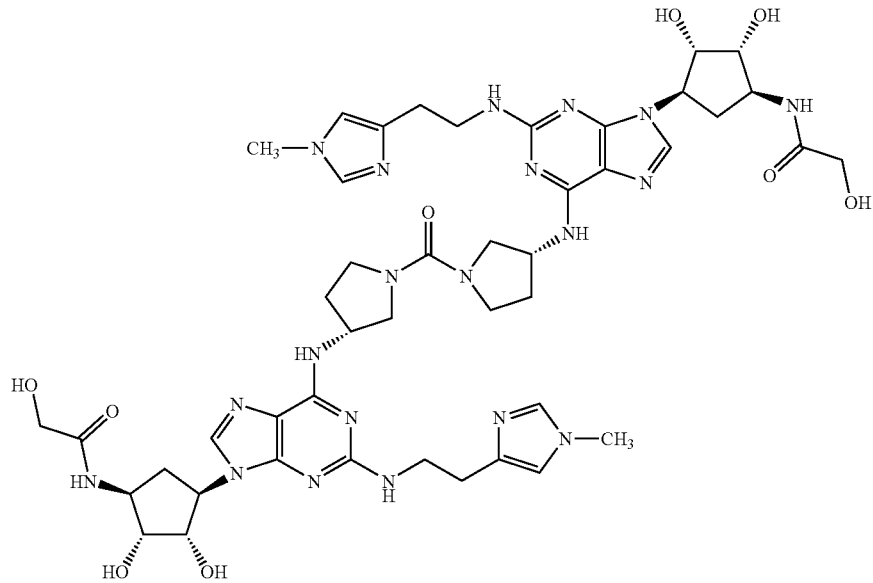
125
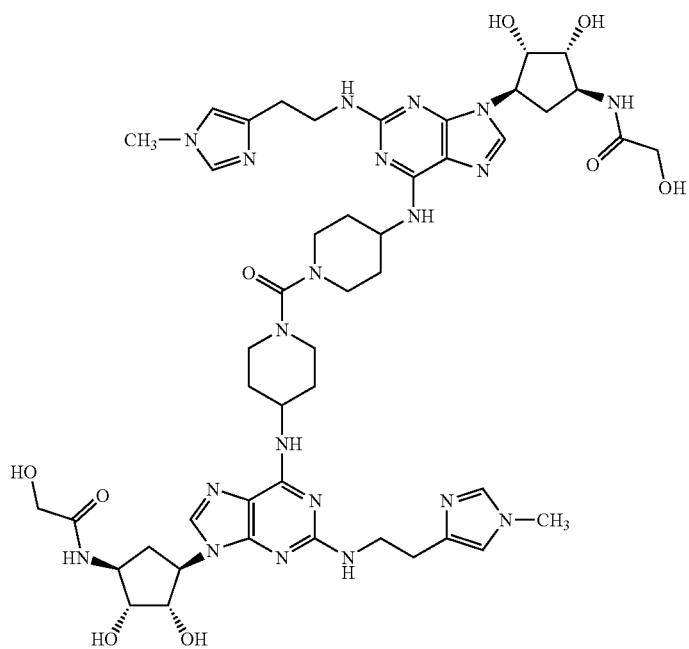

126
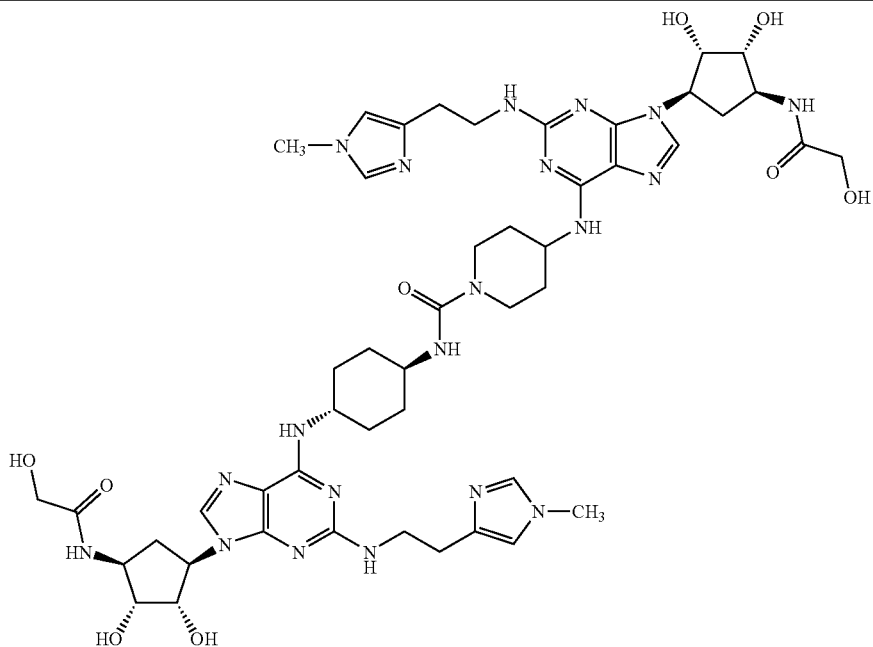
127
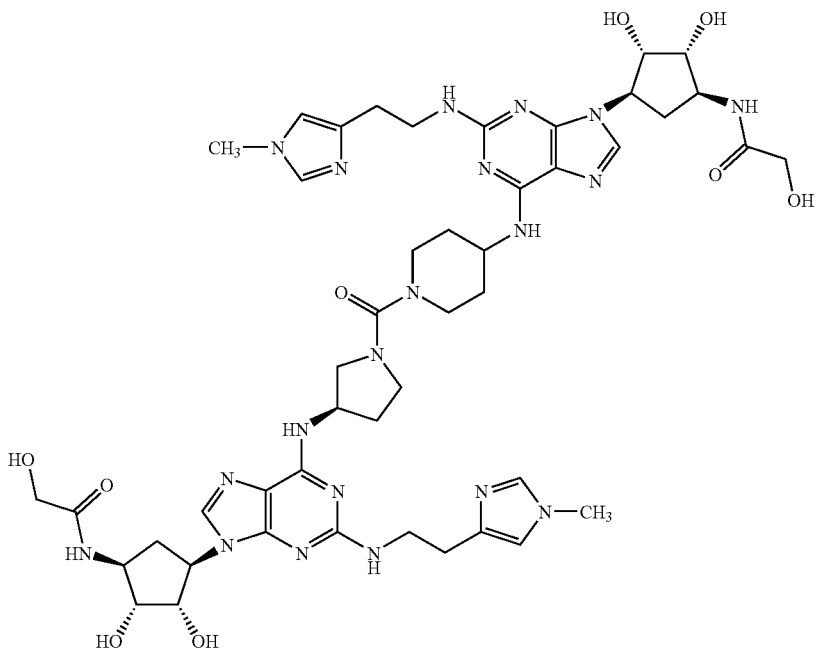

| 128 | 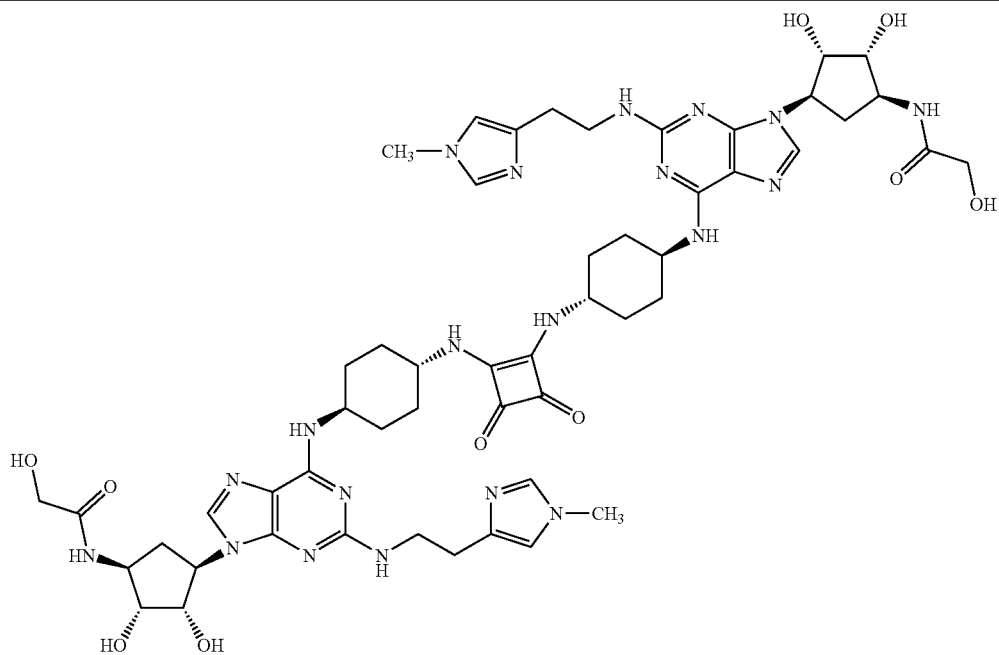 |
|---|---|
| 129 | 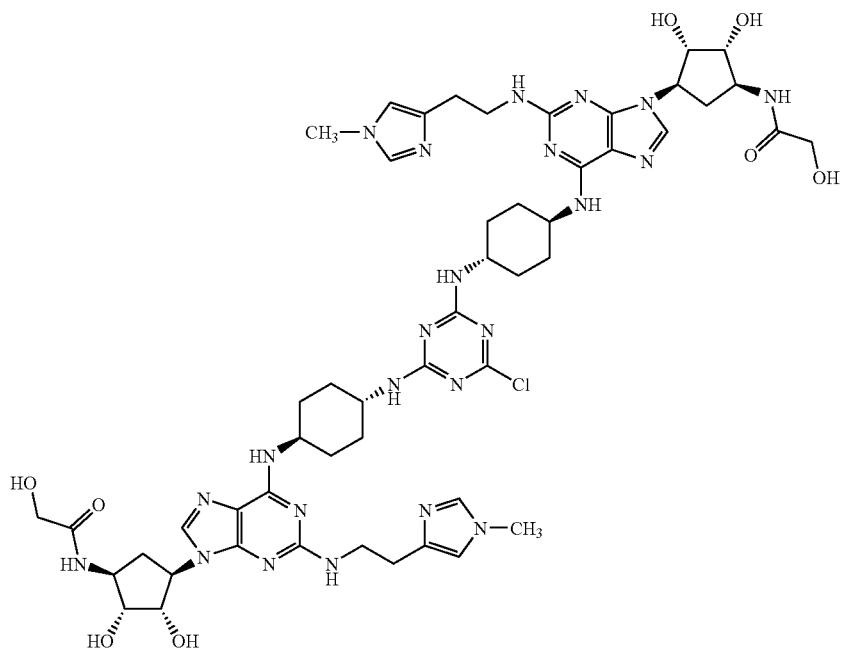 |

130
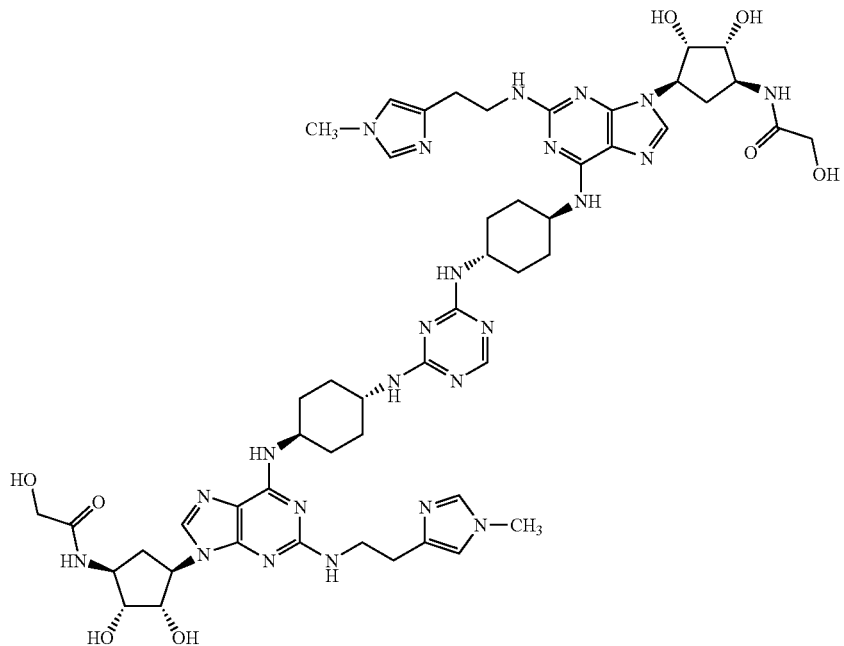
131
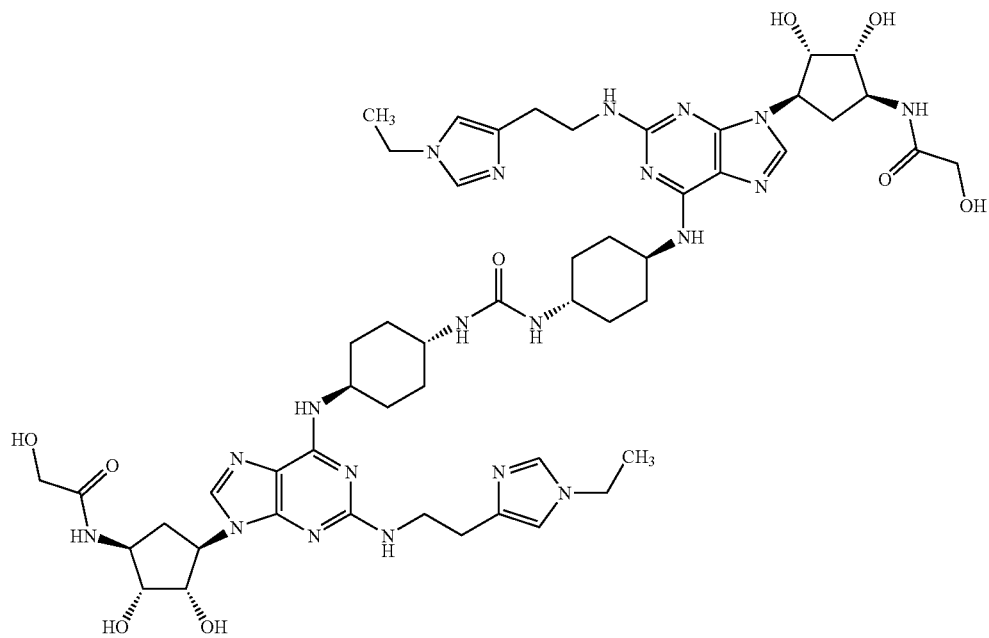

132
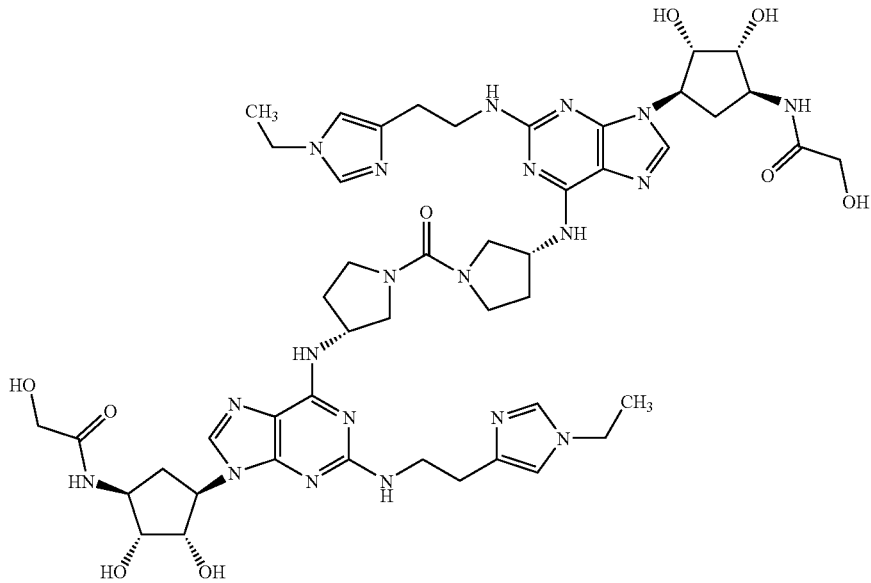
133
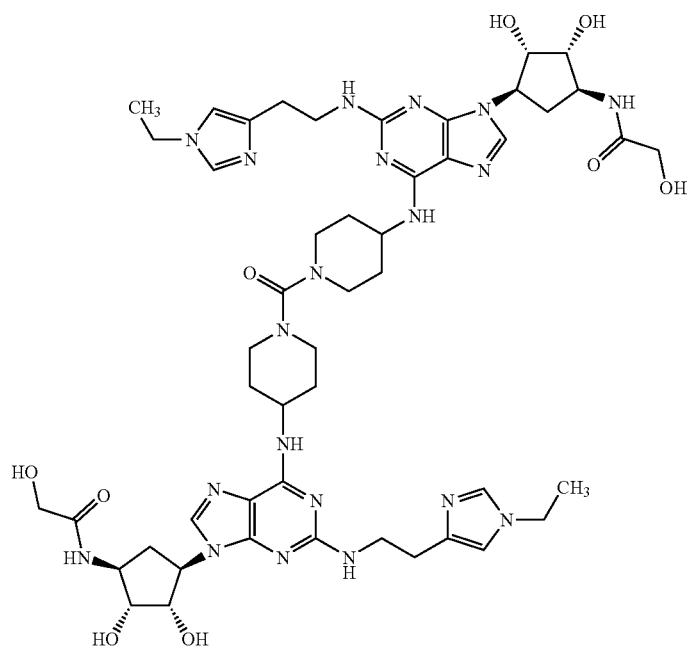

134
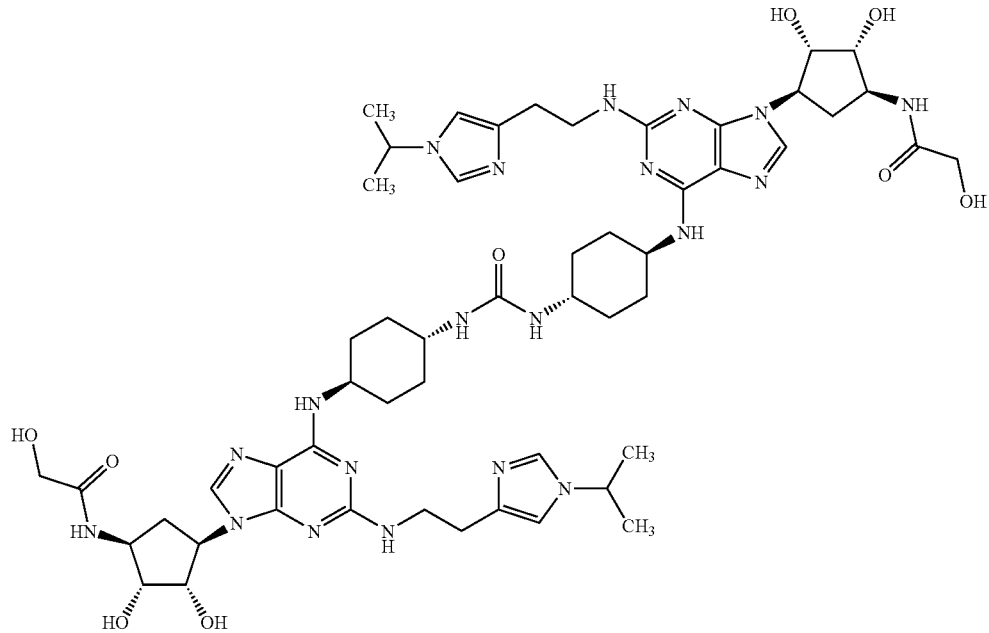
135
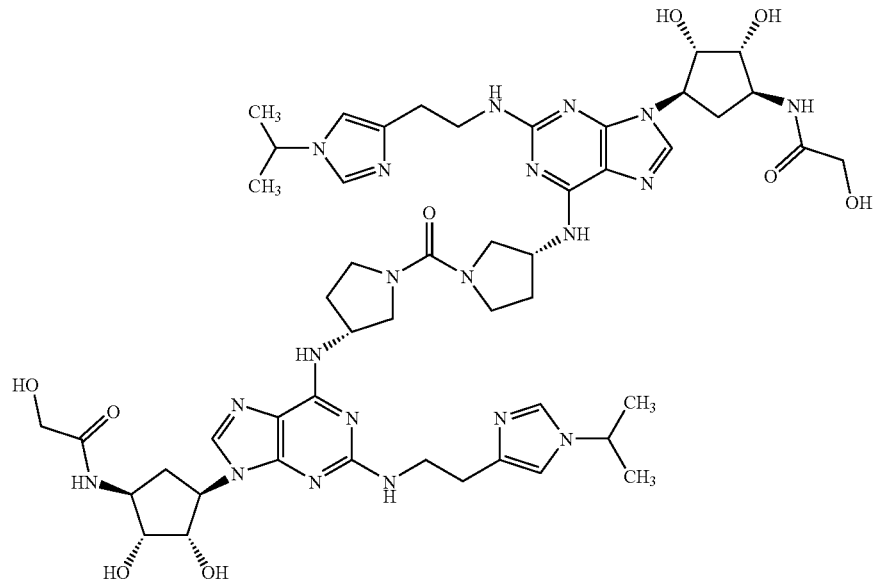

136
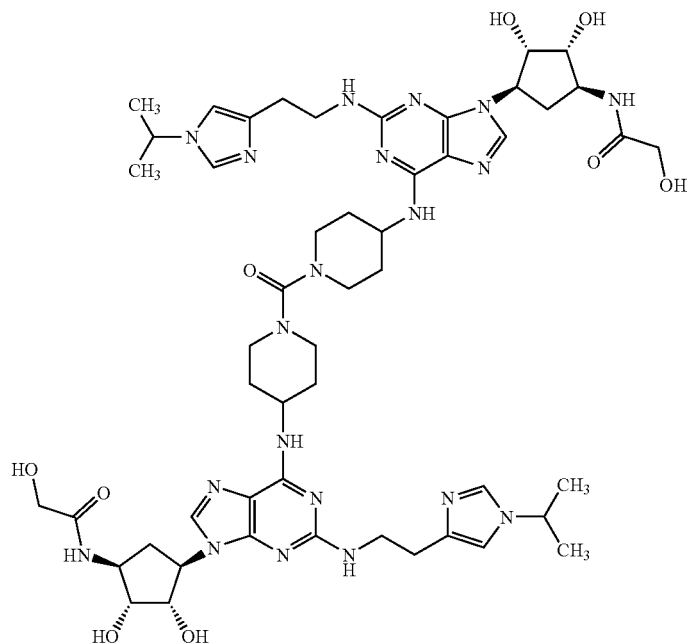
137
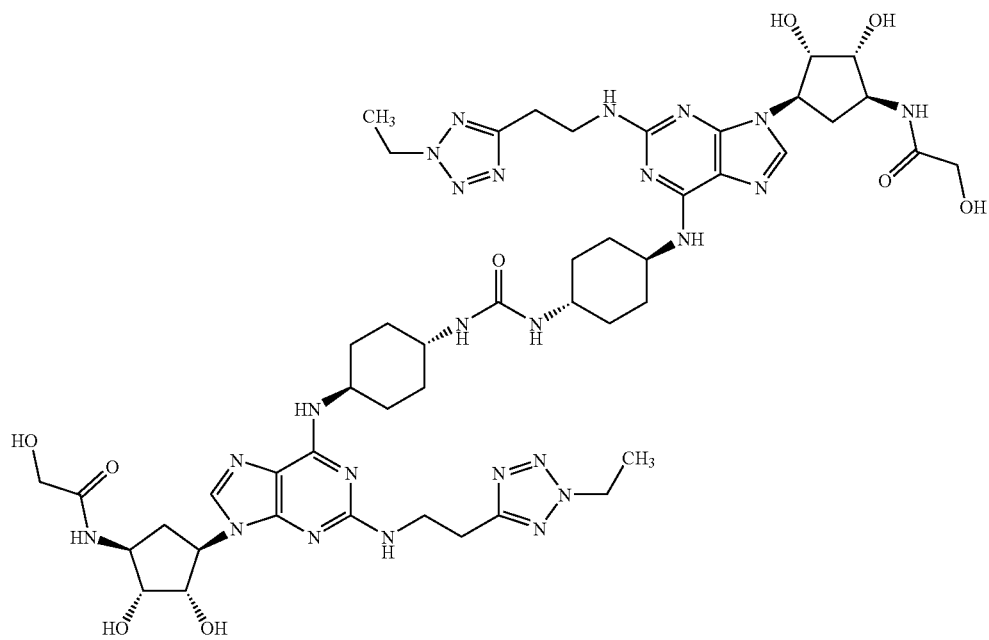

138
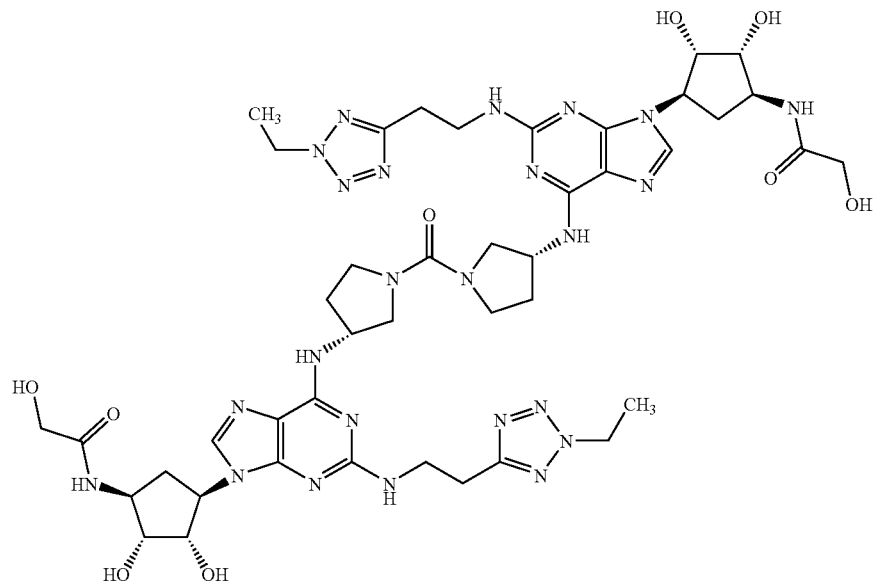
139
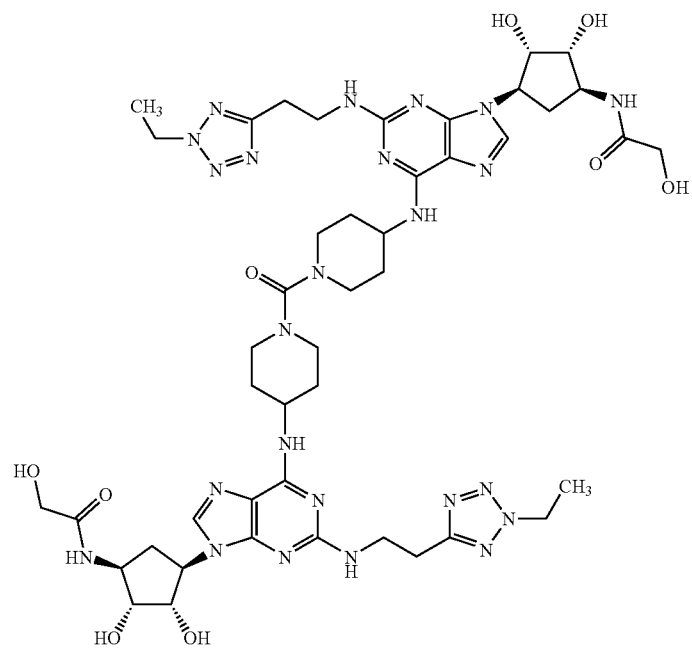

-continued
140
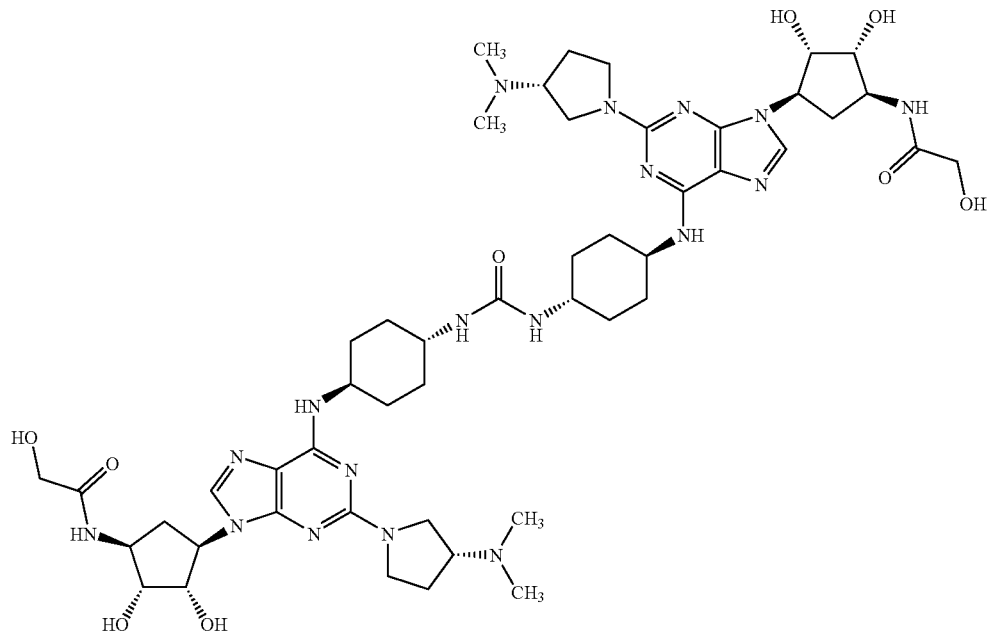
141
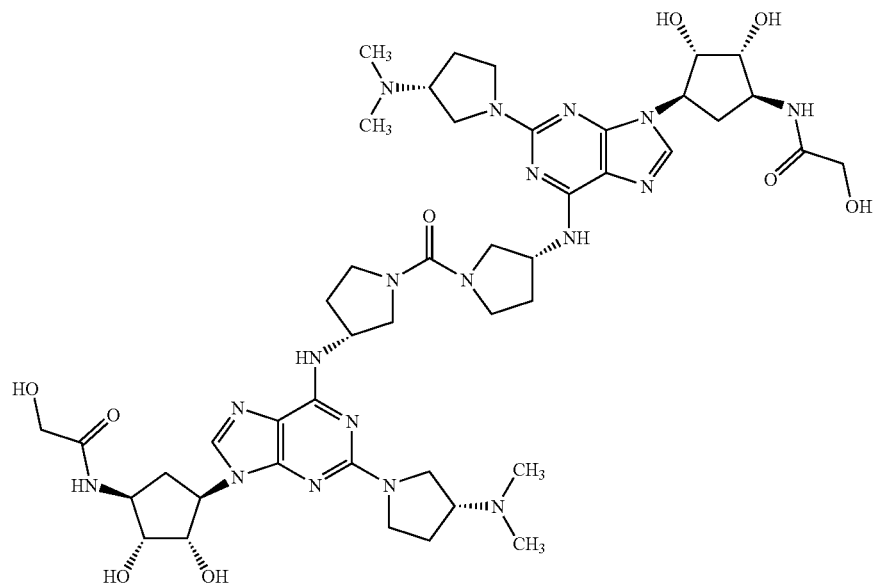

142
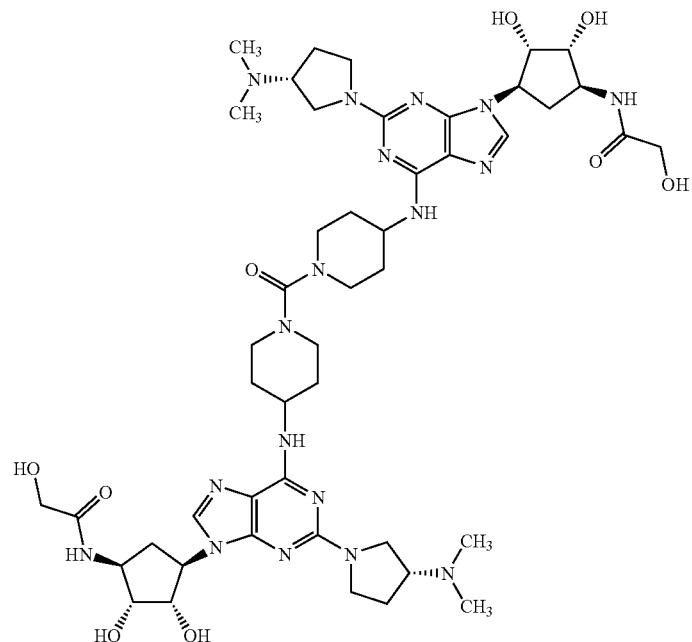
143
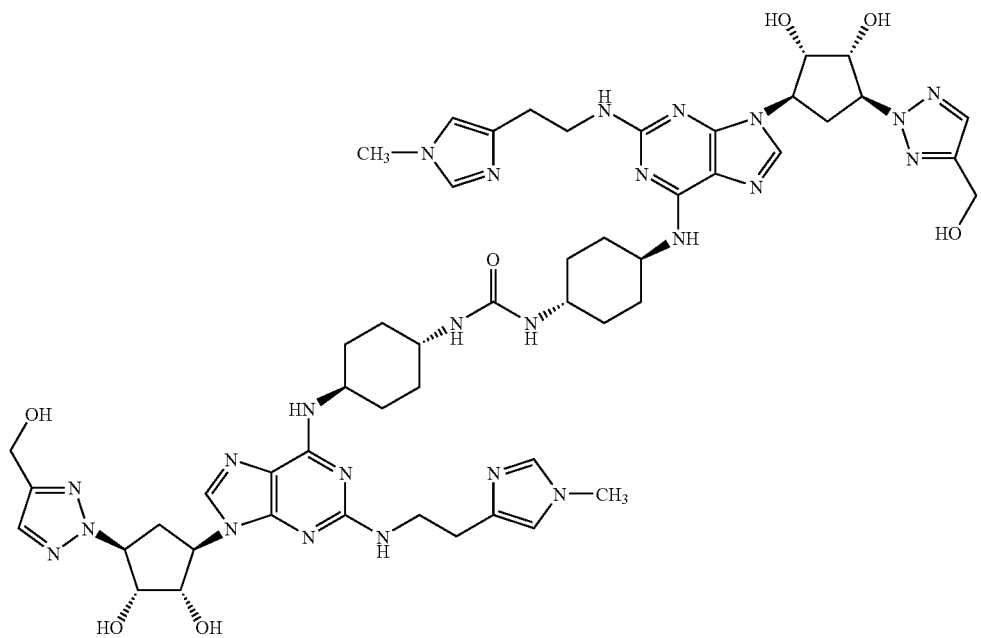

144
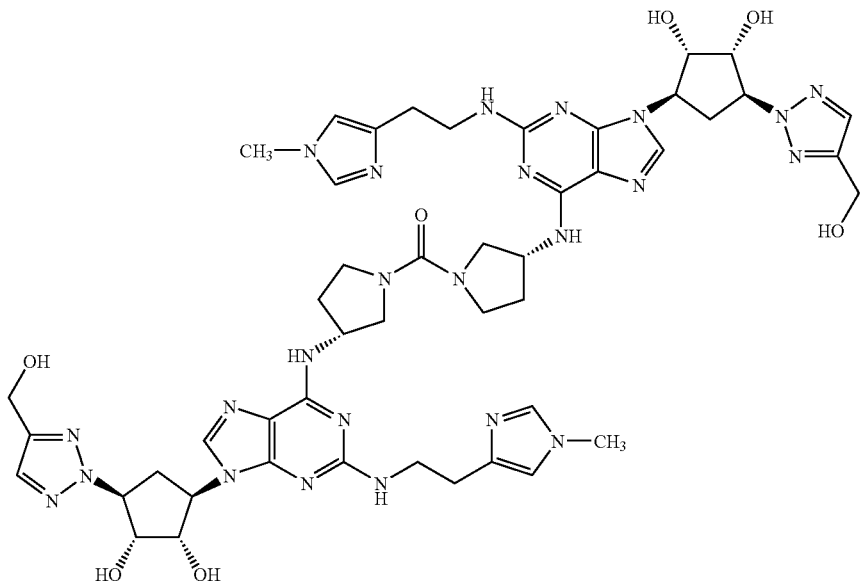
145
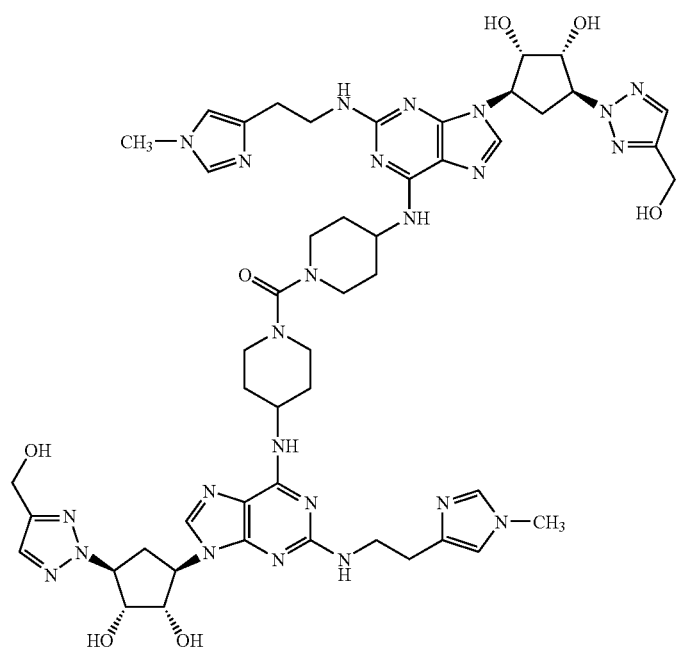

146
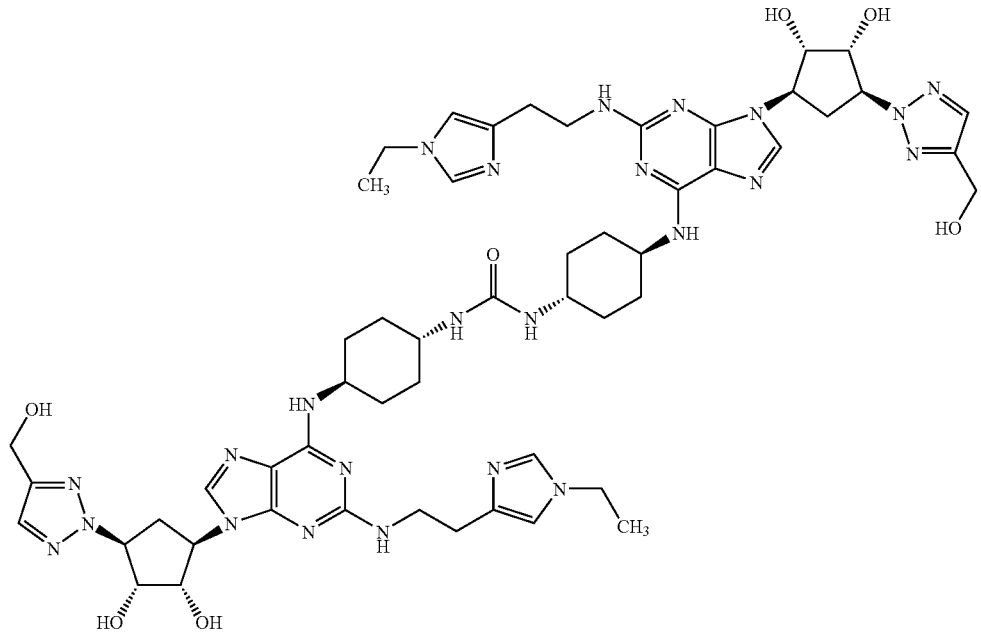
147
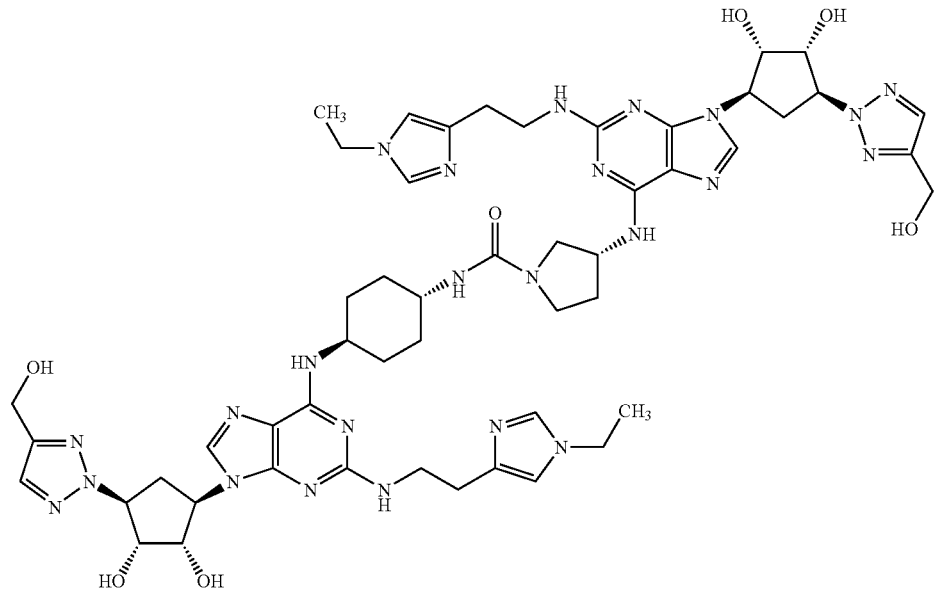

148
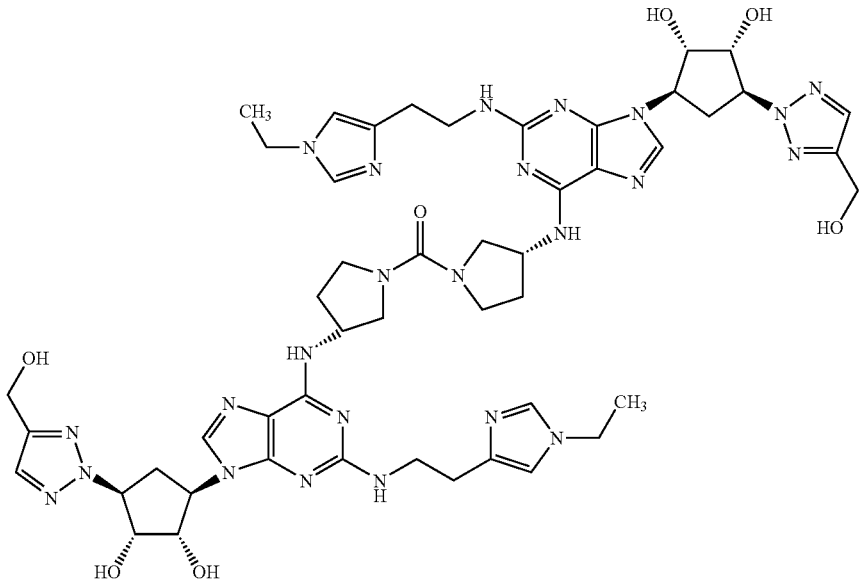
149
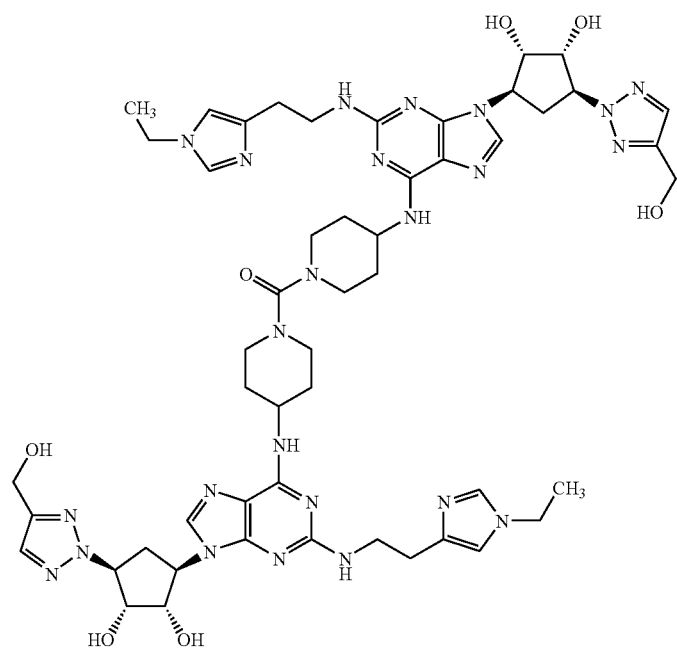

150
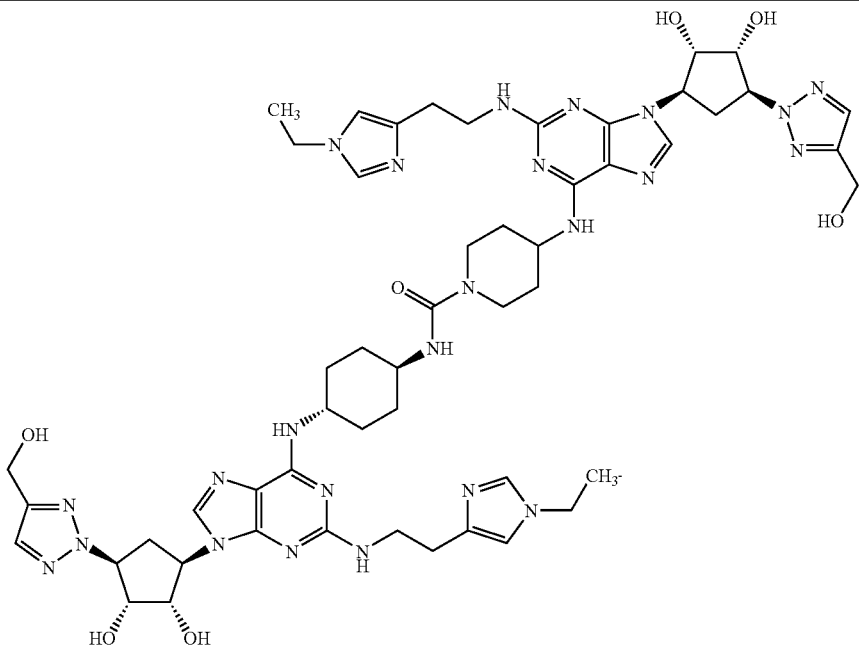
151
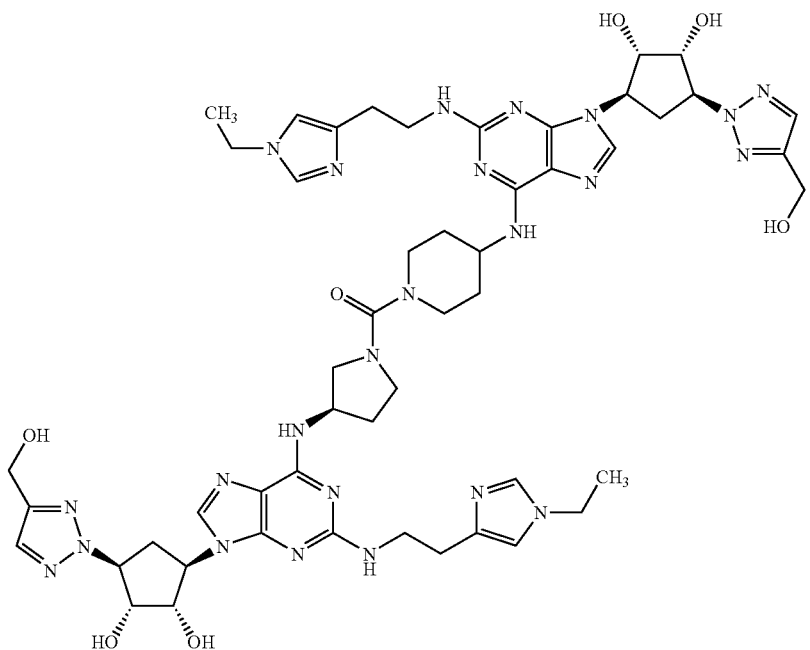

152 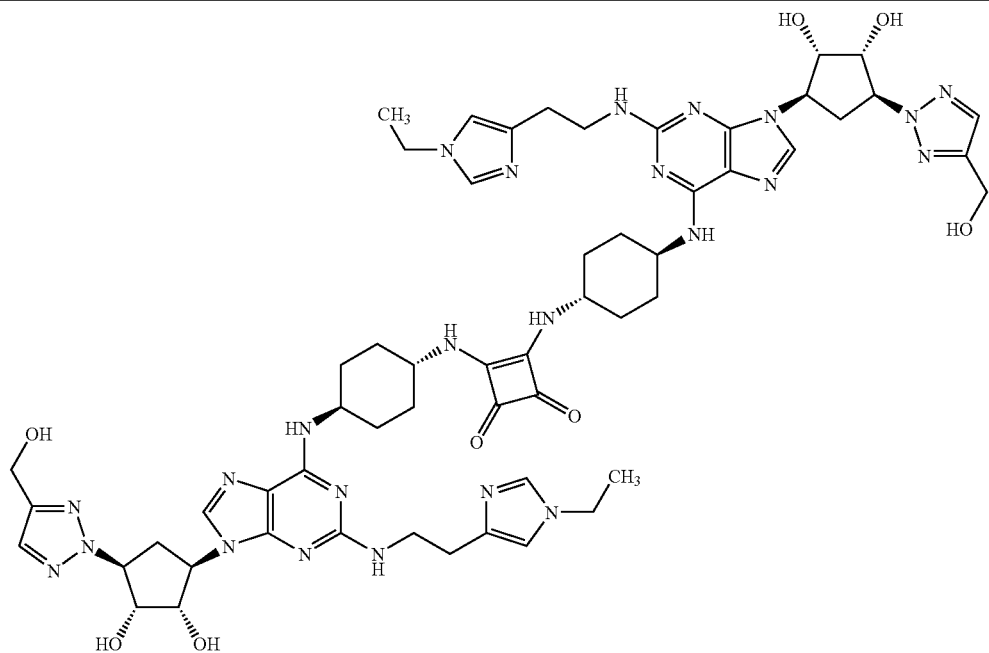
153 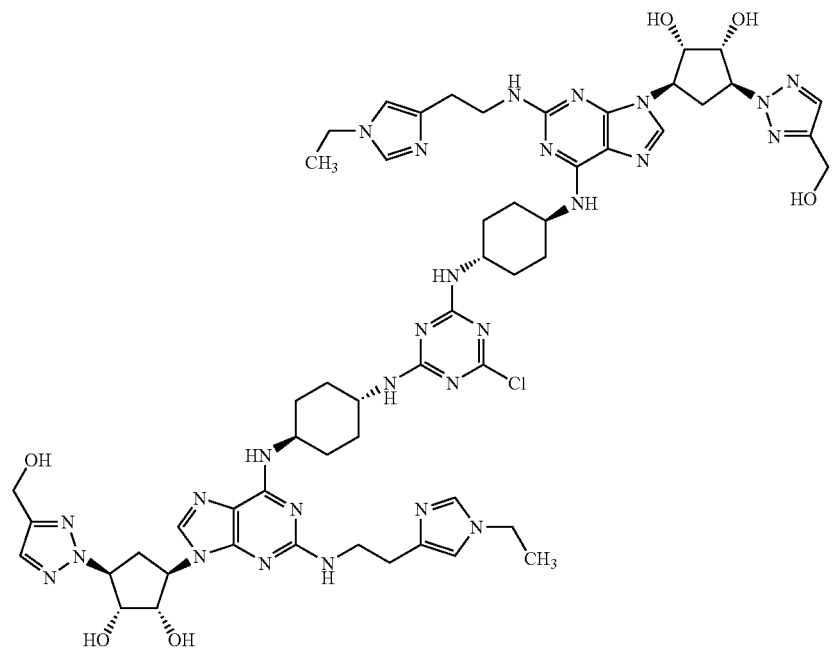

154
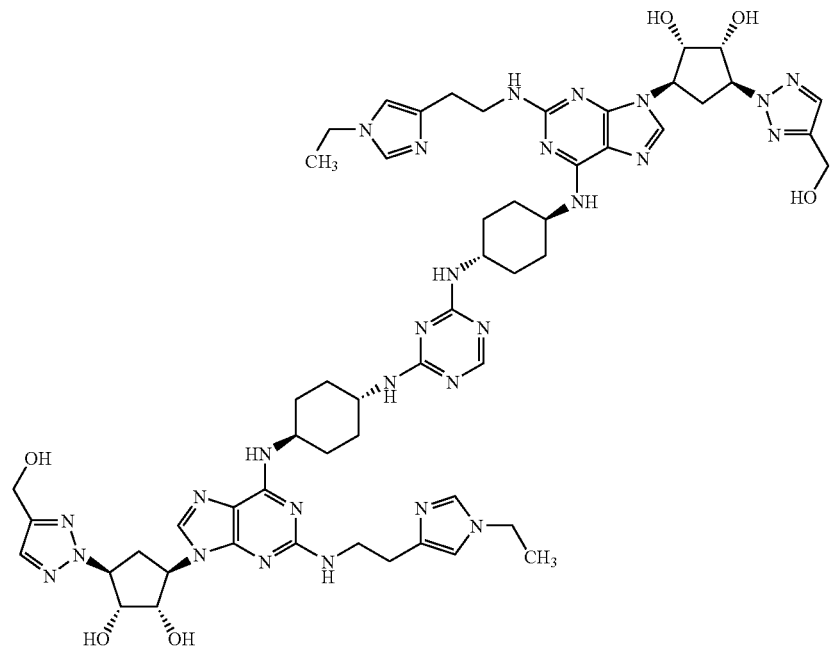
155
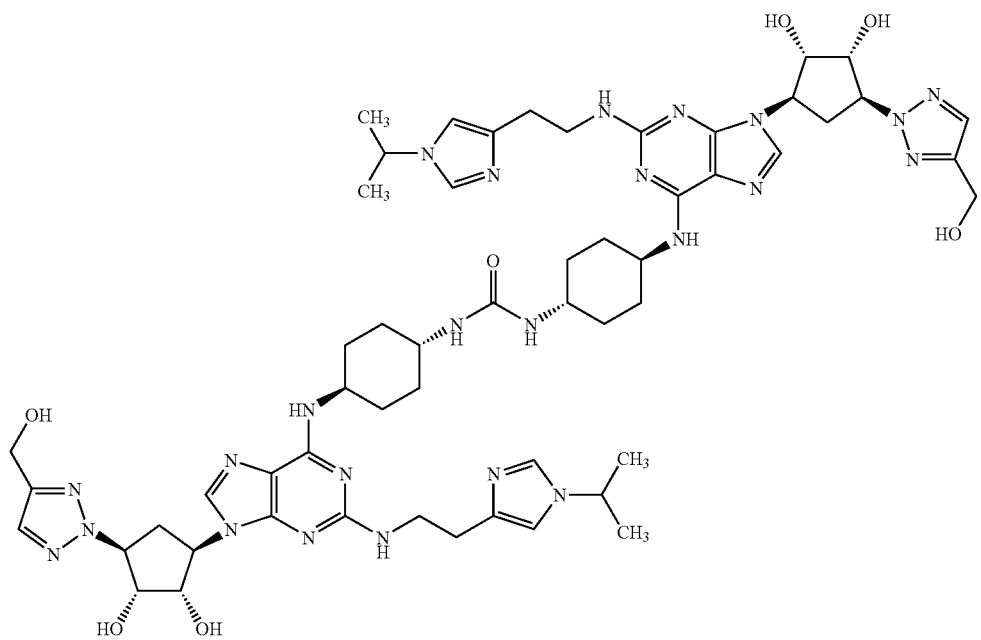

156
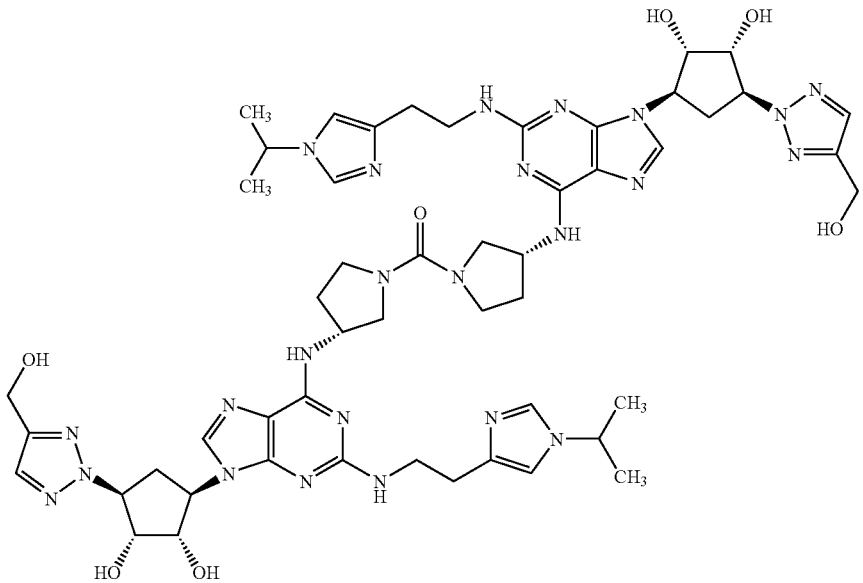
157
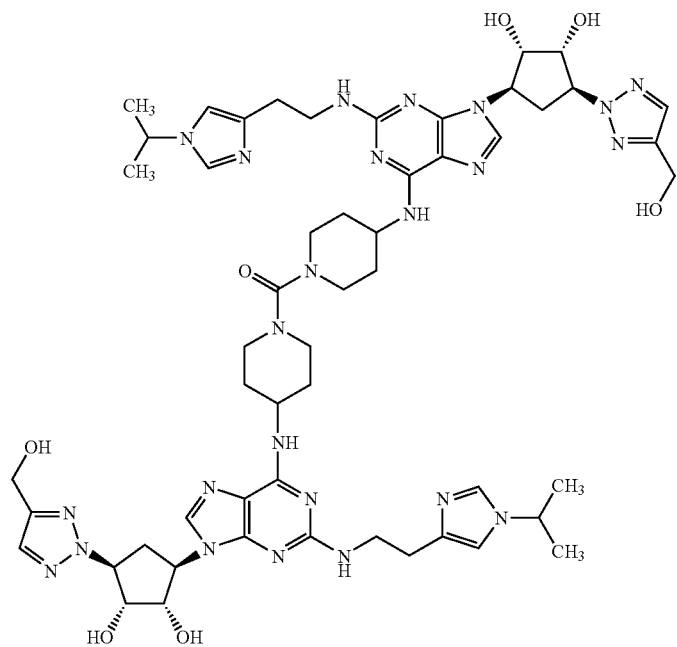

158
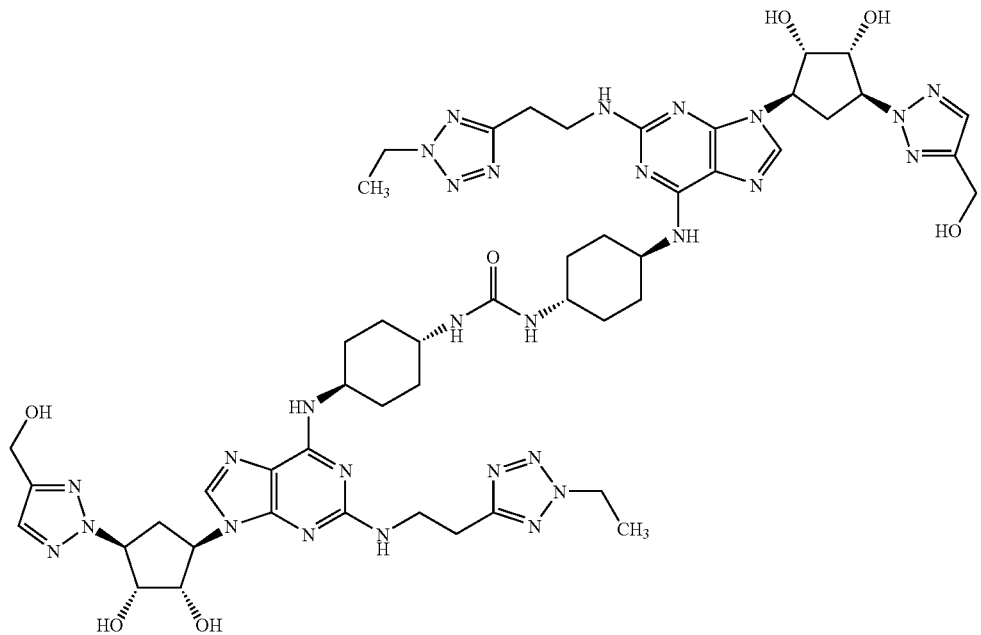
159
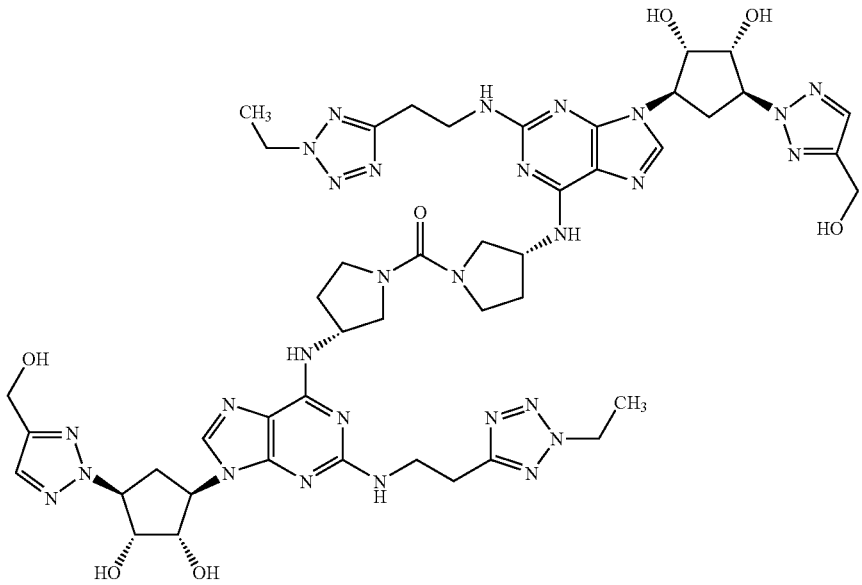

160
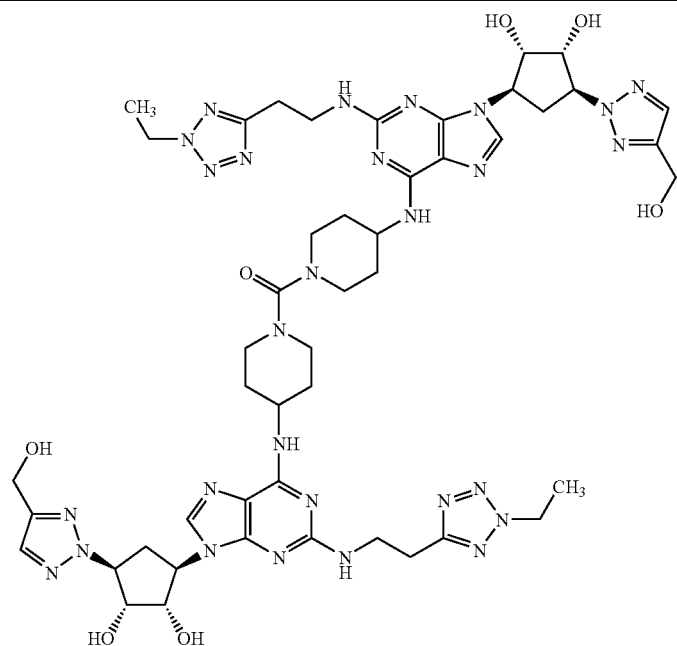
161
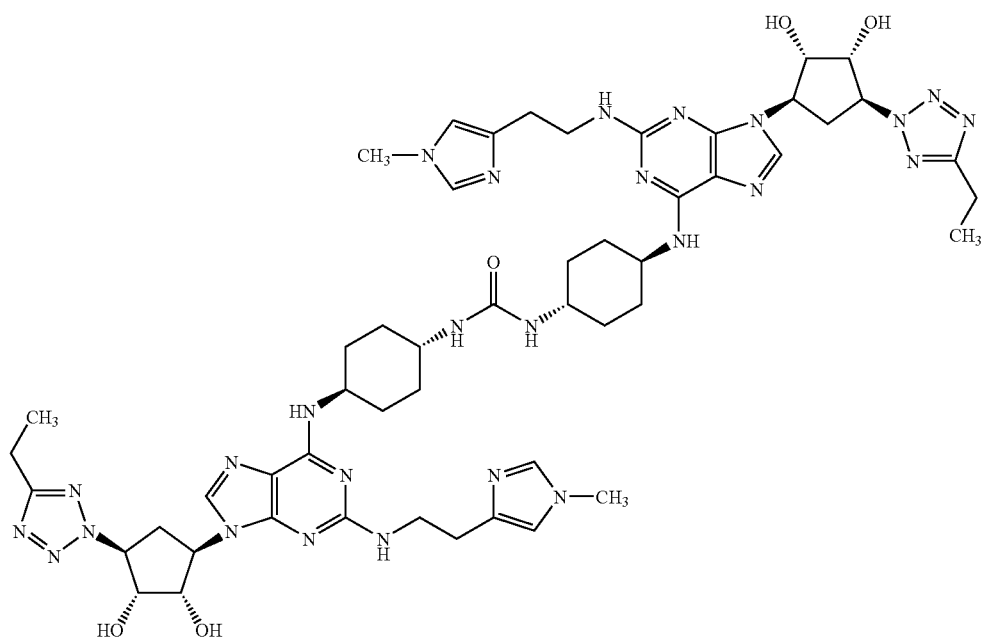

| 162 | 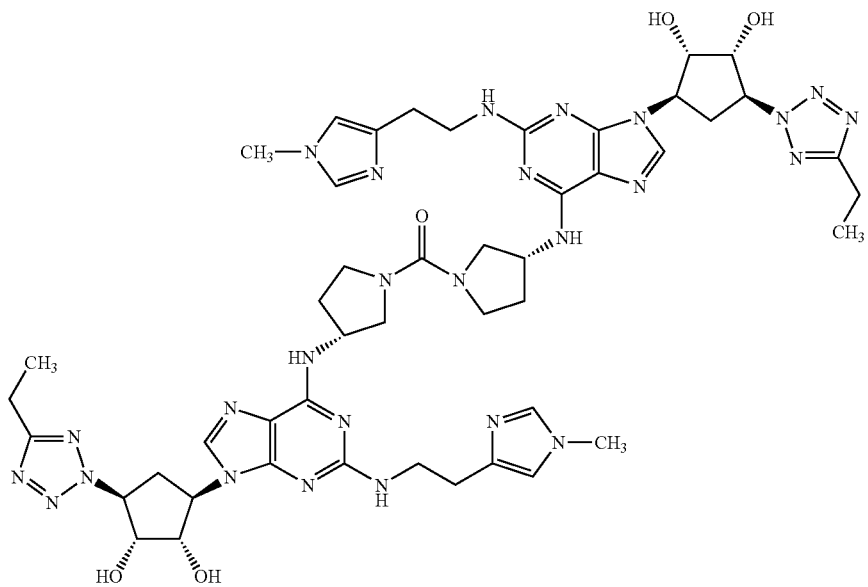 |
|---|---|
| 163 | 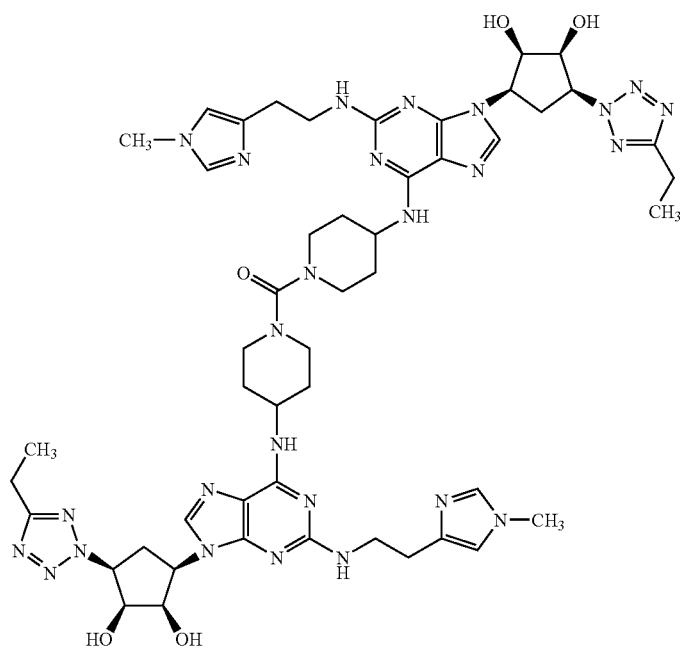 |
| Ex | R¹¹ | R¹² | A |
|---|---|---|---|
| 91 | 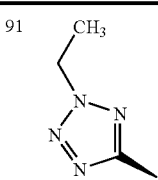 | 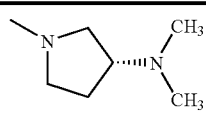 | 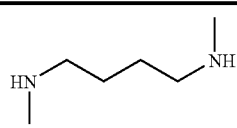 |
| 92 | 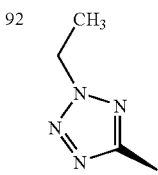 | 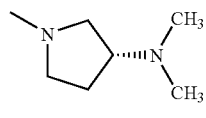 | 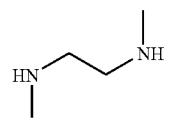 |

| | | | |
|---|---|---|---|
| 93 | 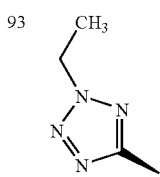 | 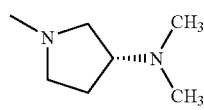 | 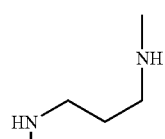 |
| 94 | 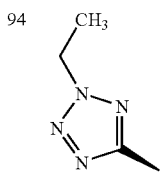 | 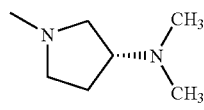 | 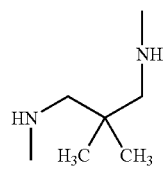 |
| 95 | 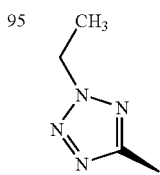 | 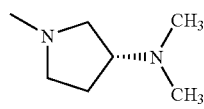 | 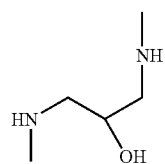 |
| 96 | 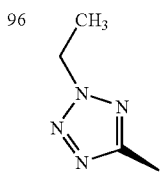 | 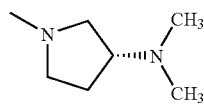 | 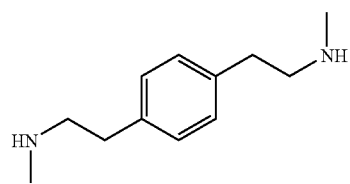 |
| 97 | 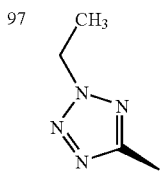 | 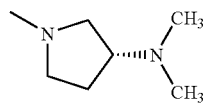 | 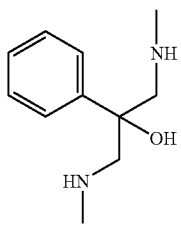 |
| 98 | 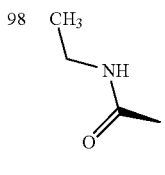 | 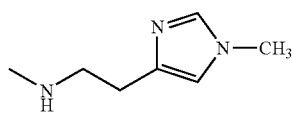 | 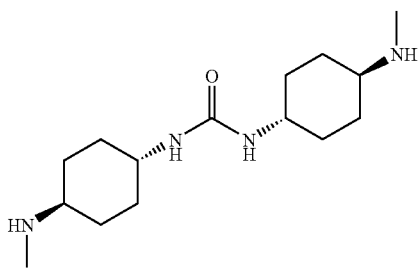 |
| 99 | 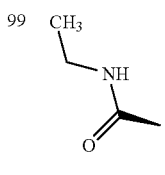 | 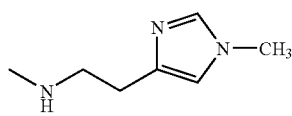 | 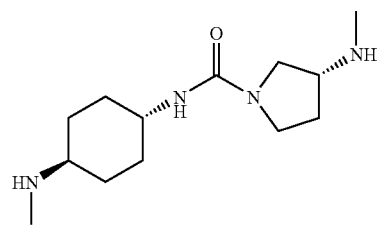 |

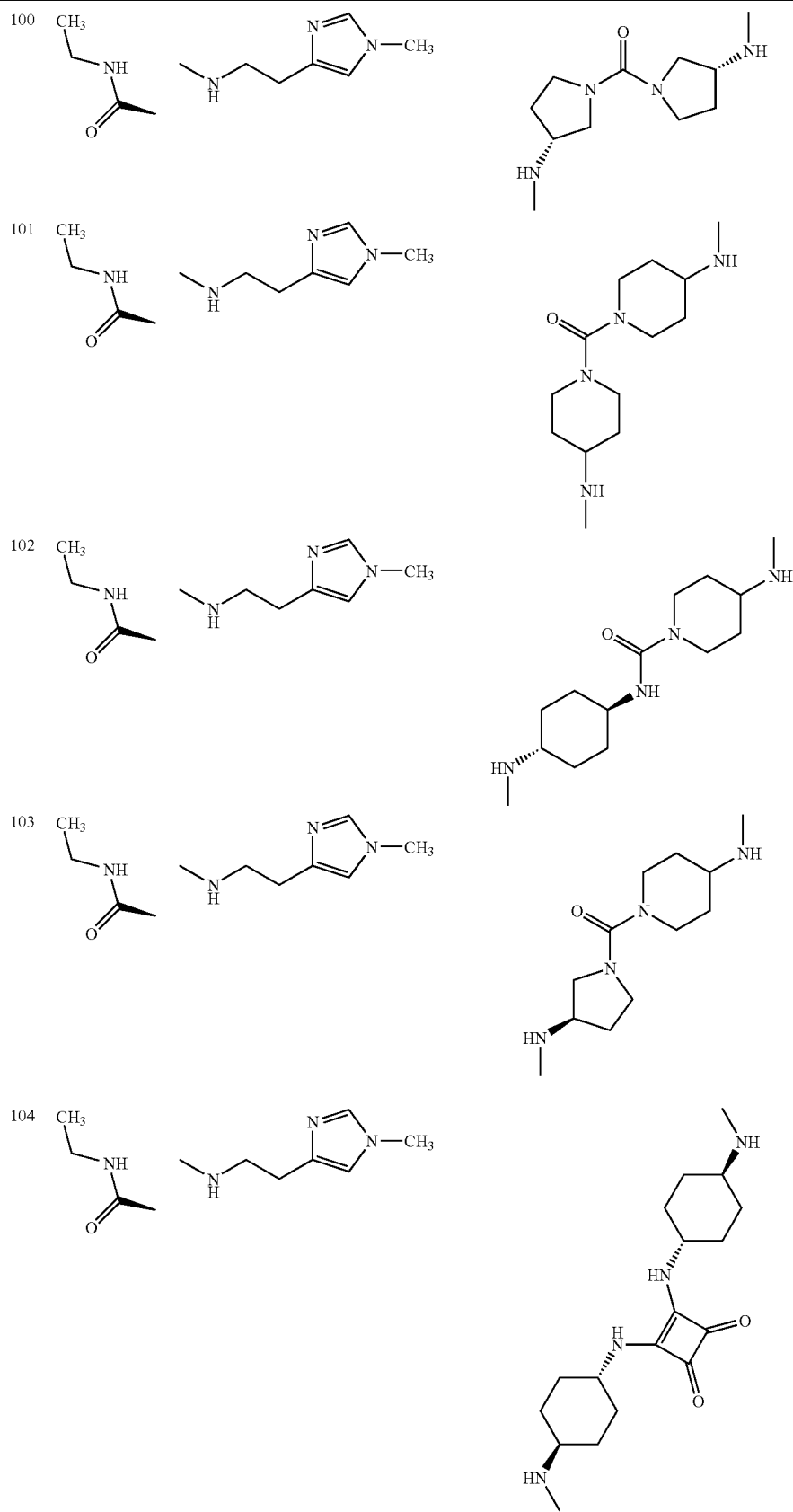

-continued
| | | | |
|---|---|---|---|
| 105 | 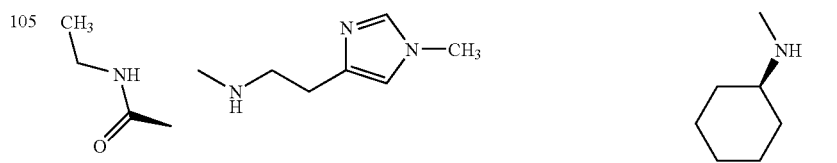 | | |
| 106 | | | |
| 107 | | 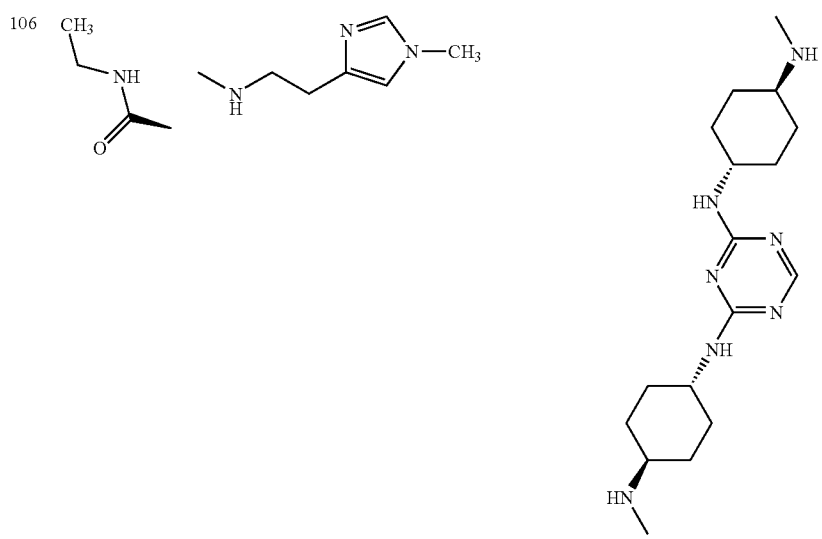 | |
| 108 | | 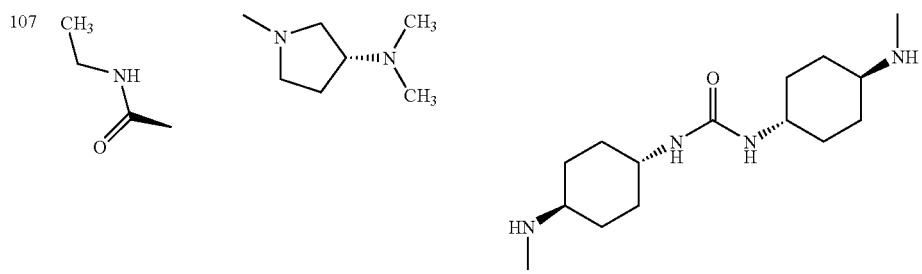 | |
| | | 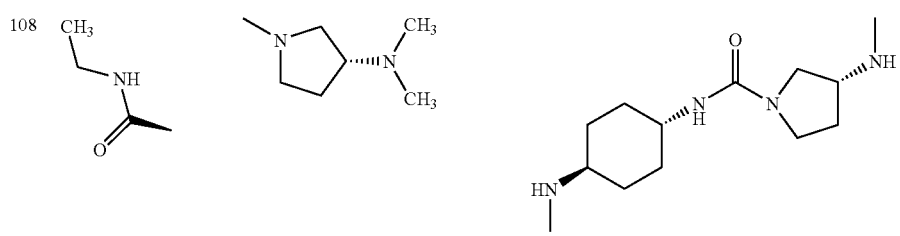 | |

US 8,193,164 B2
339 340
-continued
| | | | |
|---|---|---|---|
| 109 | 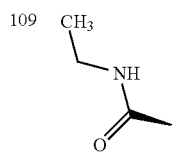 | 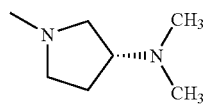 | 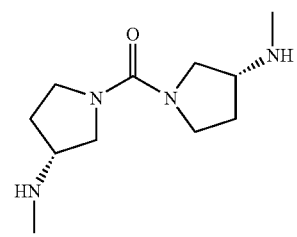 |
| 110 | 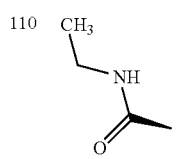 | 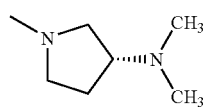 | 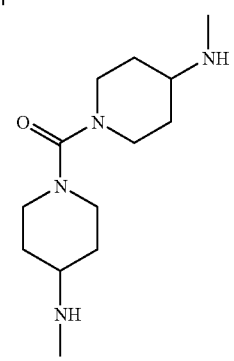 |
| 111 | 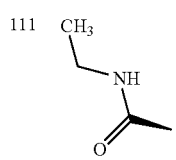 | 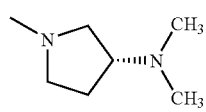 | 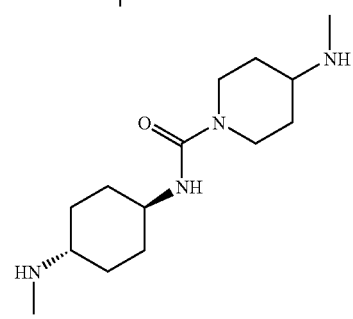 |
| 112 | 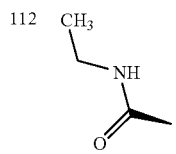 | 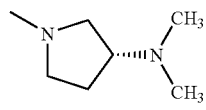 | 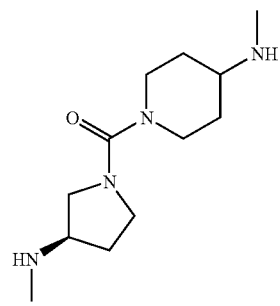 |
| 113 | 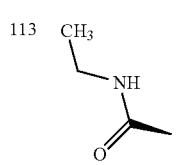 | 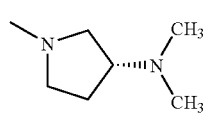 | 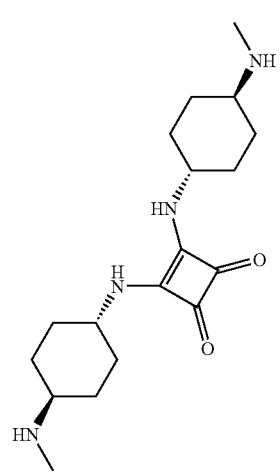 |

-continued
| 114 | 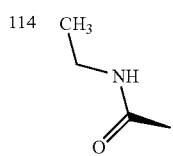 | 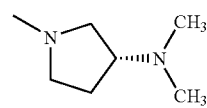 | 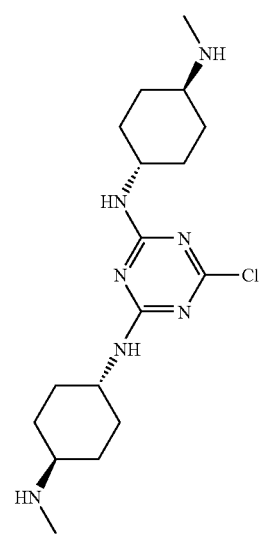 |
| 115 | 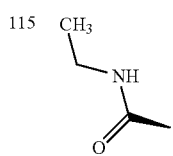 | 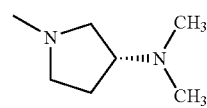 | 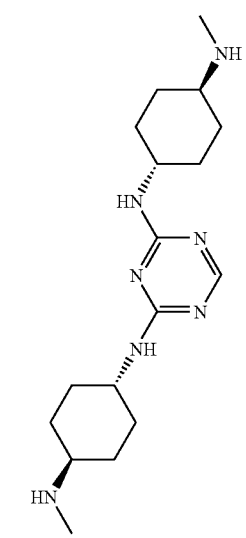 |
| 116 | 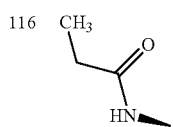 | 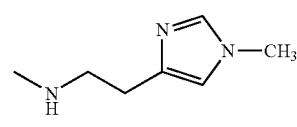 | 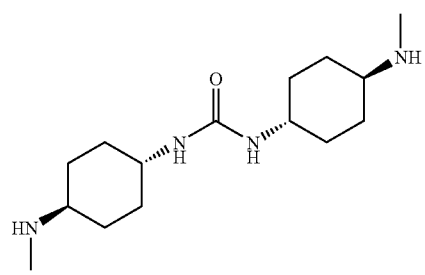 |
| 117 | 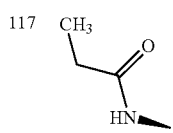 | 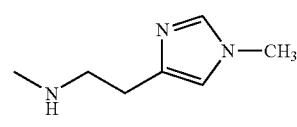 | 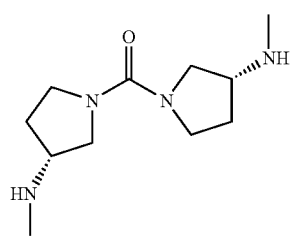 |

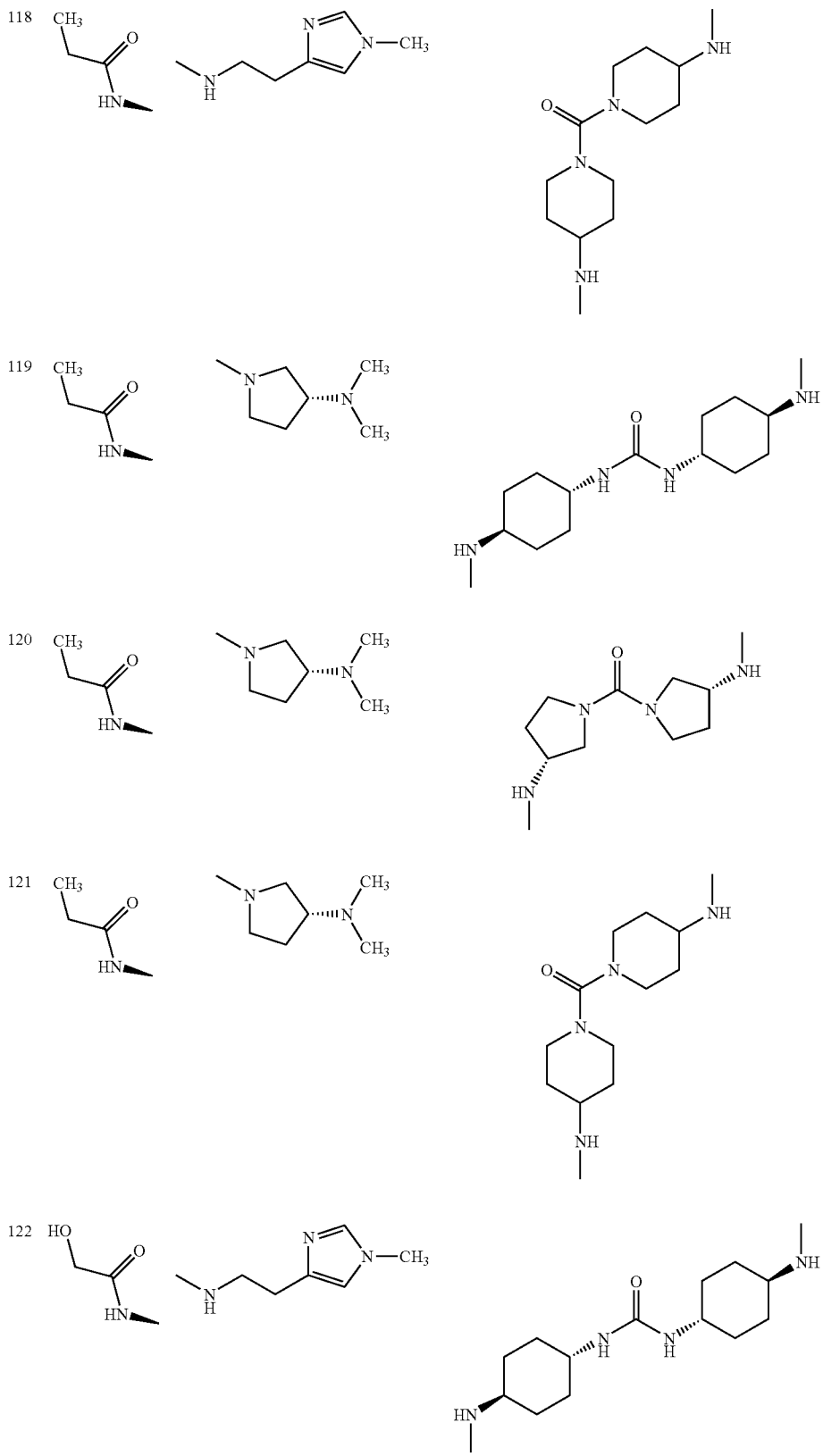

-continued
| 123 | 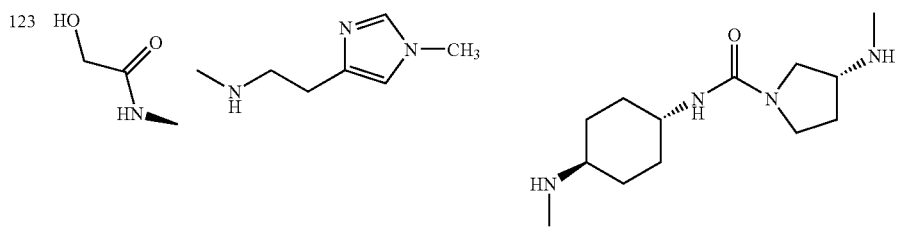 |
| 124 | 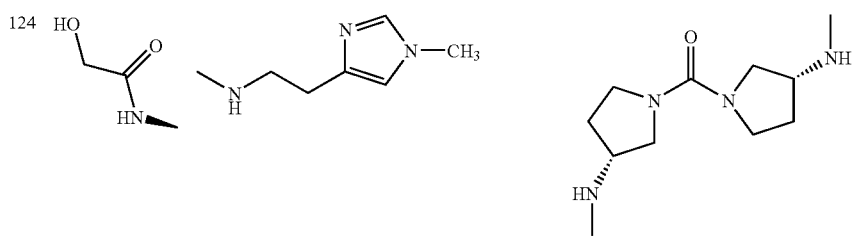 |
| 125 | 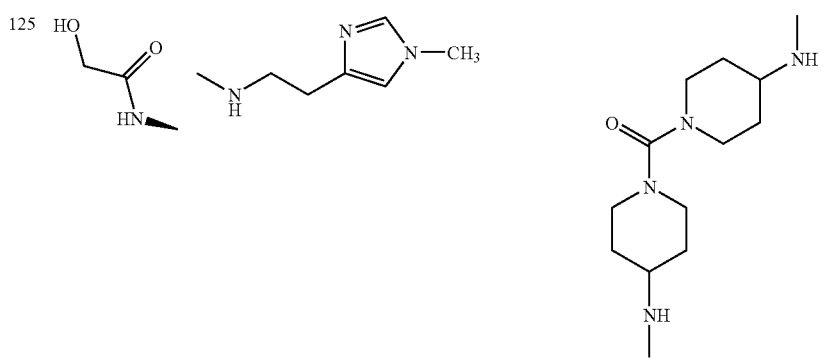 |
| 126 | 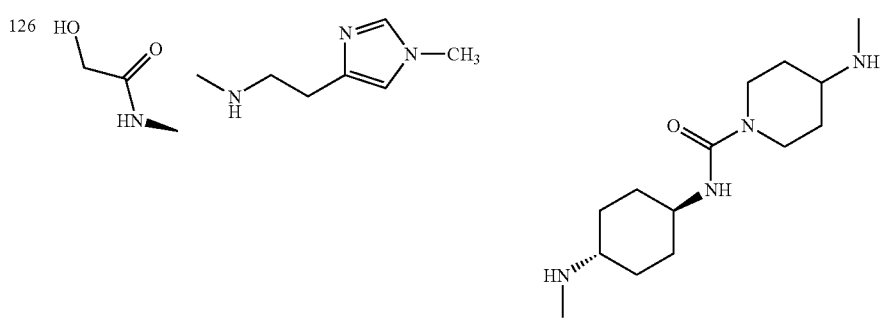 |
| 127 | 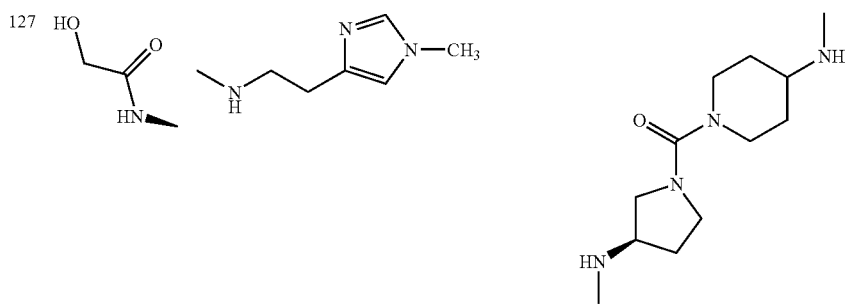 |

-continued
128 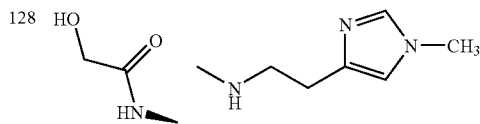 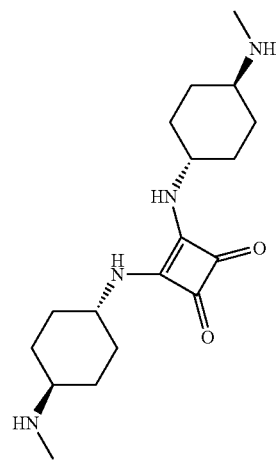
129 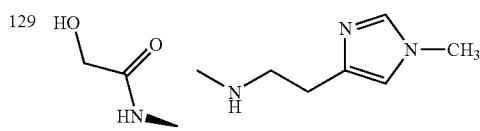 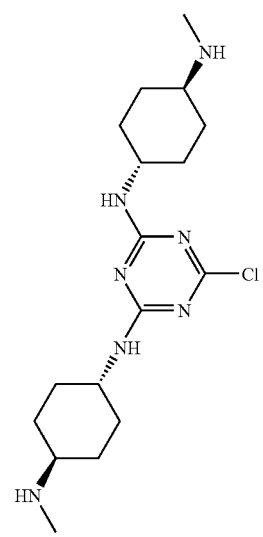
130 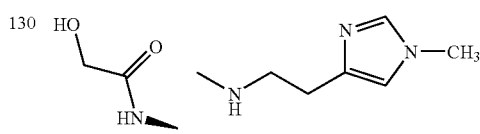 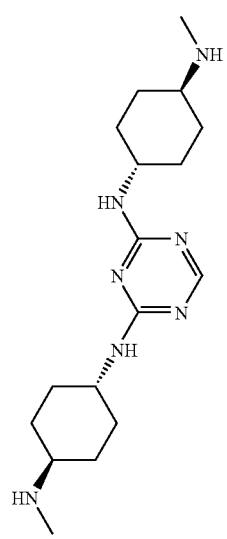

| | | |
|---|---|---|
| 131 | 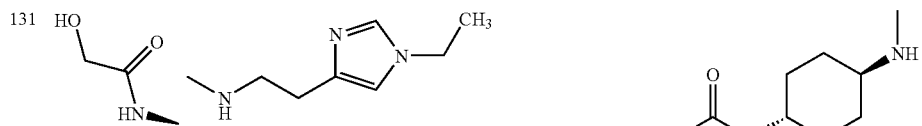 | 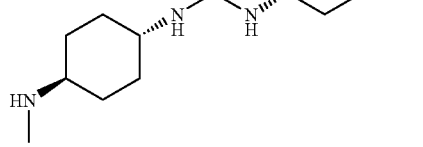 |
| 132 | 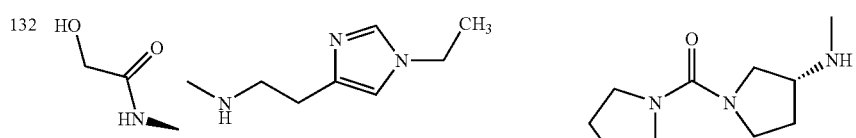 |  |
| 133 | 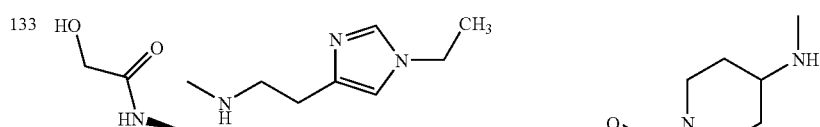 | 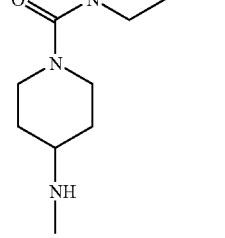 |
| 134 | 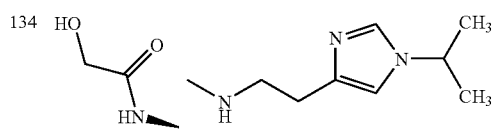 | 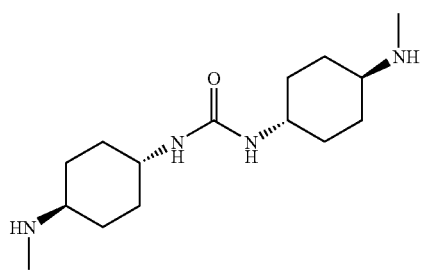 |
| 135 | 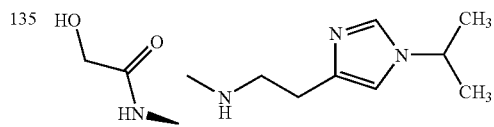 | 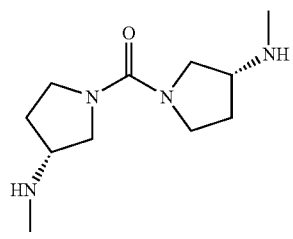 |

-continued
| | | |
|---|---|---|
| 136 | 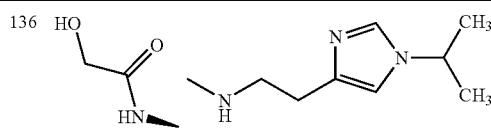 | 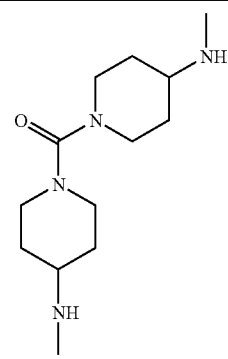 |
| 137 | 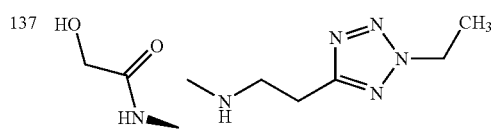 | 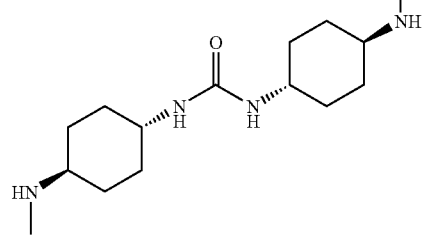 |
| 138 | 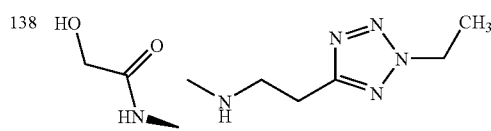 | 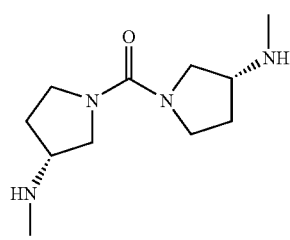 |
| 139 | 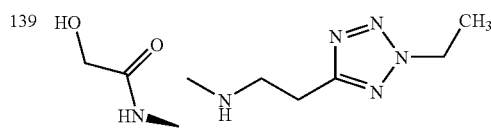 | 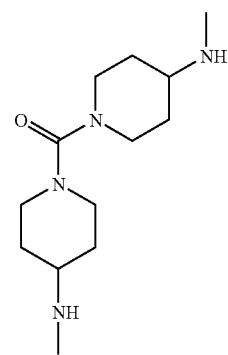 |
| 140 | 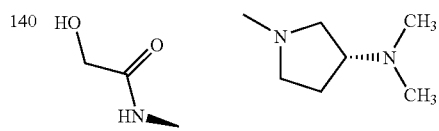 | 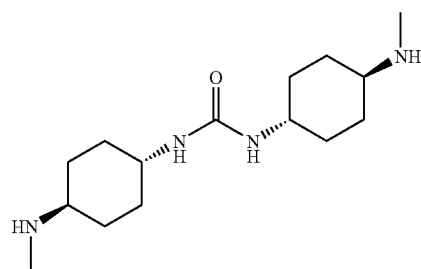 |

| | | | |
|---|---|---|---|
| 141 | 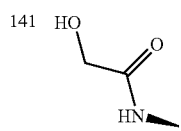 | 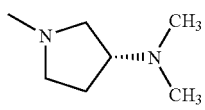 | 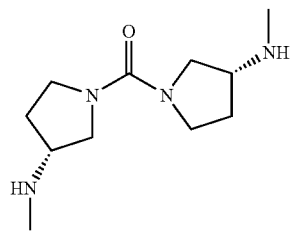 |
| 142 | 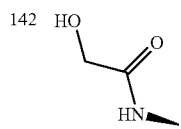 | 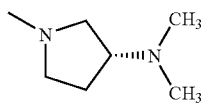 | 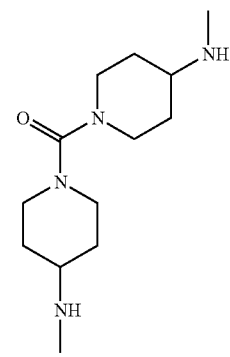 |
| 143 | 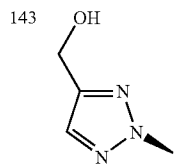 | 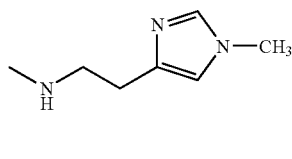 | 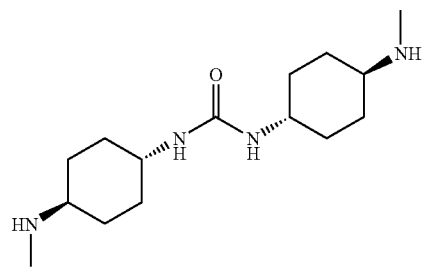 |
| 144 | 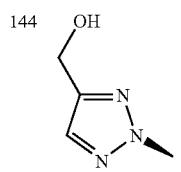 | 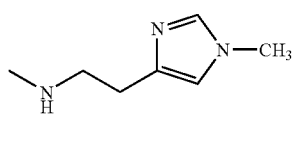 | 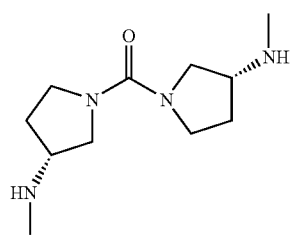 |
| 145 | 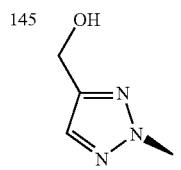 | 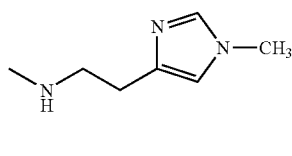 | 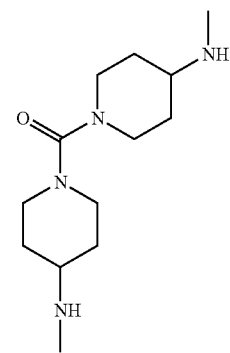 |

| 355 | 356 |
|---|---|
| 146 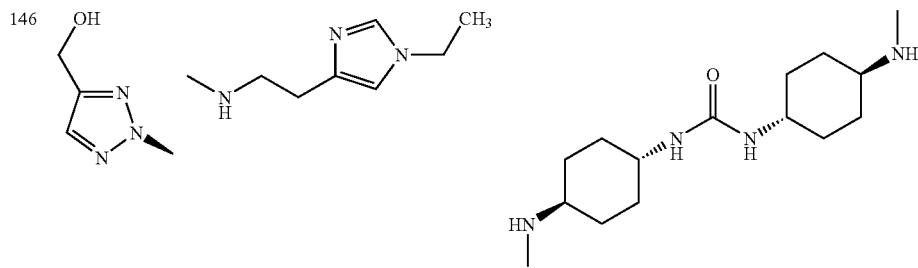 | |
| 147 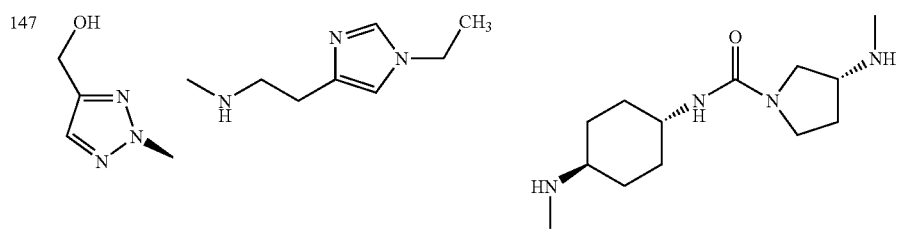 | |
| 148 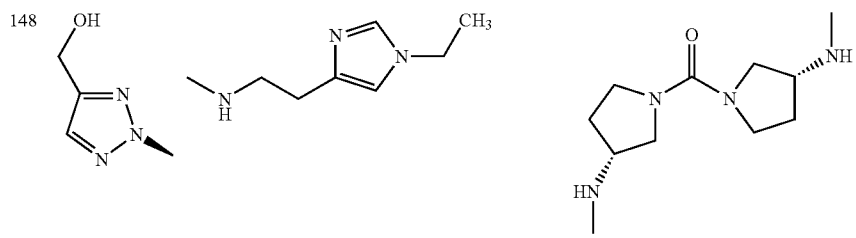 | |
| 149 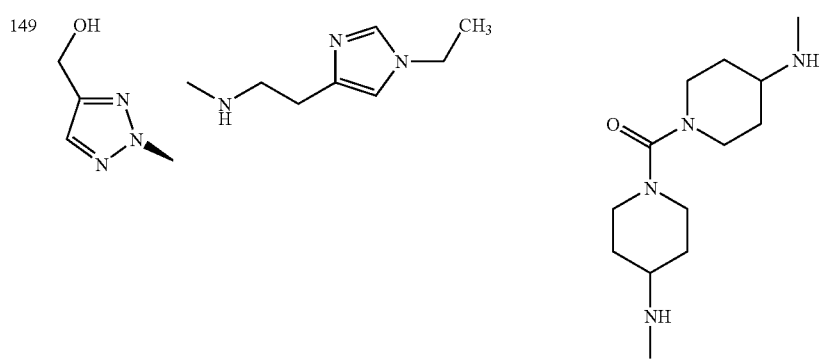 | |
| 150 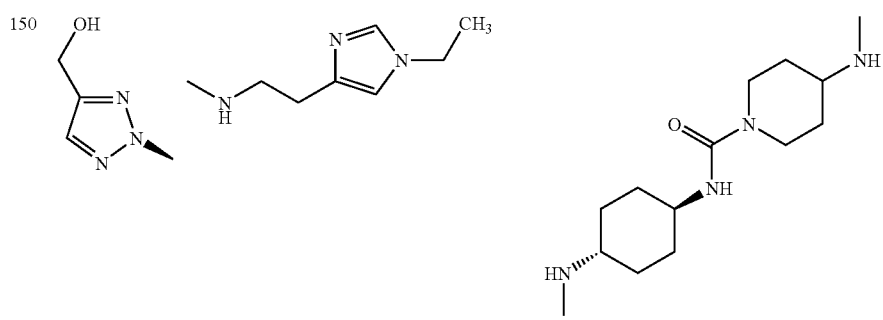 | |

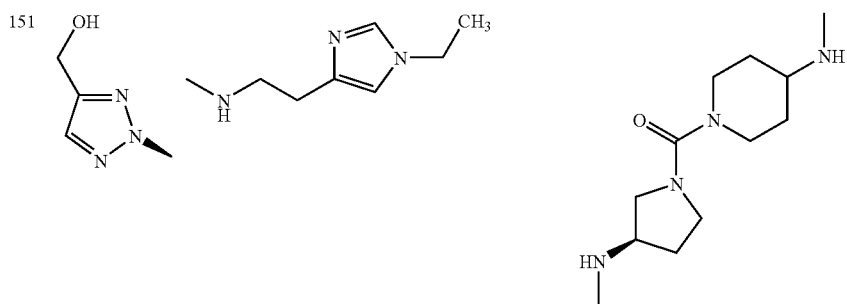
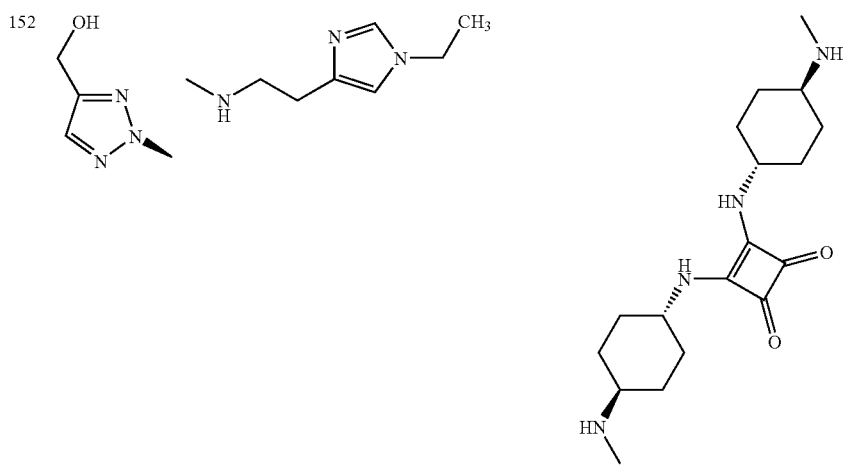
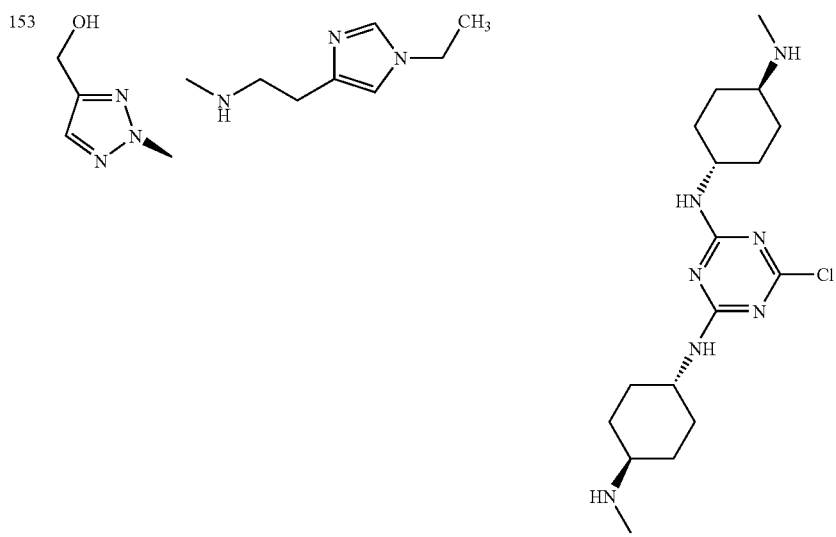

| | | | |
|---|---|---|---|
| 154 | 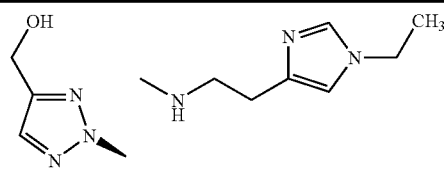 | | 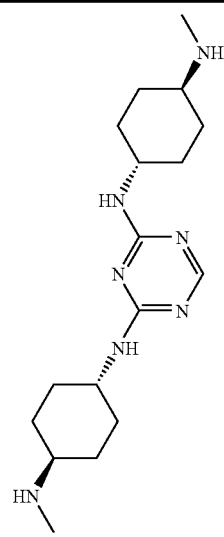 |
| 155 | 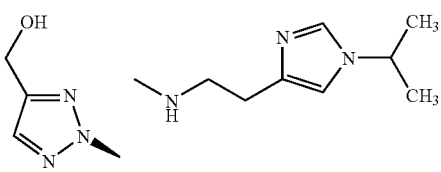 | | 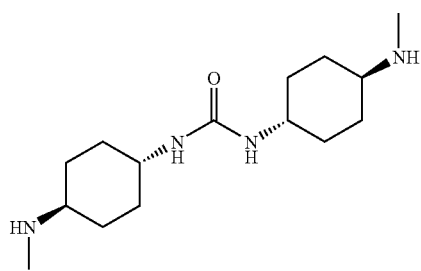 |
| 156 | 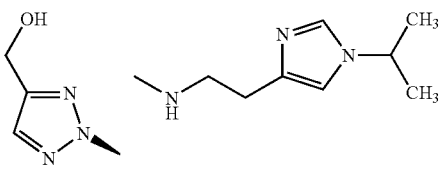 | | 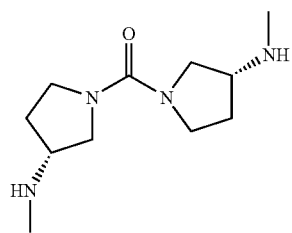 |
| 157 | 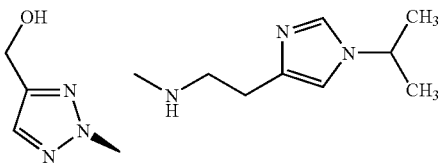 | | 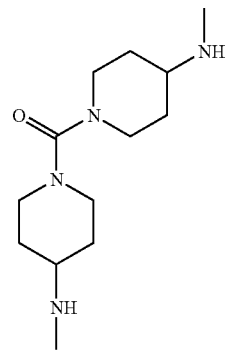 |

| 361 | 362 |
|---|---|
| 158 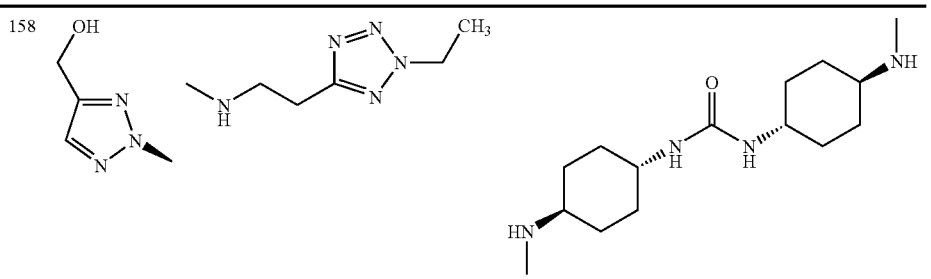 | |
| 159 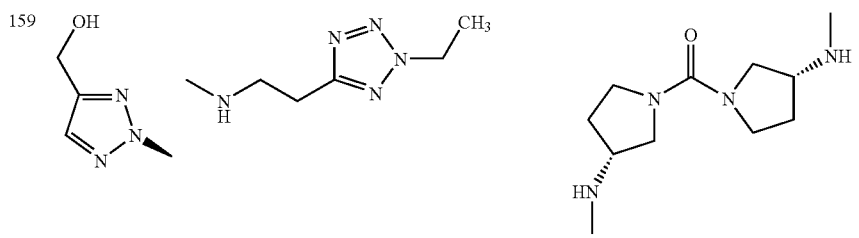 | |
| 160 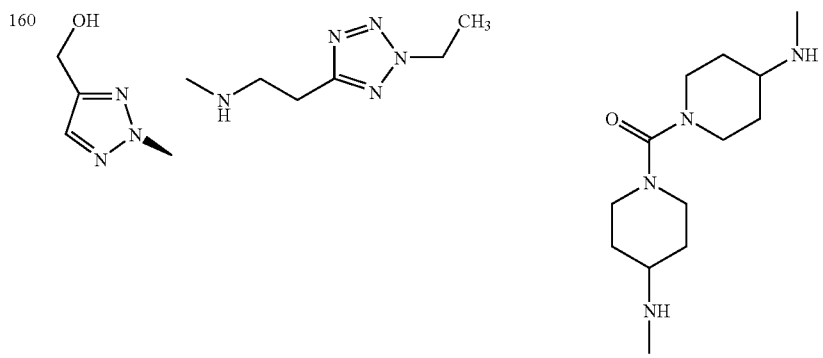 | |
| 161 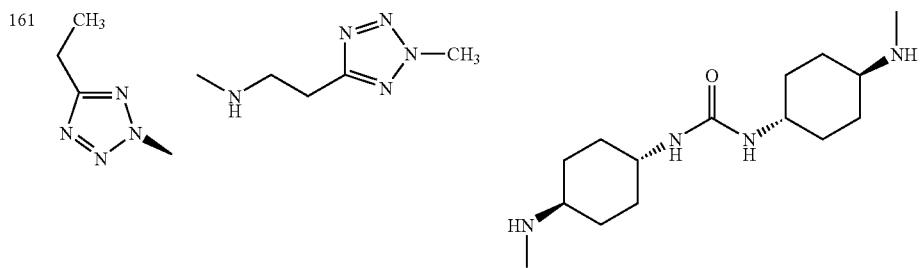 | |
| 162 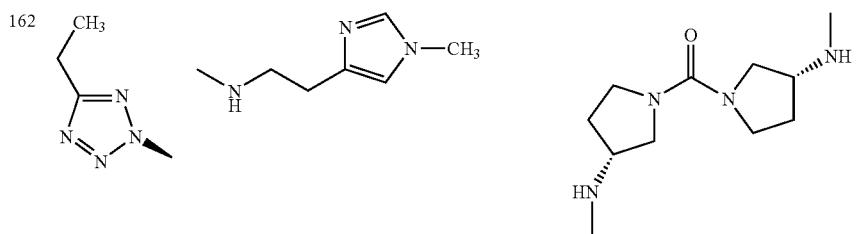 | |

-continued
| 163 | 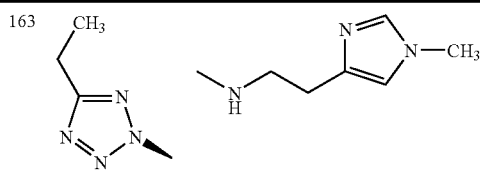 | 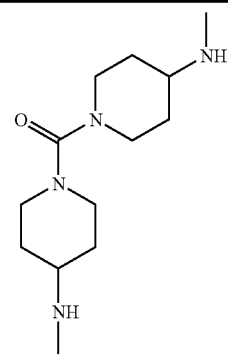 |
Examples 164-180
Additional compounds of formula (X) are shown in the following table. Methods of preparing such compounds are described hereinafter.
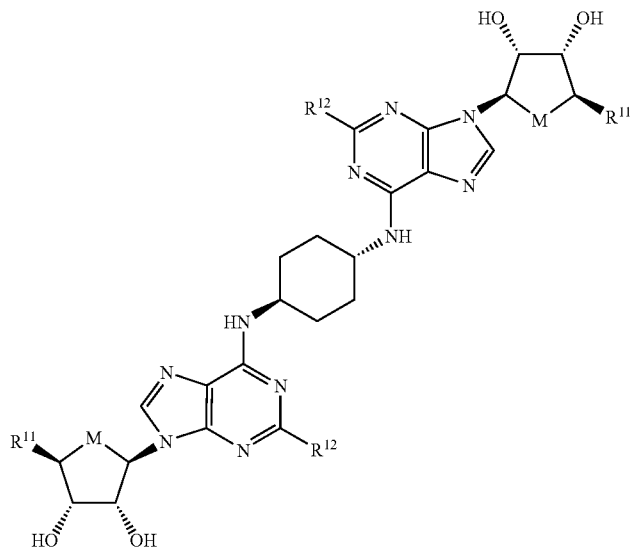
(X)
M is CH$_2$ except in Example P169 where M is O
| Ex | Structure | R$^{11}$ | R$^{12}$ |
|----|-----------|----------|----------|
| 164 | 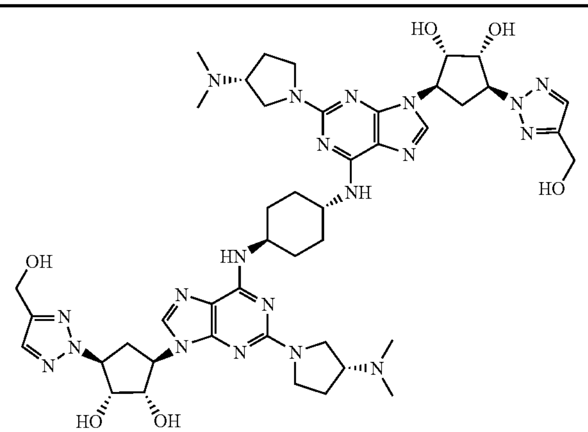 | | |

| 165 | 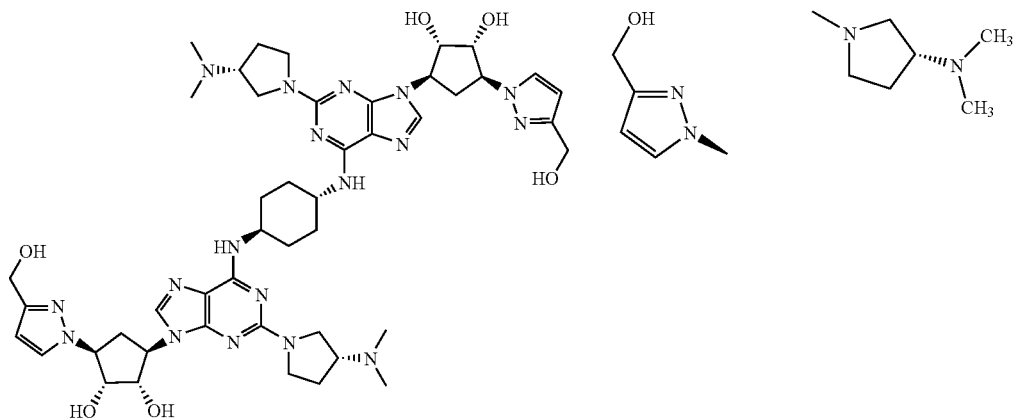 |
| 166 | 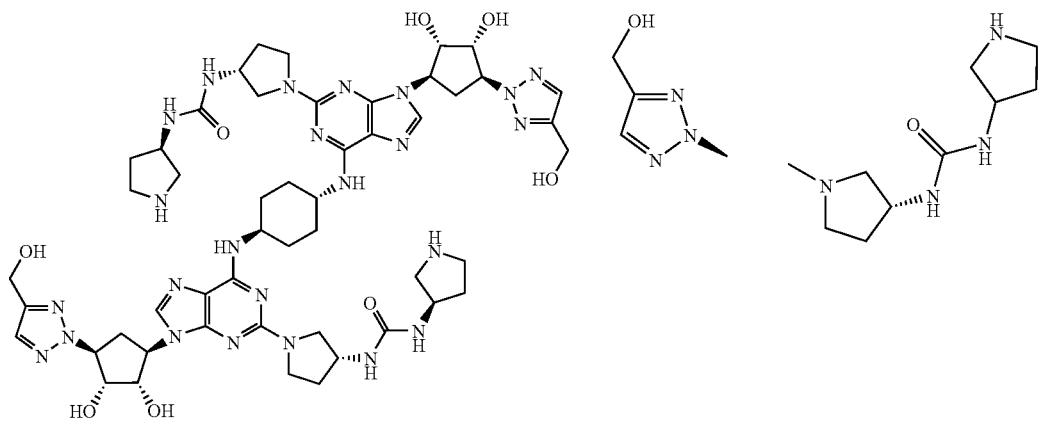 |
| 167 | 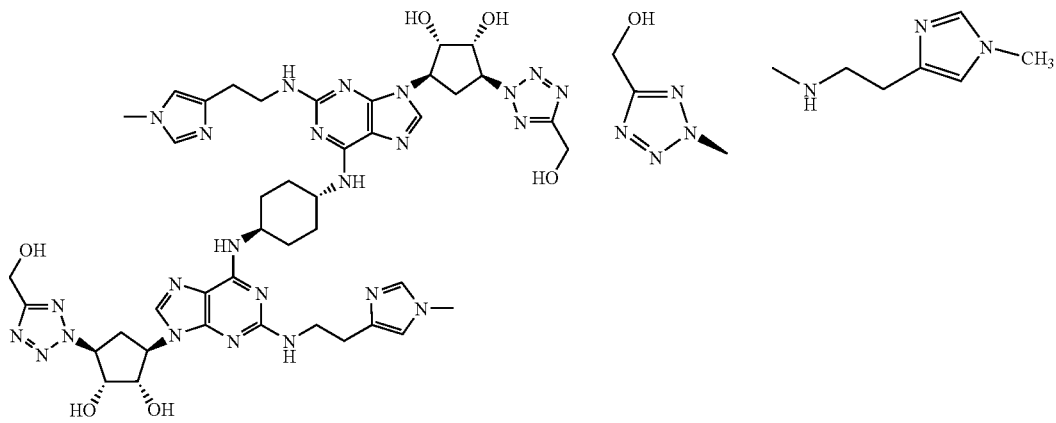 |

| 168 | 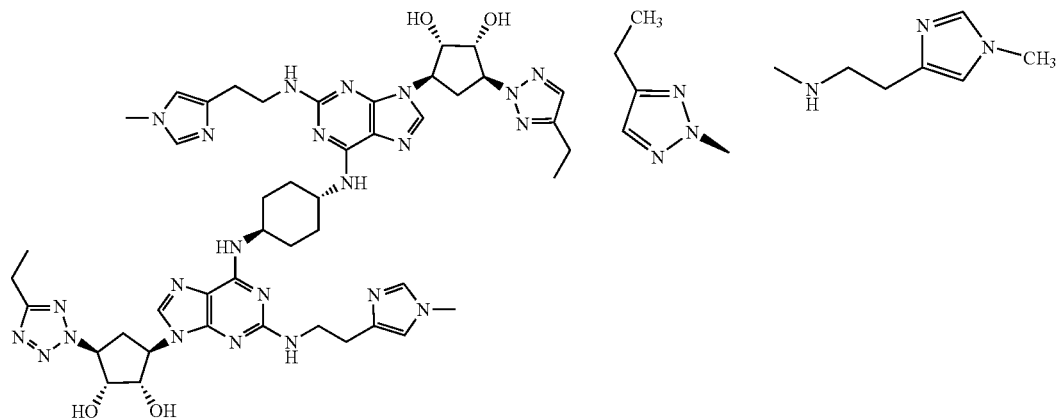 |
| 169 | 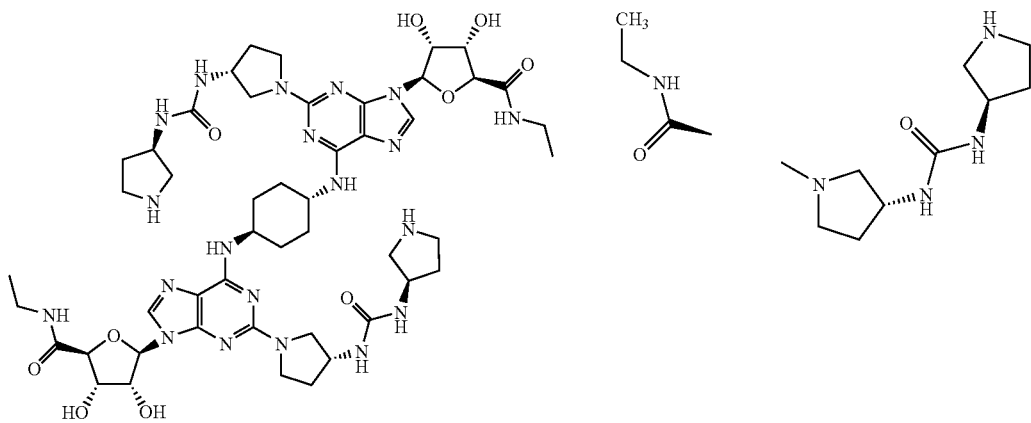 |
| 170 | 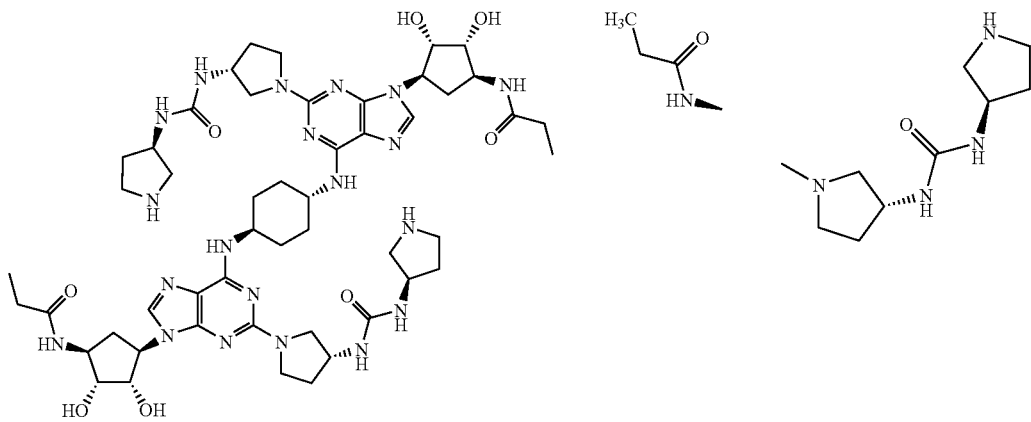 |

| 171 | 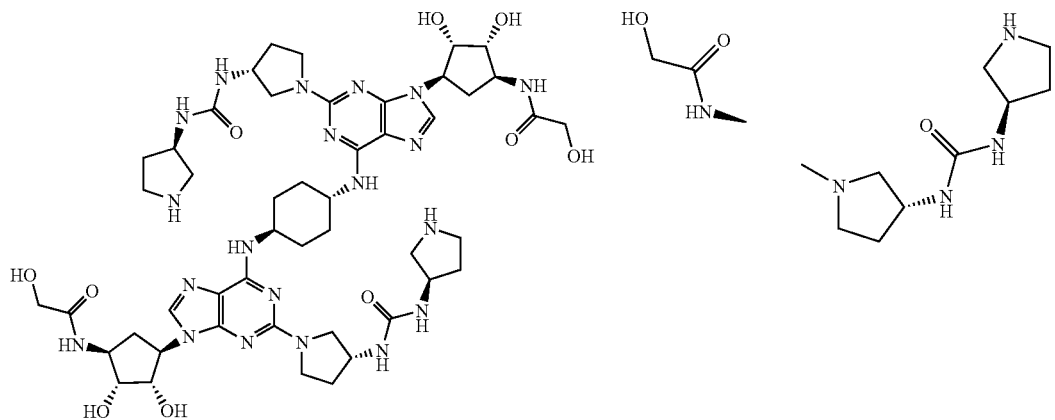 |
| 172 | 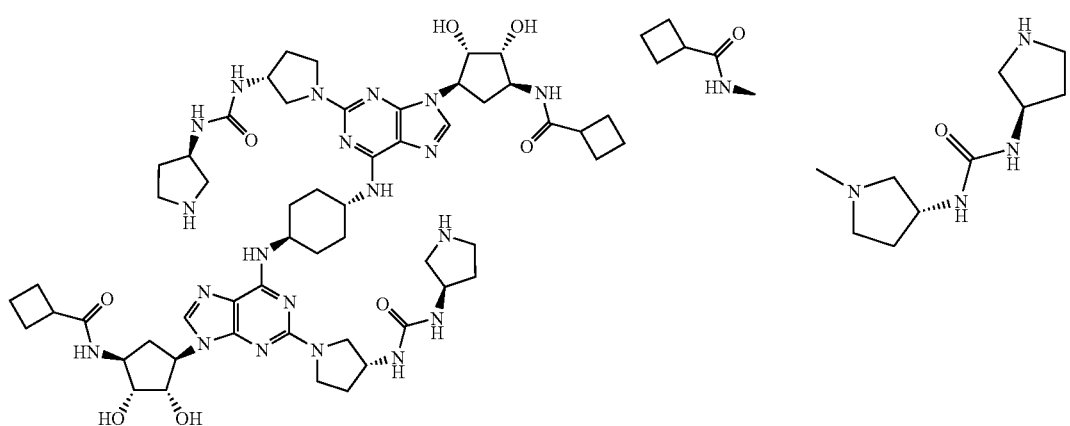 |
| 173 | 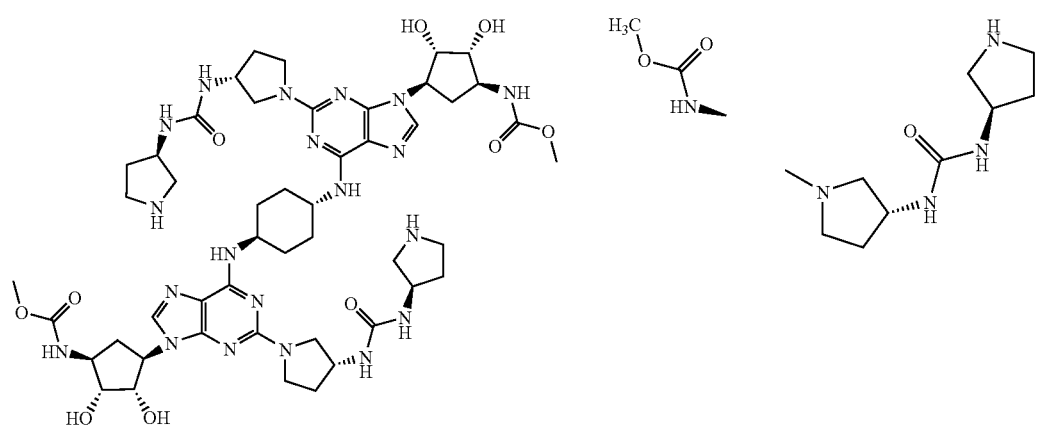 |

| 174 | 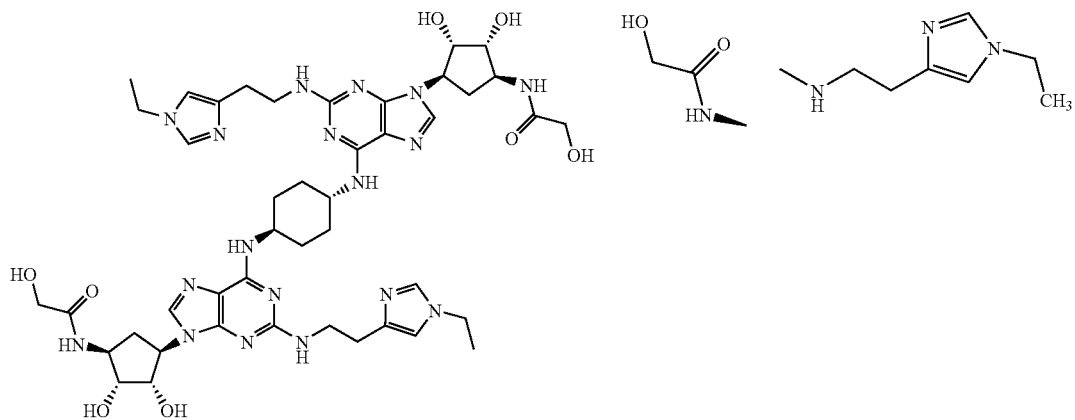 |
| 175 | 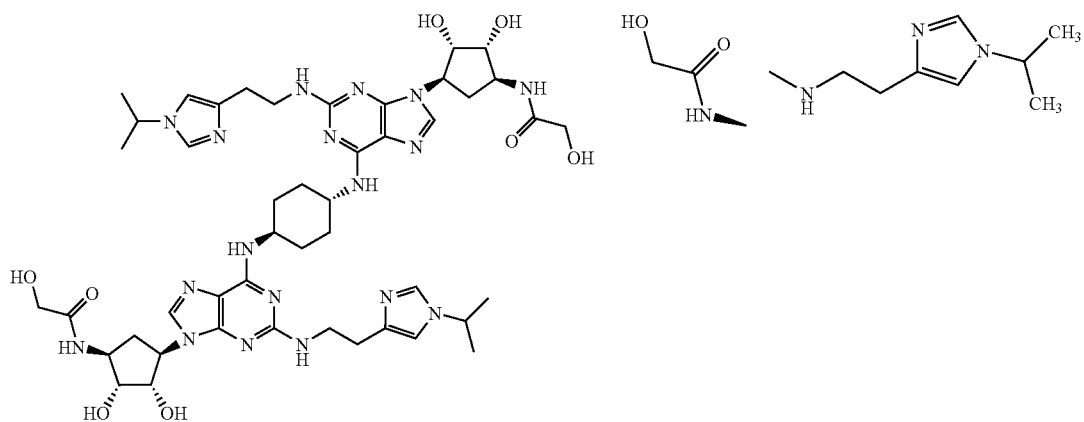 |
| 176 | 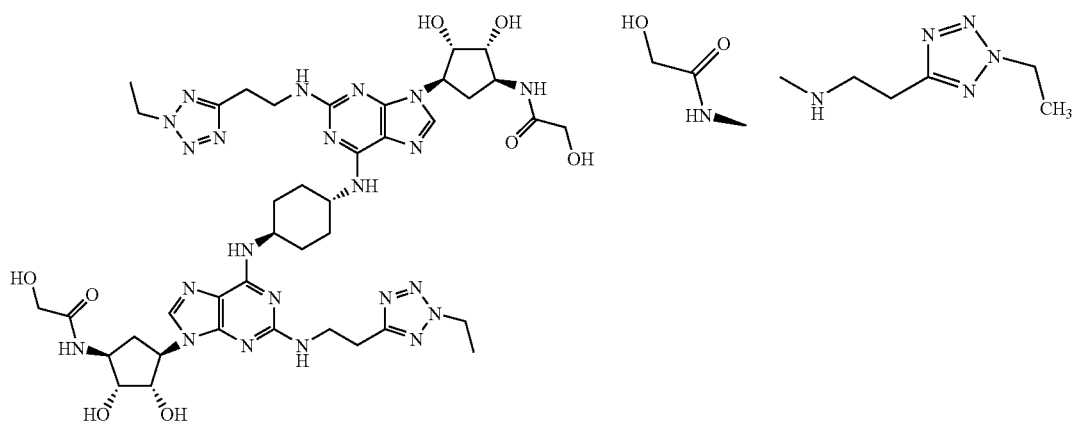 |

| 373 | 374 |
|---|---|
| 177 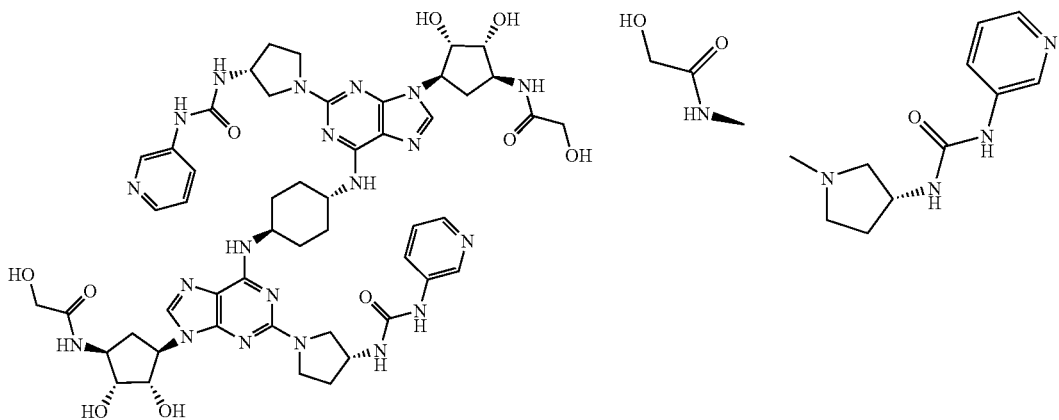 | |
| 178 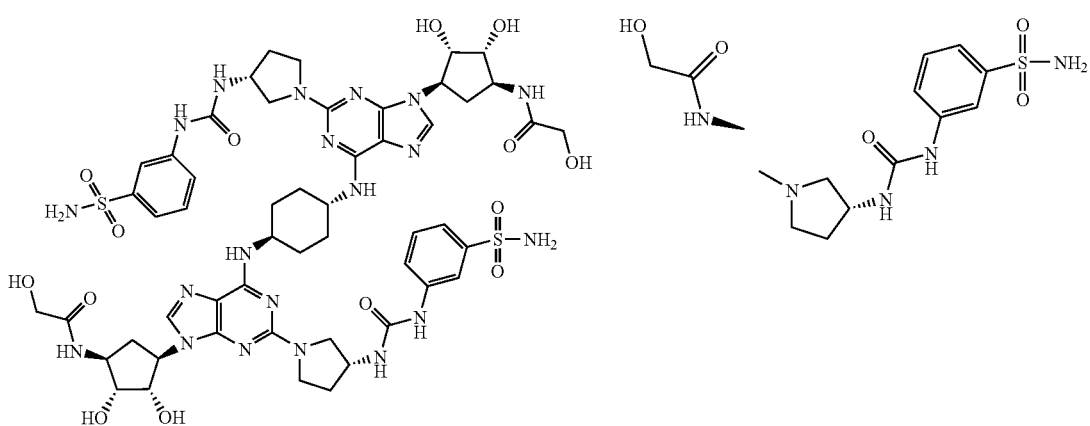 | |
| 179 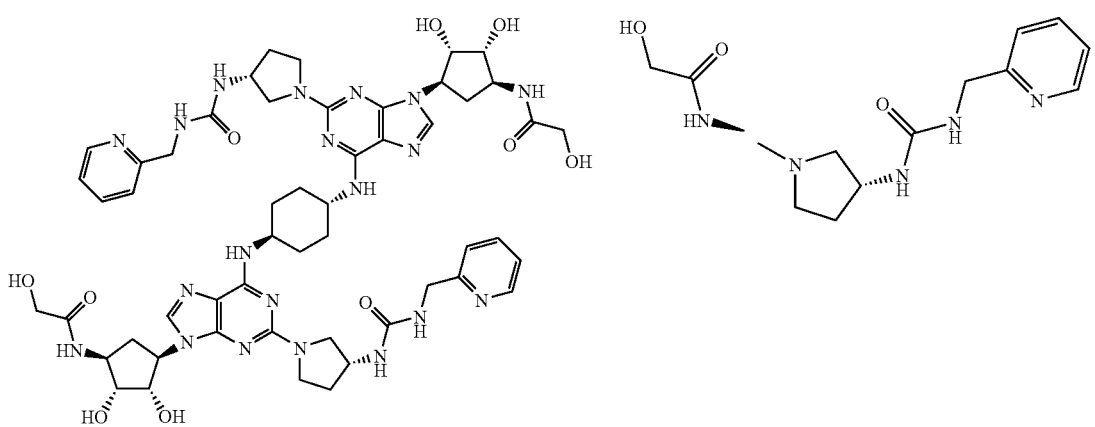 | |

| 180 | 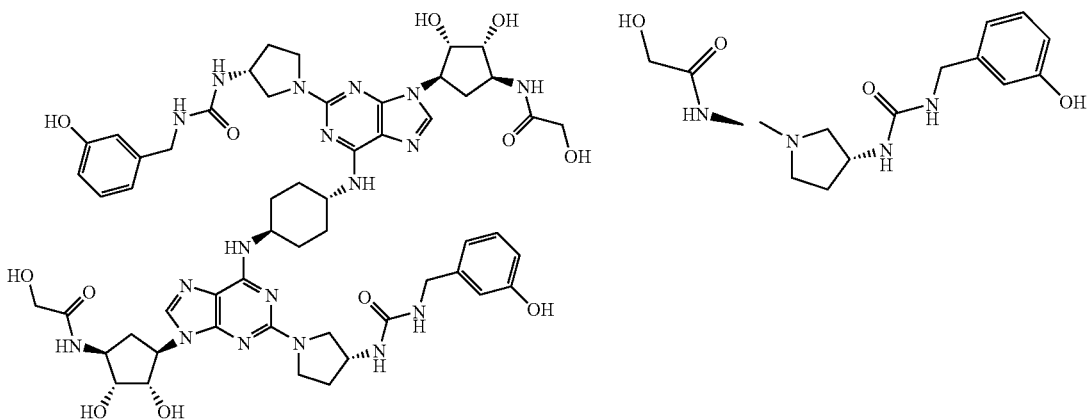 |
Examples 181-188
Compounds of formula (X3) are shown in the following table. Methods of preparing such compounds are described hereinafter.
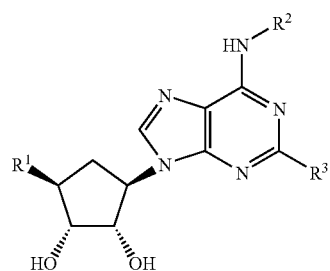
(X3)
| Ex | Structure |
|---|---|
| 181 | 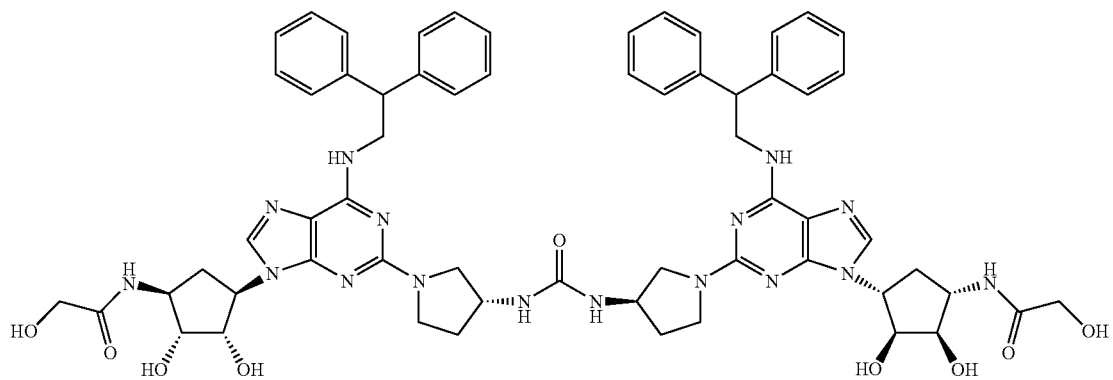 |

| 182 | 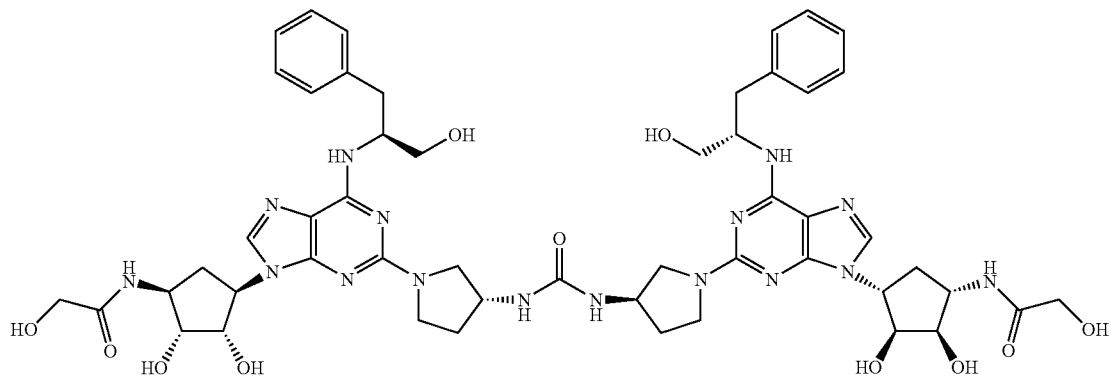 |
|---|---|
| 183 | 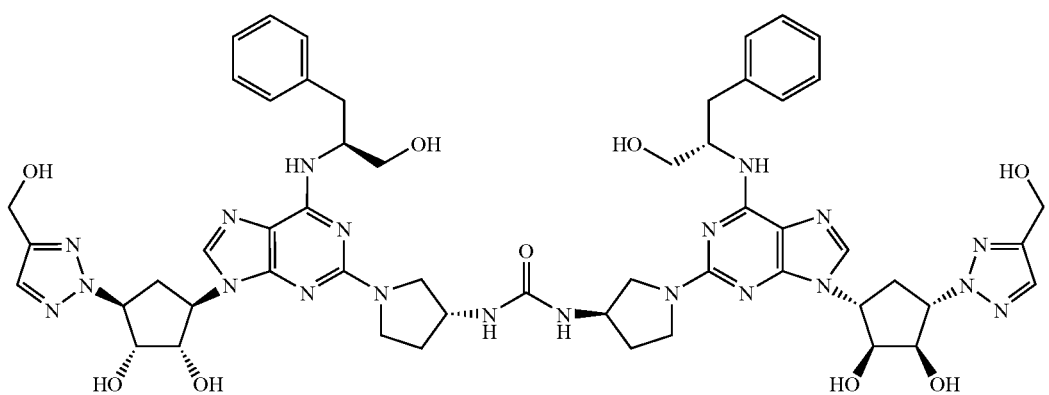 |
| 184 | 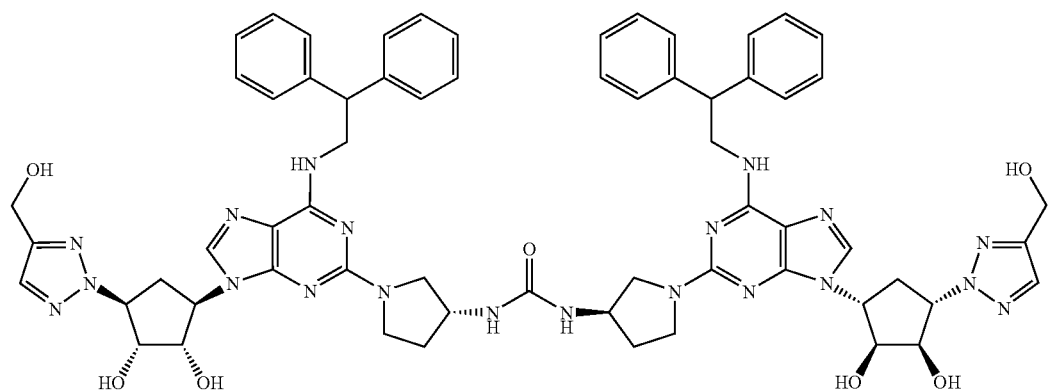 |
| 185 | 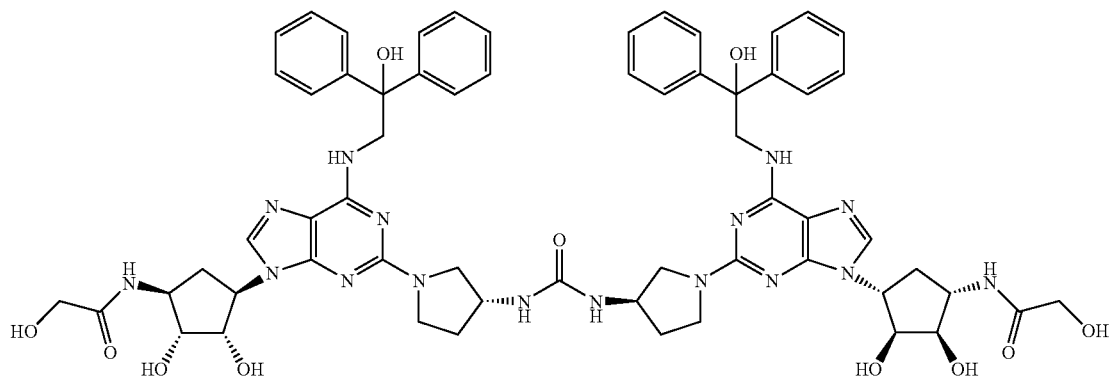 |

| | 379 | 380 |
|---|---|---|
| | -continued | |
| 186 | 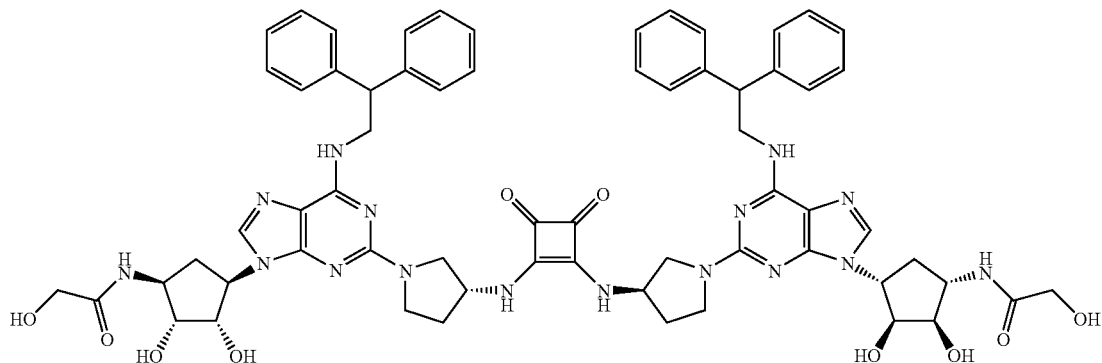 | |
| 187 | 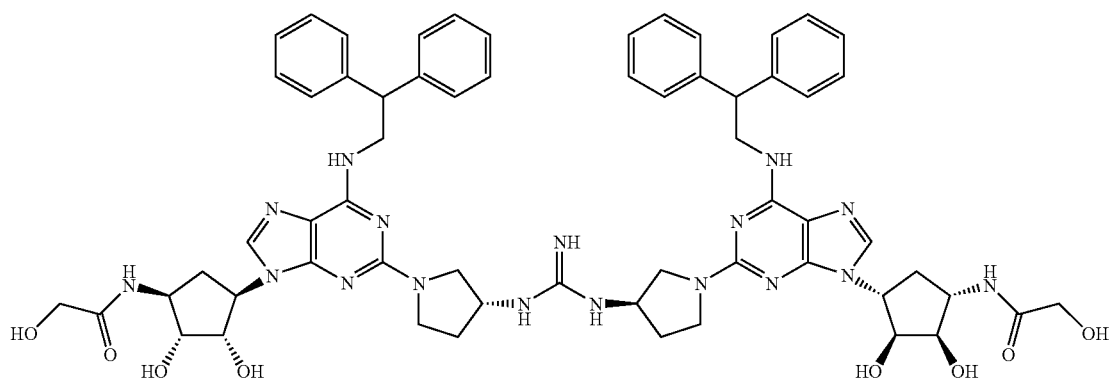 | |
| 188 | 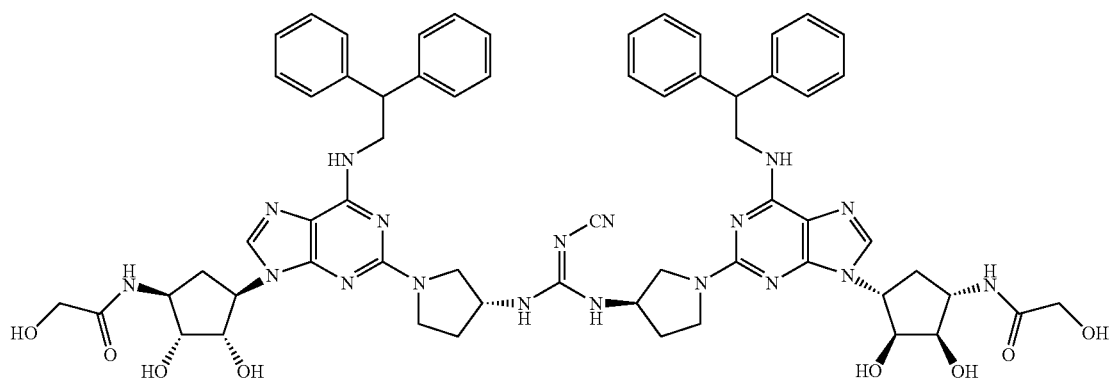 | |
| Ex | R¹ | R² | R³ |
|---|---|---|---|
| 181 | 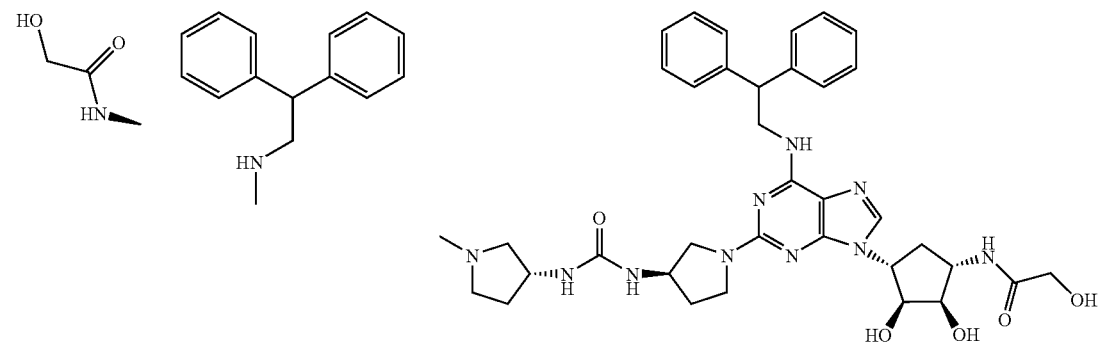 | | |

| 182 | 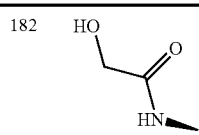 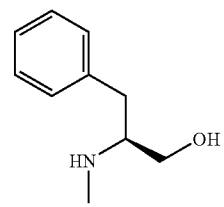 | 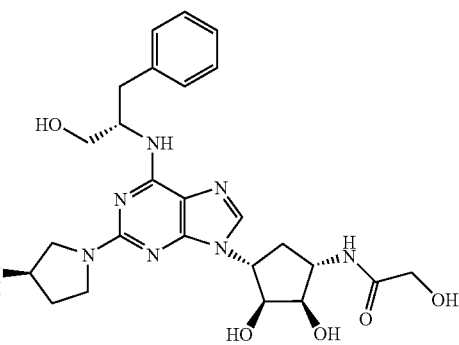 |
| --- | --- | --- |
| 183 | 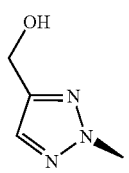 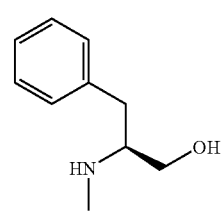 | 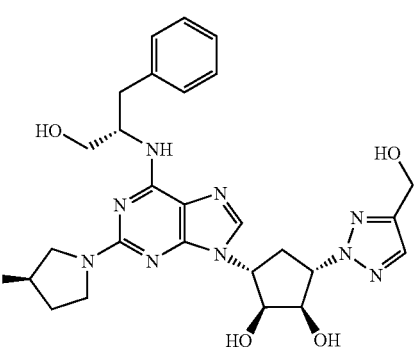 |
| 184 | 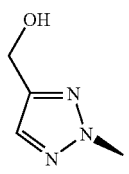 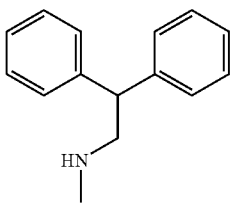 | 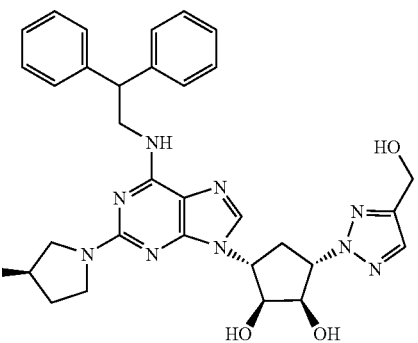 |
| 185 | 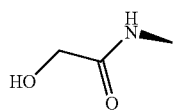 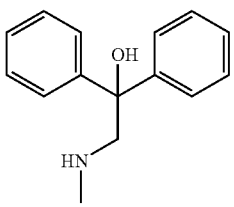 | 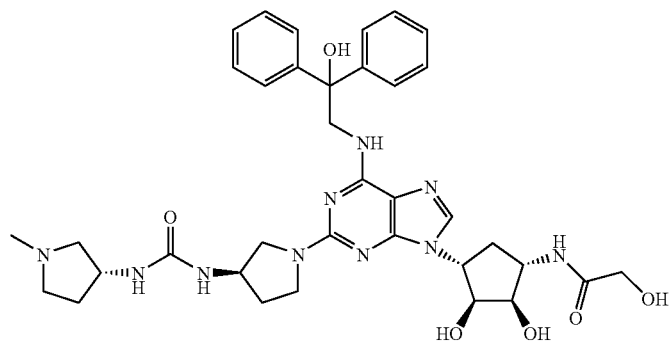 |

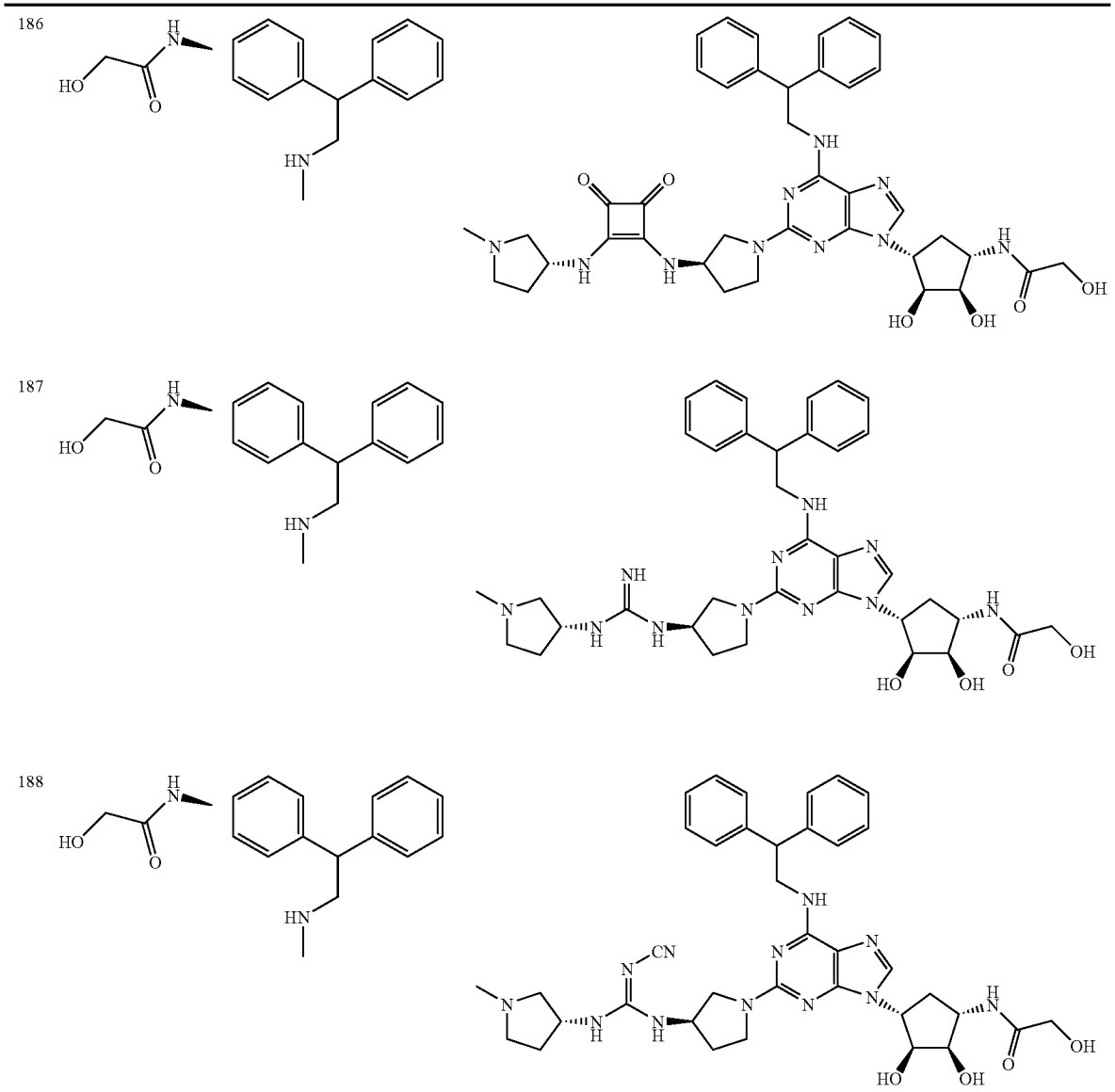
Preparation of Examples
Examples 27-36 can be prepared as follows:
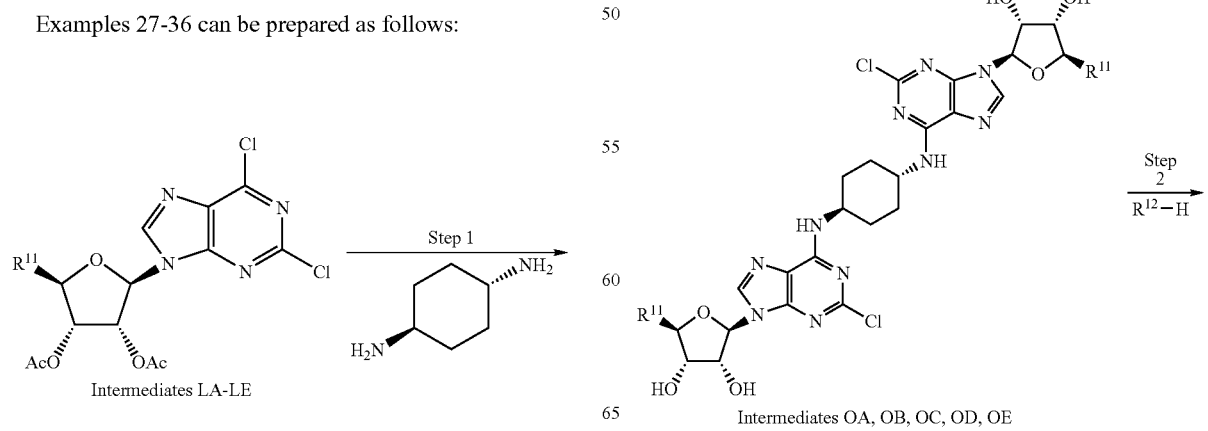

-continued

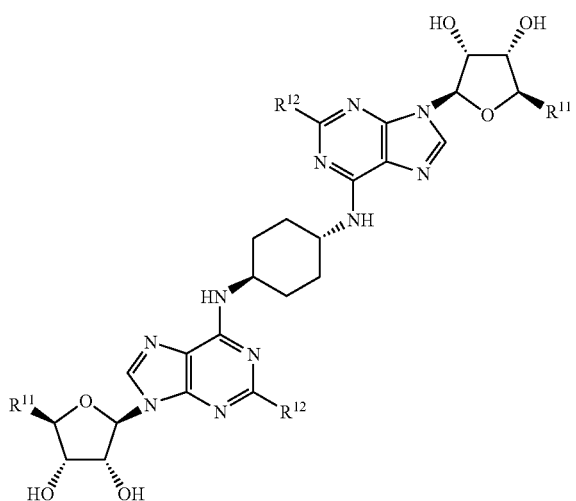
Examples 27-36

Step 1

Intermediates OA-OE can be prepared from Intermediates LA-LE using methods described in WO 05/116037 (Stages 2 and 3).

Step 2

Examples 27-36 can be prepared from Intermediates OA-OE using thermal or microwave methods as described in Examples 1 and 13 using the appropriate amines.

Examples 37-44 and 47-50 can be prepared as follows:

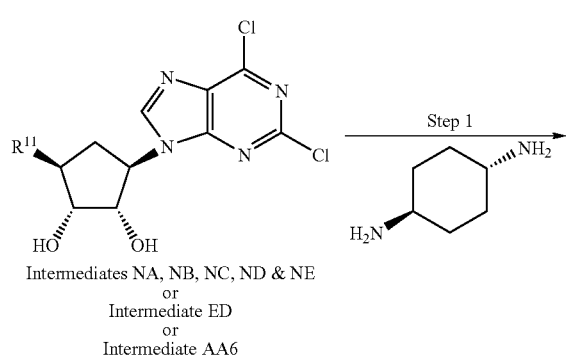

Intermediates NA, NB, NC, ND & NE
or
Intermediate ED
or
Intermediate AA6

-continued

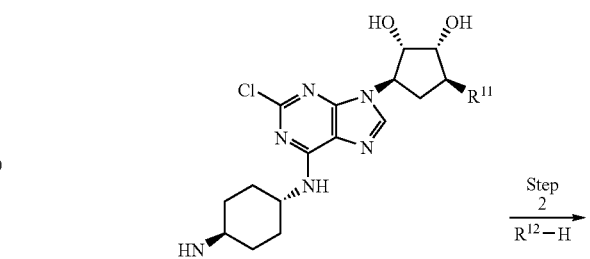
Intermediates PA, PB, PC, PD, PE, PF & PG

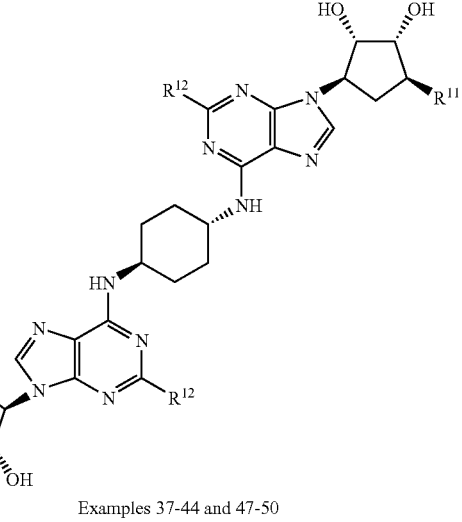
Examples 37-44 and 47-50

Step 1

Intermediates PA-PG can be prepared from Intermediates NA-NE or Intermediate ED or Intermediate AA6 using methods described in WO 05116037 (stages 2 and 3).

Step 2

Examples 37-44 and 47-50 can be prepared from Intermediates PA-PG using thermal or microwave methods as described in Examples 1, 13 and 24 using the appropriate amines.

For example:

Example 43

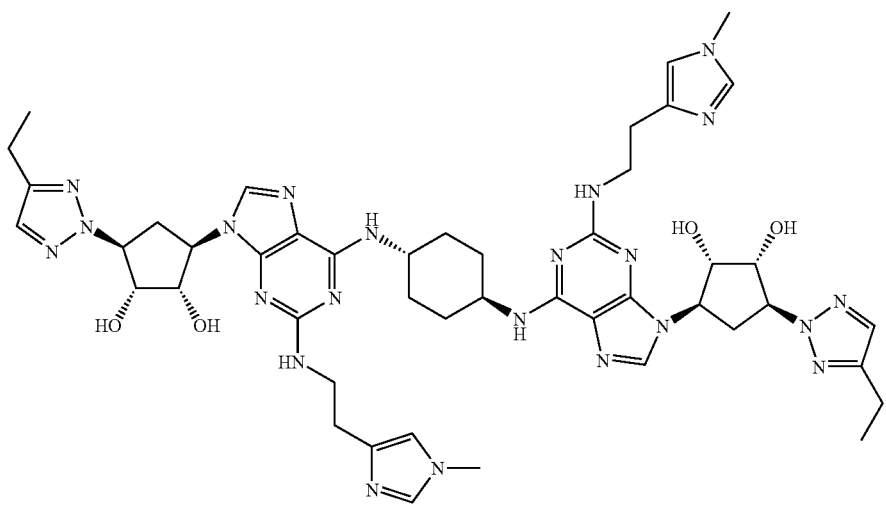

This compound is prepared analogously to Example 24 by replacing (3R)-(+)-3-dimethylaminopyrrolidine (Step 2) with 2-(1-methyl-1H-imidazol-4-yl)-ethylamine. [M/2]H+ 494.

Example 45
Step 1

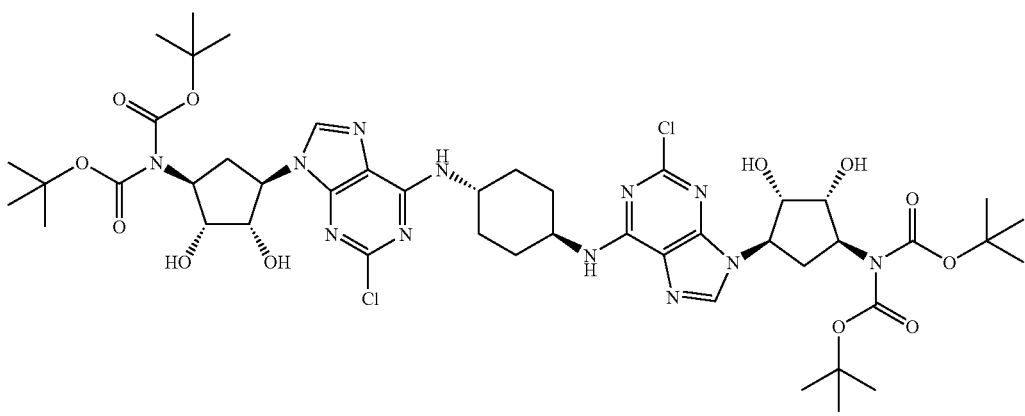

(1S,2R,3S,5R)-3-(Di-Boc-amino)-5-(2,6-dichloro-purin-9-yl)-cyclopentane-1,2-diol (Step AA4) (0.5 g, 0.992 mmol) in IPA (5 mL) is treated with diamine (trans-1,4)cyclohexane (56.6 mg, 0.446 mmol) and DIPEA (0.432 mL, 2.48 mmol). The suspension is heated at 83° C. over night and after cooling to RT, the solvent is removed in vacuo. The resulting solid is triturated with water/MeOH to afford the product as a beige solid. [MH+ 1049/1052].

Step 2

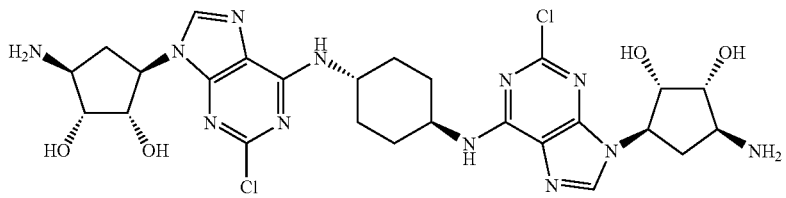

The product from Step 1 (0.2932 g, 0.279 mmol) is dissolved in MeOH (5 mL) and treated with 4 M HCl in dioxane (3 mL). The resulting orange mixture is RT for 2 hours and then concentrated in vacuo to afford the desired product as a dihydrochloride salt. [MH+ 651].

Step 3

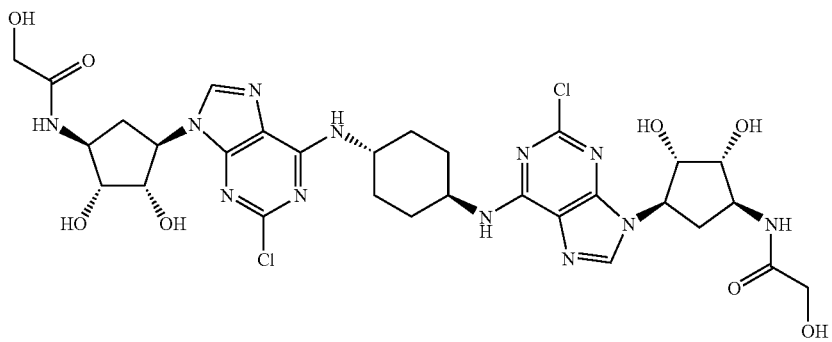

The product from Step 2 (0.1 g, 0.119 mmol) in THF (1 mL) and MeOH (1 mL) is treated with TEA (0.25 mL, 1.78 mmol) and stirred at RT for 1 hour. Acetoxychloride (0.0.384 mL, 0.714 mmol) is then added and stirring continued for 14 days. The solvent is removed in vacuo and the resulting residue is treated with MeOH and potassium carbonate (20 mg) in water (0.5 mL). The mixture is stirred at RT over night and then purification is carried out by reverse phase column chromatography (Isolute™ C18, 100% water followed by 100% MeOH) to yield desired product. [MH$^+$ 765/767]

Step 4

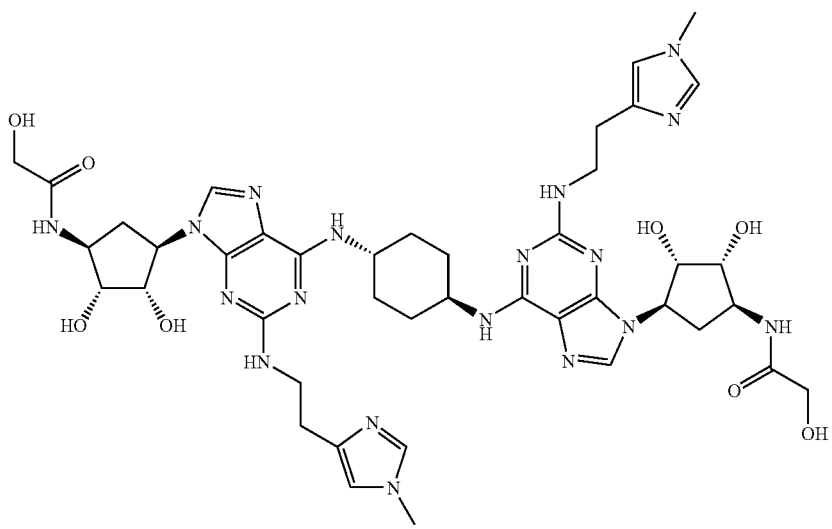

This compound is prepared from the product of Step 3 analogously to Example 24, Step 2. [M/2]H$^+$ 472.

Example 46

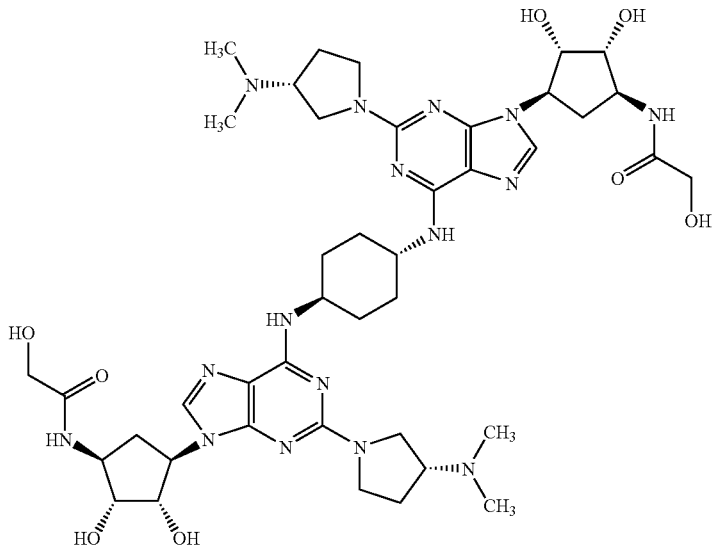

This compound is prepared analogously to Example 45 with the appropriate amine.

Examples 51-66 and 91-115 can be prepared as follows:

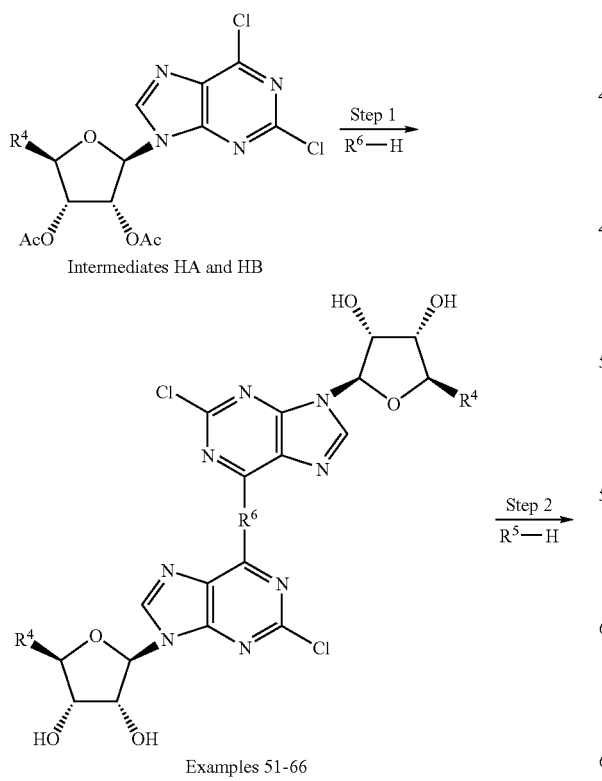

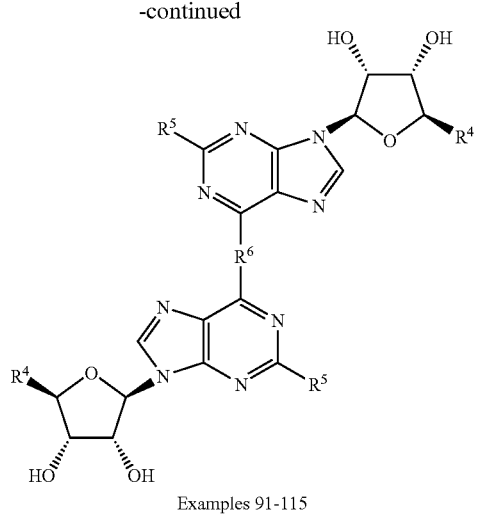

Step 1

Examples 51-66 can be prepared from Intermediates described herein using methods described in WO 05/116037 (Stages 2 and 3).

Step 2

Examples 91-115 can be prepared from Examples 51-66 using thermal or microwave methods as described in Examples 1 and 13 using the appropriate amines.

Examples 67-90 and 116-163 can be prepared as follows:

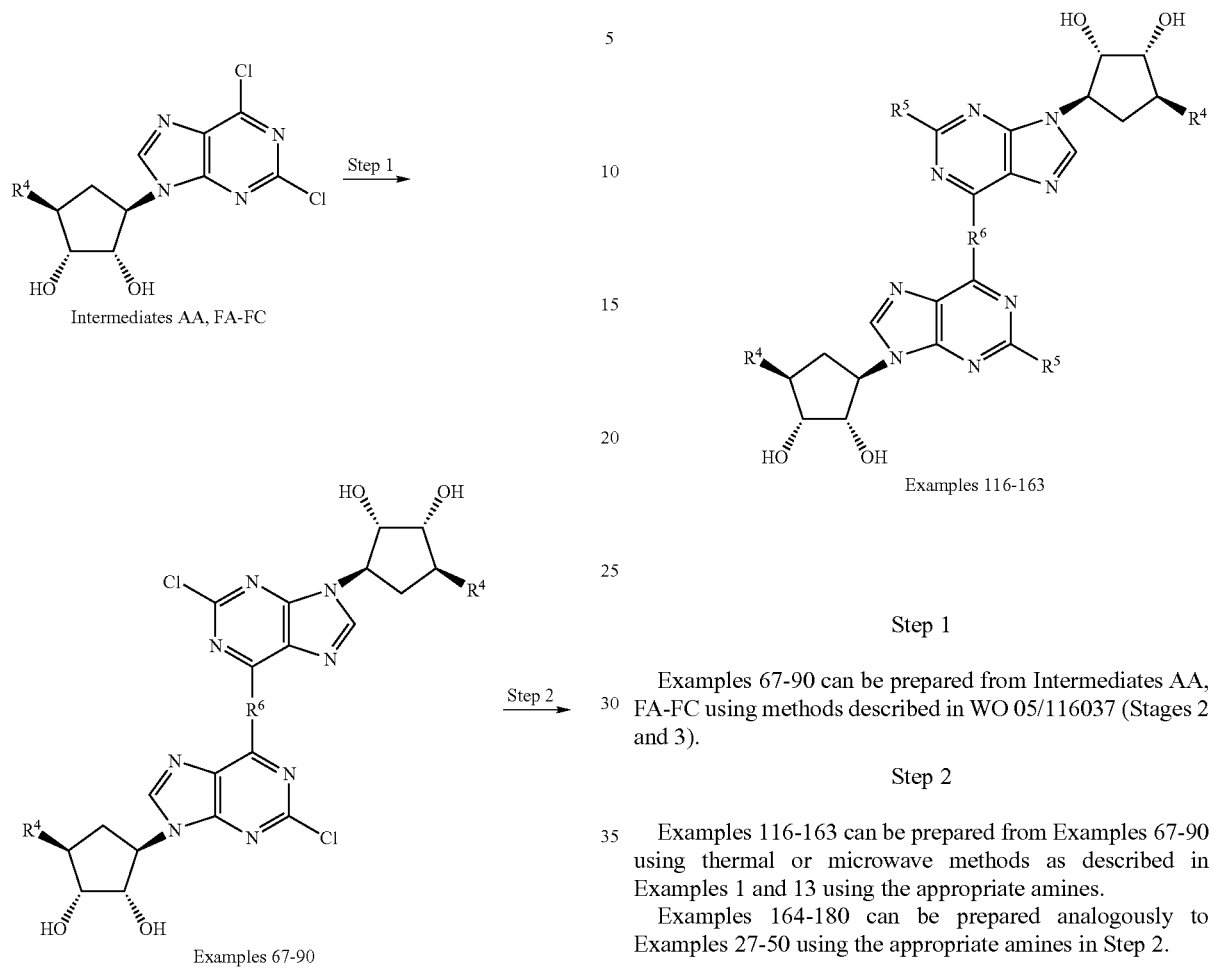

Step 1

Examples 67-90 can be prepared from Intermediates AA, FA-FC using methods described in WO 05/116037 (Stages 2 and 3).

Step 2

Examples 116-163 can be prepared from Examples 67-90 using thermal or microwave methods as described in Examples 1 and 13 using the appropriate amines.

Examples 164-180 can be prepared analogously to Examples 27-50 using the appropriate amines in Step 2.

Example 181

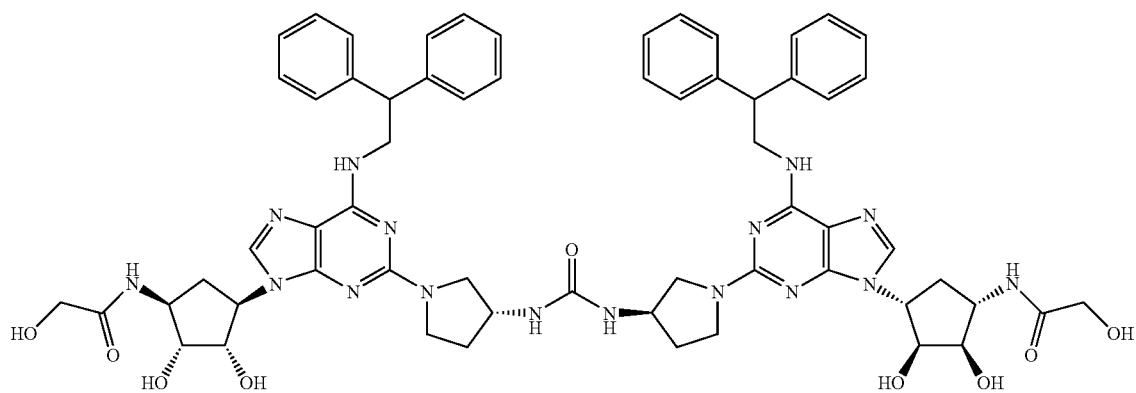

A solution of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-hydroxy-acetamide trifluoroacetate (Intermediate ZF) (150 mg, 0.26 mmol) in NMP (3 mL) is treated with TEA (139 µL, 1 mmol) followed by phenyl chloroformate (45 mg, 0.29 mmol). The resulting mixture is stirred at RT for 20 minutes and then treated with N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-hydroxy-acetamide trifluoroacetate (Intermediate ZF) (150 mg, 0.26 mmol). After heating at 100° C. over night, the mixture is treated with EtOH (10 mL) and the resulting precipitate is collected by filtration. Purification of this solid by reverse phase column chromatography (Isolute™ C18, 0-100% acetonitrile in water—0.3% NH$_3$) affords the desired product as a solid. [M/2]H$^+$ 586.43

Examples 181-188 can be prepared analogously to Example 4 by replacing N-((1S,2R,3S,4R)-4-{2-chloro-6-[2-(4-fluoro-phenyl)-2-phenyl-ethylamino]-purin-9-yl}-2,3-dihydroxy-cyclopentyl)-propionamide trifluoroacetate (Intermediate AD) with the appropriate Intermediate the preparations of which are described herein.

For example:

Example 182

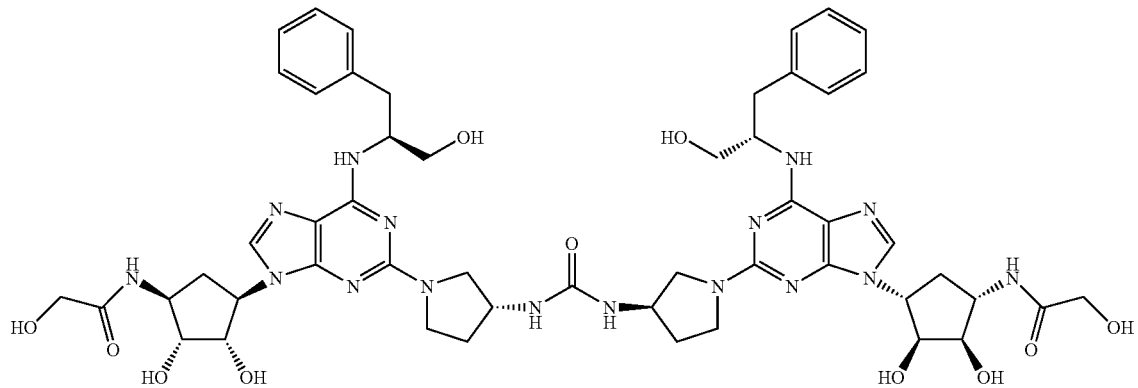

This compound is prepared analogously to Example 4 by replacing N-((1S,2R,3S,4R)-4-{2-chloro-6-[2-(4-fluoro-phenyl)-2-phenyl-ethylamino]-purin-9-yl}-2,3-dihydroxy-cyclopentyl)-propionamide trifluoroacetate (Intermediate AD) with N-{(1S,2R,3S,4R)-4-[6-((S)-1-benzyl-2-hydroxy-ethylamino)-2-chloro-purin-9-yl]-2,3-dihydroxy-cyclopentyl}-2-hydroxy-acetamide (Intermediate GC). [M/2]H$^+$ 540.49

Examples 189-211

Compounds of formula (X4) are shown in the following table. Methods of preparing such compounds are described hereinafter.

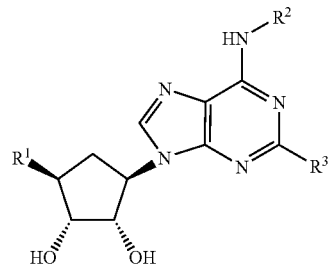
| Ex | Structure |
|---|---|
| 189 | 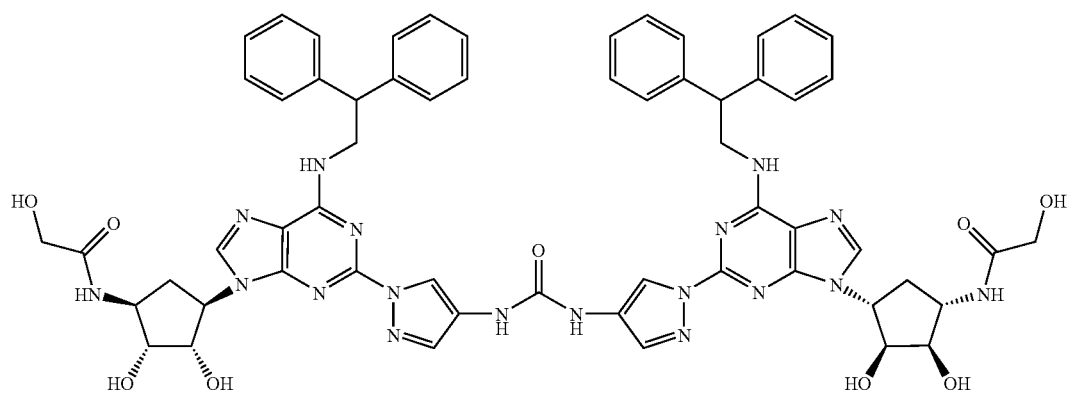 |
| 190 | 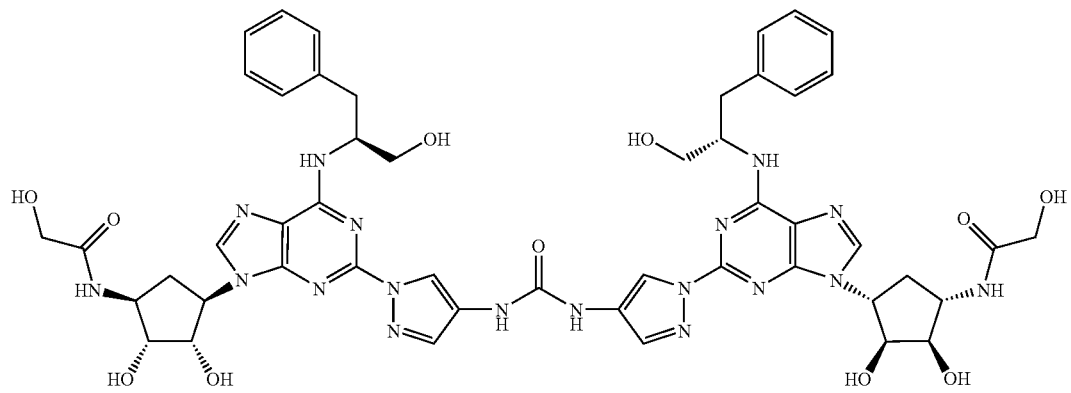 |
| 191 | 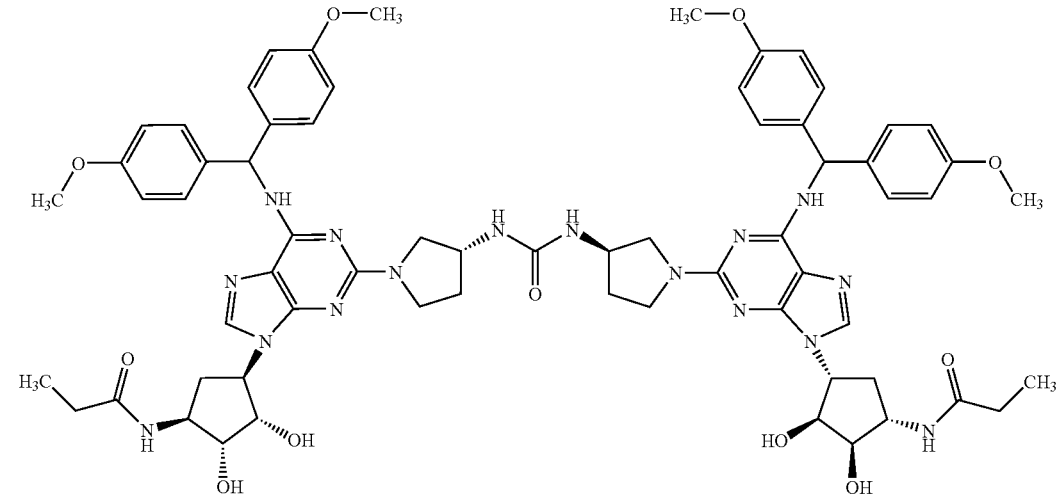 |

| 192 | 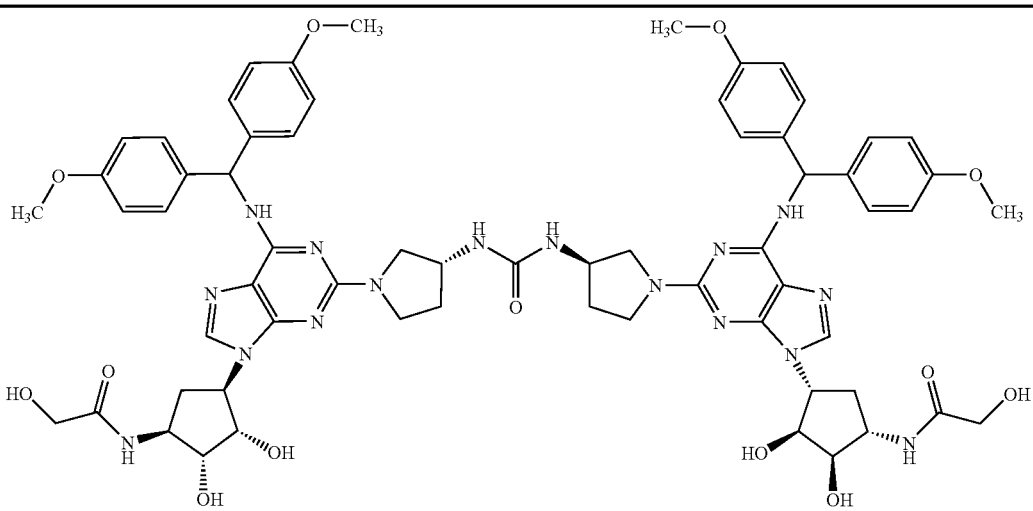 |
| --- | --- |
| 193 | 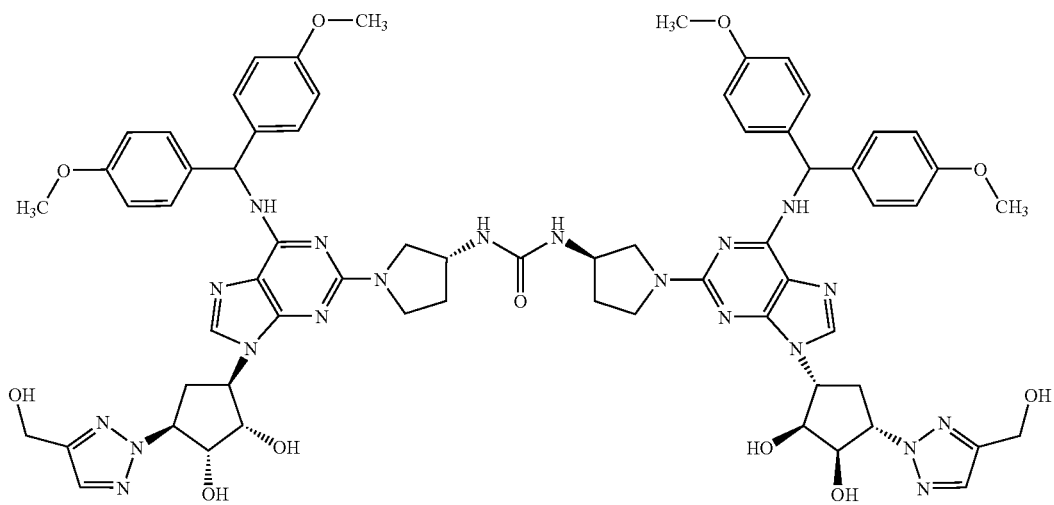 |
| 194 | 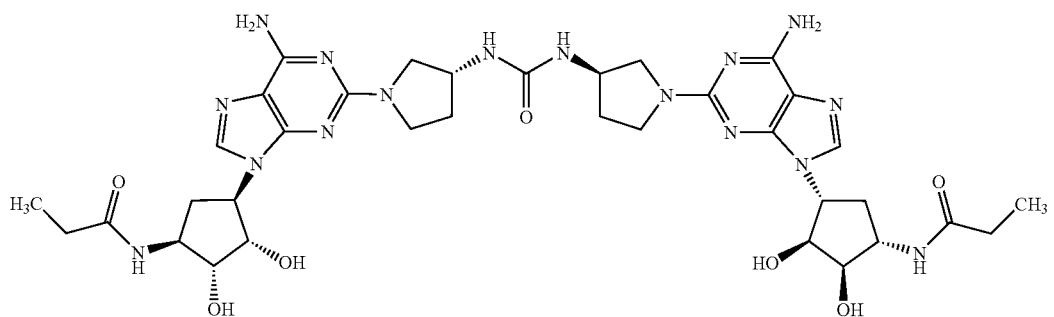 |
| 195 | 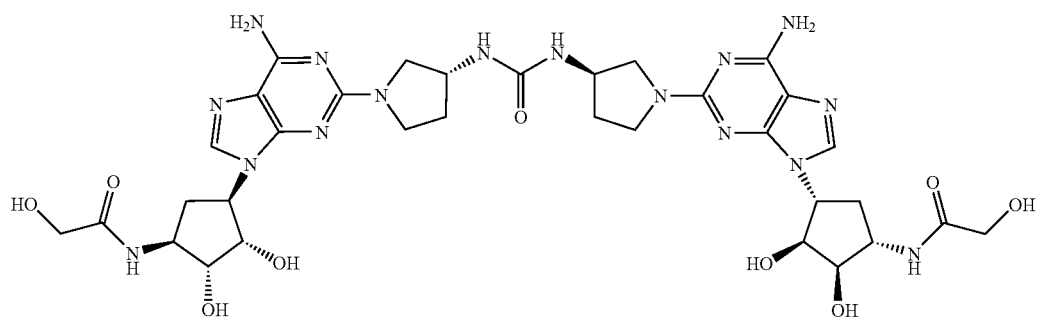 |

196
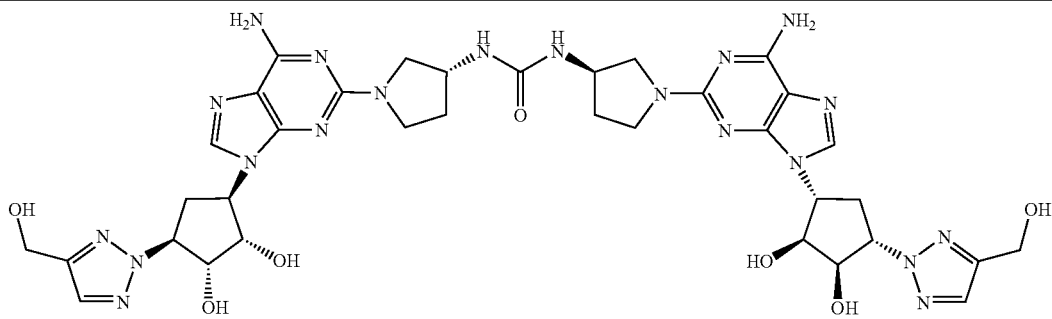
197
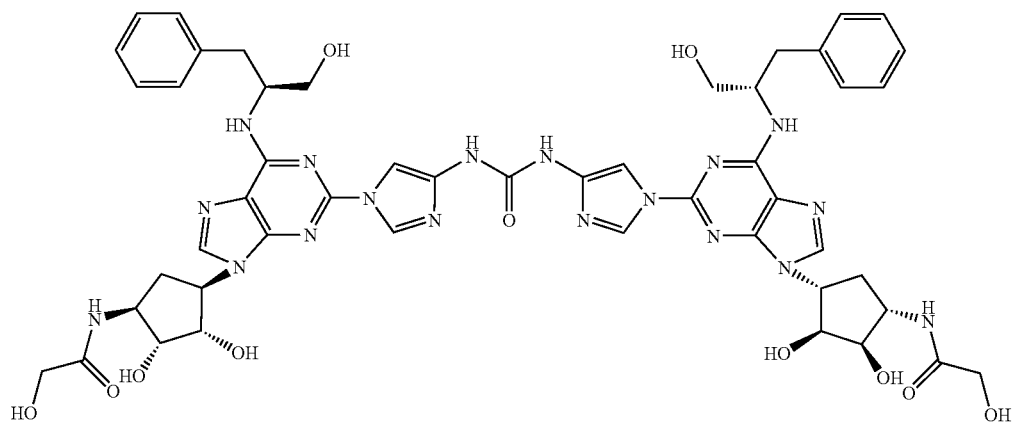
198
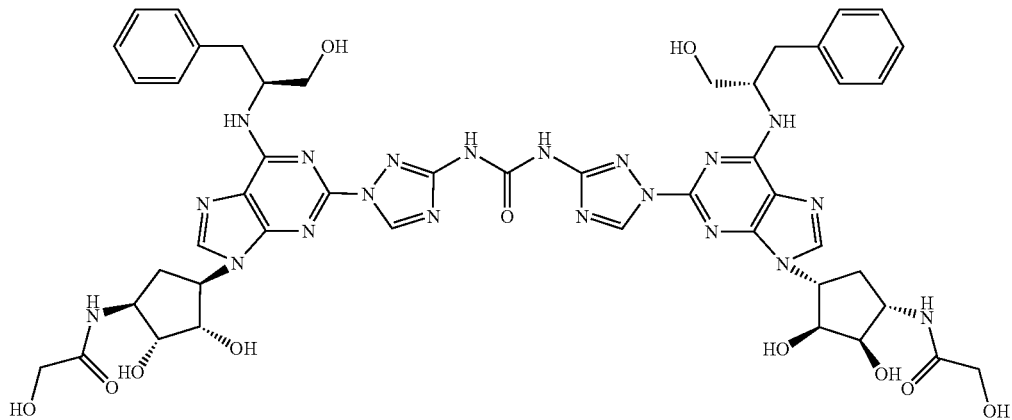

199 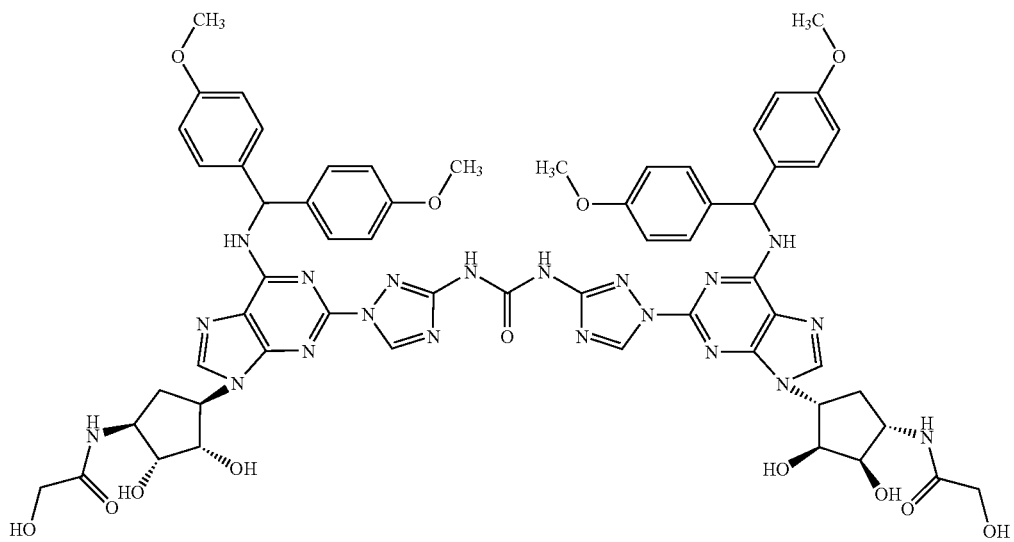
200 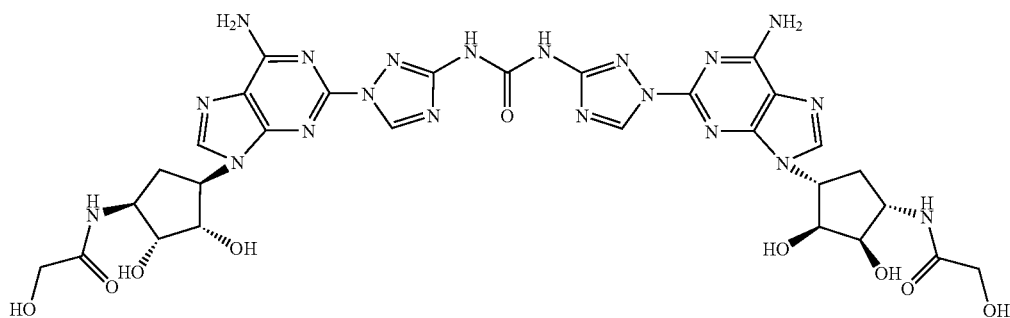
201 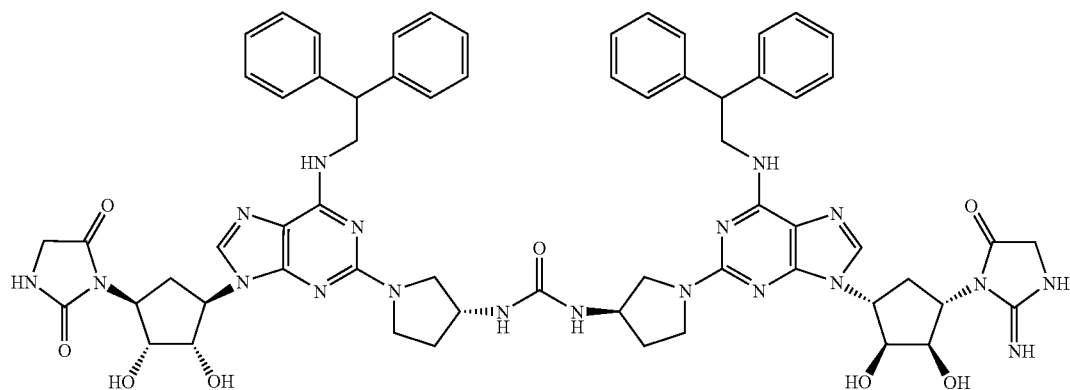
202 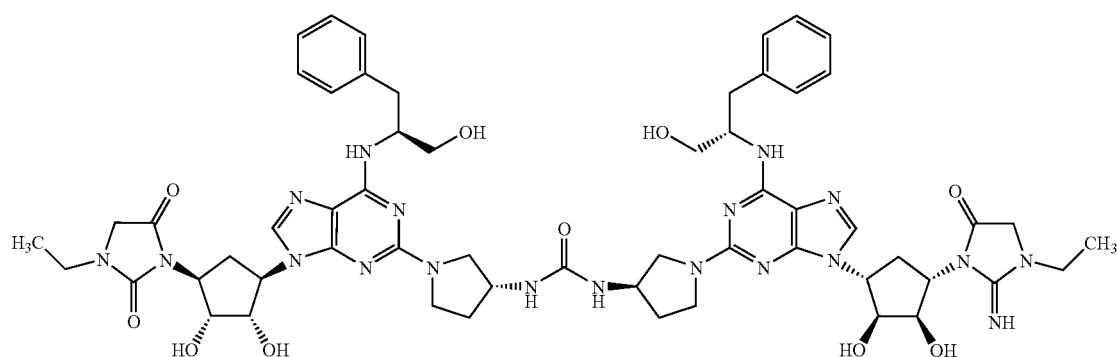

203 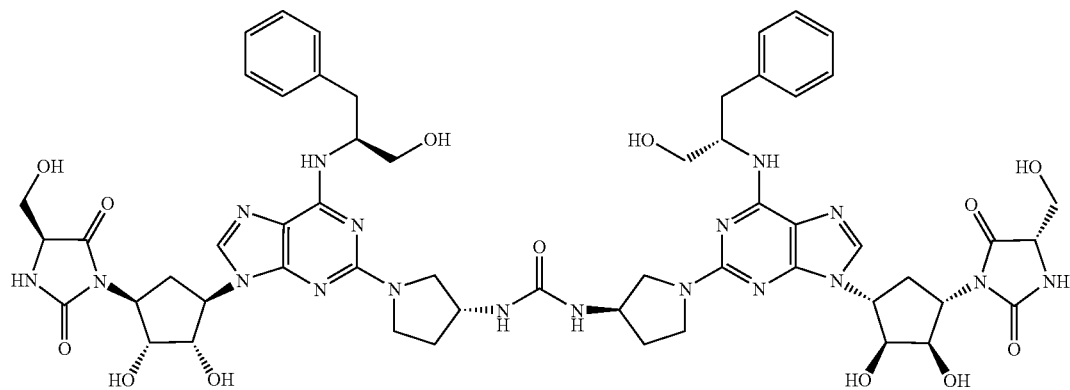
204 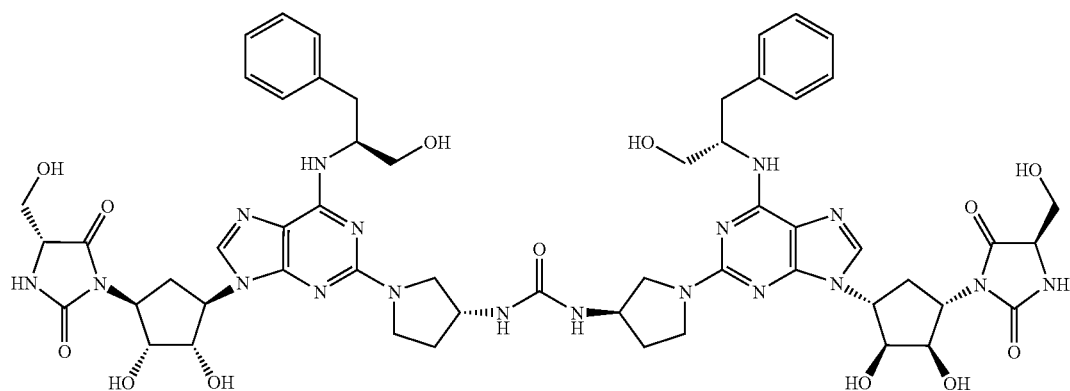
205 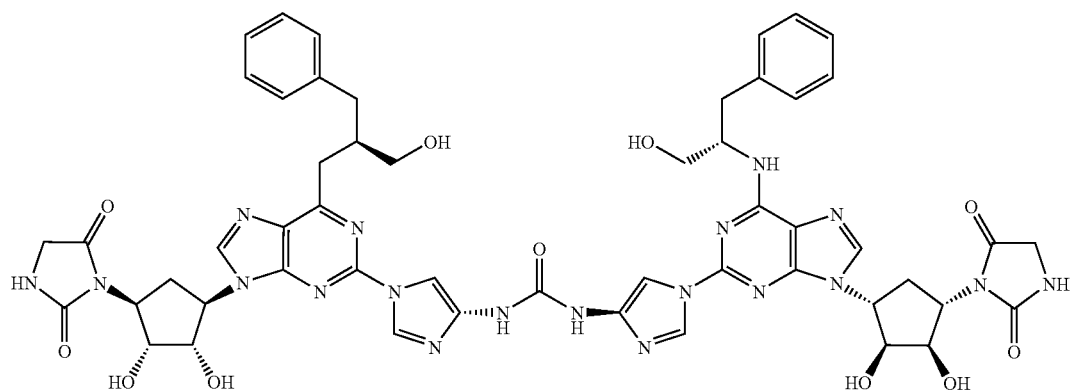
206 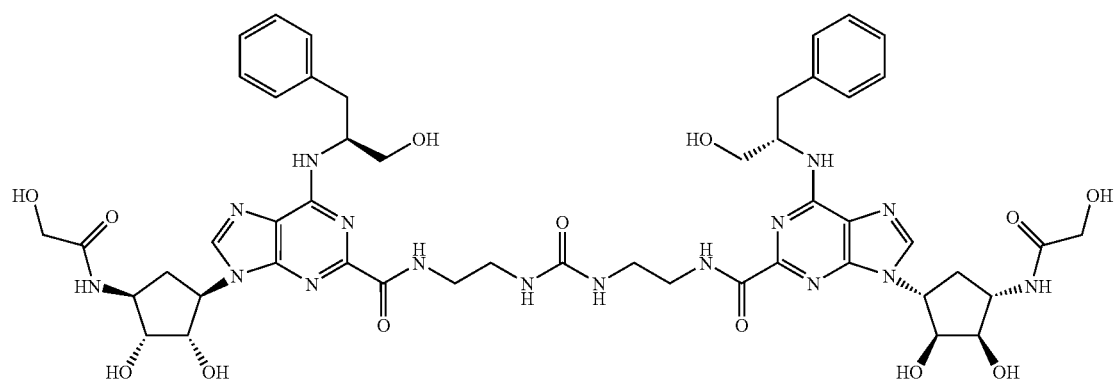

207 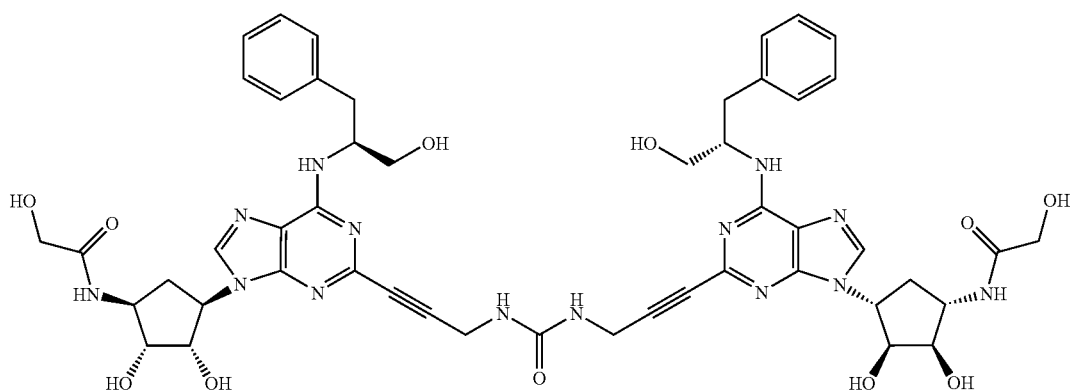
208 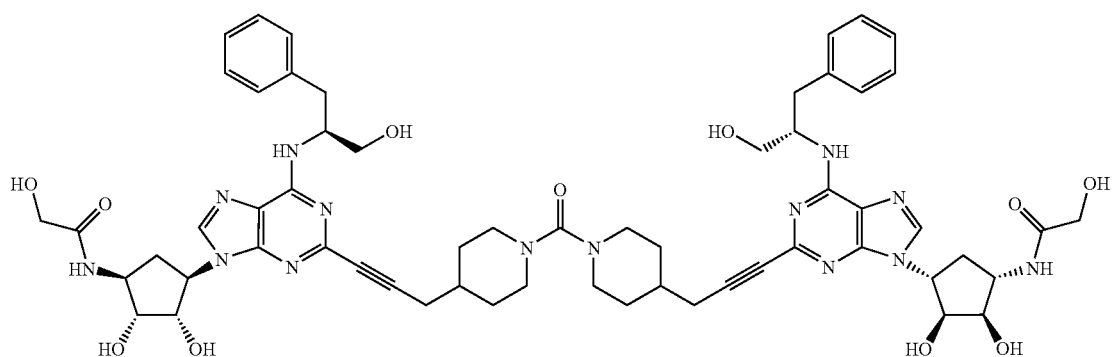
209 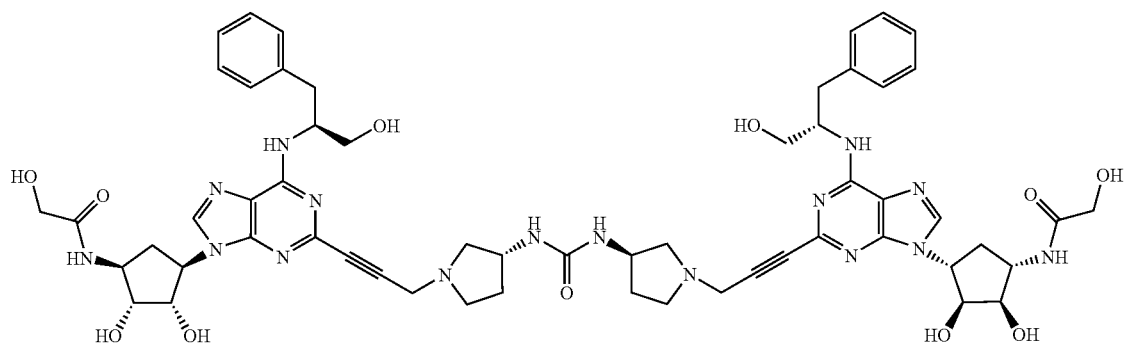
210 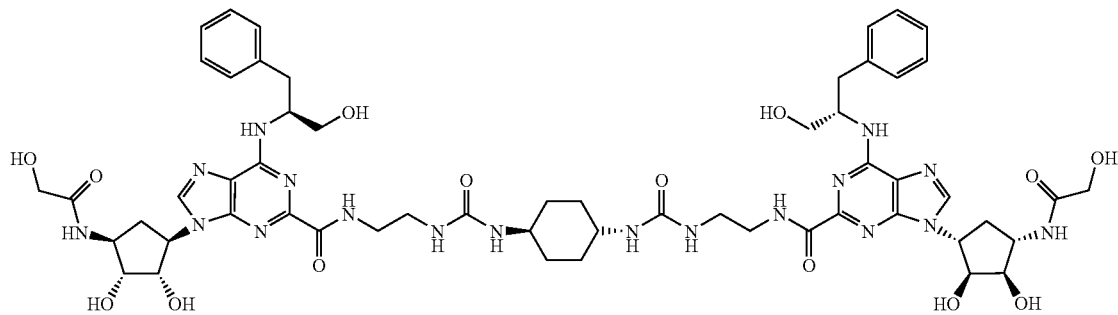

-continued
| Ex | R¹ | R² | R³ |
|---|---|---|---|
| 211 | | 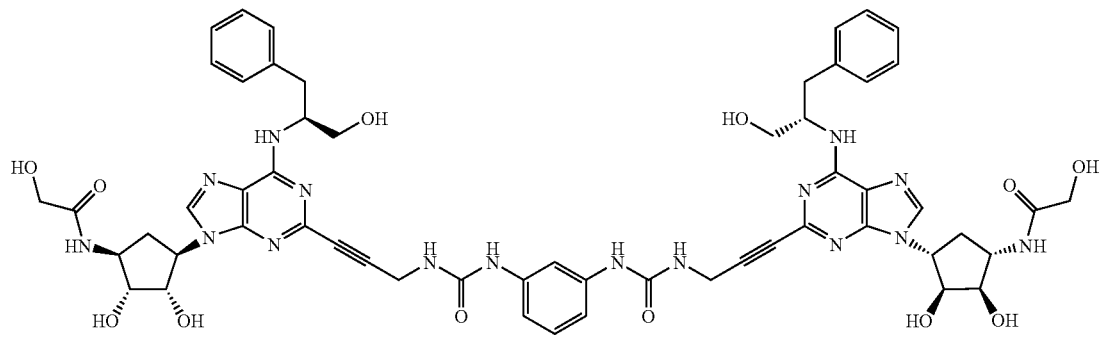 | 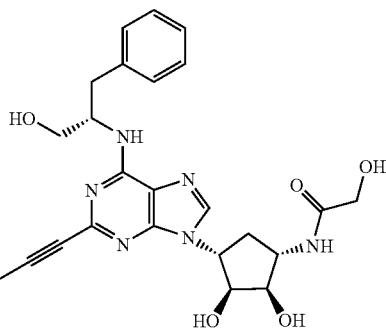 |
| 189 | 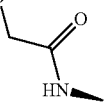 | 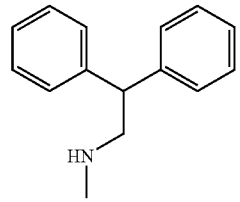 | 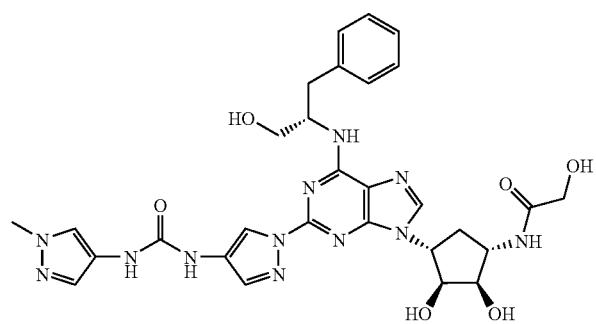 |
| 190 | 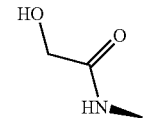 | 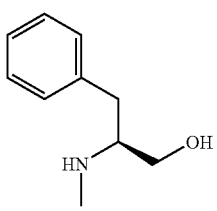 | |
| 191 | 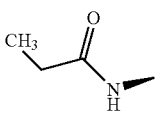 | 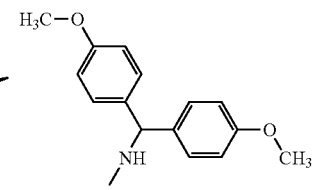 | 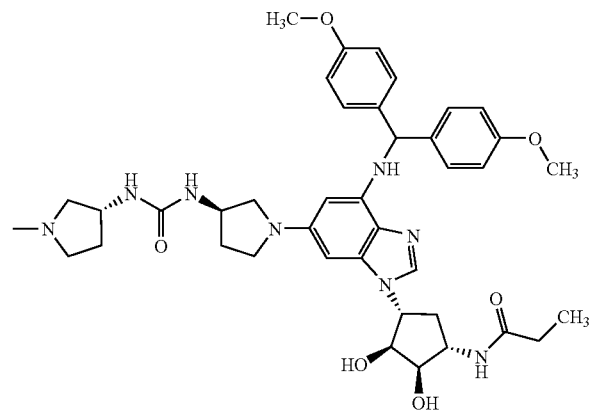 |

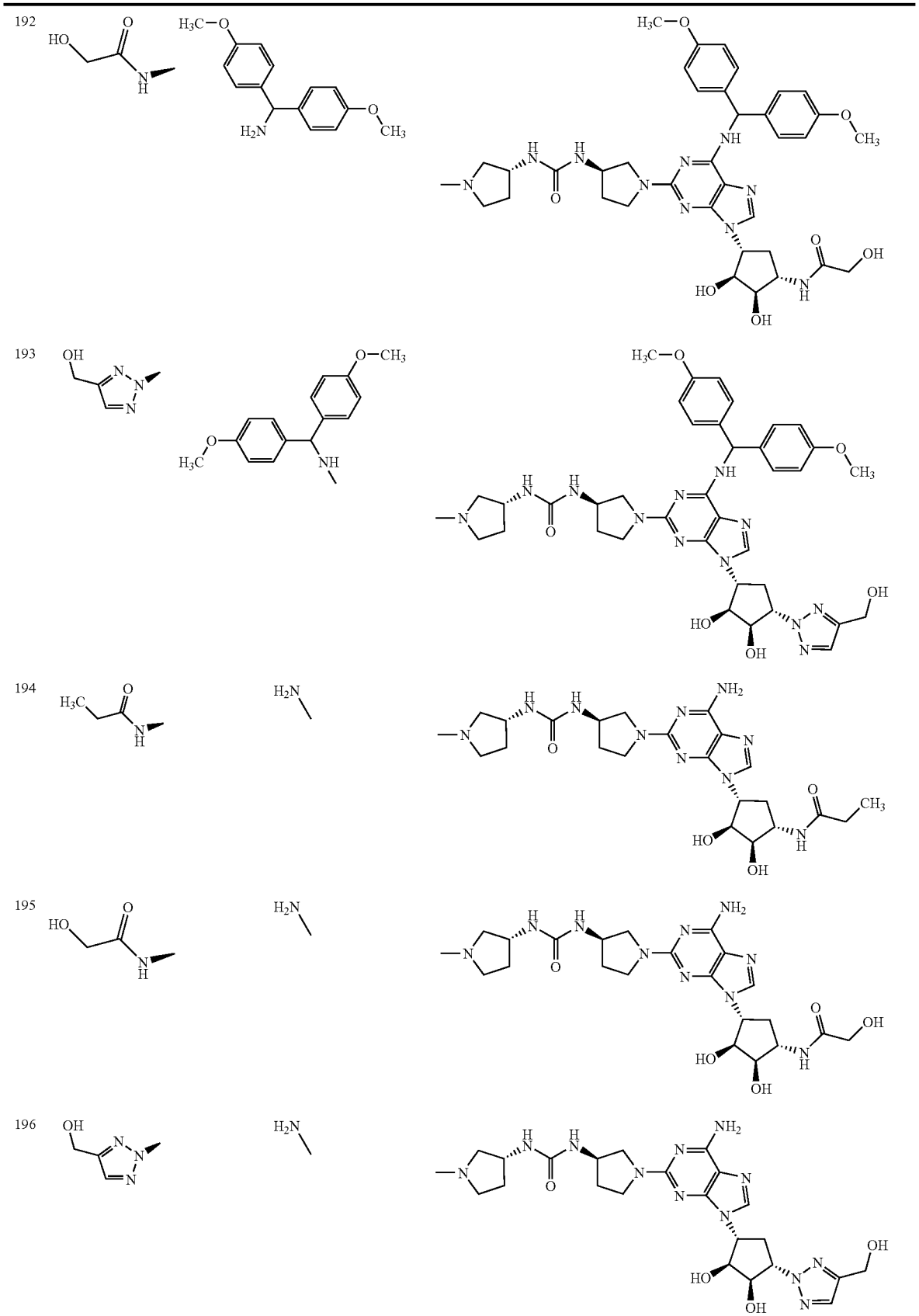

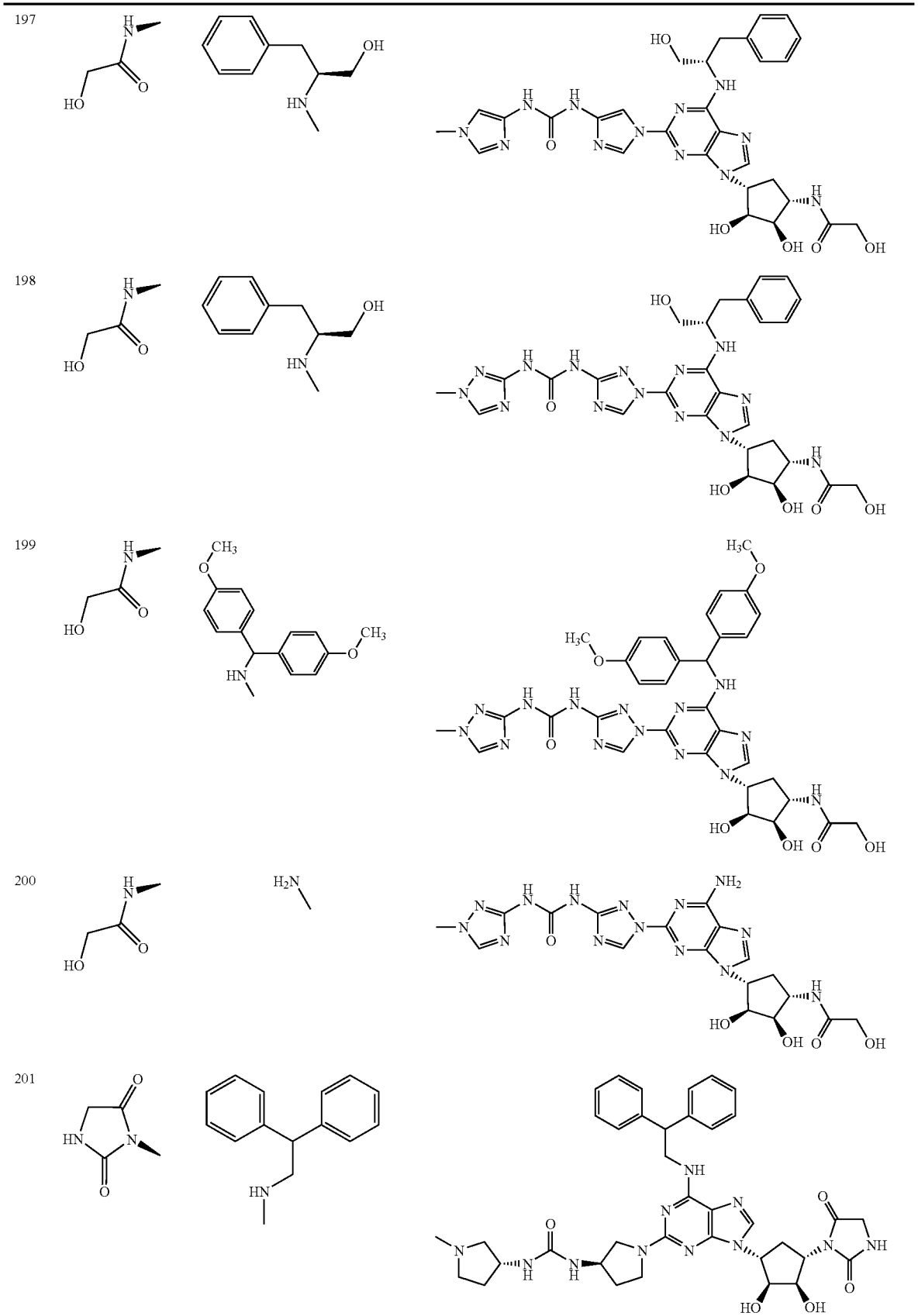

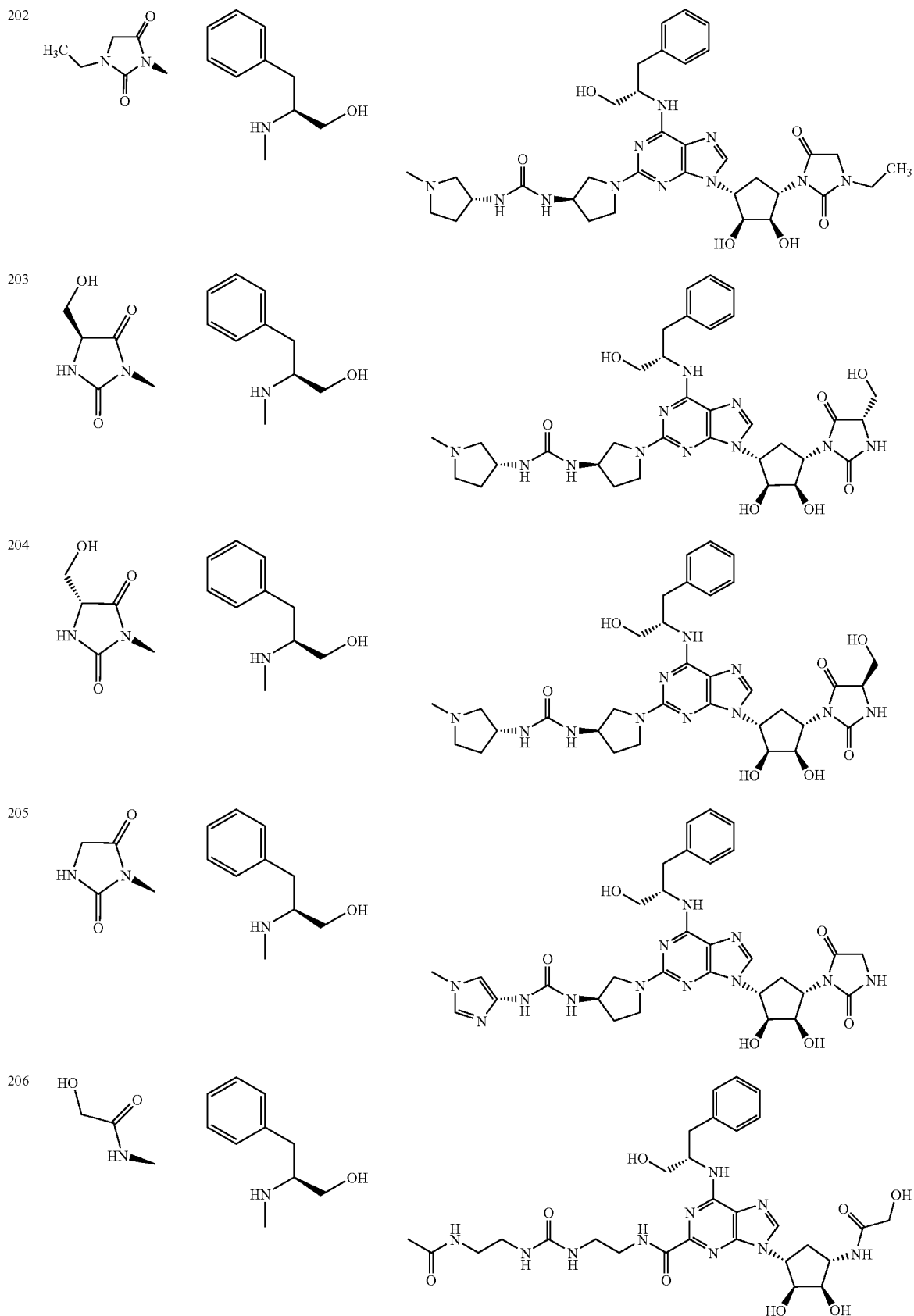

| 207 | 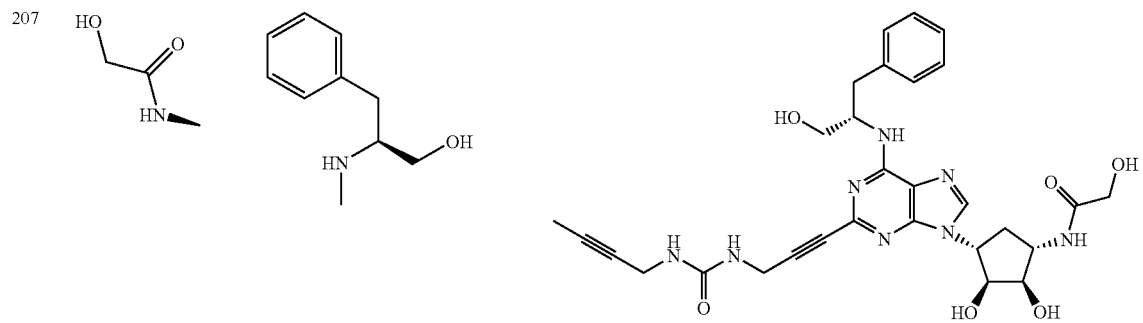 |
| 208 | 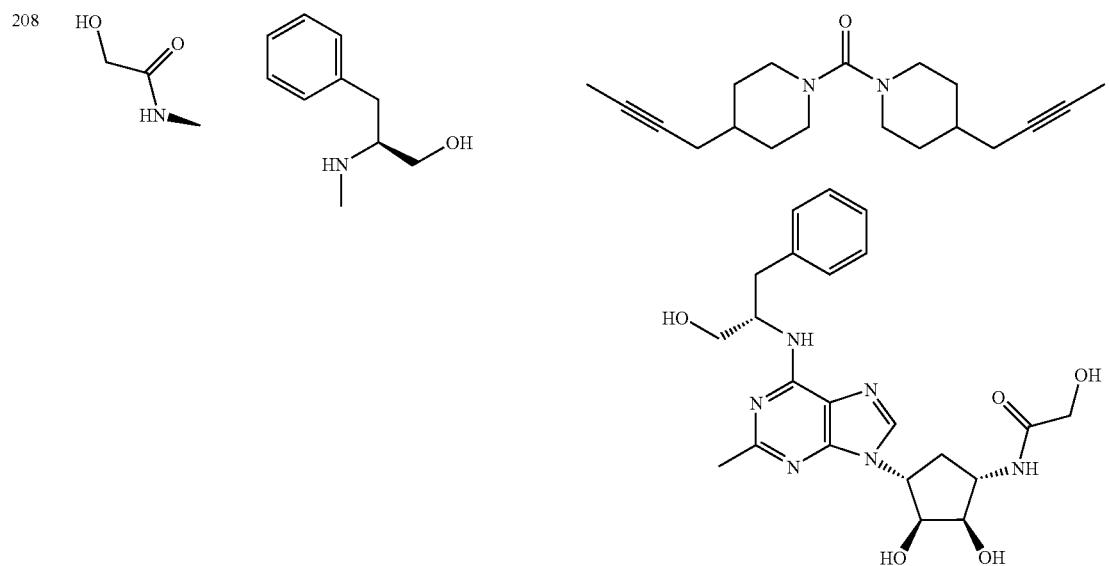 |
| 209 | 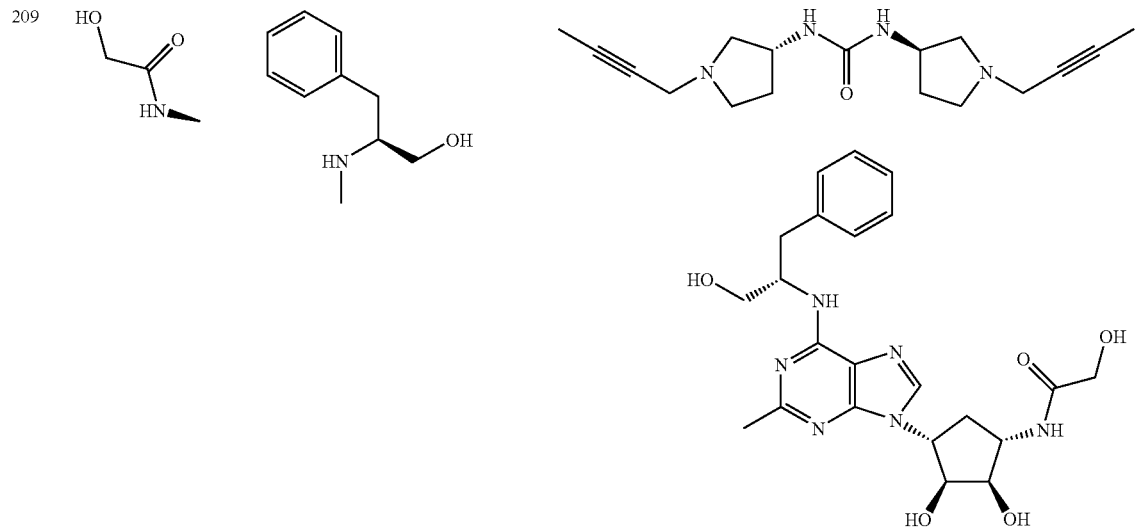 |

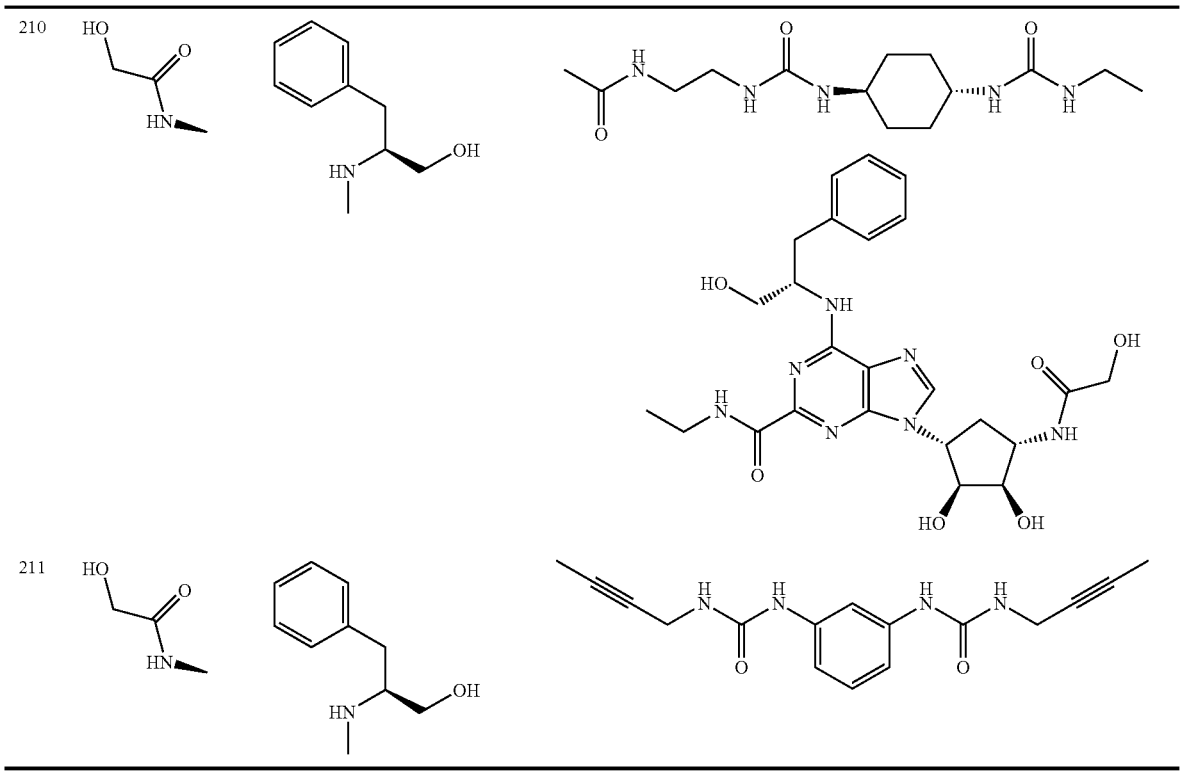

Example 189

1,3-Bis-{(1S,2R,3S,4R)-1-[6-(2,2-Diphenylethy-lamino)-9-(4-(2-hydroxyacetamido)-2,3-dihydroxy-cyclopentyl)-9H-purin-2-yl]-1H-pyrazol-4-yl}-urea The title compound can be synthesised by combining {1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazol-4-yl}-carbamic acid phenyl ester (Intermediate QH) and N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate QF) in 1,4-dioxane, and heating to 100° C. for 15 minutes by microwave irradiation.

Example 190

1,3-Bis {1-[9-[(1R,2S,3R,4S)-2,3-Dihydroxy-4-(2-hydroxy-acetylamino)-cyclopentyl]-6-((S)-1-hydroxymethyl-2-phenyl-ethylamino)-9H-purin-2-yl]-1H-pyrazol-4-yl}-urea The title compound can be synthesised by combining {1-[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purin-2-yl]-1H-pyrazol-4-yl}-carbamic acid phenyl ester (Intermediate QI) and N-{(1S,2R,3S,4R)-4-[2-(4-amino-pyrazol-1-yl)-6-((S)-1-hydroxymethyl-2-phenyl-ethylamino)-purin-9-yl]-2,3-dihydroxy-cyclopentyl}-2-hydroxy-acetamide (Intermediate QG) in 1,4-dioxane, and heating to 100° C. for 15 minutes by microwave irradiation.

Example 191

1,3-Bis-{1-(R)-[(1S,2R,3S,4R)-6-{[bis-(4-methoxyphenyl)-methyl]-amino}-9-(2,3-dihydroxy-4-propionamido-cyclopentyl)-9H-purin-2-yl]-pyrrolidin-3-yl}-urea The title compound can be prepared analogously to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate AA) with (1R,2S,3R,5S)-3-(6-{[bis-(4-methoxy-phenyl)-methyl]-amino}-2-chloro-purin-9-yl)-5-(4-hydroxymethyl-[1,2,3]triazol-2-yl)-cyclopentane-1,2-diol (Intermediate RA).

Example 192

1,3-Bis-{1-(R)-[(1S,2R,3S,4R)-6-{[bis-(4-methoxyphenyl)-methyl]-amino}-9-(2,3-dihydroxy-4-(2-acetoxyacetamido)-cyclopentyl)-9H-purin-2-yl]-pyrrolidin-3-yl}-urea The title compound can be prepared analogously to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate AA) with acetic acid [(1S,2R,3S,4R)-4-(6-{[bis-(4-methoxy-phenyl)-methyl]-amino}-2-chloro-purin-9-yl)-2,3-dihydroxy-cyclopentylcarbamoyl]-methyl ester (Intermediate RB).

Example 193

1,3-Bis-{1-(R)-[(1S,2R,3S,4R)-6-{[bis-(4-methoxyphenyl)-methyl]-amino}-9-(2,3-dihydroxy-4-(4-hydroxymethyl-[1,2,3]triazol-2-yl)-cyclopentyl)-9H-purin-2-yl]-pyrrolidin-3-yl}-urea The title compound can be prepared analogously to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate AA) with (1R,2S,3R,5S)-3-(6-{[bis-(4-methoxy-phenyl)-methyl]-amino}-2-chloro-purin-9-yl)-5-(4-hydroxymethyl-[1,2,3]triazol-2-yl)-cyclopentane-1,2-diol. (Intermediate RC).

Example 194

1,3-Bis-{1-(R)-[(1S,2R,3S,4R)-6-amino-9-(2,3-dihydroxy-4-propionamido-cyclopentyl)-9H-purin-2-yl]-pyrrolidin-3-yl}-urea (Paper)

The title compound can be prepared by dissolving Example 191 1,3-bis-{1-(R)-[(1S,2R,3S,4R)-6-{[bis-(4-methoxyphenyl)-methyl]-amino}-9-(2,3-dihydroxy-4-propionamido-cyclopentyl)-9H-purin-2-yl]-pyrrolidin-3-yl}-urea in DCM, chilling on ice/water to 0° C., and adding trifluoroacetic acid to 33% concentration with stirring. Once complete, volatile components are removed under reduced pressure, and the crude product purified.

Example 195

1,3-Bis-{1-(R)-[(1S,2R,3S,4R)-6-amino-9-(2,3-dihydroxy-4-(2-hydroxyacetamido)-cyclopentyl)-9H-purin-2-yl]-pyrrolidin-3-yl}-urea The title compound can be prepared analogously to Example 194 1,3-bis-{1-(R)-[(1S,2R,3S,4R)-6-amino-9-(2,3-dihydroxy-4-propionamido-cyclopentyl)-9H-purin-2-yl]-pyrrolidin-3-yl}-urea.

Example 196

1,3-Bis-{1-(R)-[(1S,2R,3S,4R)-6-amino-9-(2,3-dihydroxy-4-(4-hydroxymethyl-[1,2,3]triazol-2-yl)-cyclopentyl)-9H-purin-2-yl]-pyrrolidin-3-yl}-urea The title compound can be prepared analogously to Example 194 1,3-bis-{1-(R)-[(1S,2R,3S,4R)-6-amino-9-(2,3-dihydroxy-4-propionamido-cyclopentyl)-9H-purin-2-yl]-pyrrolidin-3-yl}-urea.

Example 197

1,3-Bis {1-[9-[(1R,2S,3R,4S)-2,3-Dihydroxy-4-(2-hydroxy-acetylamino)-cyclopentyl]-6-((8)-1-hydroxymethyl-2-phenyl-ethylamino)-9H-purin-2-yl]-1H-imidazol-4-yl}-urea The title compound can be synthesised by combining {1-[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purin-2-yl]-1H-imidazol-4-yl}-carbamic acid phenyl ester (Intermediate SF) and N-{(1S,2R,3S,4R)-4-[2-(4-amino-imidazol-1-yl)-6-((S)-1-hydroxymethyl-2-phenyl-ethylamino)-purin-9-yl]-2,3-dihydroxy-cyclopentyl}-2-hydroxy-acetamide (Intermediate SC), as described for Example 189 1,3-bis-{(1S,2R,3S,4R)-1-[6-(2,2-diphenylethylamino)-9-(4-(2-hydroxyacetamido)-2,3-dihydroxycyclopentyl)-9H-purin-2-yl]-1H-pyrazol-4-yl}-urea.

Example 198

1,3-Bis {1-[9-[(1R,2S,3R,4S)-2,3-Dihydroxy-4-(2-hydroxy-acetylamino)-cyclopentyl]-6-((8)-1-hydroxymethyl-2-phenyl-ethylamino)-9H-purin-2-yl]-1H-[1,2,4]triazol-3-yl}-urea The title compound can be synthesised by combining {1-[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purin-2-yl]-1H-[1,2,4]triazol-3-yl}-carbamic acid phenyl ester (Intermediate SG) and N-{(1S,2R,3S,4R)-4-[2-(3-amino-[1,2,4]triazol-1-yl)-6-((S)-1-hydroxymethyl-2-phenyl-ethylamino)-purin-9-yl]-2,3-dihydroxy-cyclopentyl}-2-hydroxy-acetamide (Intermediate SD), as described for Example 189 1,3-bis-{(1S,2R,3S,4R)-1-[6-(2,2-diphenylethylamino)-9-(4-(2-hydroxyacetamido)-2,3-dihydroxycyclopentyl)-9H-purin-2-yl]-1H-pyrazol-4-yl}-urea.

Example 199

The title compound can be synthesised by combining (1-{6-{[bis-(4-methoxy-phenyl)-methyl]-amino}-9-[(1R,2S,3R,4S)-2,3-dihydroxy-4-(2-hydroxy-acetylamino)-cyclopentyl]-9H-purin-2-yl}-1H-[1,2,4]triazol-3-yl)-carbamic acid phenyl ester (Intermediate SH) and N-{(1S,2R,3S,4R)-4-[6-{[bis-(4-methoxy-phenyl)-methyl]-amino}-2-(3-nitro-[1,2,4]triazol-1-yl)-purin-9-yl]-2,3-dihydroxy-cyclopentyl}-2-hydroxy-acetamide (Intermediate SE), as described for Example 189 1,3-bis-{(1S,2R,3S,4R)-1-[6-(2,2-diphenylethylamino)-9-(4-(2-hydroxyacetamido)-2,3-dihydroxy-cyclopentyl)-9H-purin-2-yl]-1H-pyrazol-4-yl}-urea.

Example 200

The title compound can be prepared analogously to Example 194 1,3-bis-{1-(R)-[(1S,2R,3S,4R)-6-amino-9-(2,3-dihydroxy-4-propionamido-cyclopentyl)-9H-purin-2-yl]-pyrrolidin-3-yl}-urea.

Example 201

The title compound is prepared analogues to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate AA) with 3-{(1S,2R,3S,4R)-4-[2-chloro-6-(2,2-diphenyl-ethylamino)-purin-9-yl]-2,3-dihydroxy-cyclopentyl}-imidazolidine-2,4-dione (Intermediate VA).

Example 202

1,3-Bis-{(R)-1-[9-[(1R,2S,3R,4S)-4-(3-ethyl-2,5-dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-urea The title compound is prepared analogues to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate AA) with 3-{(1S,2R,3S,4R)-4-[2-chloro-6-((S)-1-hydroxymethyl-2-phenyl-ethylamino)- purin-9-yl]-2,3-dihydroxy-cyclopentyl}-1-ethyl-imidazolidine-2,4-dione (Intermediate VC).

Example 203

1,3-Bis-{(R)-1-[9-[(1R,2S,3R,4S)-2,3-dihydroxy-4-((S)-4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-urea The title compound is prepared analogues to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate AA) with (S)-3-{(1S,2R,3S,4R)-4-[2-chloro-6-((S)-1-hydroxymethyl-2-phenyl-ethylamino)-purin-9-yl]-2,3-dihydroxy-cyclopentyl}-5-hydroxymethyl-imidazolidine-2,4-dione (Intermediate VD).

Example 204

1,3-Bis-{(R)-1-[9-[(1R,2S,3R,4S)-2,3-dihydroxy-4-((R)-4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-urea The title compound is prepared analogues to Example 1 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate AA) with (R)-3-{(1S,2R,3S,4R)-4-[2-chloro-6-((S)-1-hydroxymethyl-2-phenyl-ethylamino)-purin-9-yl]-2,3-dihydroxy-cyclopentyl}-5-hydroxymethyl-imidazolidine-2,4-dione (Intermediate VE).

Example 205

The title compound can be synthesised by combining {1-[9-[(1R,2S,3R,4S)-4-(2,5-dioxo-imidazolidin-1-yl)-2,3-dihydroxy-cyclopentyl]-6-((S)-1-hydroxymethyl-2-phenyl-ethylamino)-9H-purin-2-yl]-1H-imidazol-4-yl}-carbamic acid phenyl ester (Intermediate ZE) and 3-{(1S,2R,3S,4R)-4-[2-chloro-6-((S)-1-hydroxymethyl-2-phenyl-ethylamino)-purin-9-yl]-2,3-dihydroxy-cyclopentyl}-imidazolidine-2,4-dione (Intermediate VB), as described for Example 189 1,3-bis-{(1S,2R,3S,4R)-1-[6-(2,2-diphenylethylamino)-9-(4-(2-hydroxyacetamido)-2,3-dihydroxycyclopentyl)-9H-purin-2-yl]-1H-pyrazol-4-yl)-urea.

Example 206

The title compound can be synthesised by combining (2-{[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purine-2-carbonyl]-amino}-ethyl)-carbamic acid phenyl ester (Intermediate ZA) and 9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purine-2-carboxylic acid (2-amino-ethyl)-amide (Intermediate WG), as described for Example 189 1,3-bis-{(1S,2R,3S,4R)-1-[6-(2,2-diphenylethylamino)-9-(4-(2-hydroxyacetamido)-2,3-dihydroxycyclopentyl)-9H-purin-2-yl]-1H-pyrazol-4-yl}-urea.

Example 207

The title compound can be synthesised by combining {3-[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purin-2-yl]-prop-2-ynyl}-carbamic acid phenyl ester (Intermediate ZB) and N-{(1S,2R,3S,4R)-4-[2-(3-amino-prop-1-ynyl)-6-((S)-1-hydroxymethyl-2-phenyl-ethylamino)-purin-9-yl]-2,3-dihydroxy-cyclopentyl}-2-hydroxy-acetamide (Intermediate YA), as described for Example 189 1,3-bis-{(1S,2R,3S,4R)-1-[6-(2,2-diphenylethylamino)-9-(4-(2-hydroxyacetamido)-2,3-dihydroxycyclopentyl)-9H-purin-2-yl]-1H-pyrazol-4-yl}-urea.

Example 208

The title compound can be synthesised by combining 4-{3-[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purin-2-yl]-prop-2-ynyl}-piperidine-1-carboxylic acid phenyl ester (Intermediate ZC) and N-{(1S,2R,3S,4R)-2,3-dihydroxy-4-[6-((S)-1-hydroxymethyl-2-phenyl-ethylamino)-2-(3-piperidin-4-yl-prop-1-ynyl)-purin-9-yl]-cyclopentyl}-2-hydroxy-acetamide (Intermediate YB), as described for Example 189 1,3-bis-{(1S,2R,3S,4R)-1-[6-(2,2-diphenylethylamino)-9-(4-(2-hydroxyacetamido)-2,3-dihydroxycyclopentyl)-9H-purin-2-yl]-1H-pyrazol-4-yl}-urea.

Example 209

The title compound can be synthesised by combining ((R)-1-{3-[9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purin-2-yl]-prop-2-ynyl}-pyrrolidin-3-yl)-carbamic acid phenyl ester (Intermediate ZD) and N-{(1S,2R,3S,4R)-4-[2-[3-((R)-3-amino-pyrrolidin-1-yl)-prop-1-ynyl]-6-((S)-1-hydroxymethyl-2-phenyl-ethylamino)-purin-9-yl]-2,3-dihydroxy-cyclopentyl}-2-hydroxy-acetamide (Intermediate YC), as described for Example 189 1,3-bis-{(1S,2R,3S,4R)-1-[6-(2,2-diphenylethylamino)-9-(4-(2-hydroxyacetamido)-2,3-dihydroxycyclopentyl)-9H-purin-2-yl]-1H-pyrazol-4-yl}-urea.

Example 210

A solution comprising 9-[(1R,2S,3R,4S)-2,3-dihydroxy-4-(2-hydroxy-acetylamino)-cyclopentyl]-6-((S)-1-hydroxymethyl-2-phenyl-ethylamino)-9H-purine-2-carboxylic acid (2-amino-ethyl)-amide (Intermediate WG) (2 eq.) in dry THF is treated with 1,4-diisocyanato-cyclohexane (1 eq.) and stirred at RT for 3 days. The title compound is obtained by column chromatography.

Example 211

A solution comprising N-{(1S,2R,3S,4R)-4-[2-(3-amino-prop-1-ynyl)-6-((S)-1-hydroxymethyl-2-phenyl-ethylamino)-purin-9-yl]-2,3-dihydroxy-cyclopentyl}-2-hydroxy-acetamide (Intermediate YA) (2 eq.) in dry THF is treated with 1,3-diisocyanato-benzene (1 eq.) and stirred at RT for 3 days. The title compound is obtained by column chromatography.

The invention claimed is:

1. A compound or stereoisomers or pharmaceutically acceptable salts thereof, wherein the compound is of formula (Ia):

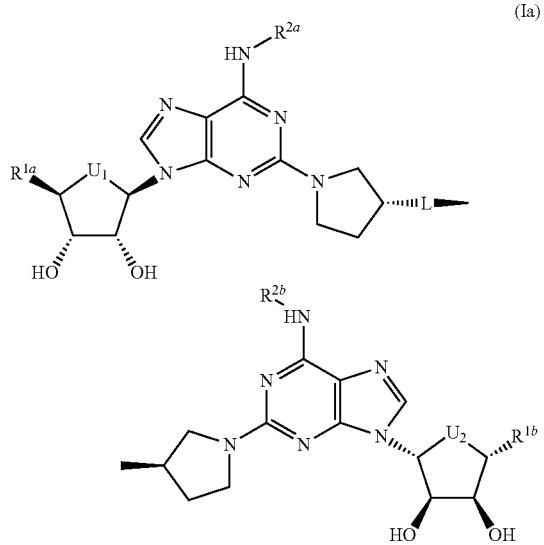

wherein
U₁ and U₂ are independently selected from CH₂ and O with the proviso that when U₁ is O then $R^{1a}$ is not a N-bonded substituent, and when U₂ is O then $R^{1b}$ is not a N-bonded substituent;
$R^{1a}$ and $R^{1b}$ are independently selected from a 3- to 12-membered heterocyclic group containing from 1 to 4 ring nitrogen atoms and optionally containing from 1 to 4 other heteroatoms selected from the group consisting of oxygen and sulfur, that group being optionally substituted by $C_1$-$C_8$-alkyl, or
$R^{1a}$ and $R^{1b}$ are independently selected from —NH—$C_1$-$C_8$-alkylcarbonyl, and —NH—$C_3$-$C_8$-cycloalkylcarbonyl, or
$R^{1a}$ and $R^{1b}$ are independently selected from NH—$C_1$-$C_8$-alkyl, NHC(O)$C_1$-$C_8$-hydroxyalkyl, NHCO₂$C_1$-$C_8$-alkyl, and NHCO₂$C_1$-$C_8$-hydroxyalkyl;
$T^{1a}$ and $R^{1b}$ are independently selected from $C_1$-$C_8$-hydroxyalkyl, and CH₂—O—$C_1$-$C_8$-alkyl;
$R^{2a}$ and $R^{2b}$ are independently selected from hydrogen, $C_1$-$C_8$-alkyl optionally substituted by OH, $C_3$-$C_{15}$-carbocyclic group, or $C_6$-$C_{10}$-aryl optionally substituted by OH, halogen, or O—$C_1$-$C_8$-alkyl, or
$R^{2a}$ and $R^{2b}$ are independently $C_7$-$C_{14}$-aralkyl optionally substituted by OH, halogen, or CN; and
L is selected from

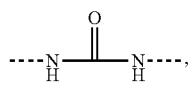

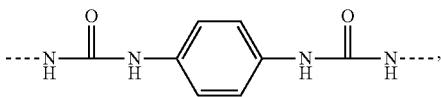

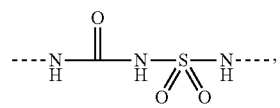

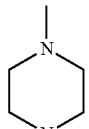

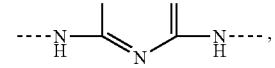

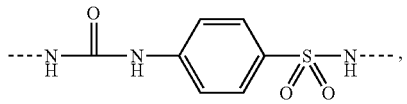

and

2. A compound or its pharmaceutically acceptable salt selected from the group consisting of 427 428
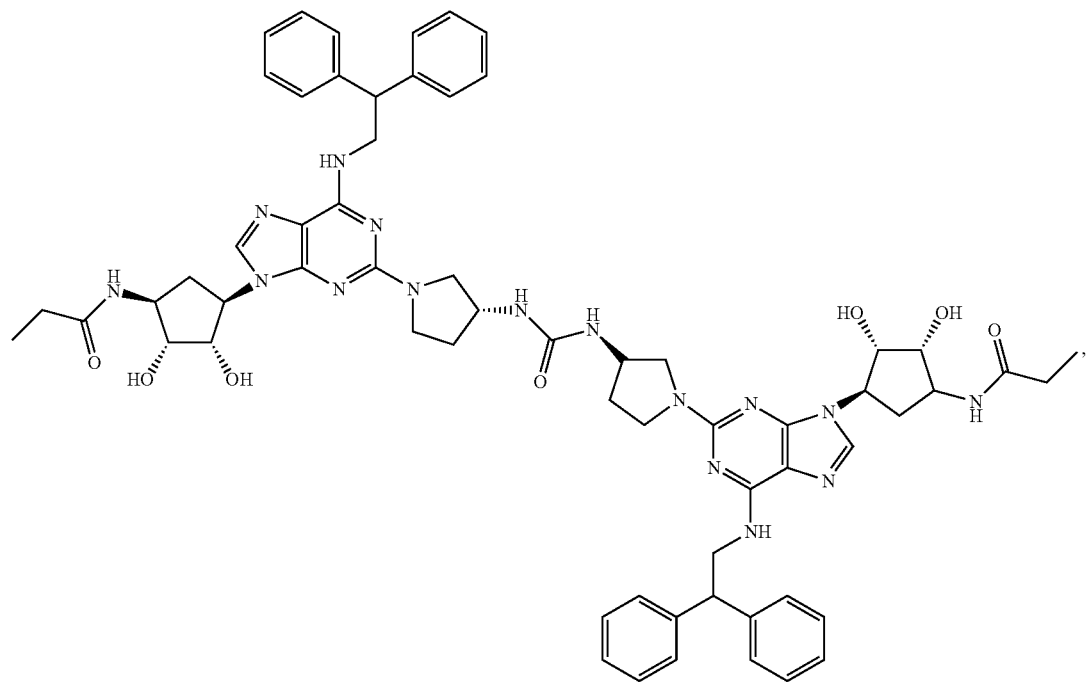
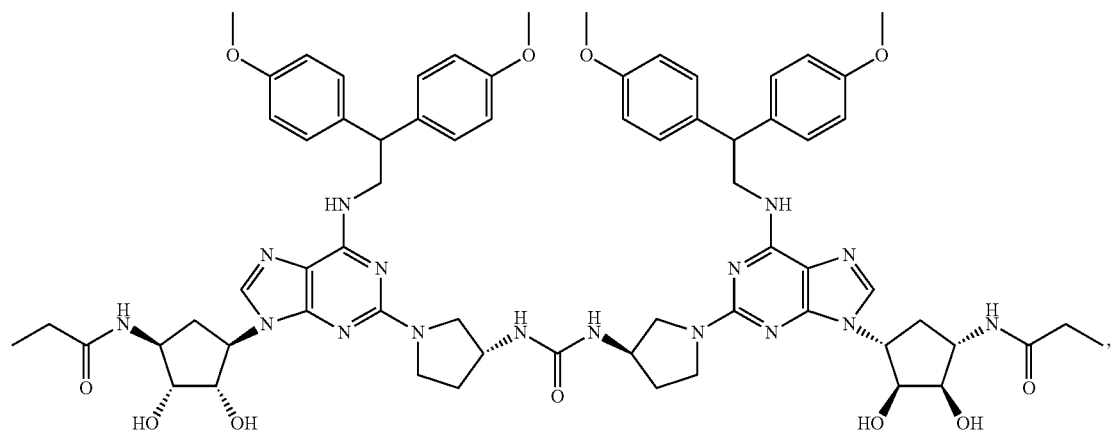
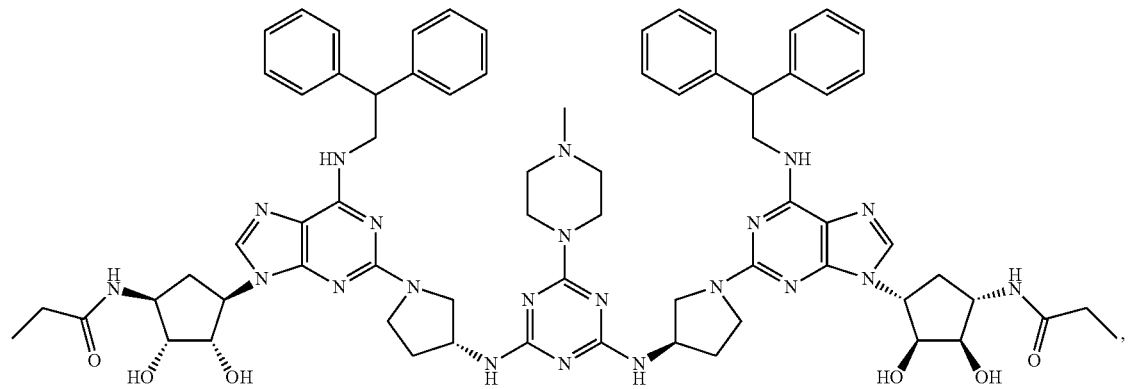

429
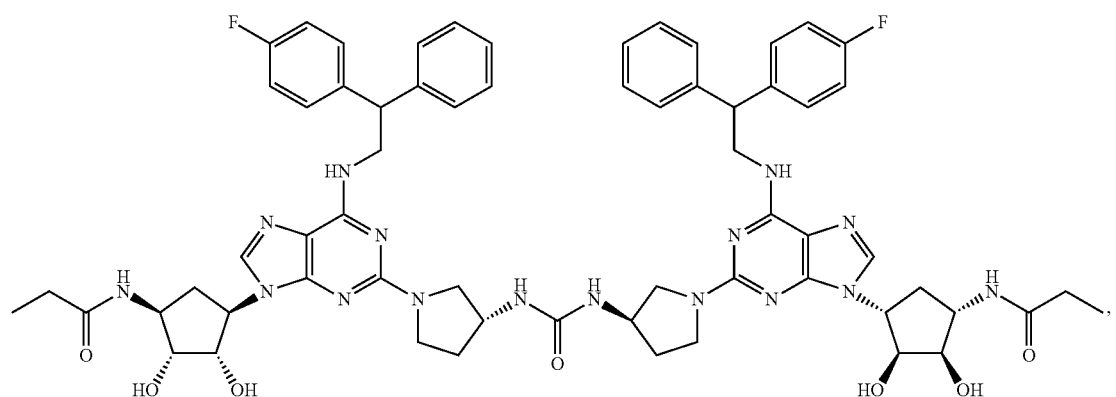
430
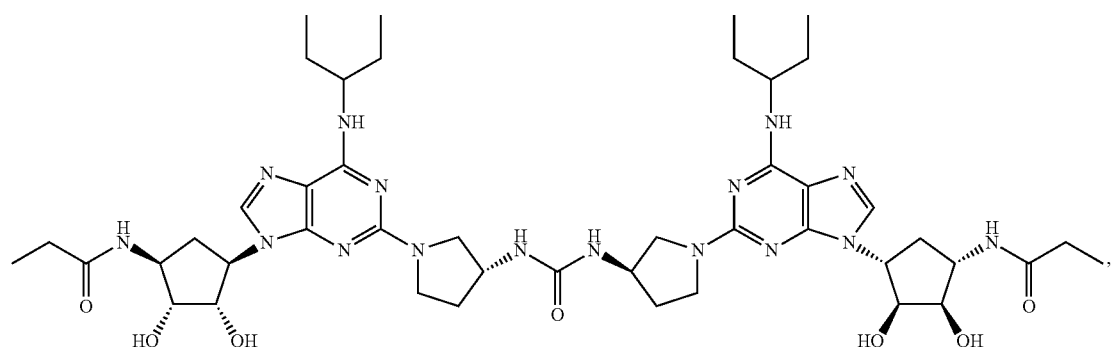
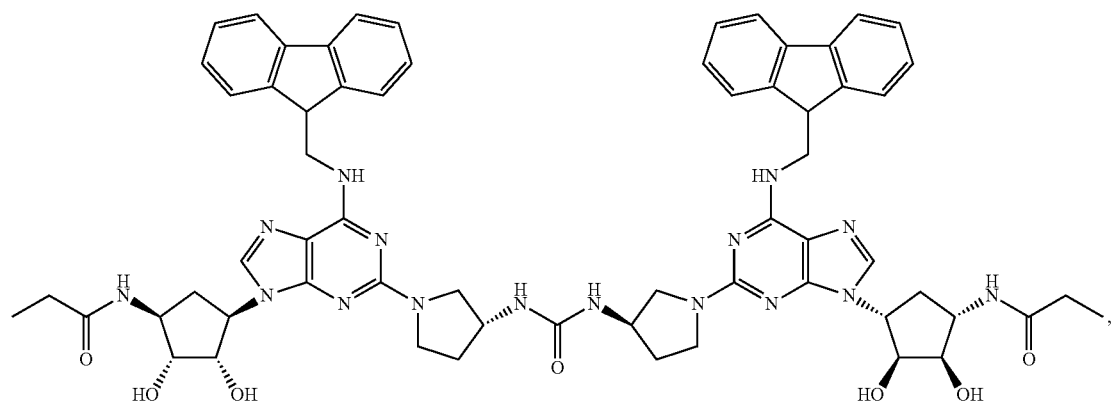
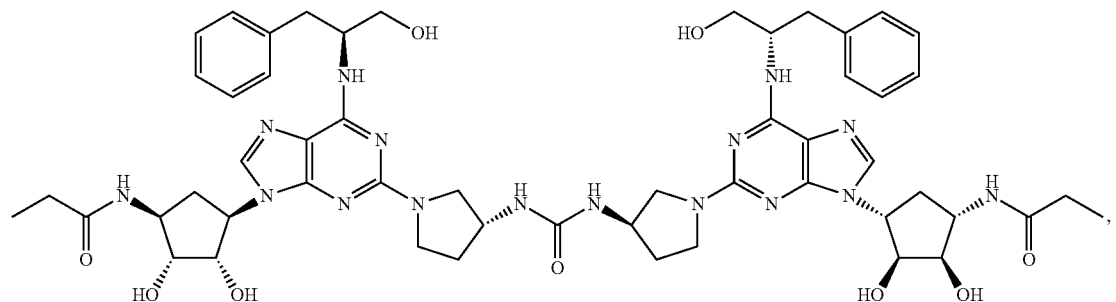

431                                             432
-continued
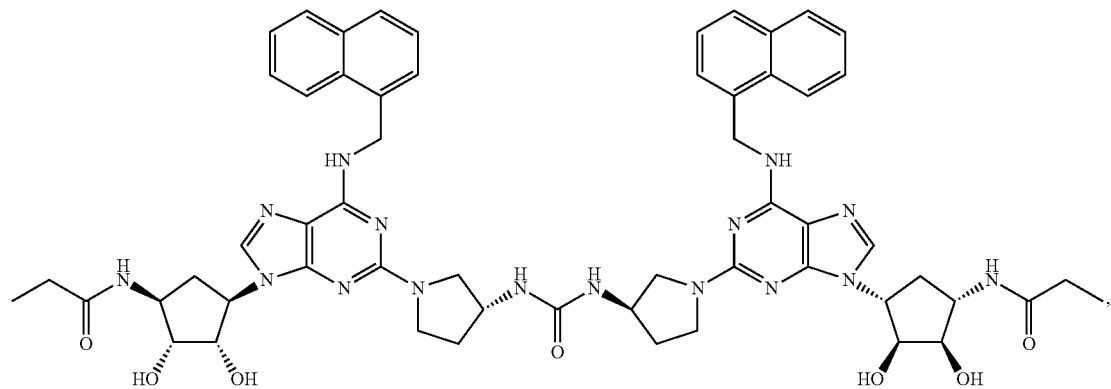
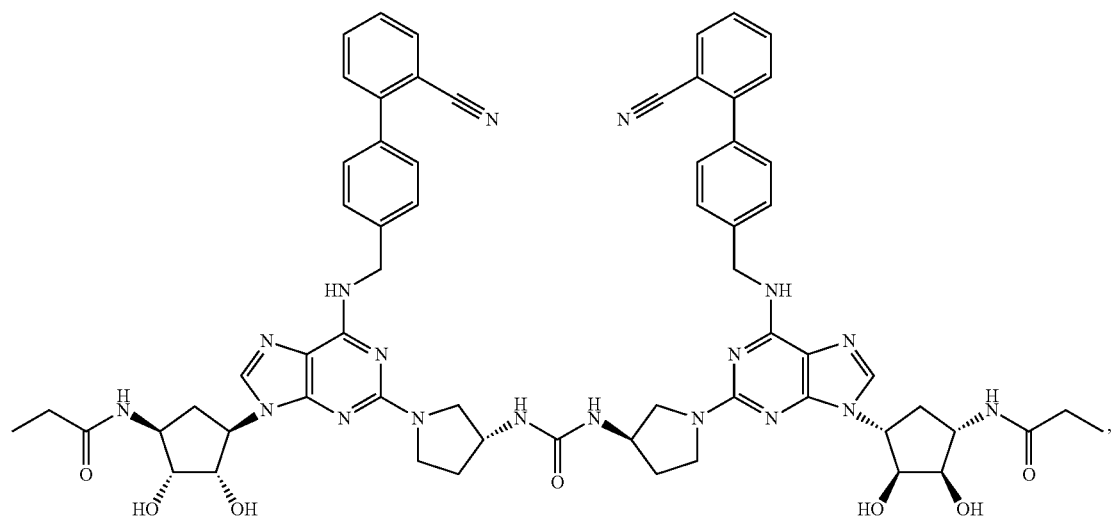
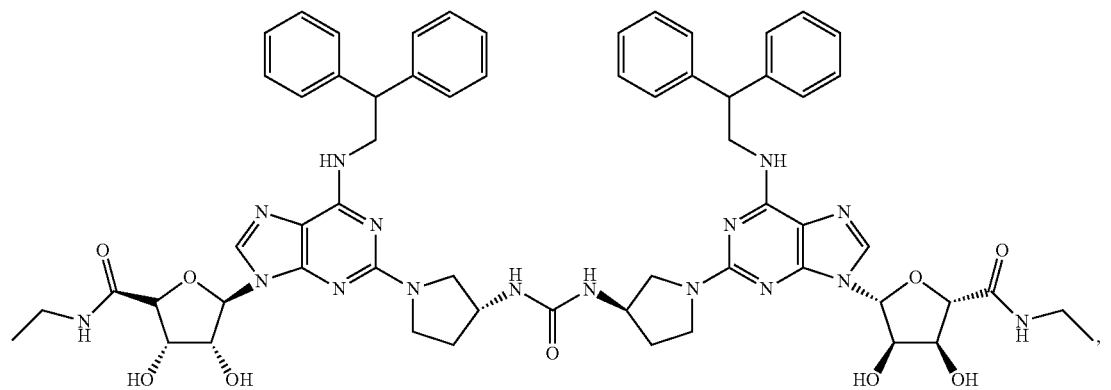
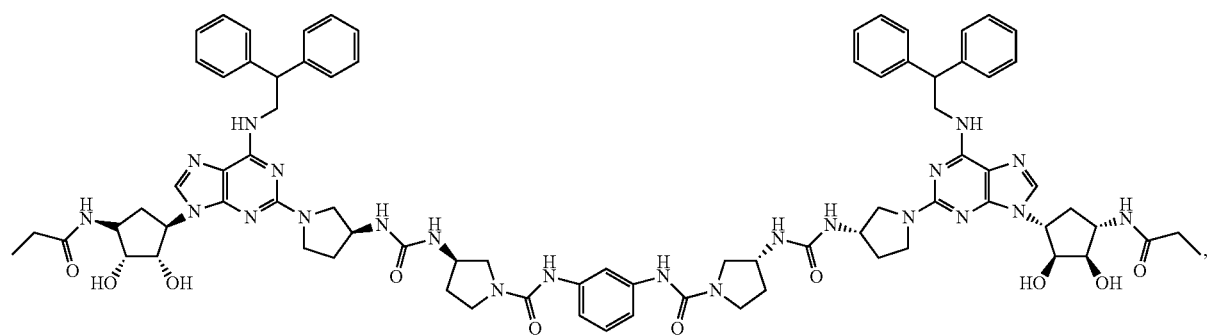

433
-continued
434
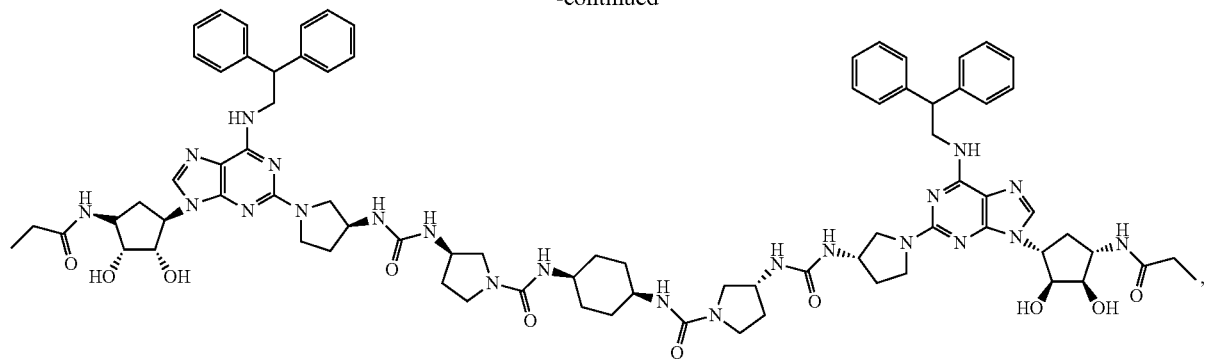
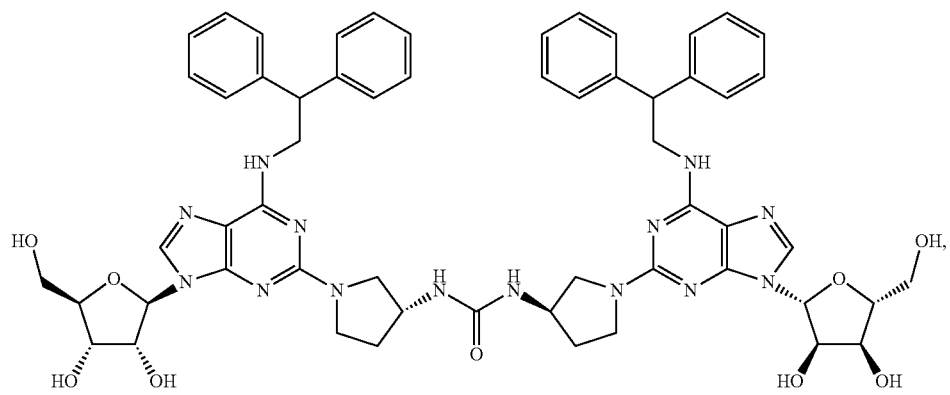
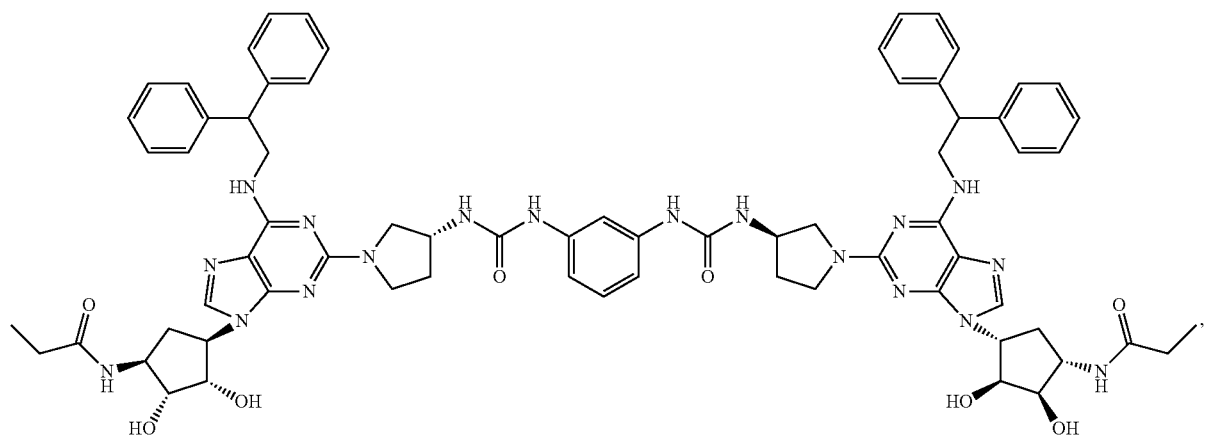
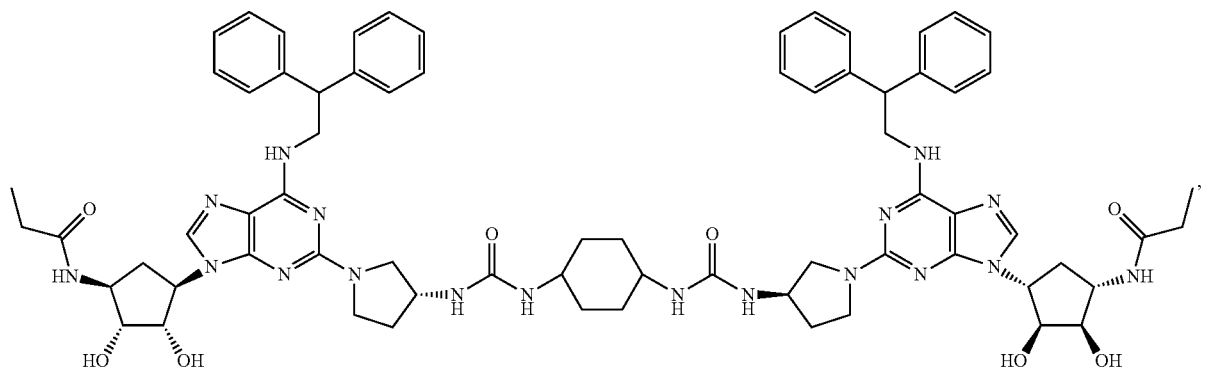

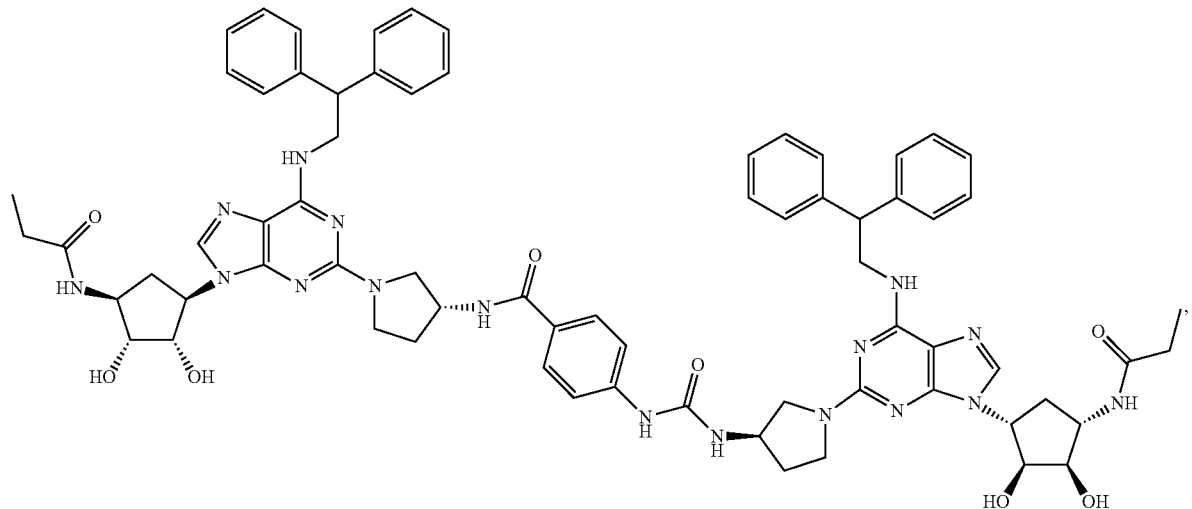
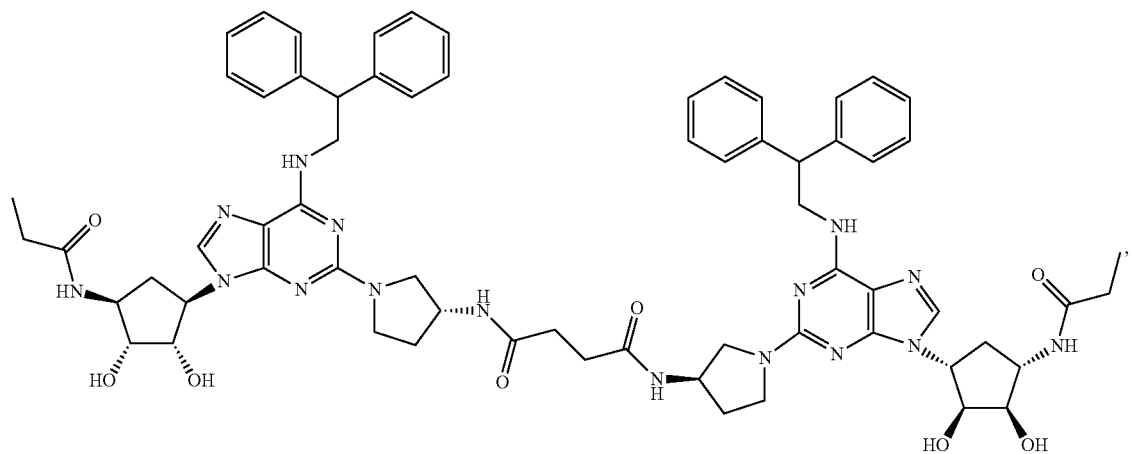
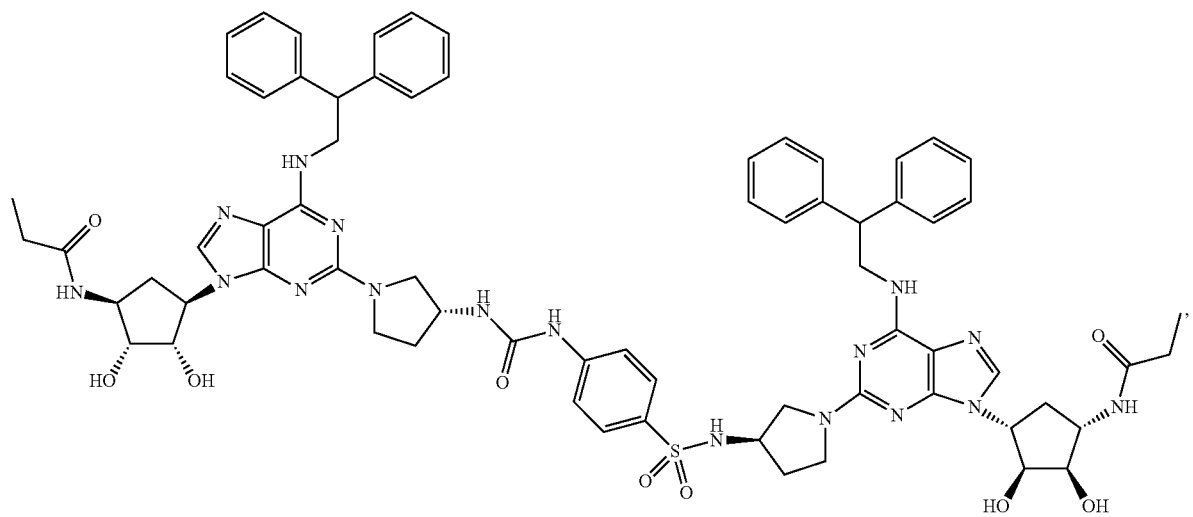

437 438
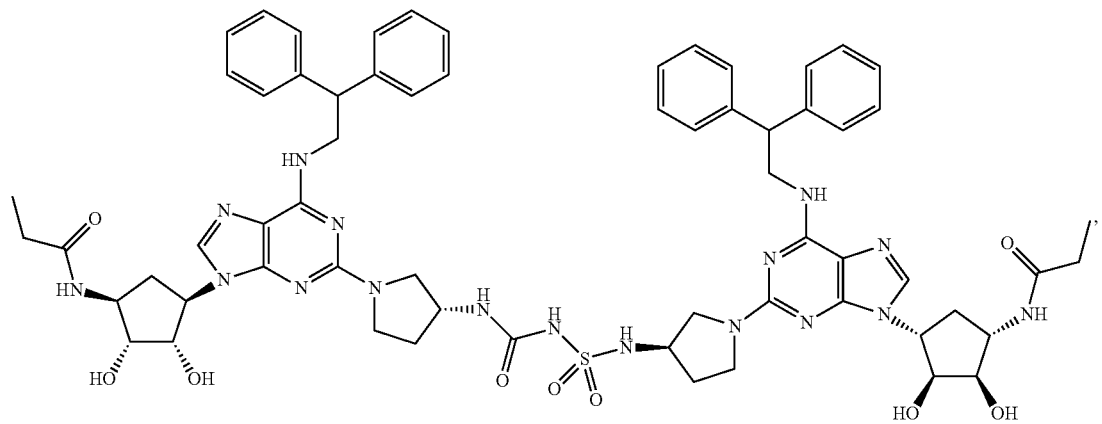
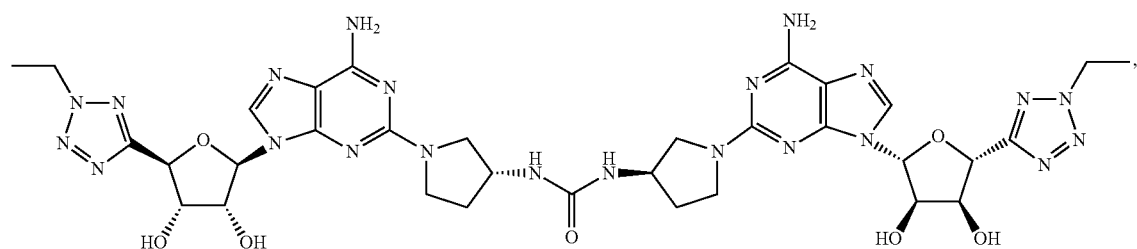
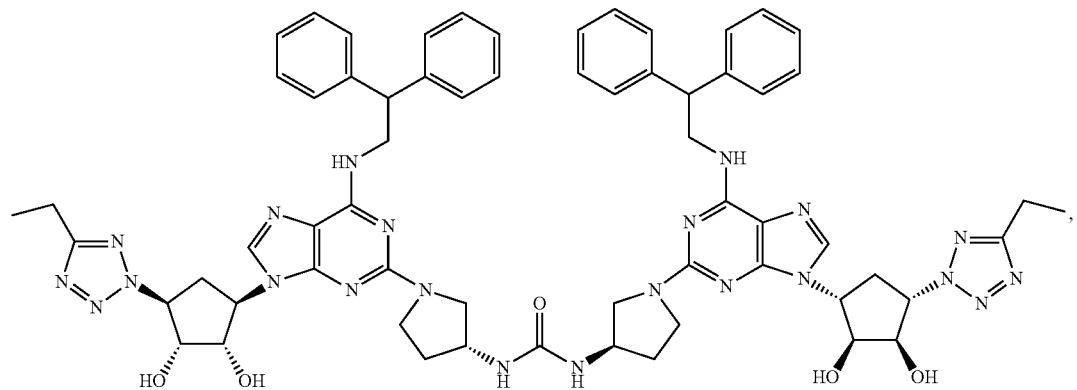
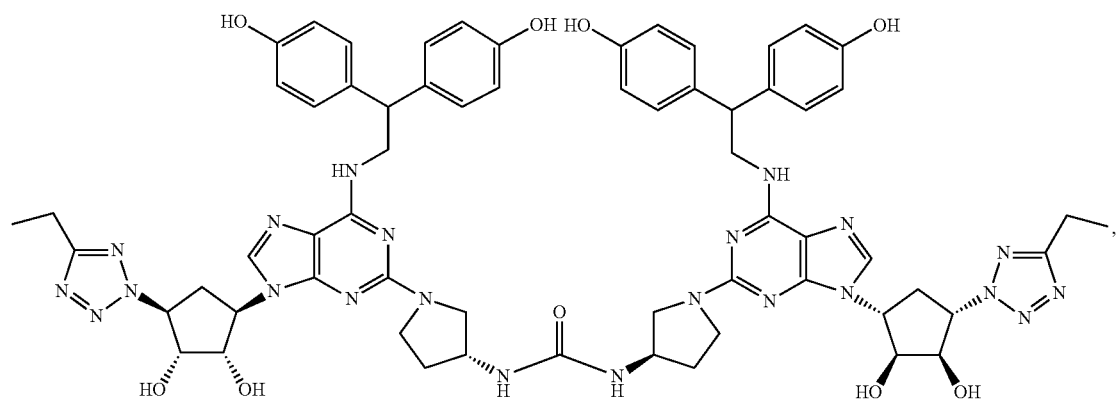

-continued
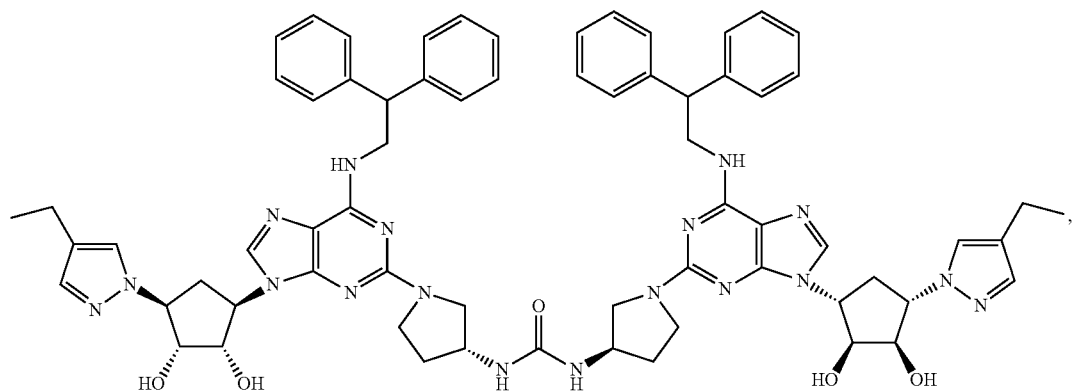
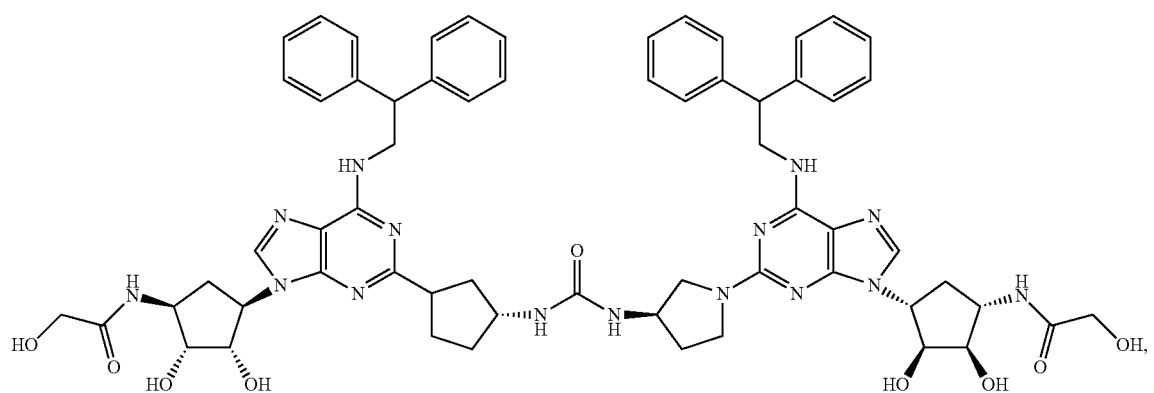
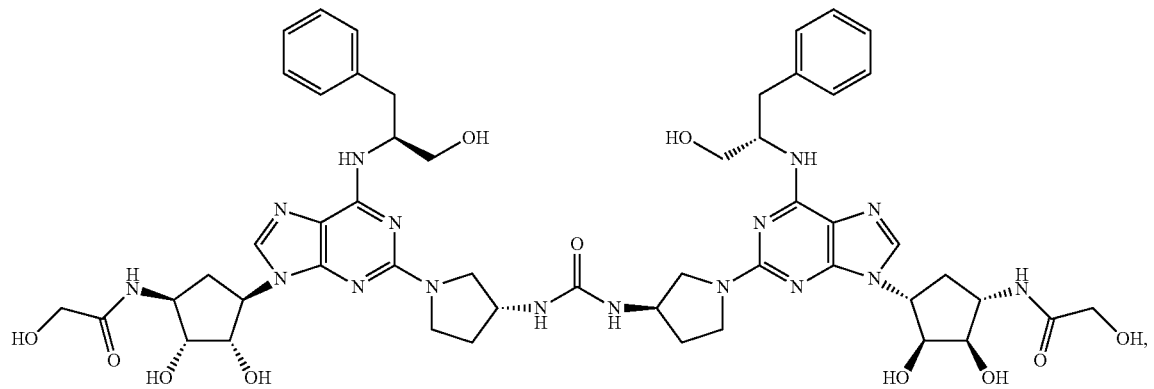
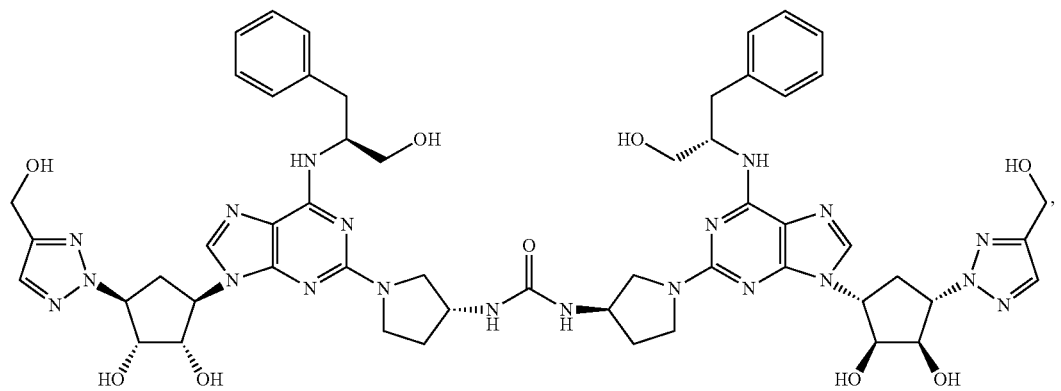

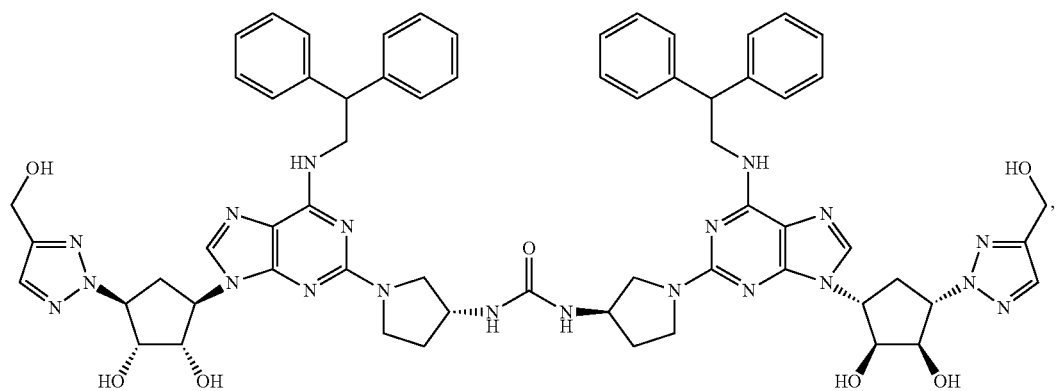
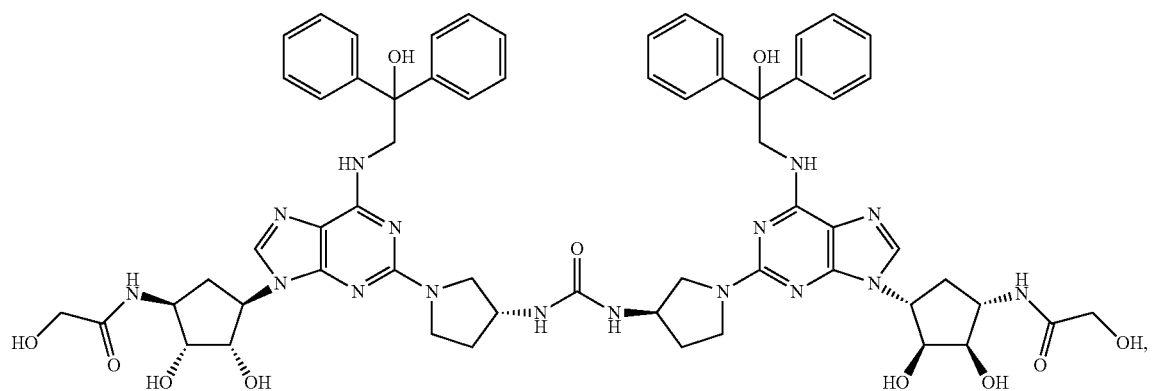
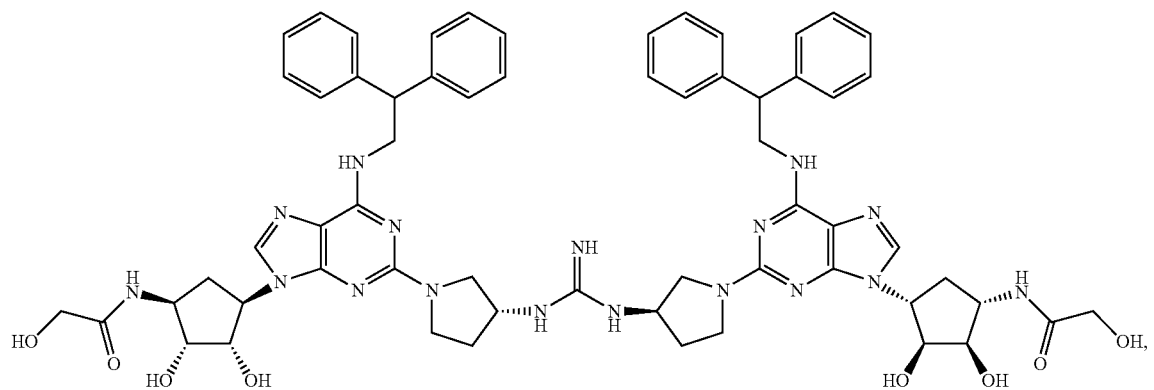
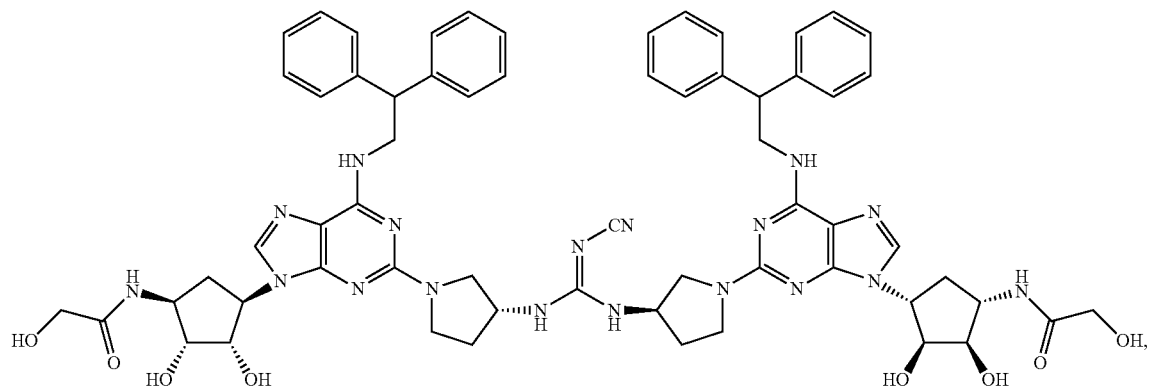

443 444
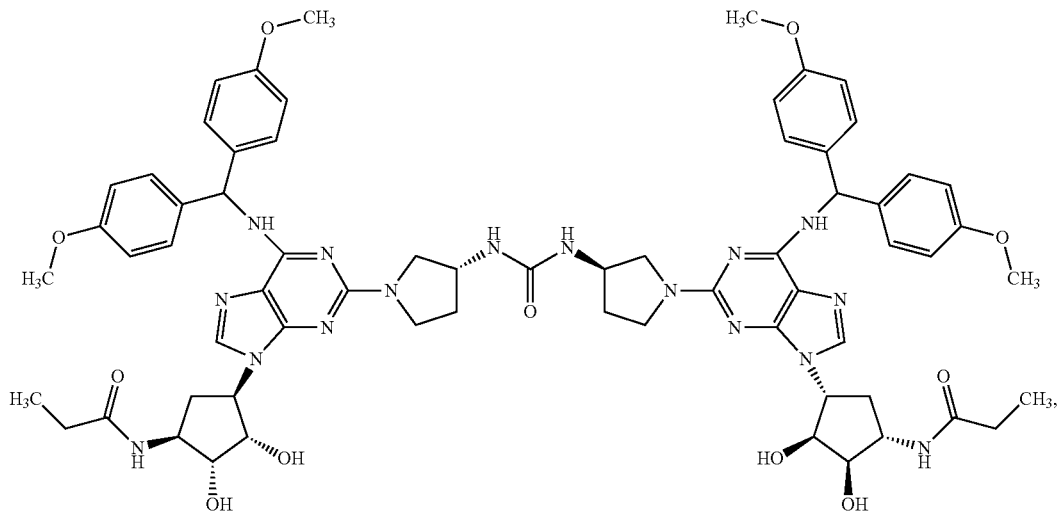
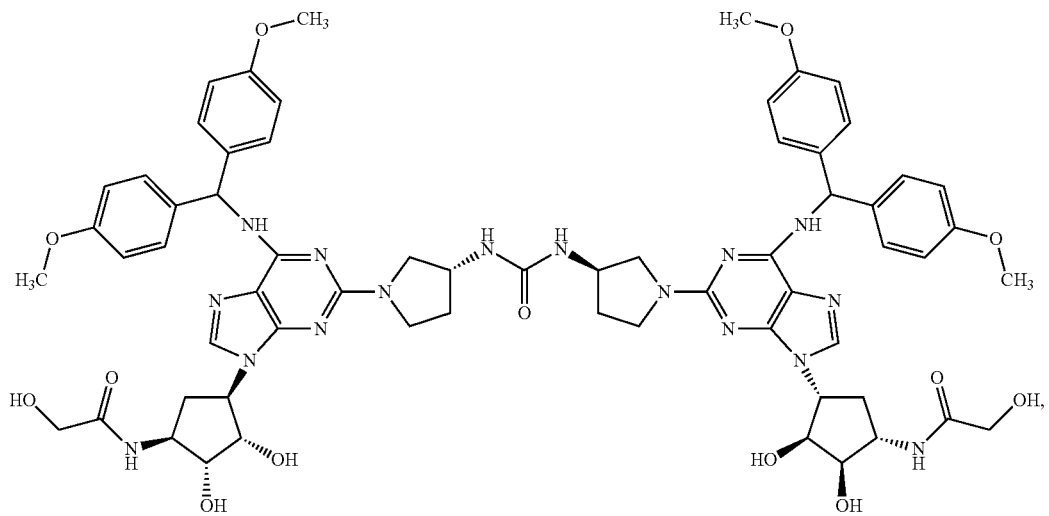
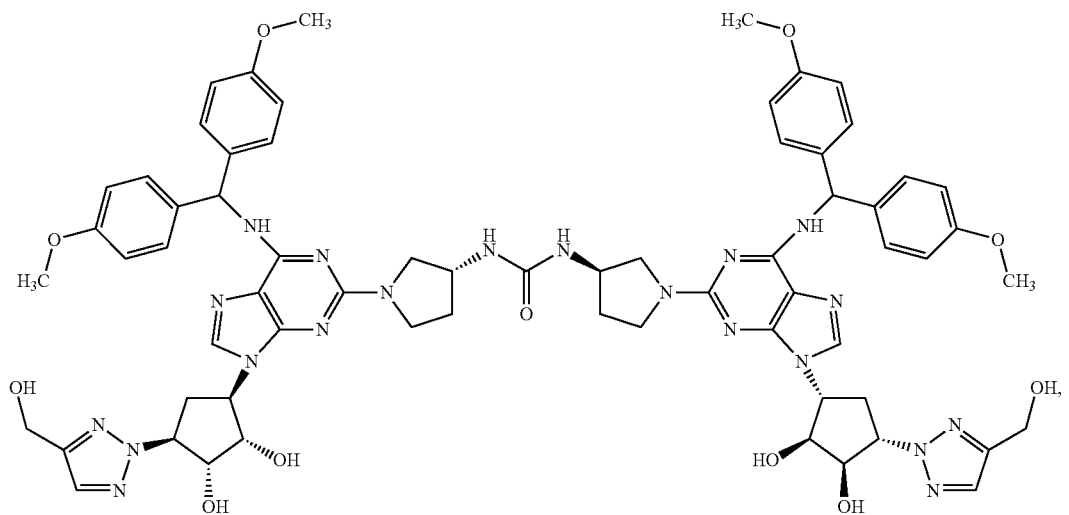

445 446
-continued
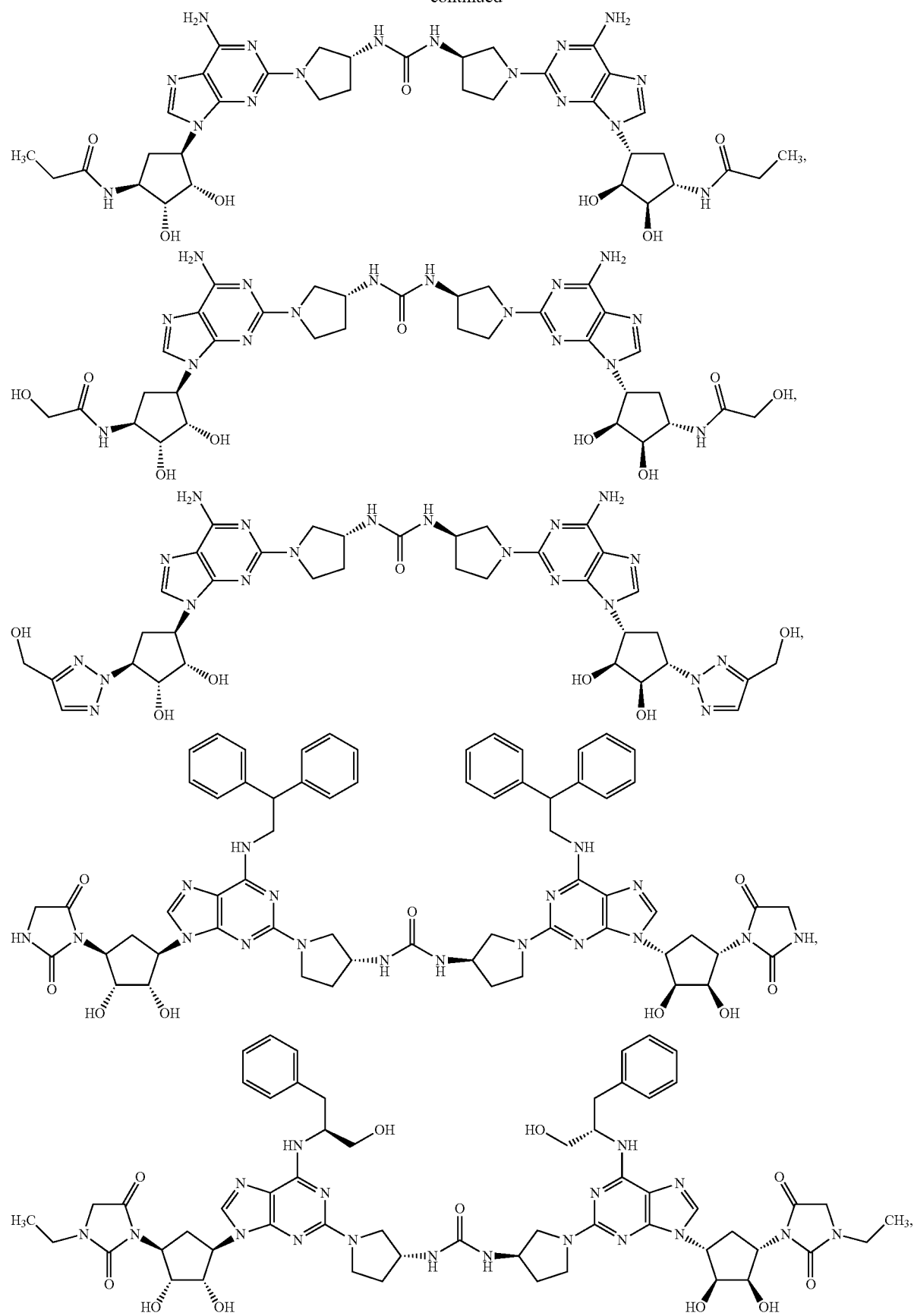

-continued

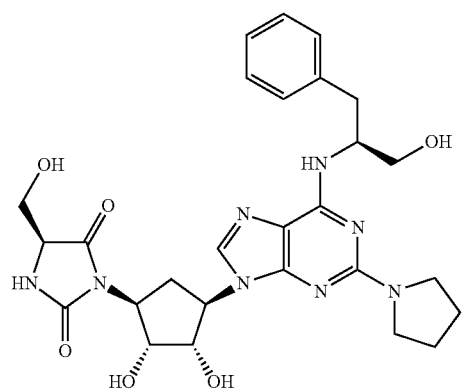 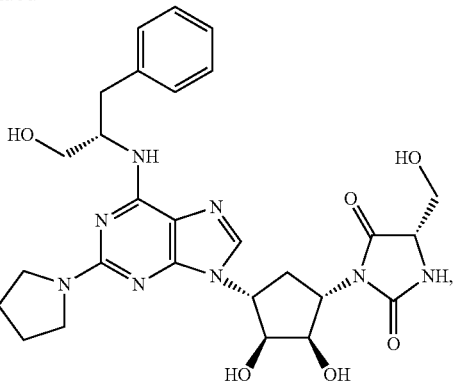

, and

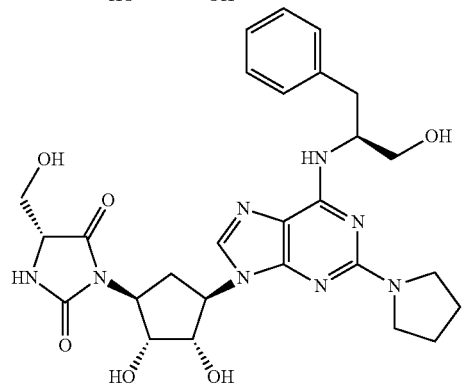 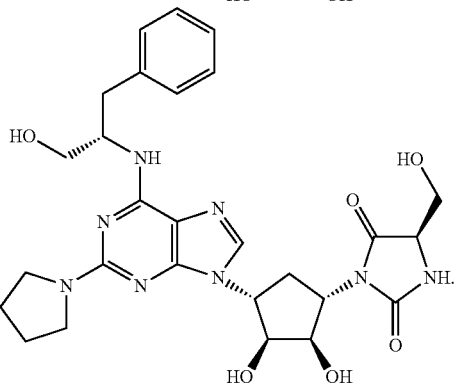

.

3. A pharmaceutical combination, comprising:
the compound according to claim 1, and
an anti-inflammatory, bronchodilatory, anti-histamine or anti-tussive drug substance, said compound and said drug substance being in the same or different pharmaceutical composition.

4. A pharmaceutical composition, comprising:
the compound according to claim 1, and
a pharmaceutically acceptable diluent or carrier.

* * * * *